(12) United States Patent
Lambrecht et al.

(10) Patent No.: US 7,658,765 B2
(45) Date of Patent: *Feb. 9, 2010

(54) RESILIENT INTERVERTEBRAL DISC IMPLANT

(75) Inventors: Gregory H. Lambrecht, Natick, MA (US); Robert Kevin Moore, Natick, MA (US); Jacob Einhorn, Brookline, MA (US); Sean Kavanaugh, Eastham, MA (US); Chris Tarapata, North Andover, MA (US); Thomas Boyajian, Wilmington, MA (US)

(73) Assignee: Intrinsic Therapeutics, Inc., Woburn, MA (US)

( * ) Notice: Subject to any disclaimer, the term of this patent is extended or adjusted under 35 U.S.C. 154(b) by 439 days.

This patent is subject to a terminal disclaimer.

(21) Appl. No.: 10/972,106

(22) Filed: Oct. 22, 2004

(65) Prior Publication Data

US 2005/0240269 A1 Oct. 27, 2005

Related U.S. Application Data

(63) Continuation of application No. 10/970,589, filed on Oct. 21, 2004, now Pat. No. 7,553,329, and a continuation-in-part of application No. 10/194,428, filed on Jul. 10, 2002, now Pat. No. 6,936,072, and a continuation-in-part of application No. 10/055,504, filed on Oct. 25, 2001, now Pat. No. 7,258,700, which is a continuation-in-part of application No. 09/696,636, filed on Oct. 25, 2000, now Pat. No. 6,508,839, which is a continuation-in-part of application No. 09/642,450, filed on Aug. 18, 2000, now Pat. No. 6,482,235, which is a continuation-in-part of application No. 09/608,797, filed on Jun. 30, 2000, now Pat. No. 6,425,919.

(60) Provisional application No. 60/513,437, filed on Oct. 22, 2003, provisional application No. 60/613,958, filed on Sep. 28, 2004, provisional application No. 60/311,586, filed on Aug. 10, 2001, provisional application No. 60/149,490, filed on Aug. 18, 1999, provisional application No. 60/161,085, filed on Oct. 25, 1999, provisional application No. 60/172,996, filed on Dec. 21, 1999.

(51) Int. Cl.
*A61F 2/44* (2006.01)
(52) U.S. Cl. .................................. 623/17.11; 623/17.16
(58) Field of Classification Search ... 623/17.11–17.16; 606/213
See application file for complete search history.

(56) References Cited

U.S. PATENT DOCUMENTS 3,526,567 A 9/1970 Macone (Continued)

FOREIGN PATENT DOCUMENTS

EP 0298233 1/1989

(Continued)

OTHER PUBLICATIONS

Bagga C.S., Williams P., Highma P.A., Bao B.Q. "Development of Fatigue Test Model for a Spinal Nucleus Prosthesis with Preliminary Results for a Hydrogel Spinal Prosthetic Nucleus." Proceedings of the 1997 Bioengineering Conference, 441-442: BED-vol. 35, Sunriver, Oregon, Jun. 11-15, 1997.

(Continued)

*Primary Examiner*—Bruce E Snow
(74) *Attorney, Agent, or Firm*—Knobbe, Martens, Olson & Bear, LLP; Sean Kavanaugh, Intrinsic

(57) ABSTRACT

Resilient surgical meshes that, in some aspects, can be compressed or otherwise configured, for minimally invasive delivery in the intervertebral discs are provided. According to one or more embodiments, the surgical mesh can be robust, fatigue resistant, stable and capable of withstanding the dynamic environment generic to intervertebral discs.

6 Claims, 97 Drawing Sheets

U.S. PATENT DOCUMENTS

| | | |
|---|---|---|
| 3,867,728 A | 2/1975 | Stubstad et al. |
| 3,875,595 A | 4/1975 | Froning |
| 3,921,632 A | 11/1975 | Bardani |
| 4,280,954 A | 7/1981 | Yannas et al. |
| 4,349,921 A | 9/1982 | Kuntz |
| 4,473,070 A | 9/1984 | Matthews et al. |
| 4,502,161 A | 3/1985 | Wall |
| 4,532,926 A | 8/1985 | O'Holla |
| 4,665,906 A | 5/1987 | Jervis |
| 4,714,469 A | 12/1987 | Kenna |
| 4,741,330 A | 5/1988 | Hayhurst |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,821,942 A | 4/1989 | Richards et al. |
| 4,837,285 A | 6/1989 | Berg et al. |
| 4,852,568 A | 8/1989 | Kensey |
| 4,863,477 A | 9/1989 | Monson |
| 4,871,094 A | 10/1989 | Gall et al. |
| 4,873,976 A | 10/1989 | Schreiber |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,021,059 A | 6/1991 | Kensey et al. |
| 5,035,716 A | 7/1991 | Downey |
| 5,046,513 A | 9/1991 | Gatturna et al. |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,129,906 A | 7/1992 | Ross et al. |
| 5,141,515 A | 8/1992 | Eberbach |
| 5,147,374 A | 9/1992 | Fernandez |
| 5,171,252 A | 12/1992 | Friedland |
| 5,171,259 A | 12/1992 | Inoue |
| 5,171,280 A | 12/1992 | Baumgartner |
| 5,171,281 A | 12/1992 | Parsons et al. |
| 5,176,692 A | 1/1993 | Wilk et al. |
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,207,649 A | 5/1993 | Aruny |
| 5,219,359 A | 6/1993 | McQuilkin et al. |
| 5,222,974 A | 6/1993 | Kensey et al. |
| 5,239,982 A | 8/1993 | Trauthen |
| 5,242,448 A | 9/1993 | Pettine et al. |
| 5,254,133 A | 10/1993 | Seid |
| 5,258,000 A | 11/1993 | Gianturco |
| 5,258,031 A | 11/1993 | Salib et al. |
| 5,258,043 A | 11/1993 | Stone |
| 5,269,783 A | 12/1993 | Sander |
| 5,282,827 A | 2/1994 | Kensey et al. |
| 5,292,332 A | 3/1994 | Lee |
| 5,306,311 A | 4/1994 | Stone et al. |
| 5,312,435 A | 5/1994 | Nash et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,356,432 A | 10/1994 | Rutkow et al. |
| 5,366,460 A | 11/1994 | Eberbach |
| 5,368,602 A | 11/1994 | De la Torre |
| 5,370,697 A | 12/1994 | Baumgartner |
| 5,383,477 A | 1/1995 | DeMatteis |
| 5,383,905 A | 1/1995 | Golds et al. |
| 5,397,331 A | 3/1995 | Himpens et al. |
| 5,397,332 A | 3/1995 | Kammerer et al. |
| 5,397,355 A | 3/1995 | Marin et al. |
| 5,405,360 A | 4/1995 | Tovey |
| 5,425,773 A | 6/1995 | Boyd et al. |
| 5,431,658 A | 7/1995 | Moskovich |
| 5,437,631 A | 8/1995 | Janzen |
| 5,445,639 A | 8/1995 | Kuslich et al. |
| 5,456,720 A | 10/1995 | Schultz |
| 5,464,407 A | 11/1995 | McGuire |
| 5,500,000 A | 3/1996 | Feagin et al. |
| 5,507,754 A | 4/1996 | Green et al. |
| 5,514,130 A | 5/1996 | Baker |
| 5,514,180 A | 5/1996 | Heggeness et al. |
| 5,520,700 A | 5/1996 | Beyar et al. |
| 5,522,898 A | 6/1996 | Bao |
| 5,531,759 A | 7/1996 | Kensey et al. |
| 5,534,028 A | 7/1996 | Bao et al. |
| 5,534,030 A | 7/1996 | Navarro et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,552,100 A | 9/1996 | Shannon et al. |
| 5,556,428 A | 9/1996 | Shah |
| 5,556,429 A | 9/1996 | Felt |
| 5,562,689 A | 10/1996 | Green et al. |
| 5,562,736 A | 10/1996 | Ray |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,591,204 A | 1/1997 | Janzen et al. |
| 5,591,223 A | 1/1997 | Lock et al. |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,634,936 A | 6/1997 | Linden et al. |
| 5,641,373 A | 6/1997 | Shannon et al. |
| 5,645,084 A | 7/1997 | McKay |
| 5,645,597 A | 7/1997 | Krapiva |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,295 A | 10/1997 | Ray et al. |
| 5,674,296 A | 10/1997 | Bryan et al. |
| 5,676,698 A | 10/1997 | Janzen et al. |
| 5,676,701 A | 10/1997 | Yuan et al. |
| 5,681,351 A | 10/1997 | Jamiolkowski |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,705,780 A | 1/1998 | Bao |
| 5,716,408 A | 2/1998 | Eldridge et al. |
| 5,716,409 A | 2/1998 | Debbas |
| 5,716,413 A | 2/1998 | Walter et al. |

| | | | | | | |
|---|---|---|---|---|---|---|
| 5,716,416 | A | 2/1998 | Lin | 6,174,311 | B1 | 1/2001 | Branch et al. |
| 5,725,577 | A | 3/1998 | Saxon | 6,179,836 | B1 | 1/2001 | Eggers et al. |
| 5,728,150 | A | 3/1998 | McDonald et al. | 6,183,518 | B1 | 2/2001 | Ross et al. |
| 5,730,744 | A | 3/1998 | Justin et al. | 6,187,048 | B1 | 2/2001 | Milner et al. |
| 5,733,337 | A | 3/1998 | Carr, Jr. et al. | 6,190,353 | B1 | 2/2001 | Makower et al. |
| 5,743,917 | A | 4/1998 | Saxon | 6,203,735 | B1 | 3/2001 | Edwin et al. |
| 5,746,755 | A | 5/1998 | Wood et al. | 6,206,921 | B1 | 3/2001 | Guagliano et al. |
| 5,746,765 | A | 5/1998 | Kleshinski et al. | 6,214,039 | B1 | 4/2001 | Banas et al. |
| 5,755,797 | A | 5/1998 | Baumgartner | 6,224,630 | B1 | 5/2001 | Bao et al. |
| 5,766,246 | A | 6/1998 | Mulhauser et al. | 6,224,631 | B1 | 5/2001 | Kohrs |
| 5,769,864 | A | 6/1998 | Kugel | 6,231,597 | B1 | 5/2001 | Deem et al. |
| 5,769,893 | A | 6/1998 | Shah | 6,241,722 | B1 | 6/2001 | Dobak et al. |
| 5,772,661 | A | 6/1998 | Michelson | 6,245,099 | B1 | 6/2001 | Edwin et al. |
| 5,776,183 | A | 7/1998 | Kanesaka et al. | 6,245,107 | B1 | 6/2001 | Ferree |
| 5,782,844 | A | 7/1998 | Yoon et al. | 6,264,659 | B1 | 7/2001 | Ross et al. |
| 5,785,705 | A | 7/1998 | Baker | 6,264,695 | B1 | 7/2001 | Stoy |
| 5,800,549 | A | 9/1998 | Bao et al. | 6,267,834 | B1 | 7/2001 | Shannon et al. |
| 5,810,851 | A | 9/1998 | Yoon | 6,273,912 | B1 | 8/2001 | Scholz et al. |
| 5,823,994 | A | 10/1998 | Sharkey et al. | 6,280,475 | B1 | 8/2001 | Bao et al. |
| 5,824,008 | A | 10/1998 | Bolduc et al. | 6,312,462 | B1 | 11/2001 | McDermott et al. |
| 5,824,082 | A | 10/1998 | Brown | 6,325,805 | B1 | 12/2001 | Ogilvie et al. |
| 5,824,093 | A | 10/1998 | Ray et al. | 6,355,063 | B1 | 3/2002 | Calcote |
| 5,824,094 | A | 10/1998 | Serhan et al. | 6,371,990 | B1 | 4/2002 | Ferree |
| 5,827,298 | A | 10/1998 | Hart et al. | 6,383,214 | B1 | 5/2002 | Banas et al. |
| 5,836,315 | A | 11/1998 | Benderev et al. | 6,398,803 | B1 | 6/2002 | Layne et al. |
| 5,843,084 | A | 12/1998 | Hart et al. | 6,402,750 | B1 | 6/2002 | Atkinson et al. |
| 5,843,173 | A | 12/1998 | Shannon et al. | 6,416,537 | B1 | 7/2002 | Martakos et al. |
| 5,846,261 | A | 12/1998 | Kotula et al. | 6,419,704 | B1 | 7/2002 | Ferree |
| 5,860,425 | A | 1/1999 | Benderev et al. | 6,425,919 | B1 | 7/2002 | Lambrecht et al. |
| 5,860,977 | A | 1/1999 | Zucherman et al. | 6,428,575 | B2 | 8/2002 | Koo et al. |
| 5,865,845 | A | 2/1999 | Thalgott | 6,428,576 | B1 | 8/2002 | Haldimann |
| 5,865,846 | A | 2/1999 | Bryan et al. | 6,436,143 | B1 | 8/2002 | Ross et al. |
| 5,888,220 | A | 3/1999 | Felt et al. | 6,443,988 | B2 | 9/2002 | Felt et al. |
| 5,888,226 | A | 3/1999 | Rogozinski | 6,482,235 | B1 | 11/2002 | Lambrecht et al. |
| 5,893,889 | A | 4/1999 | Harrington | 6,491,690 | B1 | 12/2002 | Goble et al. |
| 5,916,225 | A | 6/1999 | Kugel | 6,503,269 | B2 | 1/2003 | Neild et al. |
| 5,919,235 | A | 7/1999 | Husson et al. | 6,508,839 | B1 | 1/2003 | Lambrecht et al. |
| 5,922,026 | A | 7/1999 | Chin | 6,520,967 | B1 | 2/2003 | Cauthen |
| 5,928,279 | A | 7/1999 | Shannon et al. | 6,530,932 | B1 | 3/2003 | Swayze et al. |
| 5,928,284 | A | 7/1999 | Mehdizadeh | 6,530,933 | B1 | 3/2003 | Yeung et al. |
| 5,935,147 | A | 8/1999 | Kensey et al. | 6,579,291 | B1 | 6/2003 | Keith et al. |
| 5,954,716 | A | 9/1999 | Sharkey et al. | 6,592,625 | B2 | 7/2003 | Cauthen |
| 5,954,767 | A | 9/1999 | Pajotin et al. | 6,610,094 | B2 | 8/2003 | Husson |
| 5,957,939 | A | 9/1999 | Heaven et al. | 6,613,074 | B1 | 9/2003 | Mitelberg et al. |
| 5,961,545 | A | 10/1999 | Lentz et al. | 6,648,915 | B2 | 11/2003 | Sazy |
| 5,972,000 | A | 10/1999 | Beyar et al. | 6,712,853 | B2 | 3/2004 | Kuslich |
| 5,972,007 | A | 10/1999 | Sheffield et al. | 6,719,797 | B1 | 4/2004 | Ferree |
| 5,972,022 | A | 10/1999 | Huxel | 6,726,696 | B1 | 4/2004 | Houser et al. |
| 5,976,174 | A | 11/1999 | Ruiz | 6,749,605 | B2 | 6/2004 | Ashley et al. |
| 5,976,186 | A | 11/1999 | Bao et al. | 6,783,546 | B2 | 8/2004 | Zucherman et al. |
| 5,976,192 | A | 11/1999 | McIntyre et al. | 6,805,695 | B2 | 10/2004 | Keith et al. |
| 5,980,504 | A | 11/1999 | Sharkey et al. | 6,821,276 | B2 | 11/2004 | Lambrecht et al. |
| 6,001,056 | A | 12/1999 | Jassawalla et al. | 6,855,166 | B2 | 2/2005 | Kohrs |
| 6,001,130 | A | 12/1999 | Bryan et al. | 6,883,520 | B2 | 4/2005 | Lambrecht et al. |
| 6,007,570 | A | 12/1999 | Sharkey et al. | 6,932,841 | B2 | 8/2005 | Skylar et al. |
| 6,007,575 | A | 12/1999 | Samuels | 6,936,072 | B2 | 8/2005 | Lambrecht et al. |
| 6,019,792 | A | 2/2000 | Cauthen | 6,964,674 | B1 | 11/2005 | Matsuura et al. |
| 6,019,793 | A | 2/2000 | Perren et al. | 6,969,404 | B2 | 11/2005 | Ferree |
| 6,024,096 | A | 2/2000 | Buckberg | 7,033,393 | B2 | 4/2006 | Gainer et al. |
| 6,027,527 | A | 2/2000 | Asano et al. | 7,052,516 | B2 | 5/2006 | Cauthen, III et al. |
| 6,073,051 | A | 6/2000 | Sharkey et al. | 7,094,258 | B2 | 8/2006 | Lambrecht et al. |
| 6,096,044 | A | 8/2000 | Boyd et al. | 7,124,761 | B2 | 10/2006 | Lambrecht et al. |
| 6,099,791 | A | 8/2000 | Shannon et al. | 7,144,397 | B2 | 12/2006 | Lambrecht et al. |
| 6,102,930 | A | 8/2000 | Simmons, Jr. | 7,163,561 | B2 | 1/2007 | Michelson |
| 6,105,581 | A | 8/2000 | Eggers et al. | 7,198,047 | B2 | 4/2007 | Lambrecht et al. |
| 6,113,639 | A | 9/2000 | Ray et al. | 7,220,281 | B2 | 5/2007 | Lambrecht et al. |
| 6,120,539 | A | 9/2000 | Eldridge et al. | 7,223,289 | B2 | 5/2007 | Trieu et al. |
| 6,124,523 | A | 9/2000 | Banas et al. | 7,258,700 | B2 | 8/2007 | Lambrecht et al. |
| 6,126,682 | A | 10/2000 | Sharkey et al. | 7,500,978 | B2 | 3/2009 | Gorensek et al. |
| 6,132,465 | A | 10/2000 | Ray et al. | 7,524,333 | B2 | 4/2009 | Lambrecht et al. |
| 6,140,452 | A | 10/2000 | Felt et al. | 2001/0004710 | A1 | 6/2001 | Felt et al. |
| 6,146,380 | A | 11/2000 | Racz et al. | 2001/0031963 | A1 | 10/2001 | Sharkey et al. |
| 6,153,292 | A | 11/2000 | Bell et al. | 2002/0007218 | A1 | 1/2002 | Cauthen |

| | | | |
|---|---|---|---|
| 2002/0026244 A1 | 2/2002 | Trieu | |
| 2002/0045942 A1 | 4/2002 | Ham | |
| 2002/0049498 A1 | 4/2002 | Yuksel et al. | |
| 2002/0111688 A1 | 8/2002 | Cauthen | |
| 2002/0120337 A1 | 8/2002 | Cauthen | |
| 2002/0123807 A1 | 9/2002 | Cauthen, III | |
| 2002/0147496 A1 | 10/2002 | Belef et al. | |
| 2002/0151979 A1 | 10/2002 | Lambrecht et al. | |
| 2002/0151980 A1 | 10/2002 | Cauthen | |
| 2002/0165542 A1 | 11/2002 | Ferree | |
| 2002/0189622 A1 | 12/2002 | Cauthen, III et al. | |
| 2002/0198599 A1 | 12/2002 | Haldimann | |
| 2003/0004574 A1 | 1/2003 | Ferree | |
| 2003/0009227 A1 | 1/2003 | Lambrecht et al. | |
| 2003/0014118 A1 | 1/2003 | Lambrecht et al. | |
| 2003/0040796 A1 | 2/2003 | Ferree | |
| 2003/0050702 A1 | 3/2003 | Berger | |
| 2003/0074075 A1 | 4/2003 | Thomas, Jr. et al. | |
| 2003/0074076 A1 | 4/2003 | Ferree et al. | |
| 2003/0078579 A1 | 4/2003 | Ferree | |
| 2003/0093155 A1 | 5/2003 | Lambrecht et al. | |
| 2003/0125807 A1 | 7/2003 | Lambrecht et al. | |
| 2003/0130738 A1 | 7/2003 | Hovda et al. | |
| 2003/0149438 A1 | 8/2003 | Nichols | |
| 2003/0158604 A1 | 8/2003 | Cauthen et al. | |
| 2004/0002764 A1 | 1/2004 | Gainor et al. | |
| 2004/0010317 A1 | 1/2004 | Lambrecht et al. | |
| 2004/0024465 A1 | 2/2004 | Lambrecht et al. | |
| 2004/0030392 A1 | 2/2004 | Lambrecht et al. | |
| 2004/0034429 A1 | 2/2004 | Lambrecht et al. | |
| 2004/0044412 A1 | 3/2004 | Lambrecht et al. | |
| 2004/0097924 A1 | 5/2004 | Lambrecht et al. | |
| 2004/0116922 A1 | 6/2004 | Hovda et al. | |
| 2004/0133229 A1 | 7/2004 | Lambrecht et al. | |
| 2004/0138673 A1 | 7/2004 | Lambrecht et al. | |
| 2004/0260238 A1 | 12/2004 | Call | |
| 2004/0260300 A1 | 12/2004 | Gorensek et al. | |
| 2004/0260305 A1 | 12/2004 | Gorensek et al. | |
| 2004/0260397 A1 | 12/2004 | Lambrecht et al. | |
| 2005/0004578 A1 | 1/2005 | Lambrecht et al. | |
| 2005/0010205 A1 | 1/2005 | Hovda et al. | |
| 2005/0027362 A1 | 2/2005 | Williams et al. | |
| 2005/0033440 A1 | 2/2005 | Lambrecht et al. | |
| 2005/0033441 A1 | 2/2005 | Lambrecht et al. | |
| 2005/0038519 A1 | 2/2005 | Lambrecht et al. | |
| 2005/0060038 A1 | 3/2005 | Lambrecht et al. | |
| 2005/0206039 A1 | 9/2005 | Lambrecht et al. | |
| 2005/0234557 A1 | 10/2005 | Lambrecht et al. | |
| 2006/0030857 A1 | 2/2006 | de Villiers et al. | |
| 2006/0030884 A1 | 2/2006 | Yeung et al. | |
| 2006/0129156 A1 | 6/2006 | Cauthen et al. | |
| 2006/0161162 A1 | 7/2006 | Lambrecht et al. | |
| 2006/0200246 A1 | 9/2006 | Lambrecht et al. | |
| 2006/0217811 A1 | 9/2006 | Lambrecht et al. | |
| 2006/0217812 A1 | 9/2006 | Lambrecht et al. | |
| 2006/0247785 A1 | 11/2006 | Gorensek et al. | |
| 2006/0253121 A1 | 11/2006 | Gorensek et al. | |
| 2006/0282167 A1 | 12/2006 | Lambrecht et al. | |
| 2007/0061012 A1 | 3/2007 | Cauthen, III | |
| 2007/0067039 A1 | 3/2007 | Lambrecbt et al. | |
| 2007/0118133 A1 | 5/2007 | Lambrecht et al. | |
| 2007/0118226 A1 | 5/2007 | Lambrecht et al. | |
| 2007/0156244 A1 | 7/2007 | Cauthen | |
| 2007/0185497 A1 | 8/2007 | Cauthen et al. | |
| 2007/0260249 A1 | 11/2007 | Boyajian et al. | |

FOREIGN PATENT DOCUMENTS

| | | |
|---|---|---|
| EP | 0298235 | 1/1989 |
| EP | 0682910 | 3/1995 |
| EP | 0700671 A1 | 3/1996 |
| EP | 0277678 A1 | 8/1998 |
| EP | 0876808 | 11/1998 |
| EP | 0722700 B1 | 12/1998 |
| EP | 1091776 | 5/2004 |
| EP | 1214026 | 4/2005 |
| EP | 1180978 | 5/2005 |
| FR | 2639823 A1 | 6/1990 |
| JP | S64-887 | 1/1989 |
| JP | 1995-148172 | 6/1995 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| WO | S63-95043 | 4/1988 |
| WO | WO 92/10982 | 9/1992 |
| WO | H05-29694 | 7/1993 |
| WO | WO 95/26689 | 10/1995 |
| WO | WO 95/31946 | 11/1995 |
| WO | WO 95/34331 | 12/1995 |
| WO | WO96/01164 | 1/1996 |
| WO | WO 96/01598 | 1/1996 |
| WO | WO 97/26847 | 7/1997 |
| WO | WO 97/30638 | 8/1997 |
| WO | WO 98/17190 | 4/1998 |
| WO | WO 98/20939 | 5/1998 |
| WO | WO 98/34552 | 8/1998 |
| WO | WO 98/38918 | 9/1998 |
| WO | WO 99/00074 | 1/1999 |
| WO | WO 99/02108 | 1/1999 |
| WO | WO 99/02214 | 1/1999 |
| WO | WO 99/03422 | 1/1999 |
| WO | WO 99/30651 | 6/1999 |
| WO | WO 99/47058 | 9/1999 |
| WO | WO 99/61084 | 12/1999 |
| WO | WO 99/62439 | 12/1999 |
| WO | WO 00/14708 | 3/2000 |
| WO | WO 00/18328 | 4/2000 |
| WO | WO 00/42953 | 7/2000 |
| WO | WO 00/44288 | 8/2000 |
| WO | WO 00/45741 | 8/2000 |
| WO | WO 00/49978 | 8/2000 |
| WO | WO 00/62832 | 10/2000 |
| WO | WO01/71043 | 11/2000 |
| WO | WO 01/10316 | 2/2001 |
| WO | WO 01/12080 | 2/2001 |
| WO | WO 01/12107 | 2/2001 |
| WO | WO 01/21246 A1 | 3/2001 |
| WO | WO 01/28464 | 4/2001 |
| WO | WO 01/28468 A1 | 4/2001 |
| WO | WO 01/39696 | 6/2001 |
| WO | WO01/45579 | 6/2001 |
| WO | WO 01/52914 | 7/2001 |
| WO | WO 01/45577 | 6/2002 |
| WO | WO 02/051622 | 7/2002 |
| WO | WO 02/058599 A2 | 8/2002 |
| WO | WO 02/067824 A2 | 9/2002 |
| WO | WO 03/039328 | 5/2003 |
| WO | WO 03/088876 | 10/2003 |

OTHER PUBLICATIONS

Bao Q.B., Bagga C.S., "The Dynamic Mechanical Analysis of Hydrogel Elastomers." Thermochimica Acta, 226:107-113 (1993).

Martz E.O., Goel V.K., Pope M.H., Park J.B. "Materials and Design of Spinal Implants—A Review." Journal of Biomedical Materials Research, vol. 38, Issue 3:267-288 (1997).

Bao Q.B., McCullen G.M., Higham P.A., Dumbleton J.H., Yuan H.A. "The Artificial Disc: Theory, Design and Materials" Biomaterials, vol. 17, No. 12:1157-1167 (1996).

Sakalkale D.P., Bhagia S.A., Slipman C.W. "A Historical Review and Current Perspective on the Intervertebral Disc Prosthesis." Pain Physician, vol. 6, No. 2:1-4 (2003).

Lemaire J.P., Skalli W., Lavaste F., Templier A., Mendes, F., Diop A., Sauty V., Laloux E. "Intervertebral Disc Prosthesis." Clinical Orthopaedics and Related Research, No. 337:64-76 (1997).

Langrana N.A., Parsons J.R., Lee C.K., Vuono-Hawkins M., Yang S.W., Alexander H. "Materials and Design Concepts for an Intervertebral Disc Spacer. I. Fiber-Reinforced Composite Design" Journal of Applied Biomaterials, vol. 4:125-132 (1994).

Bao Q.B., Yuan H.A. "Artificial Disc Technology" Neurosurg Focus 9(4), 2000.

Hedman T.P., Kostuik J.P., Fernie G.R., Hellier W.G. "Design of an Intervertebral Disc Prosthesis" Spine 16 (Suppl. 6):S256-S260 (1991).

Husson J.L, Scharer N., Le Nihouannen J.C., Freudiger S., Baumgartner W., Polard J.L. "Nucleoplasty During Discectomy Concept and Experimental Study." Rachis vol. 9, No. 3:145-152 (1997).

Husson J.L., Baumgartner W., Le Huec J.C. "Nucléoplastie Inter-Somatique Par Voie Postérieure Per-Dissectomie: Concept et Étude Expérimentale." Restabilisation Inter-Somatique Due Rachis Lombaire: 311-320 (1996).

Ray C.D., Schonmayr R., Kavanagh S.A., Assell R. "Prosthetic Disc Nucleus Implants." Riv. Neuroradiol 1999:12 (Suppl. 1):157-162.

Schonmayr R., Busch C., Lotz C., Lotz-Metz G. "Prosthetic Disc Nucleus Implants: The Wiesbaden Feasibility Study, 2 Years follow-up in Ten patients" Riv. Neuroradiol 1999:12 (Suppl. 1):163-170.

Zelentsov E.V. "Plastic Surgery with Collagen of Intervertebral Discs for Surgical Treatment of Lumbosacral Polyradiculitis." Abstract of a thesis, Leningrad, 1990.

USSR Author's Certificate No. 1477390 "Method for Treatment of Osteochondritis." Published May 17, 1989.

USSR Author's Certificate No. 1827204 "Method for Treatment of Spinal Osteochondritis." Published May 15, 1993.

Khelimsky et al. "Plastic Surgery of Damaged Intervertebral Discs with Fast-Solidifying Glue Composition (Experimental Research)." Collected articles Experimental Traumatic Surgery and Orthopaedics Moscow, 1990, pp. 88-90.

Sheljakin S. Ju. "Percutaneous Diskectomy Skin-through Discectomy in Complex Treatment of Patients with Disc Lumbosacral Polyraduculitis." Abstract of a thesis, St. Petersburg, 1996.

Shul'man Kh.M. "Pathogenetic Therapy of Compression Type Osteochondritis of Spinal Lumbar Region." Collected articles Reconstruction-and-Restoration Treatment in Traumatic Surgery, Orthopaedics, Surgery and Neurosurgery, Kazan', 1976, pp. 17-21.

Shul'man Kh.M. "Surgical Treatment of Compression Type Osteochondritis of Spinal Lumbar Region with Intervertebral Disc Implantation." Kazan', 1980, pp. 174-185.

Shul'man Kh.M., Danilov V.I. "Biochemical Experimental Basis of Intervertebral Disc Prosthesis Implantation Method by Fast-solidifying Polyurethane CKYu-PFL in Case of Disc Degeneration or Traumatic Damage." Collected articles Reconstruction-and-Restoration Treatment in Traumatic Surgery, Orthopaedics, Surgery and Neurosugery. Kazan', 1976, pp. 22-27.

Usmanov M.M. "Intervertebral Disc Changes at Local Damage of its Elements and Implantation of Various Materials." Abstract of a thesis Moscow, 1991.

Zelentsov E.V. et al. "Application of Collagen for Experimental Plastic Surgery of Intervertebral Discs." Collected articles Integrated Treating of Pain Syndromes of Neurogenic Origin, Leningrad 1984 pp. 86-90.

Ahlgren, B.D., et al., "Anular Incision Technique on the Strength and Multidirectional Flexibility of the Healing Intervertebral Disc," Spine, 19 (8) : 948-954 (1994).

American Heritage Dictionary of the English Language, third Edition, 1992, Houghton Mifflin Company.

Balderston, R.A., et al., "The Treatment of Lumbar Disc Herniation: Simple Fragment Excision Versus Disc Space Curettage," J. of Spinal Disorders, 4 (1) : 22-25 (1991).

Barr, J.S., "Ruptured Intervertebral Disc and Sciatic Pain," J. of Bone and Joint Surgery, 29, (2) : 429-437 (1947).

Brinckmann, P., et al., "Change of Disc Height, Radial Disc Bulge, and Intradiscal Pressure From Discectomy An in Vitro Investigation on Human Lumbar Discs," Spine, 16 (6) : 641-646 (1991).

Goel, V.K., et al., "Mechanical Properties of Lumbar Spinal Motion Segments as Affected by Partial Disc Removal," Spine, 11 (10) : 1008-1012 (1986).

Hanley, E.N., Jr., et al., "The Development of Low-Back Pain After Excision of a Lumbar Disc," J. of Bone and Joint Surgery, 71A (5) : 719-721 (1989).

Heggeness, M.H., et al., "Discography of Lumbar Discs After Surgical Treatment for Disc Herniation," Spine, 22 (14) : 1606-1609 (1997).

Kayama, S., et al., "Incision of the Anulus Fibrosus Induces Nerve Root Morphologic, Vascular, and Functional Changes," Spine, 21 (22) : 2539-2543 (1996).

Postacchini, F., "Spine Update results of Surgery Compared With Conservative Management for Lumbar Disc Herniations," Spine, 21 (11) : 1383-1387 (1996).

Rogers, L.A., "Experience with Limited versus Extensive Disc Removal in Patients Undergoing Microsurgical Operations for Ruptured Lumbar Discs," Neurosurgery, 22 (1) : 82-85 (1988).

Tibrewal, S.B., et al., "Lumbar Intervertebral Disc Heights in Normal Subjects and Patients with Disc Herniation," Spine, 10 (5) : 452-454 (1985).

Tullberg, T., et al., "Radiographic Changes After Lumbar Discectomy," Spine, 18 (7) : 843-850 (1993).

Yasargil, M.G., "Microsurgical Operation of Herniated Lumbar Disc," p. 81.

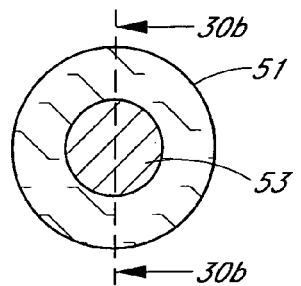 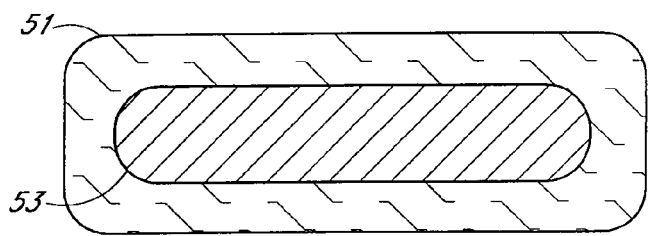
FIG. 30A    FIG. 30B
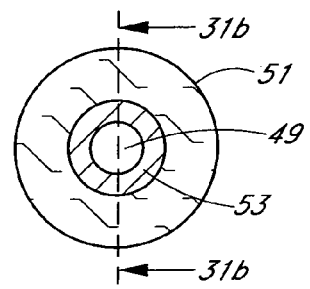 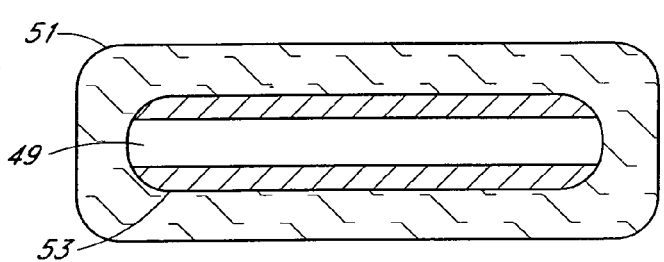
FIG. 31A    FIG. 31B
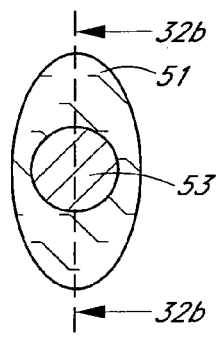 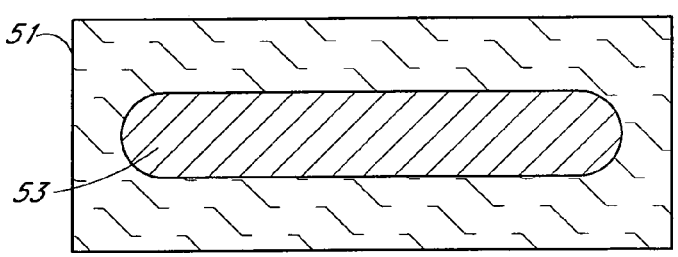
FIG. 32A    FIG. 32B
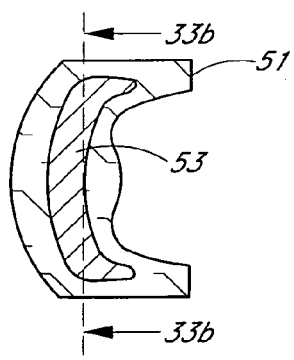 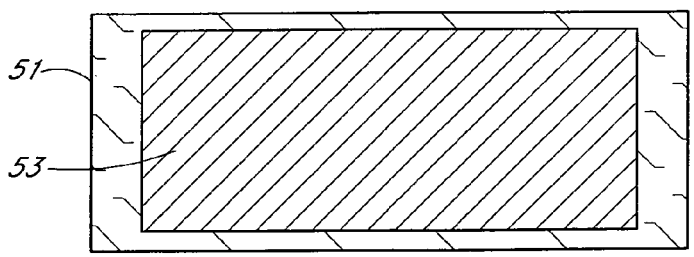
FIG. 33A    FIG. 33B

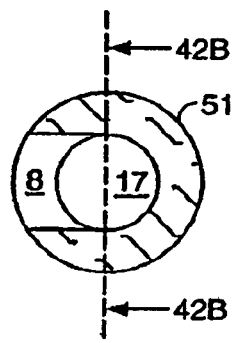
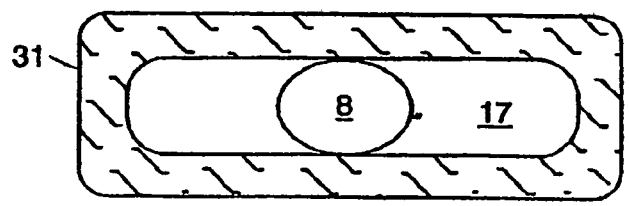
FIG. 42A          FIG. 42B
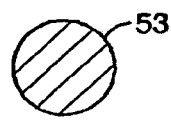
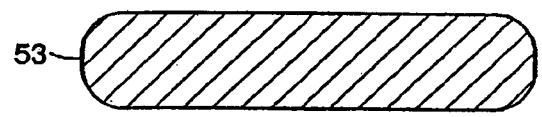
FIG. 42C          FIG. 42D
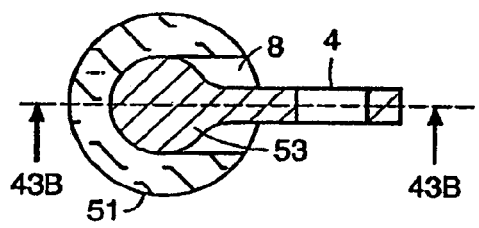
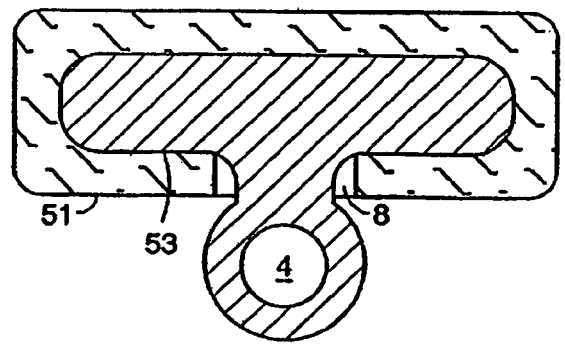
FIG. 43A          FIG. 43B

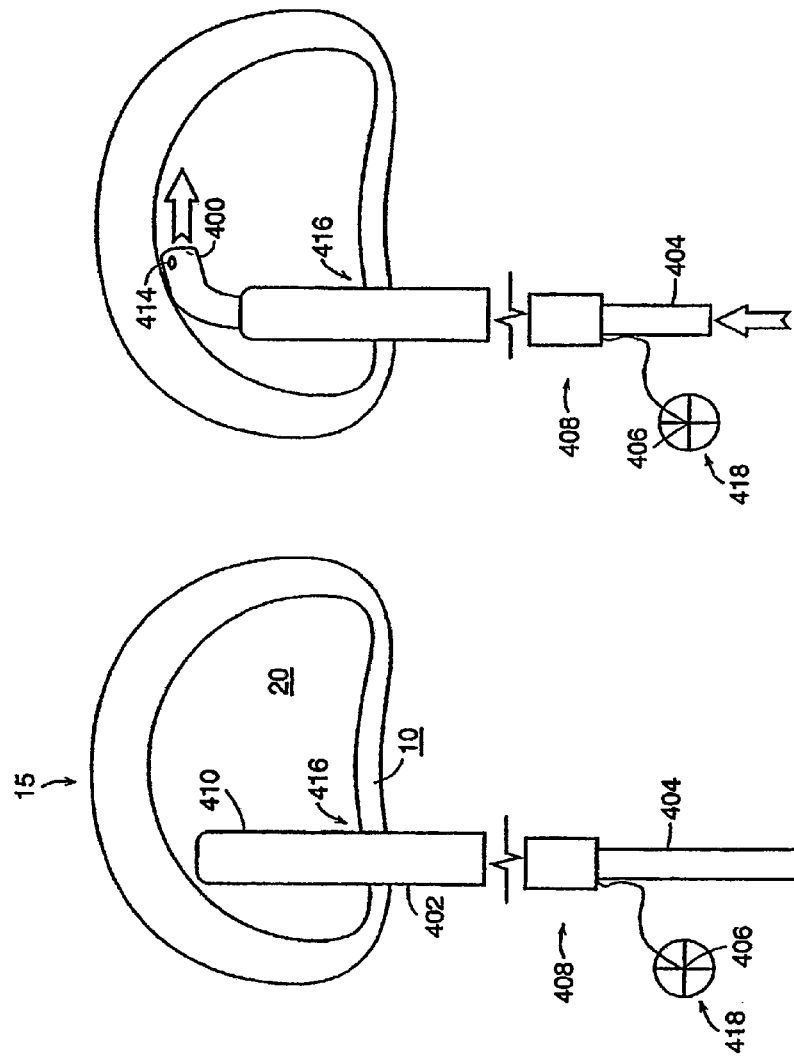

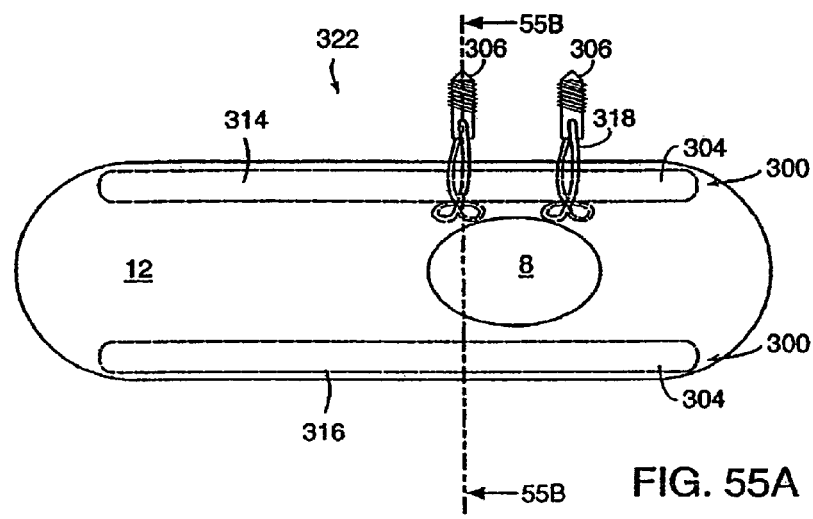
FIG. 55A
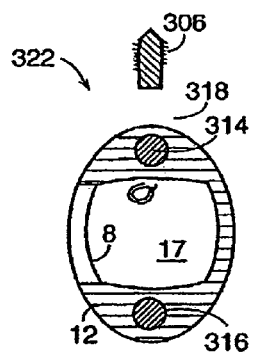
FIG. 55B
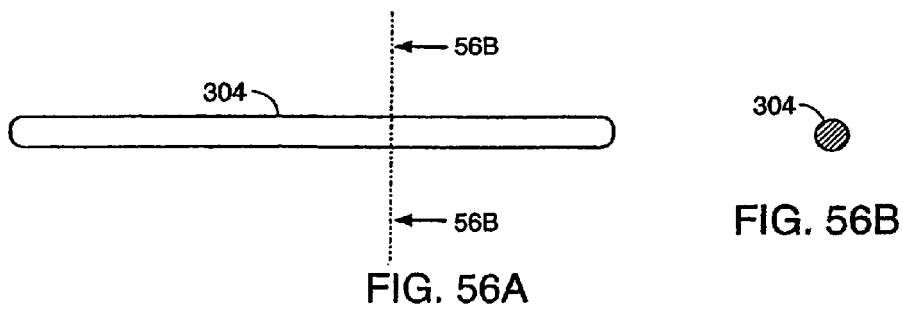
FIG. 56A
FIG. 56B

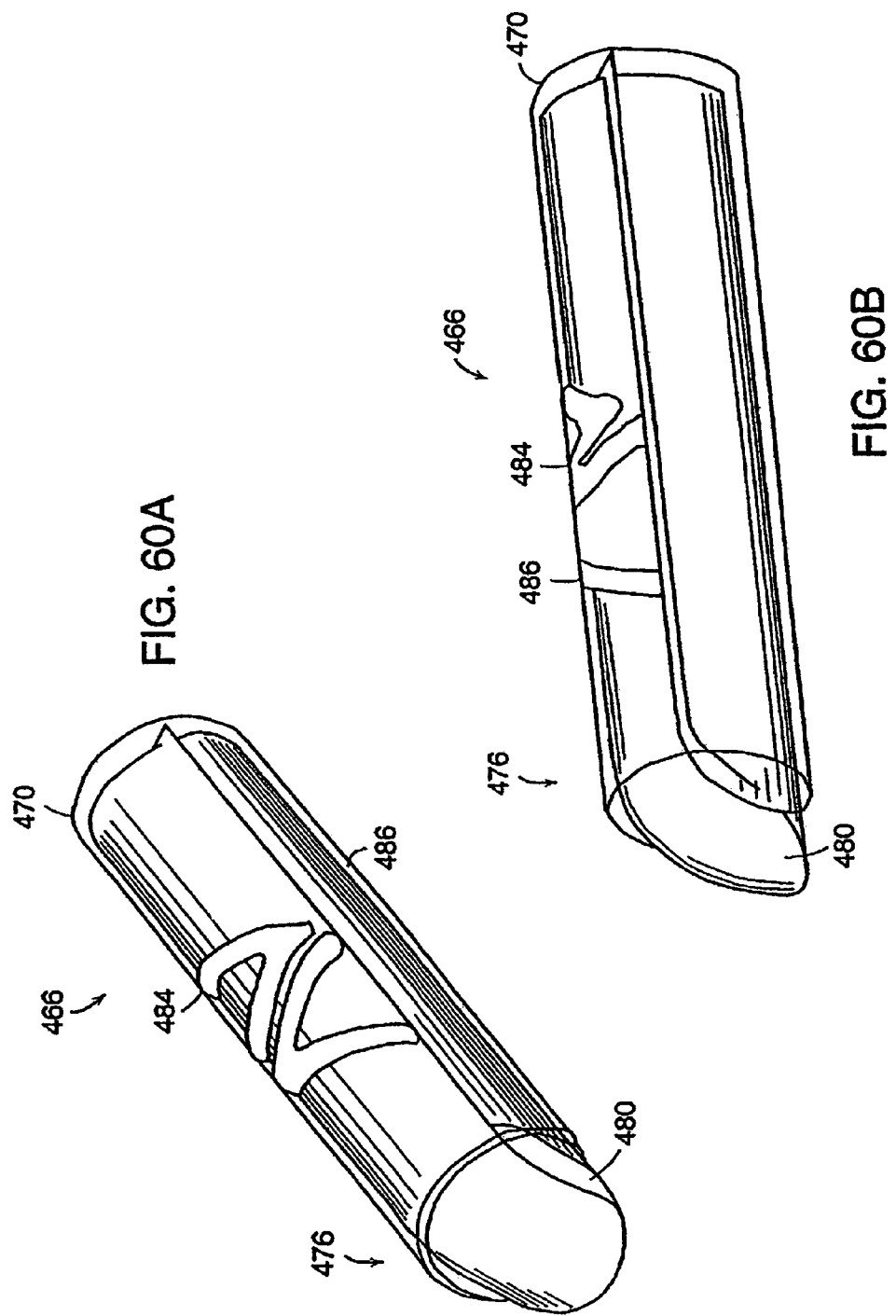

 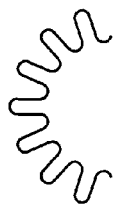 
FIG. 68A    FIG. 68B    FIG. 68C
FIG. 68D
FIG. 68E
FIG. 68F
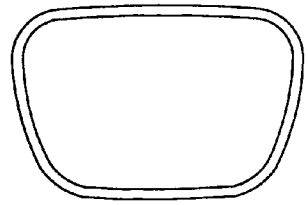
FIG. 68G

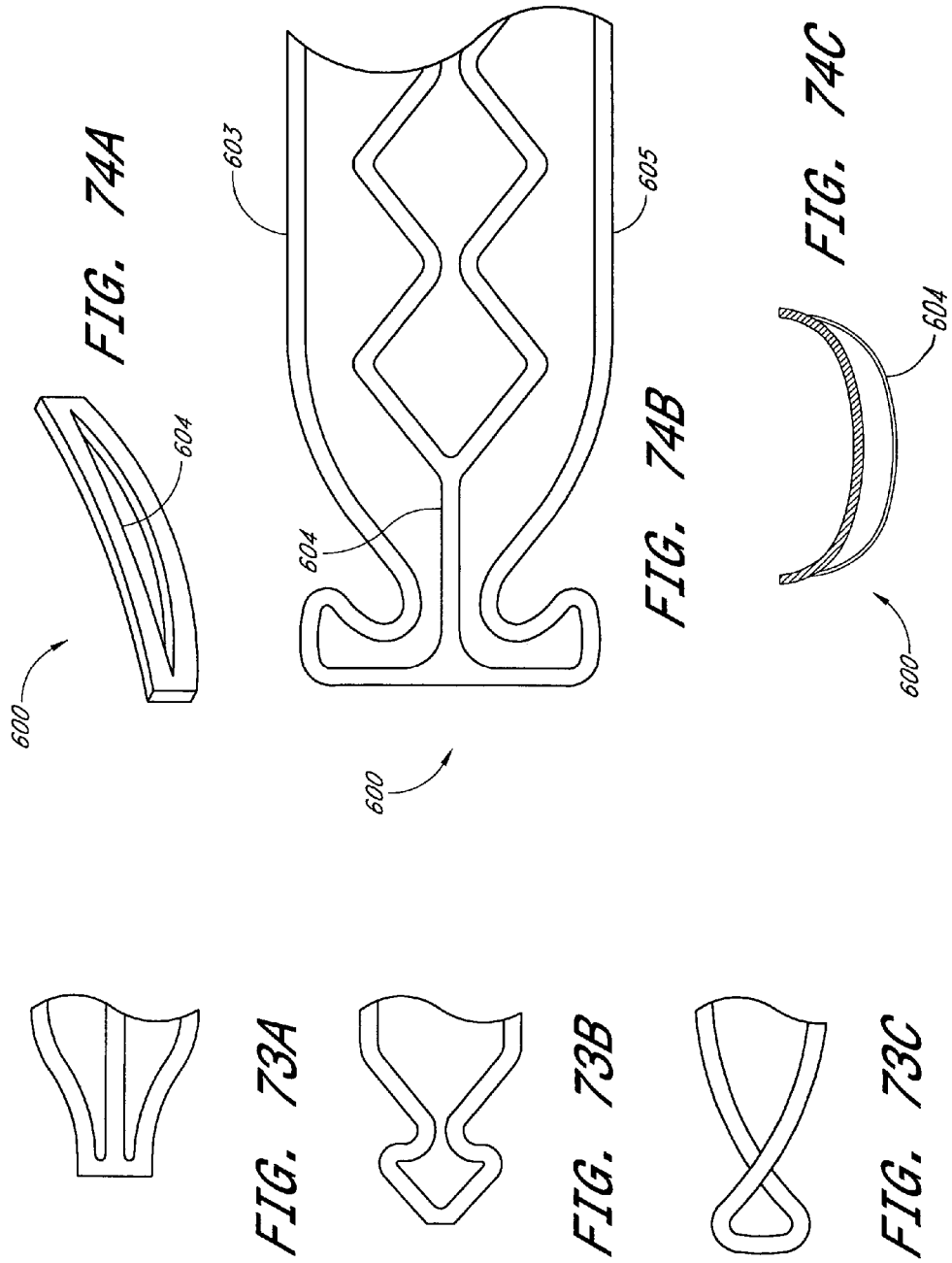

RESILIENT INTERVERTEBRAL DISC IMPLANT

RELATED APPLICATIONS

This application is a continuation of U.S. patent application Ser. No. 10/970,589, entitled "Stabilized Intervertebral Disc Barrier," filed Oct. 21, 2004, now U.S. Pat. No. 7,553,329, which claims benefit to U.S. Provisional Application No. 60/513,437, filed Oct. 22, 2003 and U.S. Provisional Application No. 60/613,958, filed Sep. 28, 2004, and is a continuation-in-part of U.S. application Ser. No. 10/194,428, filed Jul. 10, 2002, now U.S. Pat. No. 6,936,072, and is a continuation-in-part of U.S. application Ser. No. 10/055,504, filed Oct. 25, 2001, now U.S. Pat. No. 7,258,700, which is a continuation-in-part of U.S. application Ser. No. 09/696,636 filed on Oct. 25, 2000, now U.S. Pat. No. 6,508,839, which is a continuation-in-part of U.S. application Ser. No. 09/642,450 filed on Aug. 18, 2000, now U.S. Pat. No. 6,482,235, which is a continuation-in-part of U.S. application Ser. No. 09/608,797 filed on Jun. 30, 2000, now U.S. Pat. No. 6,425,919, and claims benefit to U.S. Provisional Application No. 60/311,586 filed Aug. 10, 2001, U.S. Provisional Application No. 60/149,490 filed Aug. 18, 1999, U.S. Provisional Application No. 60/161,085 filed Oct. 25, 1999 and U.S. Provisional Application No. 60/172,996 filed Dec. 21, 1999, the entire teachings of these applications being incorporated herein by reference.

BACKGROUND OF THE INVENTION

1. Field of the Invention

The present invention relates generally to the surgical treatment of intervertebral discs in the lumbar, cervical, or thoracic spine that have suffered from tears in the anulus fibrosis, herniation of the nucleus pulposus and/or significant disc height loss.

2. Description of the Related Art

The disc performs the important role of absorbing mechanical loads while allowing for constrained flexibility of the spine. The disc is composed of a soft, central nucleus pulposus (NP) surrounded by a tough, woven anulus fibrosis (AF). Herniation is a result of a weakening in the AF. Symptomatic herniations occur when weakness in the AF allows the NP to bulge or leak posteriorly toward the spinal cord and major nerve roots. The most common resulting symptoms are pain radiating along a compressed nerve and low back pain, both of which can be crippling for the patient. The significance of this problem is increased by the low average age of diagnosis, with over 80% of patients in the U.S. being under 59.

Since its original description by Mixter & Barr in 1934, discectomy has been the most common surgical procedure for treating intervertebral disc herniation. This procedure involves removal of disc materials impinging on the nerve roots or spinal cord external to the disc, generally posteriorly. Depending on the surgeon's preference, varying amounts of NP are then removed from within the disc space either through the herniation site or through an incision in the AF. This removal of extra NP is commonly done to minimize the risk of recurrent herniation.

Nevertheless, the most significant drawbacks of discectomy are recurrence of herniation, recurrence of radicular symptoms, and increasing low back pain. Re-herniation can occur in up to 21% of cases. The site for re-herniation is most commonly the same level and side as the previous herniation and can occur through the same weakened site in the AF. Persistence or recurrence of radicular symptoms happens in many patients and when not related to re-herniation, tends to be linked to stenosis of the neural foramina caused by a loss in height of the operated disc. Debilitating low back pain occurs in roughly 14% of patients. All of these failings are most directly related to the loss of NP material and AF competence that results from herniation and surgery.

Various implants, surgical meshes, patches, barriers, tissue scaffolds and the like may be used to treat intervertebral discs and are known in the art. Surgical repair meshes are used throughout the body to treat and repair damaged tissue structures such as intralinguinal hernias, herniated discs and to close iatrogenic holes and incisions as may occur elsewhere. Certain physiological environments present challenges to precise and minimally invasive delivery.

An intervertebral disc provides a dynamic environment that produces high loads and pressures. Typically implants designed for this environment must be capable of enduring such conditions for long periods of time. Also, the difficulty and danger of the implantation procedure itself, due to the proximity of the spinal cord, limits the size and ease of placement of the implant. One or more further embodiments of the invention addresses the need for a durable fatigue resistant repair mesh capable of withstanding the dynamic environment generic to intervertebral discs.

SUMMARY OF THE INVENTION

Several embodiments of the present invention relate generally to anulus augmentation devices, including, but not limited to, surgical meshes, barriers, and patches for treatment or augmentation of tissues within pathologic spinal discs. One or more embodiments comprise resilient surgical meshes that may be compressed for minimally invasive delivery and which are robust, stable, and resist fatigue and stress. These meshes are particularly well suited for intervertebral disc applications because they are durable enough to withstand intense cyclical loading and resist expulsion through a defect while not degrading over time.

Several embodiments of the present invention seek to exploit the individual characteristics of various anulus and nuclear augmentation devices to optimize the performance of both within the intervertebral disc. Accordingly, one or more of the embodiments of the present invention provide minimally invasive and removable devices for closing a defect in an anulus and augmenting the nucleus. These devices may be permanent, semi-permanent, or removable. One function of anulus augmentation devices is to prevent or minimize the extrusion of materials from within the space normally occupied by the nucleus pulposus and inner anulus fibrosus. One function of nuclear augmentation devices is to at least temporarily add material to restore diminished disc height and pressure. Nuclear augmentation devices can also induce the growth or formation of material within the nuclear space. Accordingly, the inventive combination of these devices can create a synergistic effect wherein the anulus and nuclear augmentation devices serve to restore biomechanical function in a more natural biomimetic way. Furthermore, in one embodiment, both devices may be delivered more easily and less invasively. Also, in some embodiments, the pressurized environment made possible through the addition of nuclear augmentation material and closing of the anulus serves both to restrain the nuclear augmentation and anchor the anulus augmentation in place.

As used herein, the phrase "anulus augmentation device" shall be given its ordinary meaning and shall also include devices that at least partially cover, close or seal a defect in an intervertebral disc, including, for example, barriers, meshes, patches, membranes, sealing means or closure devices. Thus, in one sense, the anulus augmentation device augments the anulus by sealing a defect in the anulus. In some embodiments, one or more barriers, meshes, patches, membranes, sealing means or closure devices comprise a support member or frame. Thus, in one embodiment, a barrier that comprises a membrane and a frame is provided. As used herein, the terms augmenting or reinforcing (and variations thereto) shall be given their ordinary meaning and shall also mean supporting, covering, closing, patching, or sealing.

In one embodiment, one or more anulus augmentation devices are provided with one or more nuclear augmentation devices. In some embodiments, the anulus barrier is integral with the nucleus augmentation. In other embodiments, at least a portion of the barrier is separate from or independent of the nuclear augmentation.

One or more of the embodiments of the present invention additionally provide an anulus augmentation device that is adapted for use with flowable nuclear augmentation material such that the flowable material cannot escape from the anulus after the anulus augmentation device has been implanted.

In one embodiment of the present invention, a disc augmentation system configured to repair or rehabilitate an intervertebral disc is provided. The system comprises at least one anulus augmentation device, and at least one nuclear augmentation material. The anulus augmentation device prevents or minimizes the extrusion of materials from within the space normally occupied by the nucleus pulposus and inner anulus fibrosus. In one application of the invention, the anulus augmentation device is configured for minimally invasive implantation and deployment. The anulus augmentation device may either be a permanent implant, or it may removable.

The nuclear augmentation material may restore diminished disc height and/or pressure. It may include factors for inducing the growth or formation of material within the nuclear space. It may either be permanent, removable, or absorbable.

The nuclear augmentation material may be in the form of liquids, gels, solids, or gases. In one embodiment, the nuclear augmentation material comprises materials selected from the group consisting of one or more of the following: steroids, antibiotics, tissue necrosis factors, tissue necrosis factor antagonists, analgesics, growth factors, genes, gene vectors, hyaluronic acid, noncross-linked collagen, collagen, fibren, liquid fat, oils, synthetic polymers, polyethylene glycol, liquid silicones, synthetic oils, saline and hydrogel. The hydrogel may be selected from the group consisting of one or more of the following: acrylonitriles, acrylic acids, polyacrylimides, acrylimides, acrylimidines, polyacrylnitriles, and polyvinyl alcohols.

Solid form nuclear augmentation materials may be in the form of geometric shapes such as cubes, spheroids, disc-like components, ellipsoid, rhombohedral, cylindrical, or amorphous. The solid material may be in powder form, and may be selected from the group consisting of one or more of the following: titanium, stainless steel, nitinol, cobalt, chrome, resorbable materials, polyurethane, polyesther, PEEK, PET, FEP, PTFE, ePTFE, PMMA, nylon, carbon fiber, Delrin, polyvinyl alcohol gels, polyglycolic acid, polyethylene glycol, silicone gel, silicone rubber, vulcanized rubber, gas-filled vesicles, bone, hydroxy apetite, collagen such as cross-linked collagen, muscle tissue, fat, cellulose, keratin, cartilage, protein polymers, transplanted nucleus pulposus, bioengineered nucleus pulposus, transplanted anulus fibrosis, and bioengineered anulus fibrosis. Structures may also be utilized, such as inflatable balloons or other inflatable containers, and spring-biased structures.

The nuclear augmentation material may additionally comprise a biologically active compound. The compound may be selected from the group consisting of one or more of the following: drug carriers, genetic vectors, genes, therapeutic agents, growth renewal agents, growth inhibitory agents, analgesics, anti-infectious agents, and anti-inflammatory drugs.

In one embodiment, the anulus augmentation device comprises materials selected from the group consisting of one or more of the following: steroids, antibiotics, tissue necrosis factors, tissue necrosis factor antagonists, analgesics, growth factors, genes, gene vectors, hyaluronic acid, noncross-linked collagen, collagen, fibren, liquid fat, oils, synthetic polymers, polyethylene glycol, liquid silicones, synthetic oils, saline, hydrogel (e.g., acrylonitriles, acrylic acids, polyacrylimides, acrylimides, acrylimidines, polyacrylnitriles, and polyvinyl alcohols), and other suitable materials.

In some embodiments, the anulus augmentation device is constructed from one or more of the following materials: titanium, stainless steel, nitinol, cobalt, chrome, resorbable materials, polyurethane, polyesther, PEEK, PET, FEP, PTFE, ePTFE, PMMA, nylon, carbon fiber, Delrin, polyvinyl alcohol gels, polyglycolic acid, polyethylene glycol, silicone gel, silicone rubber, vulcanized rubber, gas-filled vesicles, bone, hydroxy apetite, collagen such as cross-linked collagen, muscle tissue, fat, cellulose, keratin, cartilage, and protein polymers. Transplanted anulus fibrosis and bioengineered anulus fibrosis may also be used to form the barrier, sealing device, closing device or membrane. Inflatable balloons or other inflatable containers, and spring-biased structures may also be used.

The anulus augmentation device may comprise a biologically active compound. The compound may be selected from the group consisting of one or more of the following: drug carriers, genetic vectors, genes, therapeutic agents, growth renewal agents, growth inhibitory agents, analgesics, anti-infectious agents, and anti-inflammatory drugs. In some embodiments, the biologically active compound is coupled to the barrier, sealing device, closing device or membrane. In some embodiments, the biologically active compound coats the barrier, sealing device, closing device or membrane.

In one embodiment, an anulus augmentation device for reinforcing an intervertebral disc is provided. In one embodiment, the anulus augmentation device comprises a mesh frame, wherein the mesh frame comprises a plurality of flexible curvilinear members. In one embodiment, the curvalinear elements are interconnected. The interconnected curvilinear members are adapted to provide flexibility and resilience to the mesh frame. In some embodiments, the curvilinear members form a horizontal member or central strut. In one embodiment, the curvilinear members are arranged in a parallel configuration.

In one embodiment, the curvilinear members comprise a metal alloy such as steel, nickel titanium, cobalt chrome, or combinations thereof.

In some embodiments, the curvilinear members are constructed of nylon, polyvinyl alcohol, polyethylene, polyurethane, polypropylene, polycaprolactone, polyacrylate, ethylene-vinyl acetate, polystyrene, polyvinyl oxide, polyvinyl fluoride, polyvinyl imidazoles, chlorosulphonated polyolefin, polyethylene oxide, polytetrafluoroethylene, acetal, polyp-phenyleneterephtalamide) (Kevlar™), poly carbonate, carbon, graphite, or a combination thereof.

In one embodiment, a membrane encapsulates, covers or coats at least a portion of the mesh frame. In some embodiments, the membrane is coupled to the frame.

The membrane of some embodiments is constructed of polymers, elastomers, gels, elastin, albumin, collagen, fibrin, keratin, or a combination thereof. In several embodiments, the membrane comprises antibodies, antiseptics, genetic vectors, bone morphogenic proteins, steroids, cortisones, growth factors, or a combination thereof. The membrane may be a coating material.

In one embodiment, the mesh frame is concave along at least a portion of at least one axis of said mesh frame. In one embodiment, the mesh frame has a length in the range of about 0.5 cm to about 5 cm. One of skill in the art will understand that other lengths can also be used. In some embodiments, the mesh frame is sized to cover at least a portion of an interior surface of an anulus lamella. In other embodiments, the mesh frame is adapted to extend circumferentially along the entire surface of an anulus lamella.

In one embodiment, an anulus augmentation device comprising at least one projection that radiates from a mesh frame is provided. In one embodiment, the mesh frame has a vertical cross-section that is flat, concave, convex, or curvilinear. The horizontal cross-section can be concave, convex, flat, or kidney bean shaped. Other shapes can also be used.

In one embodiment of the present invention, an anulus augmentation device for reinforcing an intervertebral disc comprises a mesh frame having a horizontal axis and a vertical axis. In one embodiment, the mesh fame is concave along at least a portion the horizontal axis or the vertical axis. In one embodiment, one or more projections radiate from the horizontal axis or the vertical axis of the mesh frame. The projections are adapted to stabilize the anulus augmentation device. In one embodiment, a stabilizing projection has at least one dimension that is larger than the mesh frame. In other embodiments, the projection is smaller than the mesh frame.

In yet another embodiment of the present invention, an intervertebral disc implant comprising a posterior support member having a first terminus and a second terminus is provided. In one embodiment, an anterior projection extends outwardly from the posterior support member. The anterior projection is attached to at least the first terminus or the second terminus of the posterior support member.

In another embodiments, an intervertebral disc implant comprising a posterior support member having a first terminus and a second terminus and an anterior projection having a first end and a second end is provided. The anterior projection extends outwardly from the posterior support member. In one embodiment, the first end of the anterior projection is coupled to the first terminus of the posterior support member; and the second end of the anterior projection is coupled to the second terminus of the posterior support member, thereby substantially forming a bow-shaped implant. The posterior support member and the anterior projection can be constructed of any suitable material, including but not limited to the materials described above for the mesh frame and the membrane.

In a further embodiment of the present invention, a fatigue-resistant surgical mesh comprising rails is provided. In one embodiment, the mesh comprises a top rail, a bottom rail coupled to the top rail, wherein the top rail and said bottom rail are coupled to each other at a first end and second end. In one embodiment, the top rail and the bottom rail extend to form a gap that is defined between the rails along at least a portion of the distance between the ends.

In one embodiment of the present invention, a spinal implant for treatment of an intervertebral disc is provided. In one embodiment, a barrier or patch with a volume corresponding to the amount of material removed during a discectomy procedure is implanted. In one embodiment, the implant has a volume in a range of about 0.2 to about 2.0 cc.

In one embodiment of the invention, an intervertebral disc implant comprising a barrier forming a contiguous band is provided. In one embodiment, the band has variable heights or widths. In one embodiment, the band has different degrees of flexibility along at least one axis.

In another embodiment of the present invention, a method of repairing or rehabilitating an intervertebral disc is provided. The method comprises inserting at least one anulus augmentation device into the disc, and inserting at least one nuclear augmentation material, to be held within the disc by the anulus augmentation device. The nuclear augmentation material may conform to a first, healthy region of the anulus, while the anulus augmentation device conforms to a second, weaker region of the anulus.

In a further embodiment, a method of repairing defective regions within a spinal disc is provided. In one embodiment, the method comprises providing a surgical mesh, implanting the surgical mesh along an anulus surface, and positioning the surgical mesh at least such that about 2 mm of the device spans beyond at least one edge of the defective region of the disc.

Further features and advantages of embodiments of the present invention will become apparent to those of skill in the art in view of the detailed description of preferred embodiments which follows, when taken together with the attached drawings and claims.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 30A, 30B, 31A, 31B, 32A, 32B, 33A, and 33B depict axial and sectional views, respectively, of various embodiments of the barrier.

FIGS. 40A-D illustrate a tubular expansion means having an oval shaped cross-section. FIGS. 40E, 40F and 40I illustrate a front, back and top view, respectively of the tubular expansion means of FIG. 40A having a sealing means covering an exterior surface of an anulus face. FIGS. 40G and 40H show the tubular expansion means of FIG. 40A having a sealing means covering an interior surface of an anulus face.

FIG. 42A-D depicts cross sections of a preferred embodiment of sealing and enlarging means.

FIGS. 43A and 43B depict an alternative configuration of enlarging means.

FIGS. 49A-G illustrate a method of implanting an intradiscal implant.

FIG. 55A illustrates a barrier having stiffening rod elements.

FIG. 55B illustrates a sectional view of the barrier of FIG. 55A.

FIG. 56A illustrates a stiffening rod.

FIG. 56B illustrates a sectional view of the stiffening rod of FIG. 56A.

FIGS. 60A-C illustrate a dissector component.

FIGS. 68A-G show profiles and cross-sectional views of an anulus augmentation device (such as a mesh), e.g., "U" shaped, "C" shaped, curvilinear shaped, and "D" shaped to extend along and cover the entire inner anulus surface, or portions.

FIGS. 73A-C shows embodiments of the end or natural hinge portion of the frame, including a looped terminus.

FIGS. 74A-C show some embodiments of the central band or strut.

DETAILED DESCRIPTION OF THE PREFERRED EMBODIMENT

Several embodiments of the present invention provide for an in vivo augmented functional spine unit. A functional spine unit includes the bony structures of two adjacent vertebrae (or vertebral bodies), the soft tissue (anulus fibrosis (AF), and optionally nucleus pulposus (NP)) of the intervertebral disc, and the ligaments, musculature and connective tissue connected to the vertebrae. The intervertebral disc is substantially situated in the intervertebral space formed between the adjacent vertebrae. Augmentation of the functional spine unit can include repair of a herniated disc segment, support of a weakened, torn or damaged anulus fibrosis, or the addition of material to or replacement of all or part of the nucleus pulposus. Augmentation of the functional spine unit is provided by herniation constraining devices and disc augmentation devices situated in the intervertebral disc space.

Figure 1A:
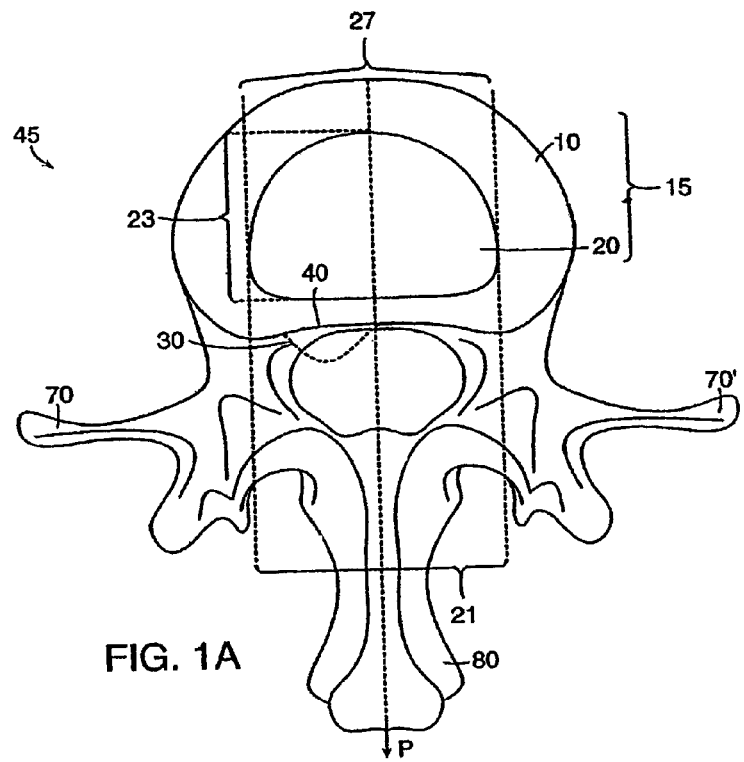
FIG. 1A shows a transverse section of a portion of a functional spine unit, in which part of a vertebra and intervertebral disc are depicted.
Figure 1B:
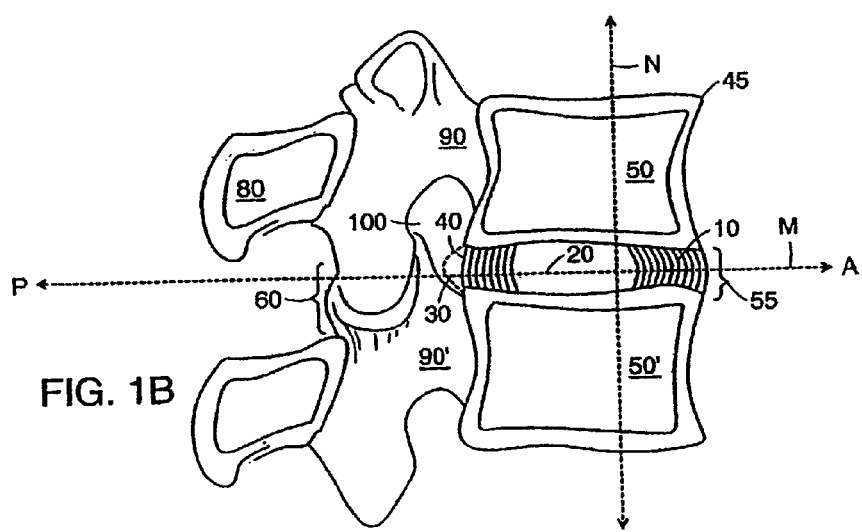
FIG. 1B shows a sagittal cross section of a portion of a functional spine unit shown in FIG. 1A, in which two lumbar vertebrae and the intervertebral disc are visible.

FIGS. 1A and 1B show the general anatomy of a functional spine unit 45. In this description and the following claims, the terms 'anterior' and 'posterior', 'superior' and 'inferior' are defined by their standard usage in anatomy, i.e., anterior is a direction toward the front (ventral) side of the body or organ, posterior is a direction toward the back (dorsal) side of the body or organ; superior is upward (toward the head) and inferior is lower (toward the feet).

FIG. 1A is an axial view along the transverse axis M of a vertebral body with the intervertebral disc 15 superior to the vertebral body. Axis M shows the anterior (A) and posterior (P) orientation of the functional spine unit within the anatomy. The intervertebral disc 15 contains the anulus fibrosis (AF) 10 which surrounds a central nucleus pulposus (NP) 20. A Herniated segment 30 is depicted by a dashed-line. The herniated segment 30 protrudes beyond the pre-herniated posterior border 40 of the disc. Also shown in this figure are the left 70 and right 70' transverse spinous processes and the posterior spinous process 80.

FIG. 1B is a sagittal section along sagittal axis N through the midline of two adjacent vertebral bodies 50 (superior) and 50' (inferior). Intervertebral disc space 55 is formed between the two vertebral bodies and contains intervertebral disc 15, which supports and cushions the vertebral bodies and permits movement of the two vertebral bodies with respect to each other and other adjacent functional spine units.

Intervertebral disc 15 is comprised of the outer AF 10 which normally surrounds and constrains the NP 20 to be wholly within the borders of the intervertebral disc space. In FIGS. 1A and 1B, herniated segment 30, represented by the dashed-line, has migrated posterior to the pre-herniated border 40 of the posterior AF of the disc. Axis M extends between the anterior (A) and posterior (P) of the functional spine unit. The vertebral bodies also include facet joints 60 and the superior 90 and inferior 90' pedicle that form the neural foramen 100. Disc height loss occurs when the superior vertebral body 50 moves inferiorly relative to the inferior vertebral body 50'.

Figure 1C:
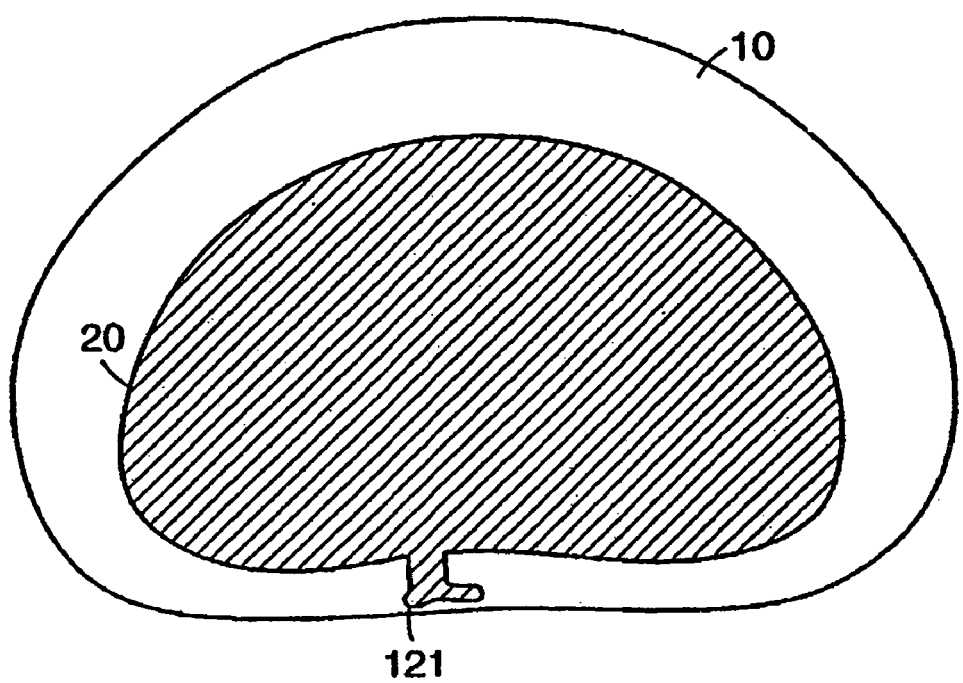
FIG. 1C shows partial disruption of the inner layers of an anulus fibrosis.

Partial disruption 121 of the inner layers of the anulus 10 without a true perforation has also been linked to chronic low back pain. Such a disruption 4 is illustrated in FIG. 1C. It is thought that weakness of these inner layers forces the sensitive outer anulus lamellae to endure higher stresses. This increased stress stimulates the small nerve fibers penetrating the outer anulus, which results in both localized and referred pain.

In one embodiment of the present invention, the disc herniation constraining devices 13 provide support for returning all or part of the herniated segment 30 to a position substantially within its pre-herniated borders 40. The disc herniation constraining device includes an anchor which is positioned at a site within the functional spine unit, such as the superior or inferior vertebral body, or the anterior medial, or anterior lateral anulus fibrosis. The anchor is used as a point against which all or part of the herniated segment is tensioned so as to return the herniated segment to its pre-herniated borders, and thereby relieve pressure on otherwise compressed neural tissue and structures. A support member is positioned in or posterior to the herniated segment, and is connected to the anchor by a connecting member. Sufficient tension is applied to the connecting member so that the support member returns the herniated segment to a pre-herniated position. In various embodiments, augmentation material is secured within the intervertebral disc space, which assists the NP in cushioning and supporting the inferior and superior vertebral bodies. An anchor secured in a portion of the functional spine unit and attached to the connection member and augmentation material limits movement of the augmentation material within the intervertebral disc space. A supporting member, located opposite the anchor, may optionally provide a second point of attachment for the connection member and further hinder the movement of the augmentation material within the intervertebral disc space.

Figure 2A:
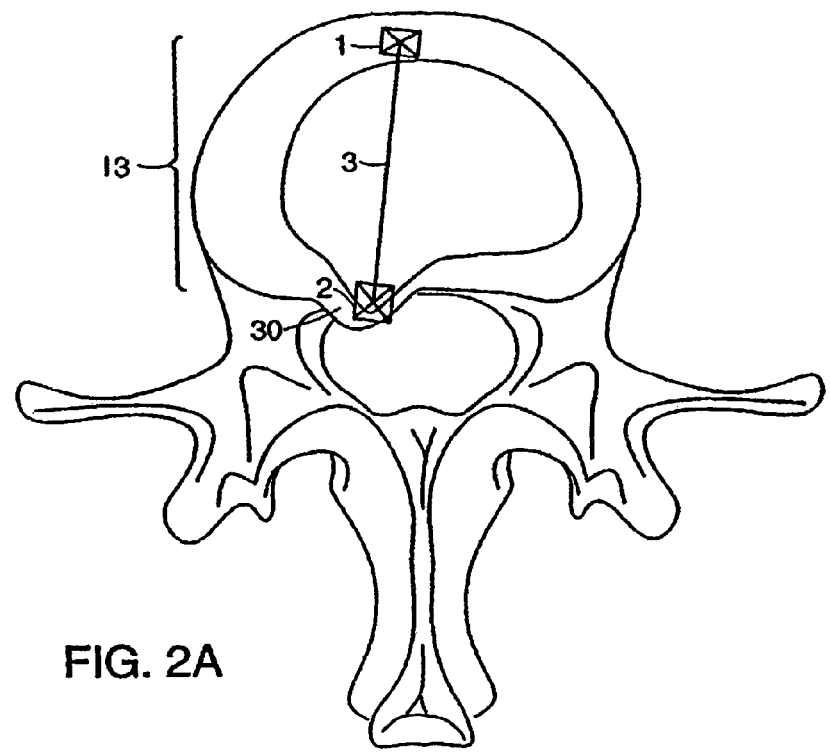
FIG. 2A shows a transverse section of one aspect of the present invention prior to supporting a herniated segment, as shown in one embodiment.
Figure 2B:
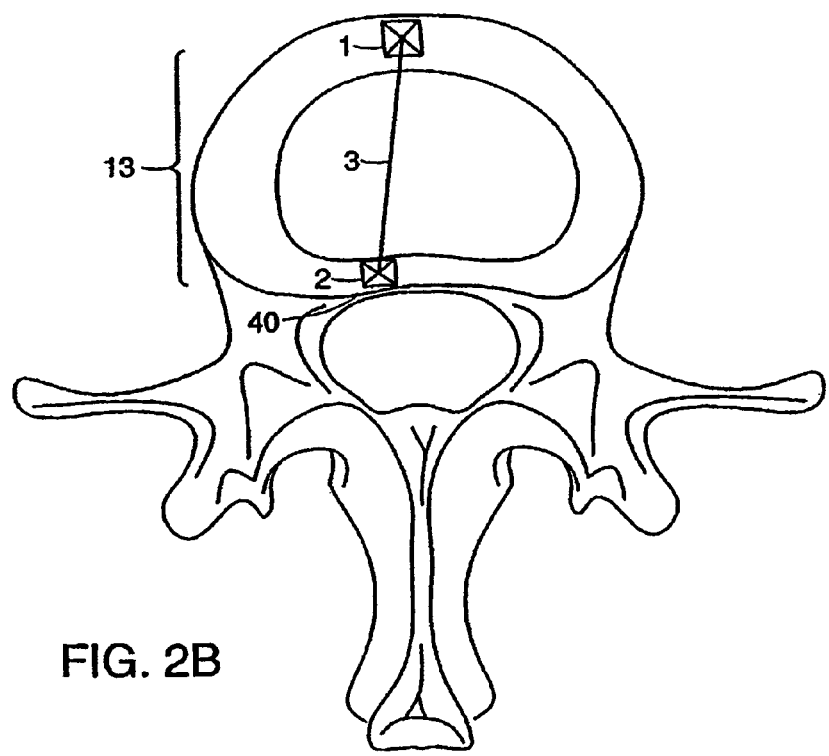
FIG. 2B shows a transverse section of the construct in FIG. 2A supporting the herniated segment.

FIGS. 2A and 2B depict one embodiment of device 13. FIG. 2A shows the elements of the constraining device in position to correct the herniated segment. Anchor 1 is securely established in a location within the functional spine unit, such as the anterior AF shown in the figure. Support member 2 is positioned in or posterior to herniated segment 30. Leading from and connected to anchor 1 is connection member 3, which serves to connect anchor 1 to support member 2. Depending on the location chosen for support member 2, the connection member may traverse through all or part of the herniated segment.

FIG. 2B shows the positions of the various elements of the herniation constraining device 13 when the device 13 is supporting the herniated segment. Tightening connection member 2 allows it to transmit tensile forces along its length, which causes herniated segment 30 to move anteriorly, i.e., in the direction of its pre-herniated borders. Once herniated segment 30 is in the desired position, connection member 3 is secured in a permanent fashion between anchor 1 and support member 2. This maintains tension between anchor 1 and support member 2 and restricts motion of the herniated segment to within the pre-herniated borders 40 of the disc. Support member 2 is used to anchor to herniated segment 30, support a weakened AF in which no visual evidence of herniation is apparent, and may also be used to close a defect in the AF in the vicinity of herniated segment 30.

Anchor 1 is depicted in a representative form, as it can take one of many suitable shapes, be made from one of a variety of biocompatible materials, and be constructed so as to fall within a range of stiffness. It can be a permanent device constructed of durable plastic or metal or can be made from a resorbable material such as polylactic acid (PLA) or polyglycolic acid (PGA). Specific embodiments are not shown, but many possible designs would be obvious to anyone skilled in the art. Embodiments include, but are not limited to, a barbed anchor made of PLA or a metal coil that can be screwed into the anterior AF. Anchor 1 can be securely established within a portion of the functional spine unit in the usual and customary manner for such devices and locations, such as being screwed into bone, sutured into tissue or bone, or affixed to tissue or bone using an adhesive method, such as cement, or other suitable surgical adhesives. Once established within the bone or tissue, anchor 1 should remain relatively stationary within the bone or tissue.

Support member 2 is also depicted in a representative format and shares the same flexibility in material and design as anchor 1. Both device elements can be of the same design, or they can be of different designs, each better suited to being established in healthy and diseased tissue respectively. Alternatively, in other forms, support member 2 can be a cap or a bead shape, which also serves to secure a tear or puncture in the AF, or it can be bar or plate shaped, with or without barbs to maintain secure contact with the herniated segment. Support member 2 can be established securely to, within, or posterior to the herniated segment.

The anchor and support member can include suture, bone anchors, soft tissue anchors, tissue adhesives, and materials that support tissue ingrowth although other forms and materials are possible. They may be permanent devices or resorbable. Their attachment to a portion of FSU and herniated segment must be strong enough to resist the tensional forces that result from repair of the hernia and the loads generated during daily activities.

Connection member 3 is also depicted in representative fashion. Member 3 may be in the format of a flexible filament, such as a single or multi-strand suture, wire, or perhaps a rigid rod or broad band of material, for example. The connection member can further include suture, wire, pins, and woven tubes or webs of material. It can be constructed from a variety of materials, either permanent or resorbable, and can be of any shape suitable to fit within the confines of the intervertebral disc space. The material chosen is preferably adapted to be relatively stiff while in tension, and relatively flexible against all other loads. This allows for maximal mobility of the herniated segment relative to the anchor without the risk of the supported segment moving outside of the pre-herniated borders of the disc. The connection member may be an integral component of either the anchor or support member or a separate component. For example, the connection member and support member could be a length of non-resorbing suture that is coupled to an anchor, tensioned against the anchor, and sewn to the herniated segment.

Figure 3A:
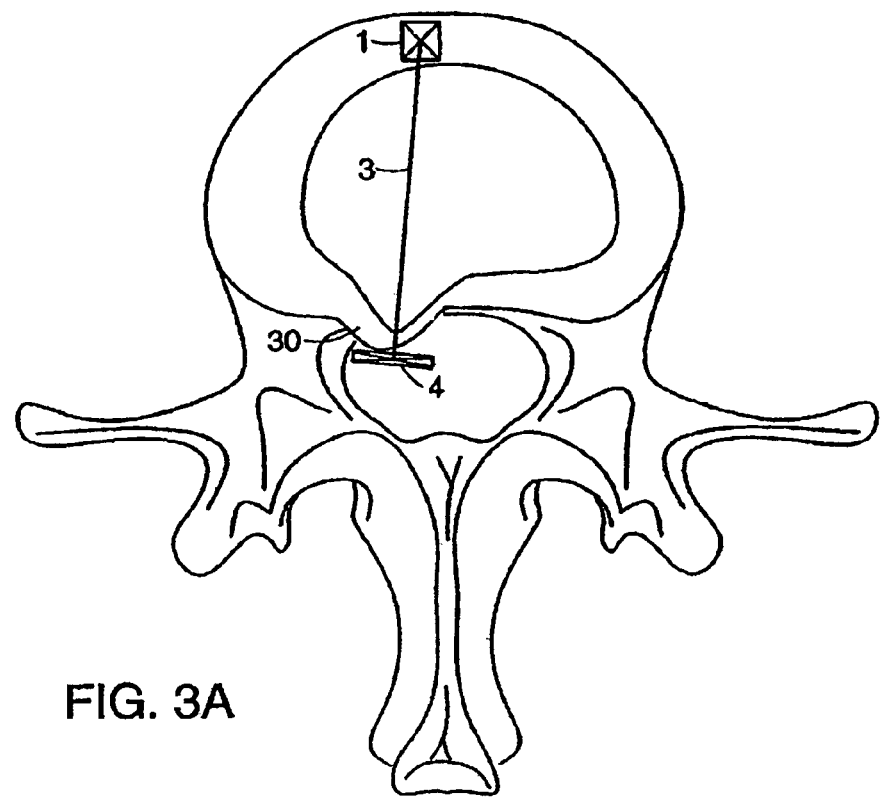
FIG. 3A shows a transverse section of another embodiment of the disclosed invention after placement of the device.
Figure 3B:
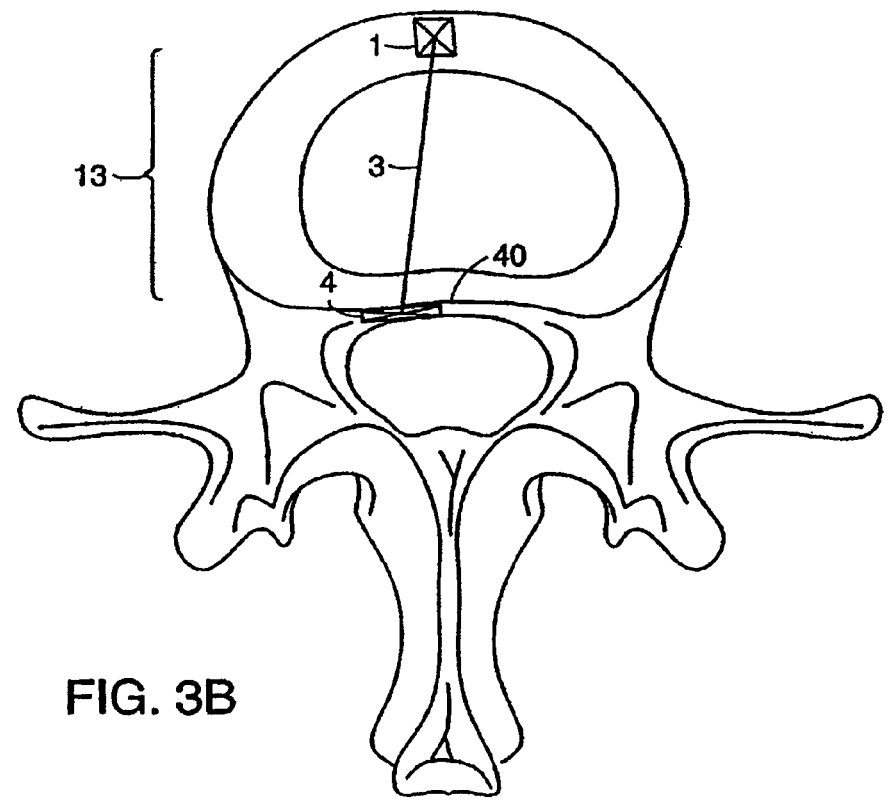
FIG. 3B shows a transverse section of the construct in FIG. 3A after tension is applied to support the herniated segment.

FIGS. 3A and 3B depict another embodiment of device 13. In FIG. 3A the elements of the herniation constraining device are shown in position prior to securing a herniated segment. Anchor 1 is positioned in the AF and connection member 3 is attached to anchor 1. Support member 4 is positioned posterior to the posterior-most aspect of herniated segment 30. In this way, support member 4 does not need to be secured in herniated segment 30 to cause herniated segment 30 to move within the pre-herniated borders 40 of the disc. Support member 4 has the same flexibility in design and material as anchor 1, and may further take the form of a flexible patch or rigid plate or bar of material that is either affixed to the posterior aspect of herniated segment 30 or is simply in a form that is larger than any hole in the AF directly anterior to support member 4. FIG. 3B shows the positions of the elements of the device when tension is applied between anchor 1 and support member 4 along connection member 3. The herniated segment is displaced anteriorly, within the pre-herniated borders 40 of the disc.

Figure 4A:
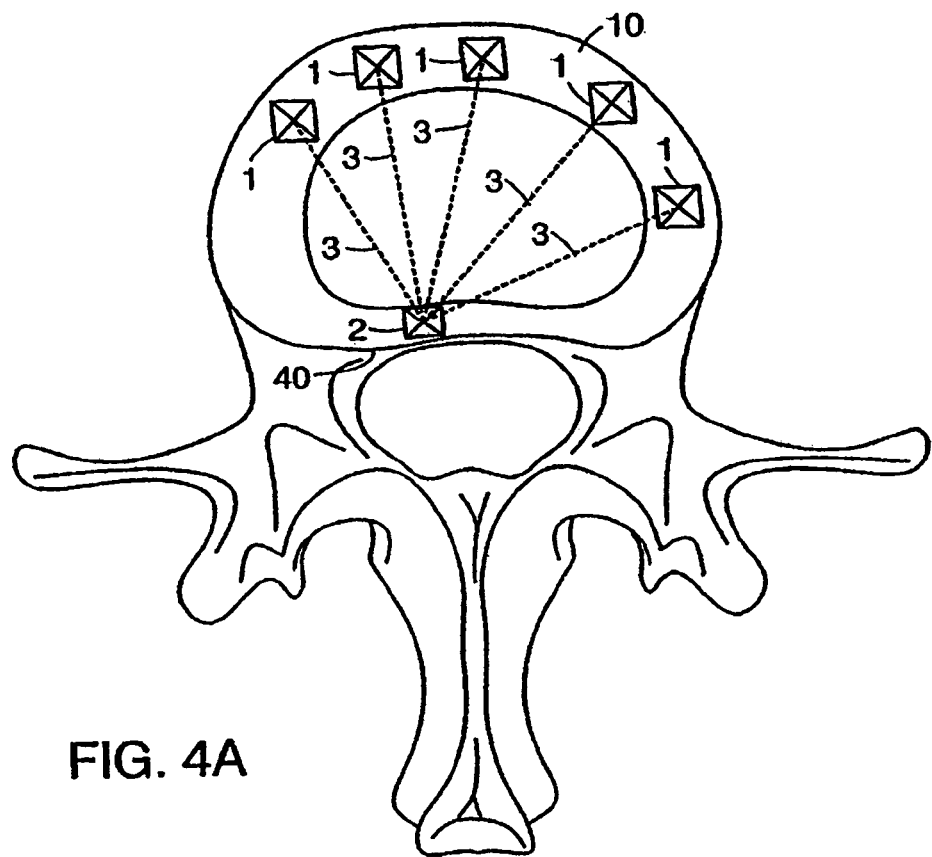
FIG. 4A shows a transverse view of an alternate embodiment of the invention.
Figure 4B:
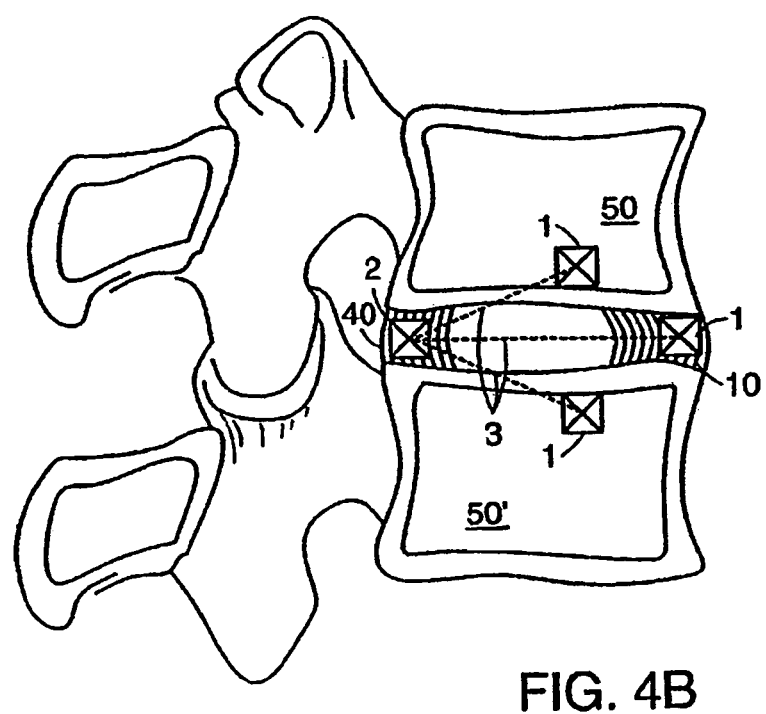
FIG. 4B shows a sagittal view of the alternate embodiment shown in FIG. 4A.

FIGS. 4A and 4B show five examples of suitable anchoring sites within the FSU for anchor 1. FIG. 4A shows an axial view of anchor 1 in various positions within the anterior and lateral AF. FIG. 4B similarly shows a sagittal view of the various acceptable anchoring sites for anchor 1. Anchor 1 is secured in the superior vertebral body 50, inferior vertebral body 50' or anterior AF 10, although any site that can withstand the tension between anchor 1 and support member 2 along connection member 3 to support a herniated segment within its pre-herniated borders 40 is acceptable.

Generally, a suitable position for affixing one or more anchors is a location anterior to the herniated segment such that, when tension is applied along connection member 3, herniated segment 30 is returned to a site within the pre-herniated borders 40. The site chosen for the anchor should be able to withstand the tensile forces applied to the anchor when the connection member is brought under tension. Because most symptomatic herniations occur in the posterior or posterior lateral directions, the preferable site for anchor placement is anterior to the site of the herniation. Any portion of the involved FSU is generally acceptable, however the anterior, anterior medial, or anterior lateral AF is preferable. These portions of the AF have been shown to have considerably greater strength and stiffness than the posterior or posterior lateral portions of the AF. As shown in FIGS. 4A and 4B, anchor 1 can be a single anchor in any of the shown locations, or there can be multiple anchors 1 affixed in various locations and connected to a support member 2 to support the herniated segment. Connection member 3 can be one continuous length that is threaded through the sited anchors and the support member, or it can be several individual strands of material each terminated under tension between one or more anchors and one or more support members.

In various forms of the invention, the anchor(s) and connection member(s) may be introduced and implanted in the patient, with the connection member under tension. Alternatively, those elements may be installed, without introducing tension to the connection member, but where the connection member is adapted to be under tension when the patient is in a non-horizontal position, e.g., resulting from loading in the intervertebral disc.

Figure 5A:
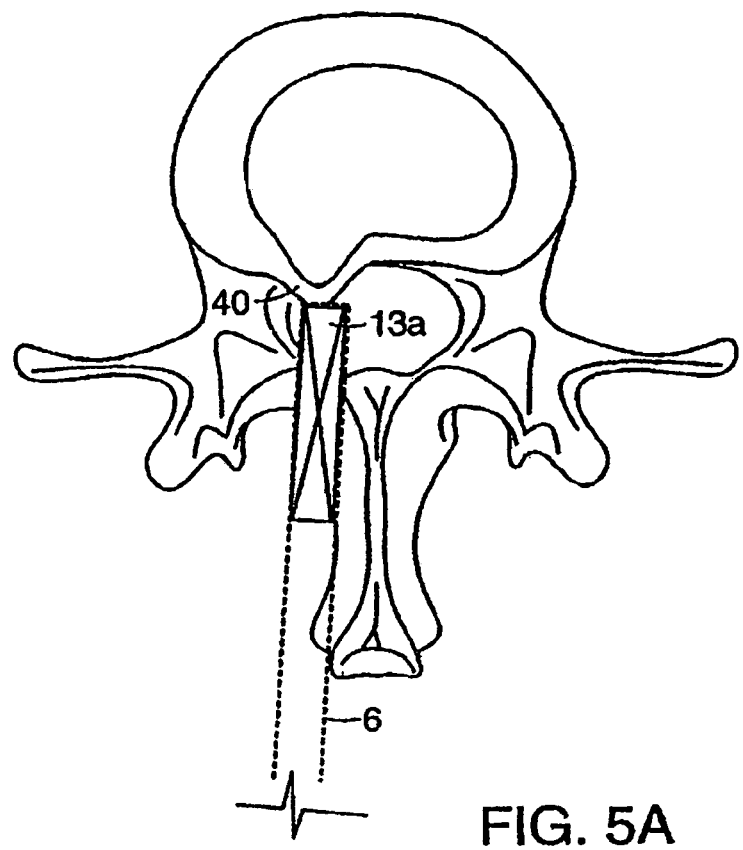
FIG. 5A shows a transverse view of another aspect of the present invention, as shown in one embodiment.
Figure 5B:
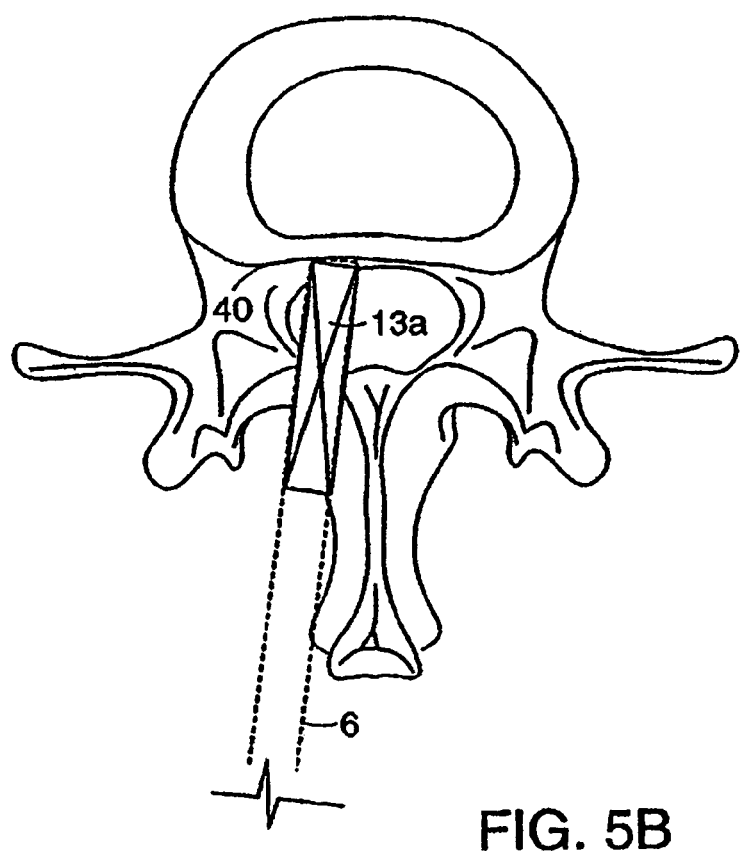
FIG. 5B shows the delivery tube of FIG. 5A being used to displace the herniated segment to within its pre-herniated borders.
Figure 5C:
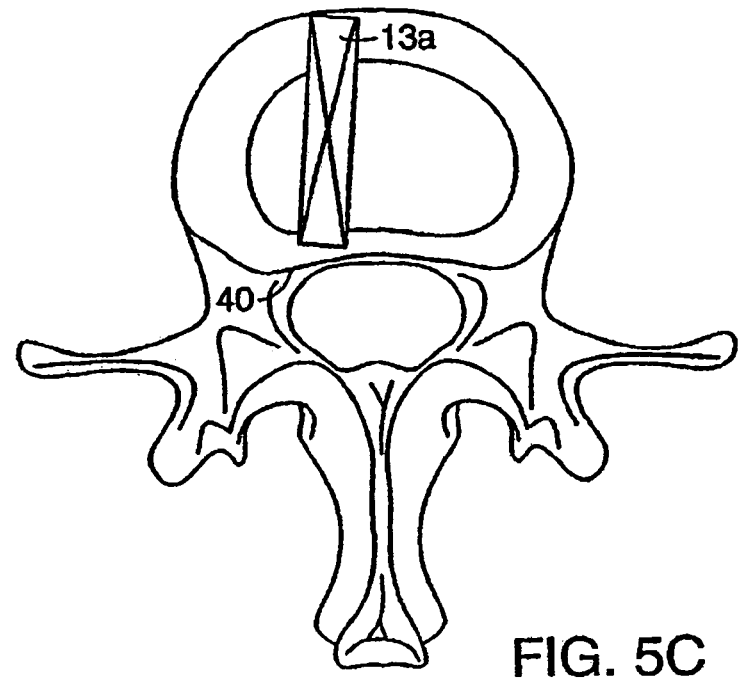
FIG. 5C shows a one-piece embodiment of the invention in an anchored and supporting position.

FIGS. 5A-C show an alternate embodiment of herniation constraining device 13A. In this series of figures, device 13A, a substantially one-piece construct, is delivered through a delivery tube 6, although device 13A could be delivered in a variety of ways including, but not limited to, by hand or by a hand held grasping instrument. In FIG. 5A, device 13A in delivery tube 6 is positioned against herniated segment 30. In FIG. 5B, the herniated segment is displaced within its pre-herniated borders 40 by device 13A and/or delivery tube 6 such that when, in FIG. 5C, device 13A has been delivered through delivery tube 6, and secured within a portion of the FSU, the device supports the displaced herniated segment within its pre-herniated border 40. Herniation constraining device 13A can be made of a variety of materials and have one of many possible forms so long as it allows support of the herniated segment 30 within the pre-herniated borders 40 of the disc. Device 13A can anchor the herniated segment 30 to any suitable anchoring site within the FSU, including, but not limited to the superior vertebral body, inferior vertebral body, or anterior AF. Device 13A may be used additionally to close a defect in the AF of herniated segment 30. Alternatively, any such defect may be left open or may be closed using another means.

Figure 6:
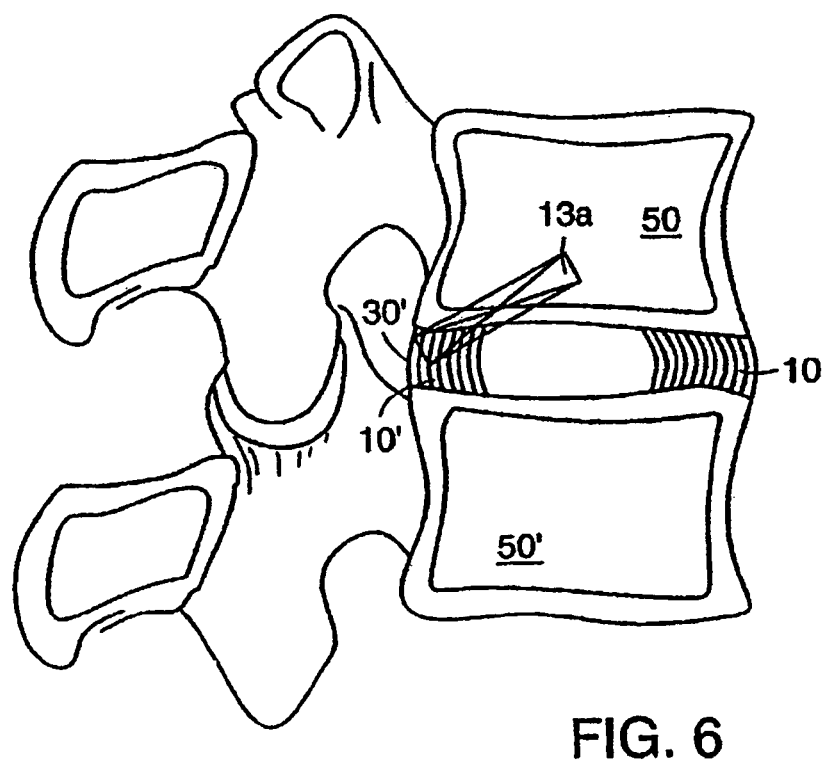
FIG. 6 shows one embodiment of the invention supporting a weakened posterior anulus fibrosis.

FIG. 6 depicts the substantially one-piece device 13A supporting a weakened segment 30' of the posterior AF 10'. Device 13A is positioned in or posterior to the weakened segment 30' and secured to a portion of the FSU, such as the superior vertebral body 50, shown in the figure, or the inferior vertebral body 50' or anterior or anterior-lateral anulus fibrosis 10. In certain patients, there may be no obvious herniation found at surgery. However, a weakened or torn AF that may not be protruding beyond the pre-herniated borders of the disc may still induce the surgeon to remove all or part of the NP in order to decrease the risk of herniation. As an alternative to discectomy, any of the embodiments of the invention may be used to support and perhaps close defects in weakened segments of AF.

Figure 7A:
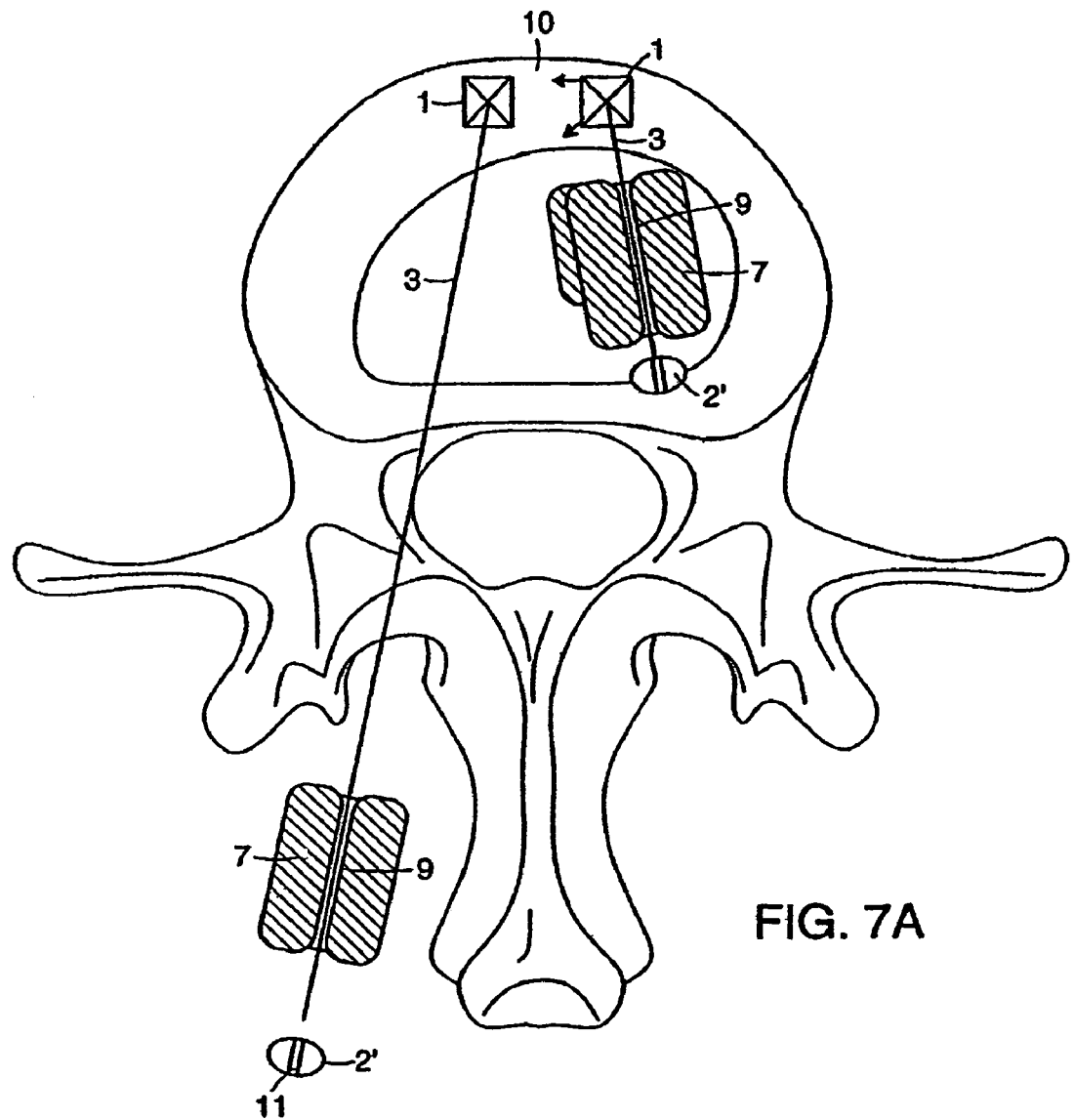
FIG. 7A shows a transverse section of another aspect of the disclosed invention demonstrating two stages involved in augmentation of the soft tissues of the disc.
Figure 7B:
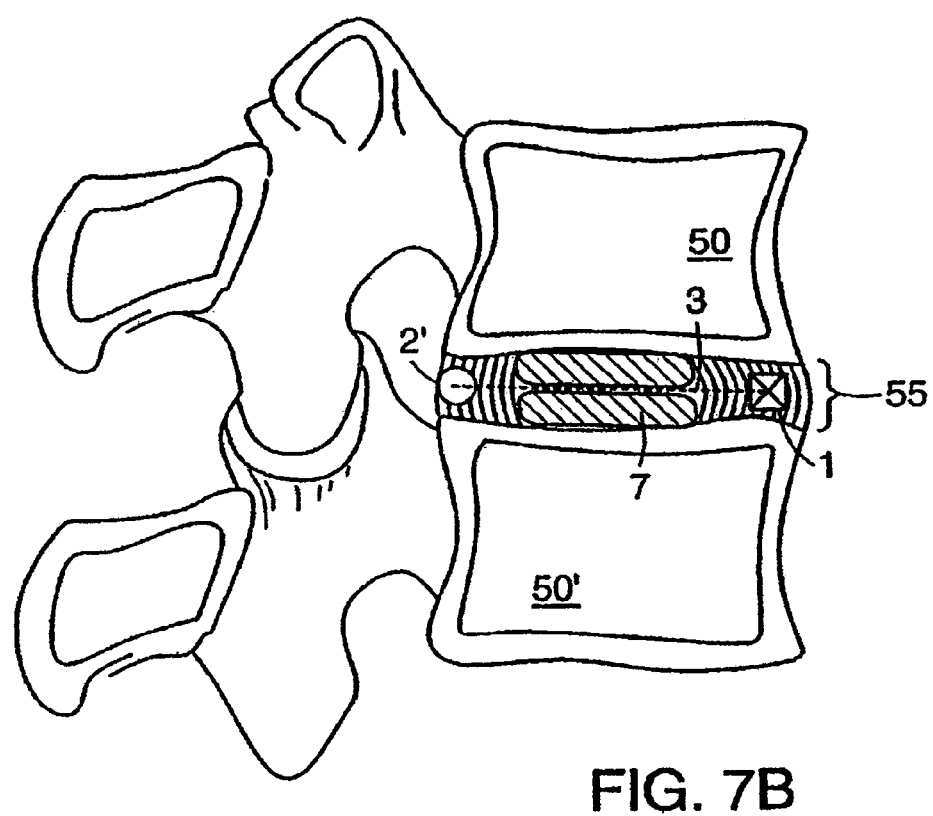
FIG. 7B shows a sagittal view of the invention shown in FIG. 7A.
Figure 8:
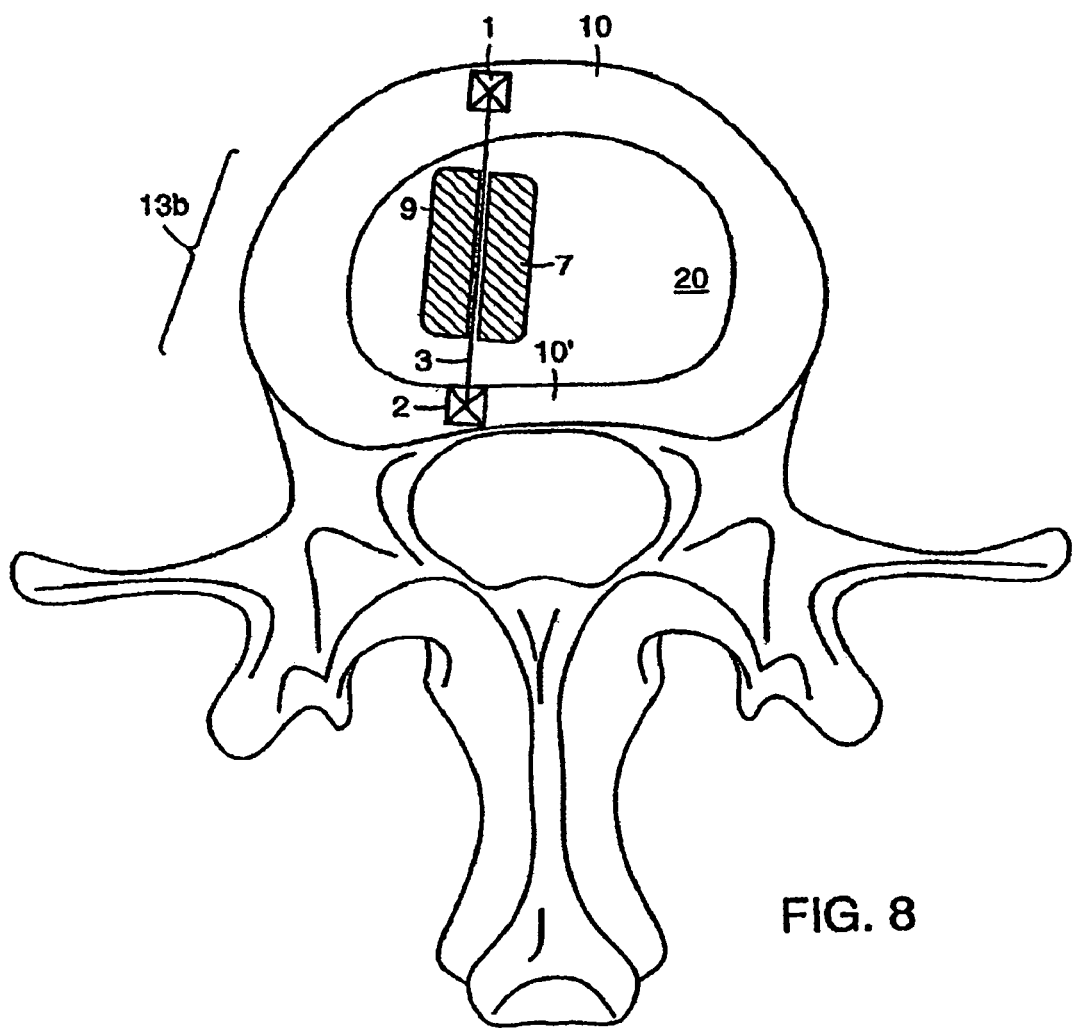
FIG. 8 shows a transverse section of one aspect of the disclosed invention involving augmentation of the soft tissues of the disc and support/closure of the anulus fibrosis.

A further embodiment of the present invention involves augmentation of the soft tissues of the intervertebral disc to avoid or reverse disc height loss. FIGS. 7A and 7B show one embodiment of device 13 securing augmentation material in the intervertebral disc space 55. In the left side of FIG. 7A, anchors 1 have been established in the anterior AF 10. Augmentation material 7 is in the process of being inserted into the disc space along connection member 3 which, in this embodiment, has passageway 9. Support member 2' is shown ready to be attached to connection member 3 once the augmentation material 7 is properly situated. In this embodiment, connection member 3 passes through an aperture 11 in support member 2', although many other methods of affixing support member 2' to connection member 3 are possible and within the scope of this invention.

Augmentation material 7 may have a passageway 9, such as a channel, slit or the like, which allows it to slide along the connection member 3, or augmentation material 7 may be solid, and connection member 3 can be threaded through augmentation material by means such as needle or other puncturing device. Connection member 3 is affixed at one end to anchor 1 and terminated at its other end by a support member 2', one embodiment of which is shown in the figure in a cap-like configuration. Support member 2' can be affixed to connection member 3 in a variety of ways, including, but not limited to, swaging support member 2' to connection member 3. In a preferred embodiment, support member 2' is in a cap configuration and has a dimension (diameter or length and width) larger than the optional passageway 9, which serves to prevent augmentation material 7 from displacing posteriorly with respect to anchor 1. The right half of the intervertebral disc of FIG. 7A (axial view) and FIG. 7B (sagittal view) show augmentation material 7 that has been implanted into the disc space 55 along connection member 3 where it supports the vertebral bodies 50 and 50'. FIG. 7A shows an embodiment in which support member 2' is affixed to connection member 3 and serves only to prevent augmentation material 7 from moving off connection member 3. The augmentation device is free to move within the disc space. FIG. 7B shows an alternate embodiment in which support member 2' is embedded in a site in the functional spine unit, such as a herniated segment or posterior anulus fibrosis, to further restrict the movement of augmentation material 7 or spacer material within the disc space.

Augmentation or spacer material can be made of any biocompatible, preferably flexible, material. Such a flexible material is preferably fibrous, like cellulose or bovine or autologous collagen. The augmentation material can be plug or disc shaped. It can further be cube-like, ellipsoid, spheroid or any other suitable shape. The augmentation material can be secured within the intervertebral space by a variety of methods, such as but not limited to, a suture loop attached to, around, or through the material, which is then passed to the anchor and support member.

FIGS. 8, 9A, 9B and 10A and 10B depict further embodiments of the disc herniation constraining device 13B in use for augmenting soft tissue, particularly tissue within the intervertebral space. In the embodiments shown in FIGS. 8 and 9A, device 13B is secured within the intervertebral disc space providing additional support for NP 20. Anchor 1 is securely affixed in a portion of the FSU, (anterior AF 10 in these figures). Connection member 3 terminates at support member 2, preventing augmentation material 7 from migrating generally posteriorly with respect to anchor 1. Support member 2 is depicted in these figures as established in various locations, such as the posterior AF 10' in FIG. 8, but support member 2 may be anchored in any suitable location within the FSU, as described previously. Support member 2 may be used to close a defect in the posterior AF. It may also be used to displace a herniated segment to within the pre-herniated borders of the disc by applying tension between anchoring means 1 and 2 along connection member 3.

Figure 9A:
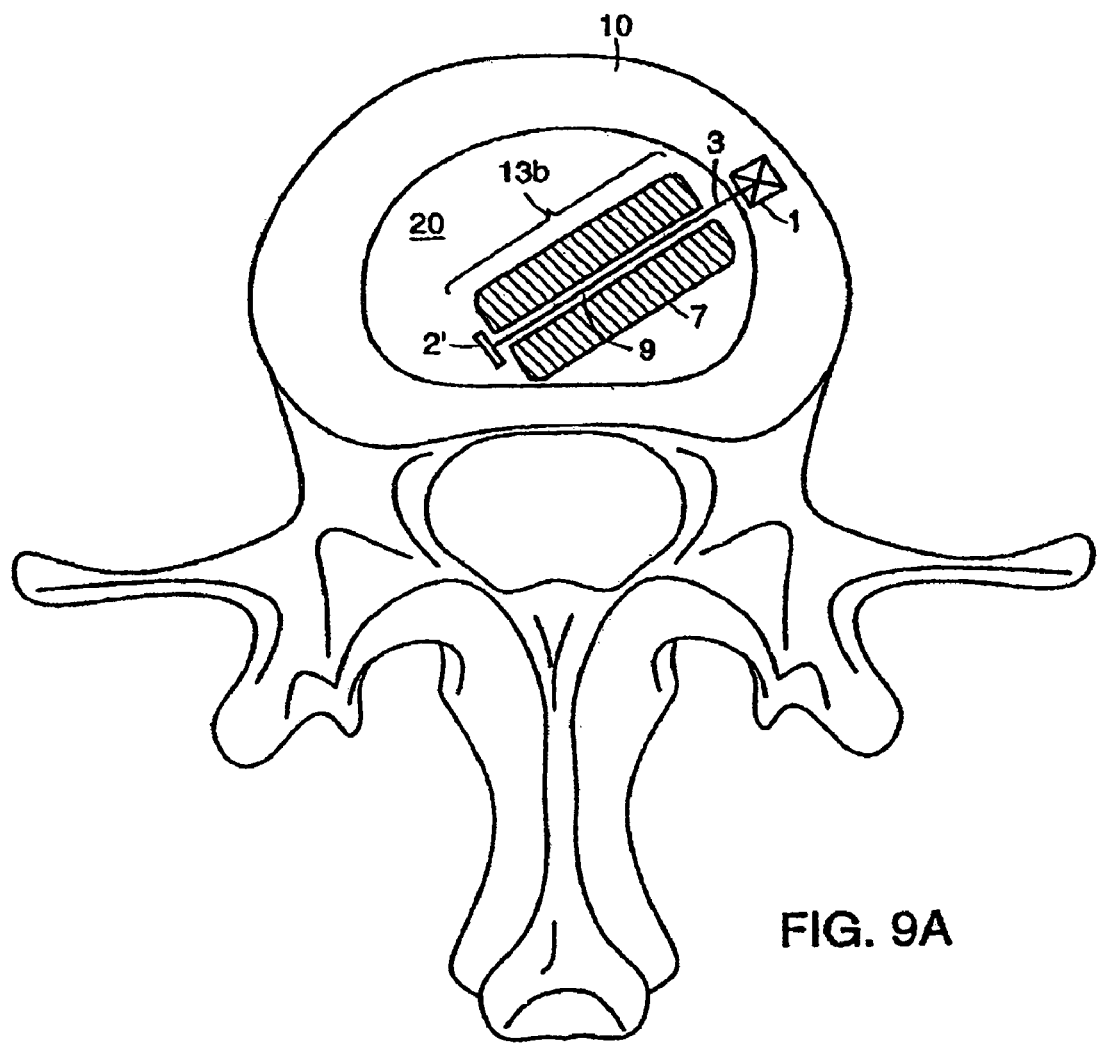
FIG. 9A shows a transverse section of one aspect of the invention involving augmentation of the soft tissues of the disc with the flexible augmentation material anchored to the anterior lateral anulus fibrosis.

FIG. 9A depicts anchor 1, connection member 3, spacer material 7 and support member 2' (shown in the "cap"-type configuration) inserted as a single construct and anchored to a site within the disc space, such as the inferior or superior vertebral bodies. This configuration simplifies insertion of the embodiments depicted in FIGS. 7 and 8 by reducing the number of steps to achieve implantation. Connection member 3 is preferably relatively stiff in tension, but flexible against all other loads. Support member 2' is depicted as a bar element that is larger than passageway 9 in at least one plane.

Figure 9B:
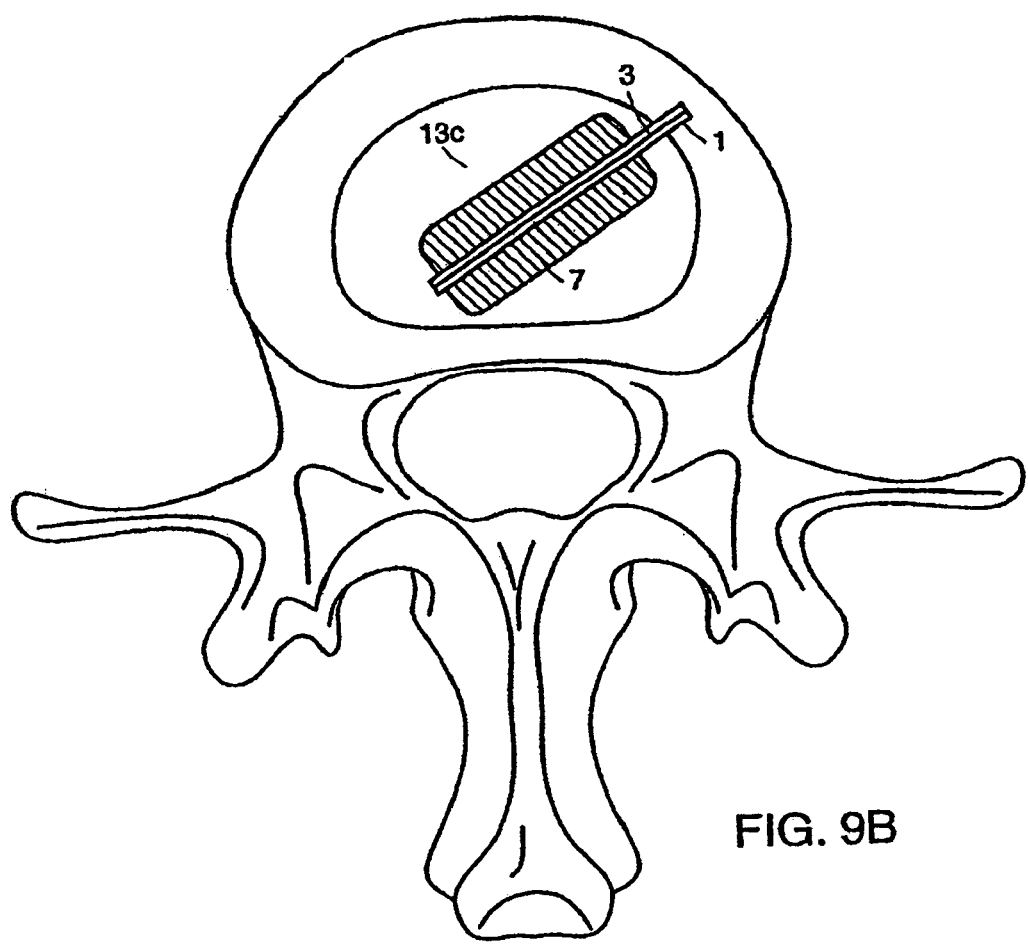
FIG. 9B shows a transverse section of one aspect of the disclosed invention involving augmentation of the soft tissues of the disc with the flexible augmentation material anchored to the anulus fibrosis by a one-piece anchor.

FIG. 9B depicts a variation on the embodiment depicted in FIG. 9A. FIG. 9B shows substantially one-piece disc augmentation device 13C, secured in the intervertebral disc space. Device 13C has anchor 1, connection member 3 and augmentation material 7. Augmentation material 7 and anchor 1 could be pre-assembled prior to insertion into the disc space 55 as a single construct. Alternatively, augmentation material 7 could be inserted first into the disc space and then anchored to a portion of the FSU by anchor 1.

Figure 10A:
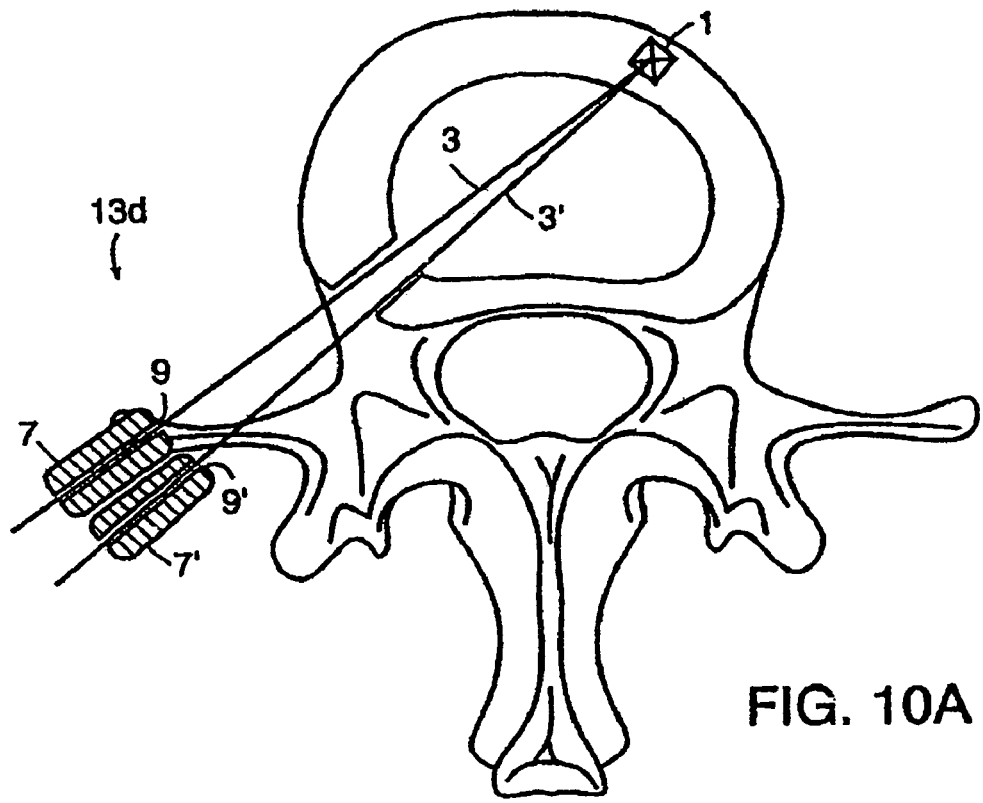
FIG. 10A shows a transverse section of one aspect of the disclosed invention involving augmentation of the soft tissues of the disc.
Figure 10B:
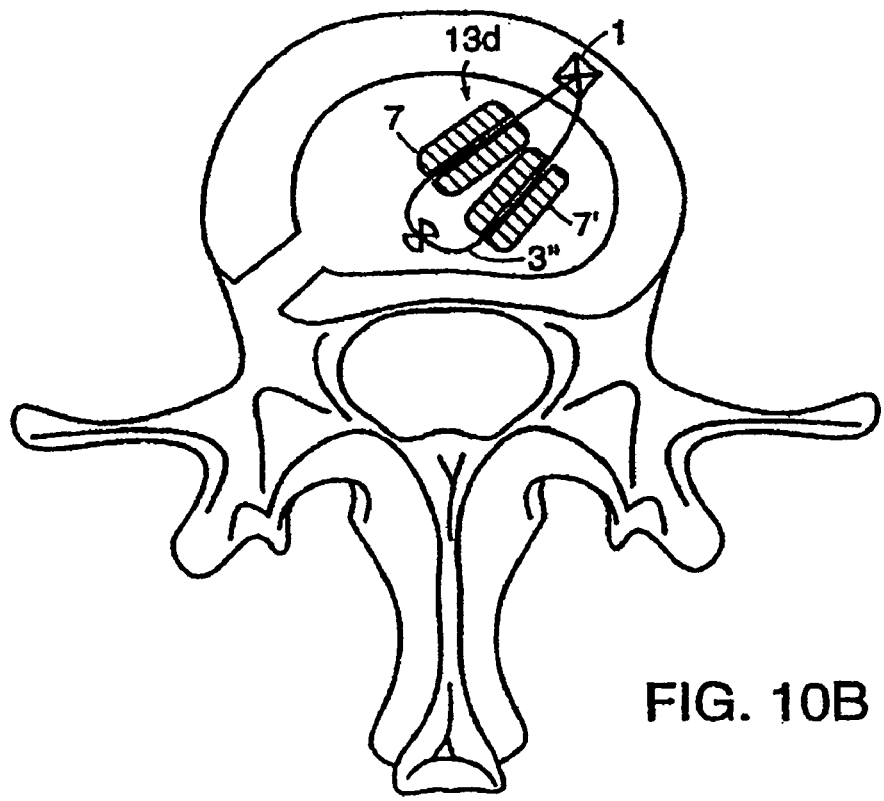
FIG. 10B shows the construct of FIG. 10A after the augmentation material has been inserted into the disc.

FIGS. 10A and 10B show yet another embodiment of the disclosed invention, 13D. In FIG. 10A, two connection members 3 and 3' are attached to anchor 1. Two plugs of augmentation material 7 and 7' are inserted into the disc space along connection members 3 and 3'. Connection members 3 and 3' are then bound together (e.g., knotted together, fused, or the like). This forms loop 3" that serves to prevent augmentation materials 7 and 7' from displacing posteriorly. FIG. 10B shows the position of the augmentation material 7 after it is secured by the loop 3" and anchor 1. Various combinations of augmentation material, connecting members and anchors can be used in this embodiment, such as using a single plug of augmentation material, or two connection members leading from anchor 1 with each of the connection members being bound to at least one other connection member. It could further be accomplished with more than one anchor with at least one connection member leading from each anchor, and each of the connection members being bound to at least one other connection member.

Any of the devices described herein can be used for closing defects in the AF whether created surgically or during the herniation event. Such methods may also involve the addition of biocompatible material to either the AF or NP. This material could include sequestered or extruded segments of the NP found outside the pre-herniated borders of the disc.

FIGS. 11-15 illustrate devices used in and methods for closing a defect in an anulus fibrosis. One method involves the insertion of a barrier or barrier means 12 into the disc 15. This procedure can accompany surgical discectomy. It can also be done without the removal of any portion of the disc 15 and further in combination with the insertion of an augmentation material or device into the disc 15.

The method consists of inserting the barrier 12 into the interior of the disc 15 and positioning it proximate to the interior aspect of the anulus defect 16. The barrier material is preferably considerably larger in area than the size of the defect 16, such that at least some portion of the barrier means 12 abuts healthier anulus fibrosis 10. The device acts to seal the anulus defect 16, recreating the closed isobaric environment of a healthy disc nucleus 20. This closure can be achieved simply by an over-sizing of the implant relative to the defect 16. It can also be achieved by affixing the barrier means 12 to tissues within the functional spinal unit. In one embodiment of the present invention, the barrier 12 is affixed to the anulus surrounding the anulus defect 16. This can be achieved with sutures, staples, glues or other suitable fixation means or fixation device 14. The barrier means 12 can also be larger in area than the defect 16 and be affixed to a tissue or structure opposite the defect 16, e.g., anterior tissue in the case of a posterior defect.

The barrier means 12 is preferably flexible in nature. It can be constructed of a woven material such as Dacron™ or Nylon™, a synthetic polyamide or polyester, a polyethylene, and can further be an expanded material, such as expanded polytetrafluroethylene (e-PTFE), for example. The barrier means 12 can also be a biologic material such as cross-linked collagen or cellulous.

The barrier means 12 can be a single piece of material. It can have an expandable means or component that allows it to be expanded from a compressed state after insertion into the interior of the disc 15. This expandable means can be active, such as a balloon, or passive, such as a hydrophilic material. The expandable means can also be a self-expanding elastically deforming material, for example.

Figure 11:
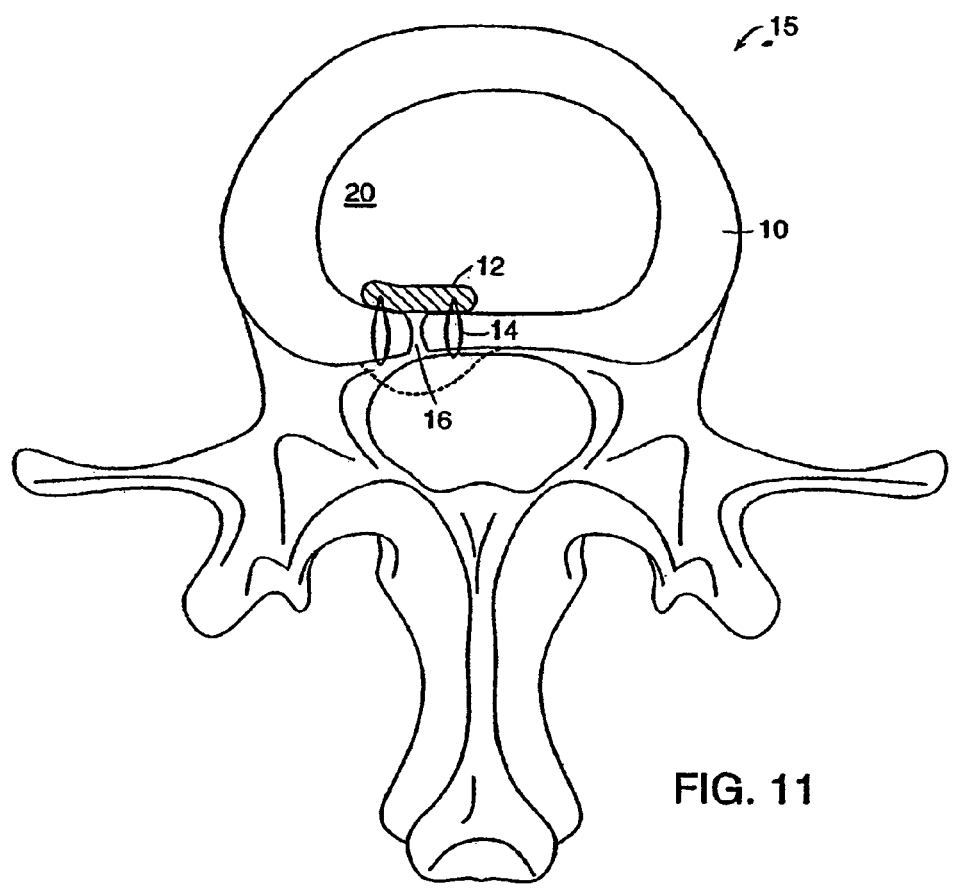
FIG. 11 illustrates a transverse section of a barrier mounted within an anulus.
Figure 12:
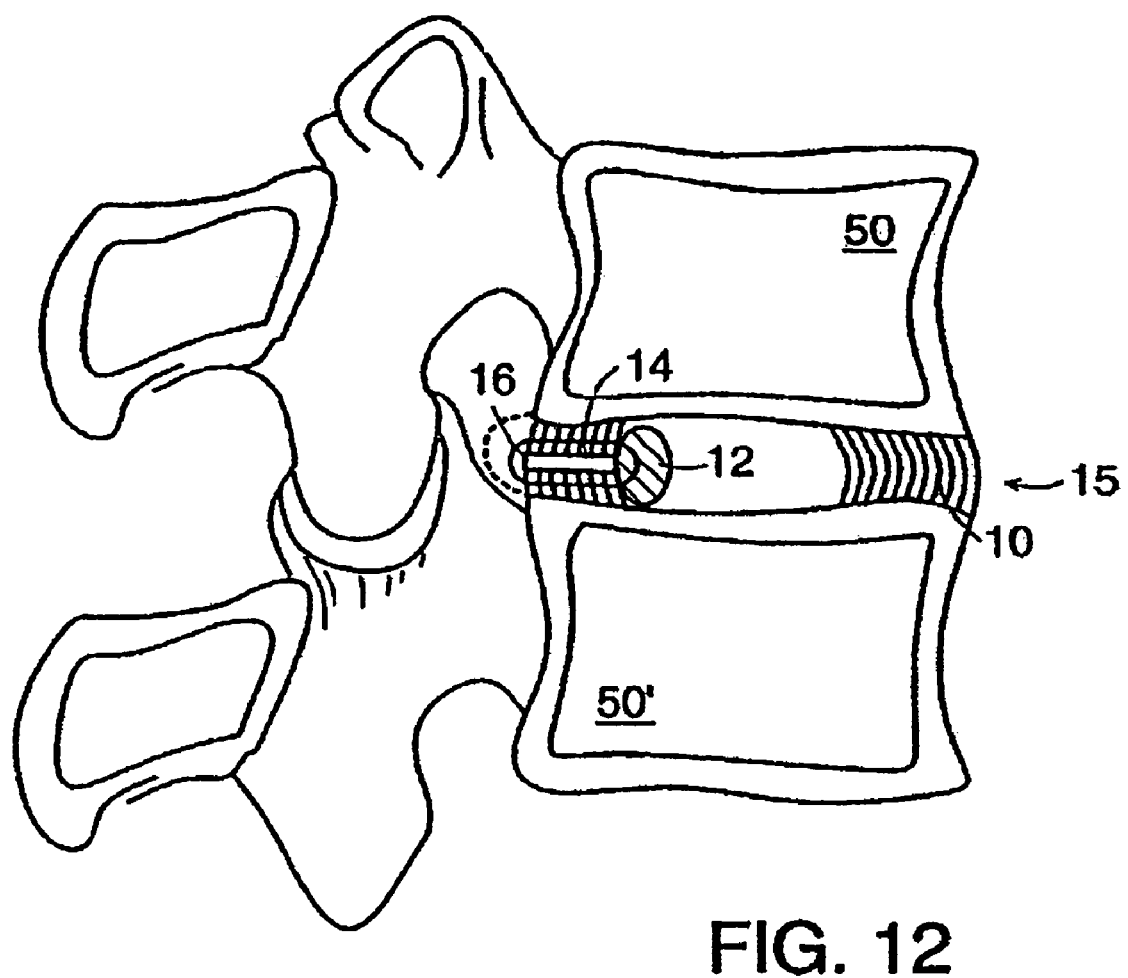
FIG. 12 shows a sagittal view of the barrier of FIG. 11.
Figure 13:
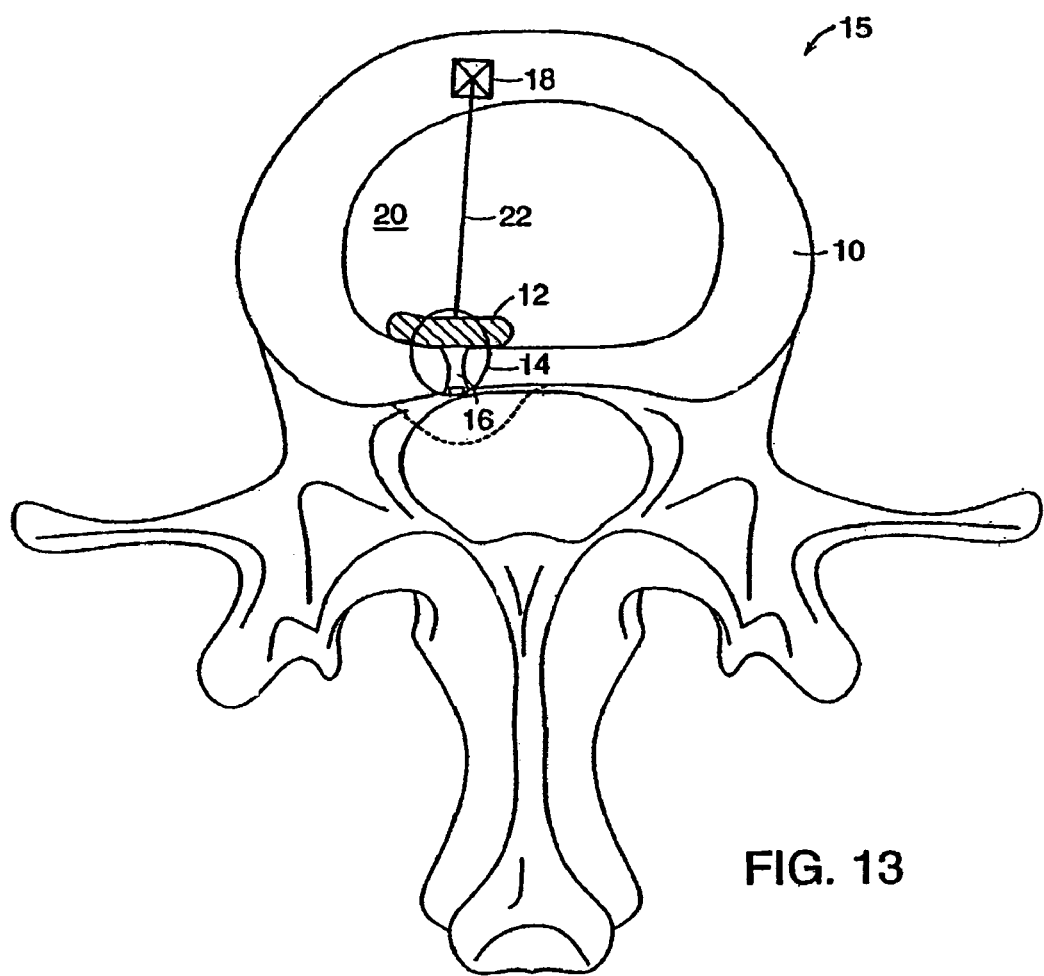
FIG. 13 shows a transverse section of a barrier anchored within a disc.
Figure 14:
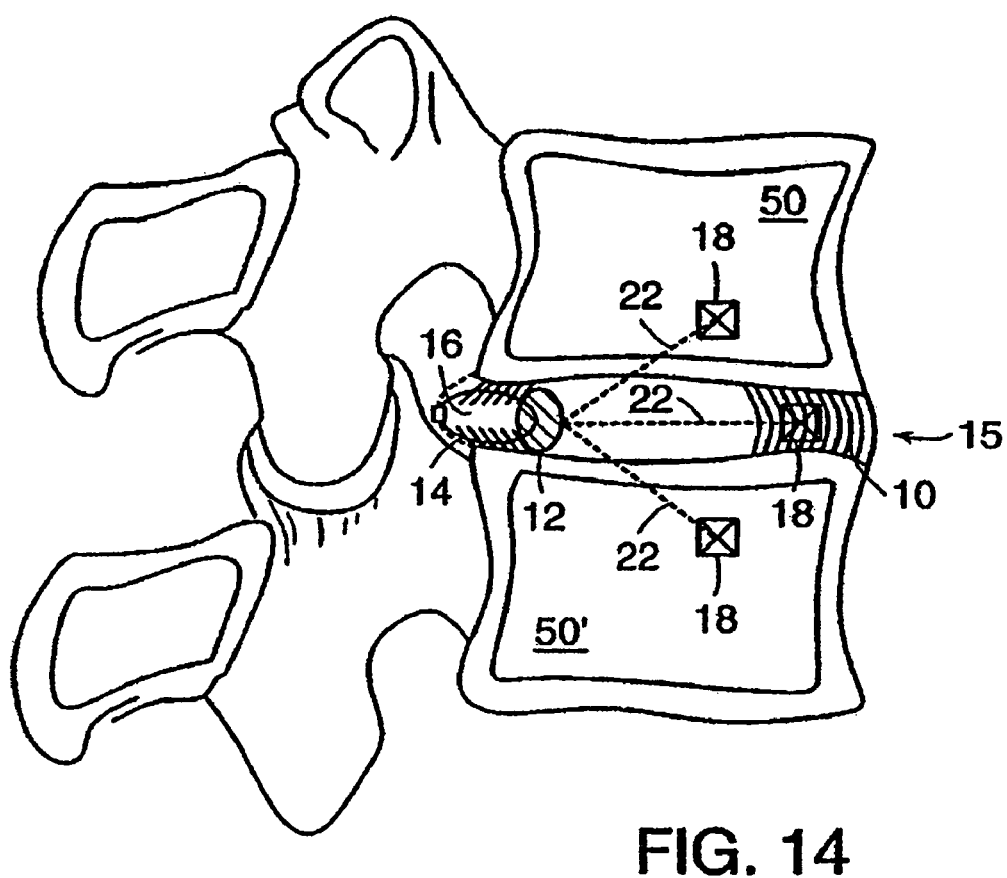
FIG. 14 illustrates a sagittal view of the barrier shown in FIG. 13.

FIGS. 11 and 12 illustrate a barrier 12 mounted within an anulus 10 and covering an anulus defect 16. The barrier 12 can be secured to the anulus 10 with a fixation mechanism or fixation means 14. The fixation means 14 can include a plurality of suture loops placed through the barrier 12 and the anulus 10. Such fixation can prevent motion or slipping of the barrier 12 away from the anulus defect 16.

The barrier means 12 can also be anchored to the disc 15 in multiple locations. In one preferred embodiment, shown in FIGS. 13 and 14, the barrier means 12 can be affixed to the anulus tissue 10 in or surrounding the defect and further affixed to a secondary fixation site opposite the defect, e.g. the anterior anulus 10 in a posterior herniation, or the inferior 50' or superior 50 vertebral body. For example, fixation means 14 can be used to attach the barrier 12 to the anulus 10 near the defect 16, while an anchoring mechanism 18 can secure the barrier 12 to a secondary fixation site. A connector 22 can attach the barrier 12 to the anchor 18. Tension can be applied between the primary and secondary fixation sites through a connector 22 so as to move the anulus defect 16 toward the secondary fixation site. This may be particularly beneficial in closing defects 16 that result in posterior herniations. By using this technique, the herniation can be moved and supported away from any posterior neural structures while further closing any defect in the anulus 10.

The barrier means 12 can further be integral to a fixation means such that the barrier means affixes itself to tissues within the functional spinal unit.

Figure 15:
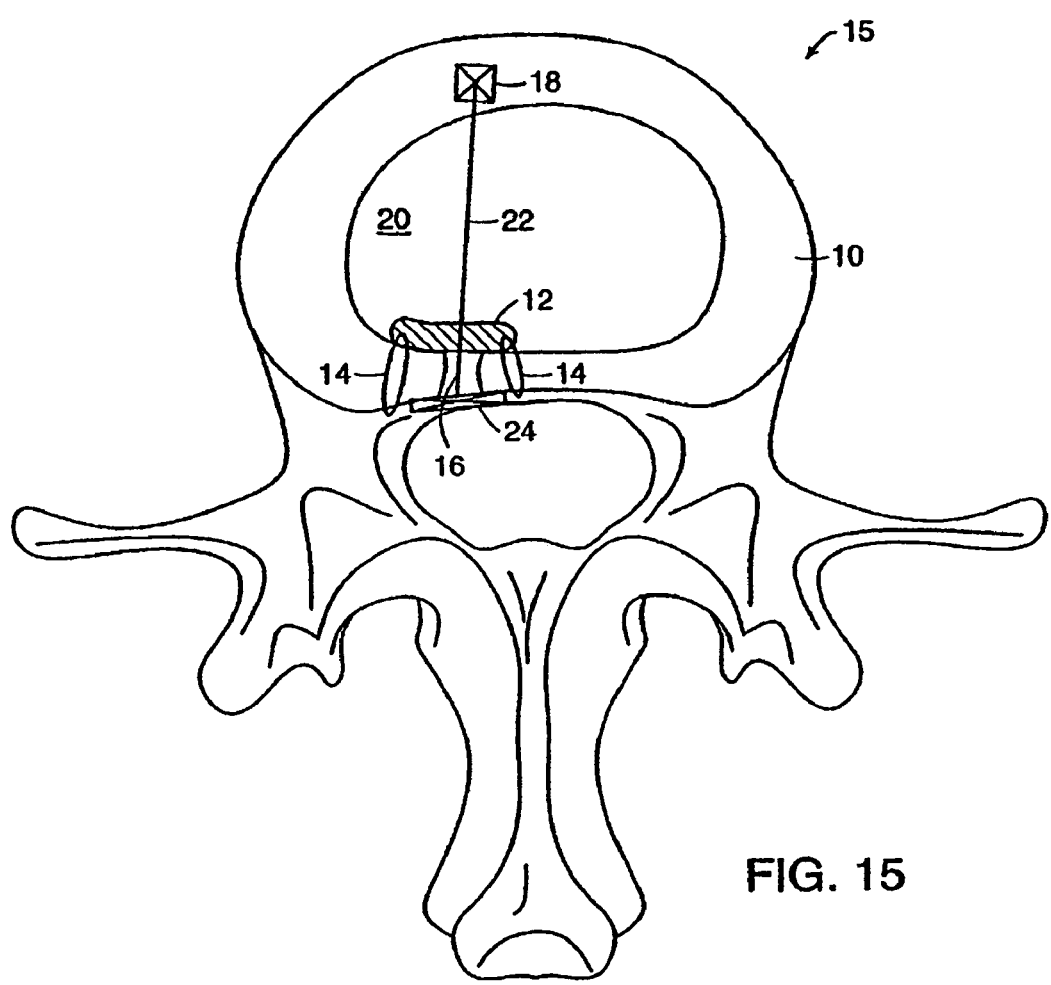
FIG. 15 illustrates the use of a second anchoring device for a barrier mounted within a disc.

Any of the methods described above can be augmented by the use of a second barrier or a second barrier means 24 placed proximate to the outer aspect of the defect 16 as shown in FIG. 15. The second barrier 24 can further be affixed to the inner barrier means 12 by the use of a fixation means 14 such as suture material.

Figure 16A:
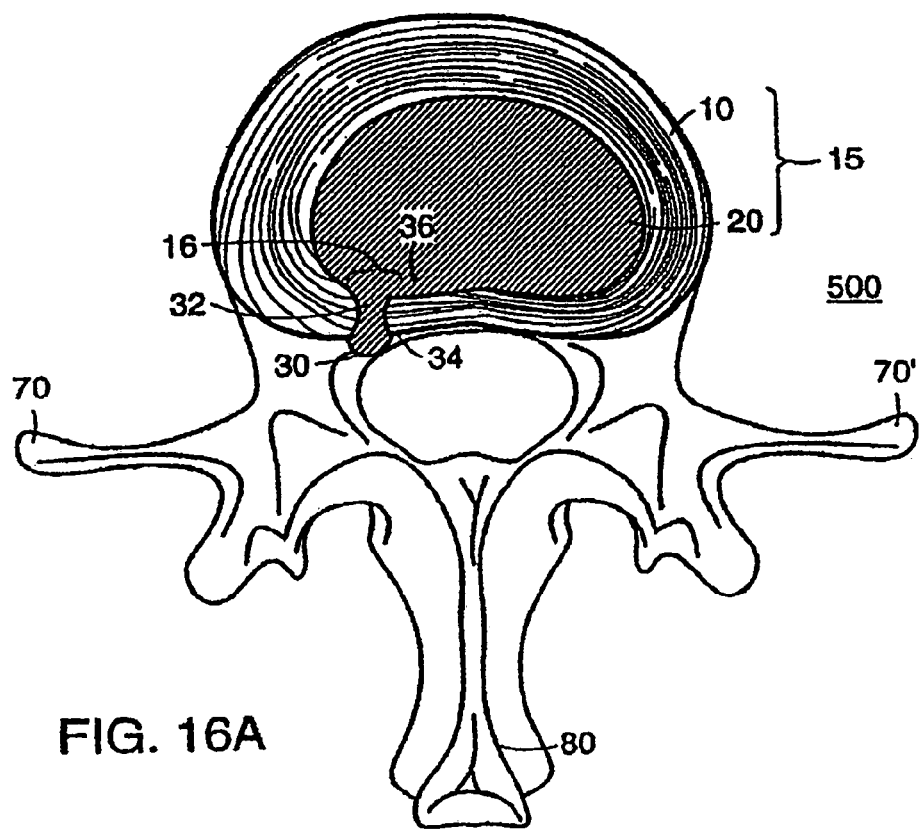
FIG. 16A is an transverse view of the intervertebral disc.
Figure 16B:
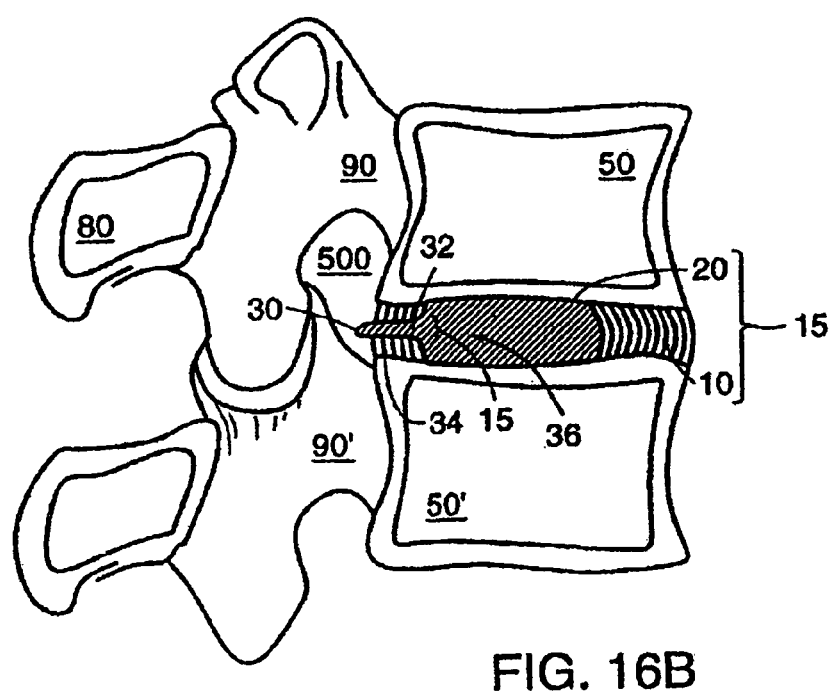
FIG. 16B is a sagittal section along the midline of the intervertebral disc.

FIGS. 16A and 16B depict intervertebral disc 15 comprising nucleus pulposus 20 and anulus fibrosis 10. Nucleus pulposus 20 forms a first anatomic region and extra-discal space 500 (any space exterior to the disc) forms a second anatomic region wherein these regions are separated by anulus fibrosis 10.

FIG. 16A is an axial (transverse) view of the intervertebral disc. A posterior lateral defect 16 in anulus fibrosis 10 has allowed a segment 30 of nucleus pulposus 20 to herniate into an extra discal space 500. Interior aspect 32 and exterior aspect 34 are shown, as are the right 70' and left 70 transverse processes and posterior process 80.

FIG. 16B is a sagittal section along the midline intervertebral disc. Superior pedicle 90 and inferior pedicle 90' extend posteriorly from superior vertebral body 95 and inferior vertebral body 95' respectively.

Figure 17:
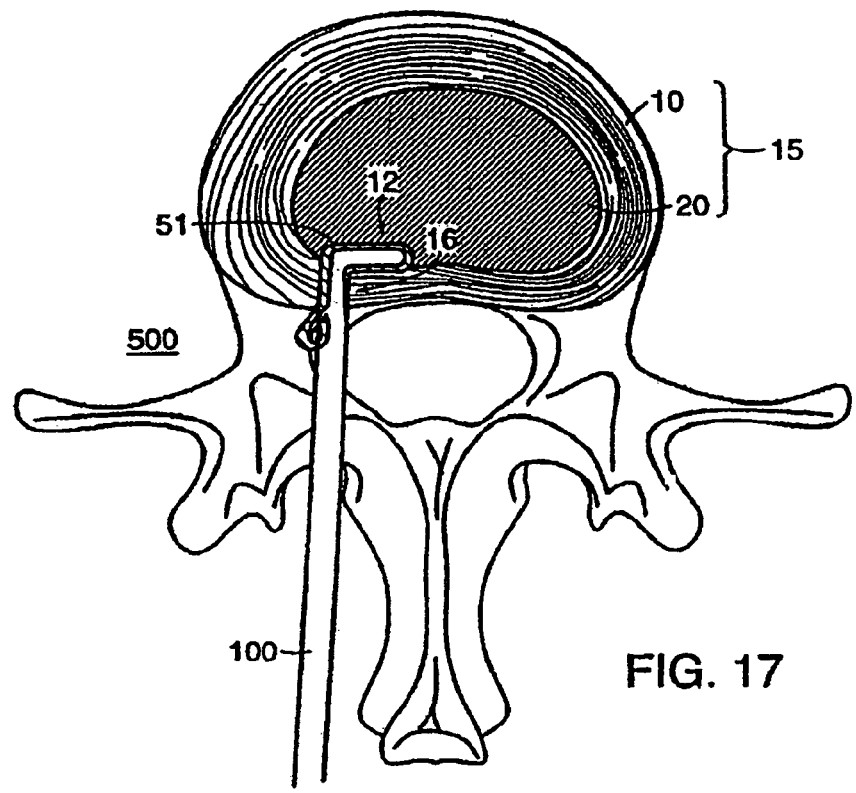
FIG. 17 is an axial view of the intervertebral disc with the right half of a sealing means of a barrier means being placed against the interior aspect of a defect in anulus fibrosis by a dissection/delivery tool.
Figure 18:
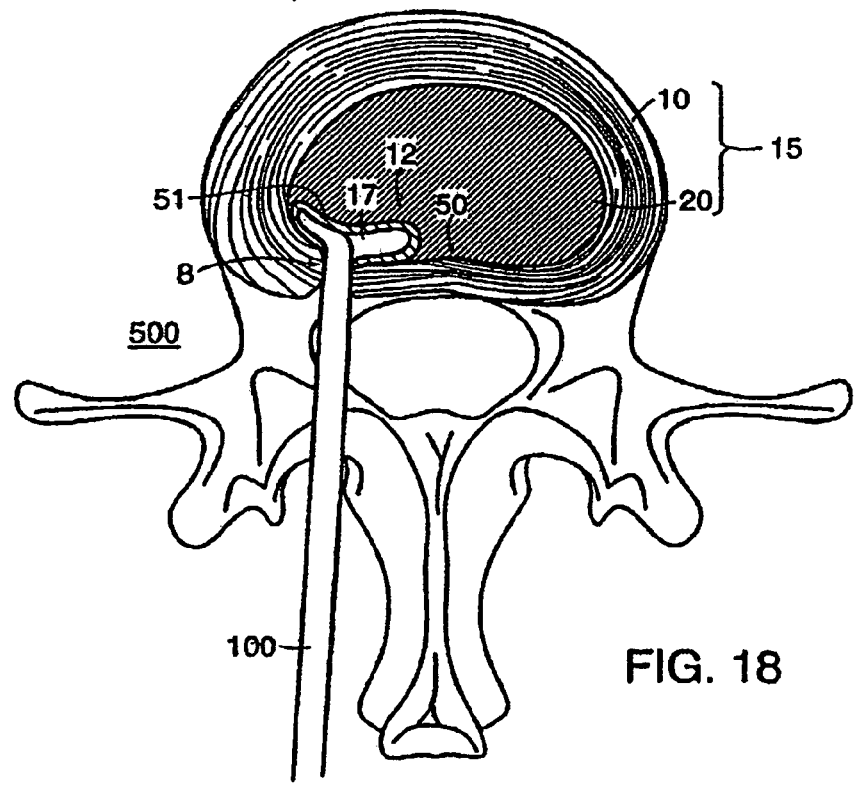
FIG. 18 illustrates a full sealing means placed on the interior aspect of a defect in anulus fibrosis.

To prevent further herniation of the nucleus 20 and to repair any present herniation, in a preferred embodiment, a barrier or barrier means 12 can be placed into a space between the anulus 10 and the nucleus 20 proximate to the inner aspect 32 of defect 16, as depicted in FIGS. 17 and 18. The space can be created by blunt dissection. Dissection can be achieved with a separate dissection instrument, with the barrier means 12 itself, or a combined dissection/barrier delivery tool 100. This space is preferably no larger than the barrier means such that the barrier means 12 can be in contact with both anulus 10 and nucleus 20. This allows the barrier means 12 to transfer load from the nucleus 20 to the anulus 10 when the disc is pressurized during activity.

In position, the barrier means 12 preferably spans the defect 16 and extends along the interior aspect 36 of the anulus 10 until it contacts healthy tissues on all sides of the defect 16, or on a sufficient extent of adjacent healthy tissue to provide adequate support under load. Healthy tissue may be non-diseased tissue and/or load bearing tissue, which may be micro-perforated or non-perforated. Depending on the extent of the defect 16, the contacted tissues can include the anulus 10, cartilage overlying the vertebral endplates, and/or the endplates themselves.

Figure 21A:
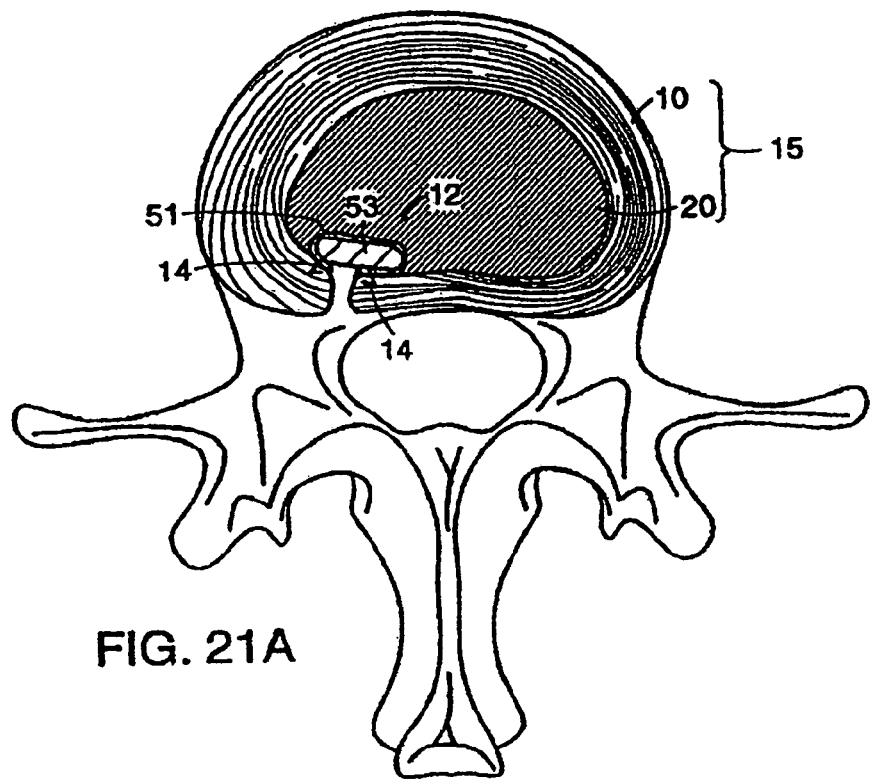
FIG. 21A depicts an axial view of the sealing means of FIG. 20 having enlarging means inserted into the interior cavity.
Figure 21B:
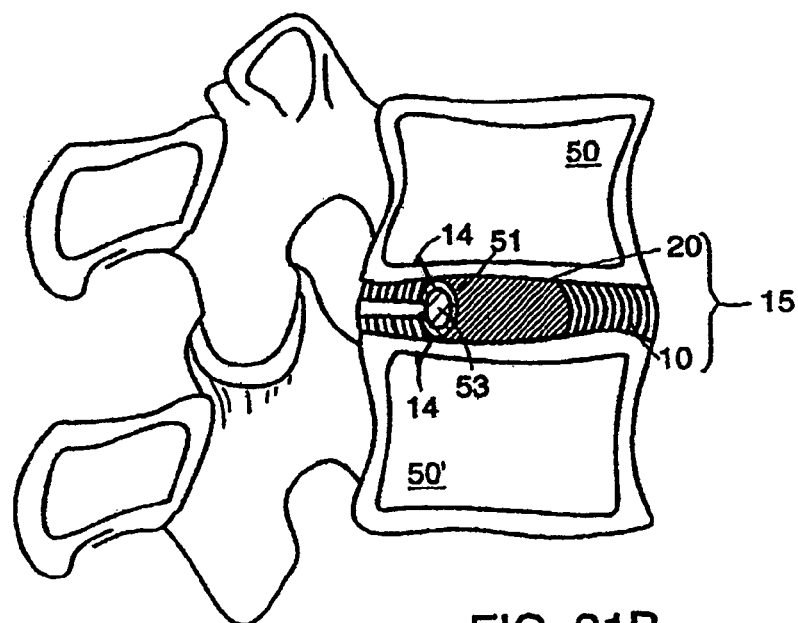
FIG. 21B depicts the construct of FIG. 21 in a sagittal section.
Figure 22A:
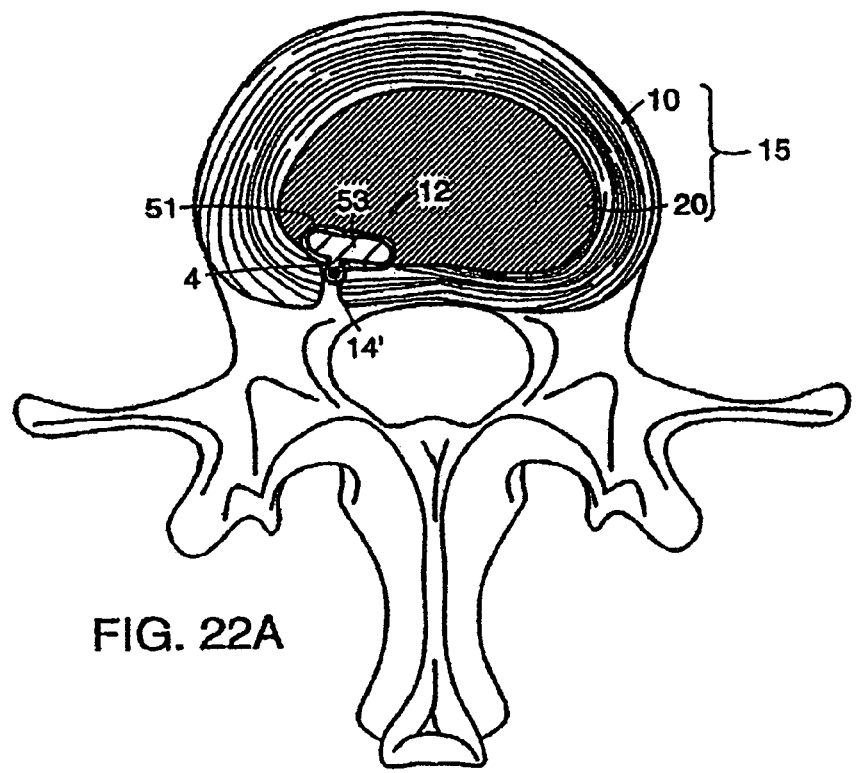
FIG. 22A shows an alternative fixation scheme for the sealing means and enlarging means.
Figure 22B:
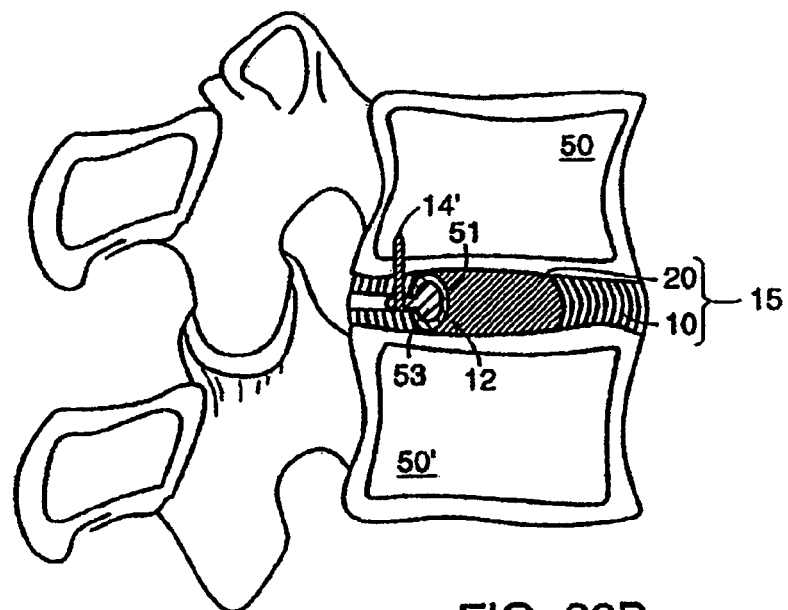
FIG. 22B shows the construct of FIG. 22A in a sagittal section with an anchor securing a fixation region of the enlarging means to a superior vertebral body in a location proximate to the defect.

In the preferred embodiment, the barrier means 12 comprises two components—a sealing means or sealing component 51 and an enlarging means or enlarging component 53, shown in FIGS. 21A and 21B.

The sealing means 51 forms the periphery of the barrier 12 and has an interior cavity 17. There is at least one opening 8 leading into cavity 17 from the exterior of the sealing means 51. Sealing means 51 is preferably compressible or collapsible to a dimension that can readily be inserted into the disc 15 through a relatively small hole. This hole can be the defect 16 itself or a site remote from the defect 16. The sealing means 51 is constructed from a material and is formed in such a manner as to resist the passage of fluids and other materials around sealing means 51 and through the defect 16. The sealing means 51 can be constructed from one or any number of a variety of materials including, but not limited to PTFE, e-PTFE, Nylon™, Marlex™, high-density polyethylene, and/or collagen. The thickness of the sealing component has been found to be optimal between about 0.001 inches (0.127 mm) and 0.063 inches (1.6 mm).

The enlarging means 53 can be sized to fit within cavity 17 of sealing means 51. It is preferably a single object of a dimension that can be inserted through the same defect 16 through which the sealing means 51 was passed. The enlarging means 53 can expand the sealing means 51 to an expanded state as it is passed into cavity 17. One purpose of enlarging means 53 is to expand sealing means 51 to a size greater than that of the defect 16 such that the assembled barrier 12 prevents passage of material through the defect 16. The enlarger 53 can further impart stiffness to the barrier 12 such that the barrier 12 resists the pressures within nucleus pulposus 20 and expulsion through the defect 16. The enlarging means 53 can be constructed from one or any number of materials including, but not limited to, silicon rubber, various plastics, stainless steel, nickel titanium alloys, or other metals. These materials may form a solid object, a hollow object, coiled springs or other suitable forms capable of filling cavity 17 within sealing means 51.

The sealing means 51, enlarging means 53, or the barrier means 12 constructs can further be affixed to tissues either surrounding the defect 16 or remote from the defect 16. In the preferred embodiment, no aspect of a fixation means or fixation device or the barrier means 12 nor its components extend posterior to the disc 15 or into the extradiscal region 500, avoiding the risk of contacting and irritating the sensitive nerve tissues posterior to the disc 15.

Figure 19:
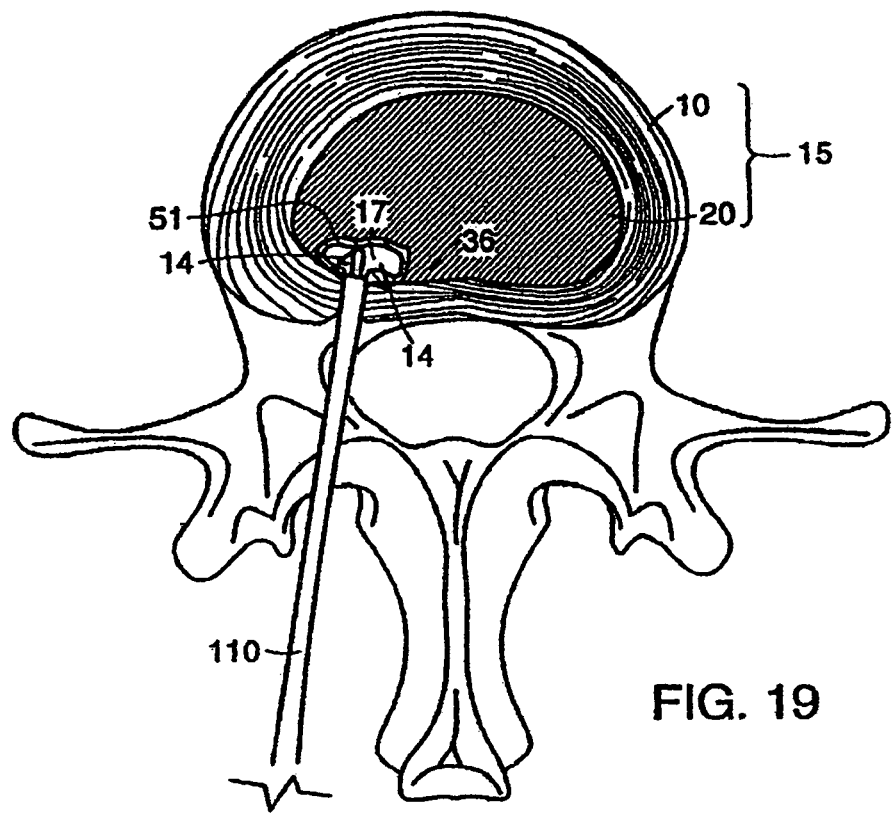
FIG. 19 depicts the sealing means of FIG. 18 being secured to tissues surrounding the defect.
Figure 20:
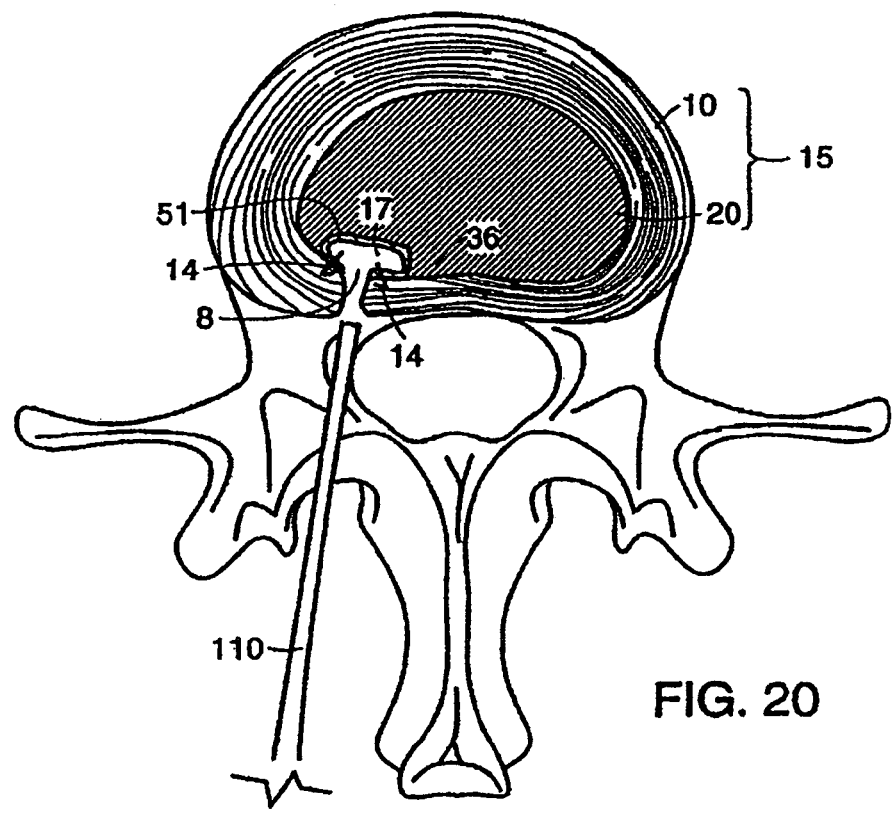
FIG. 20 depicts the sealing means of FIG. 19 after fixation means have been passed into surrounding tissues.

In a preferred embodiment, the sealing means 51 is inserted into the disc 15 proximate the interior aspect 36 of the defect. The sealing means 51 is then affixed to the tissues surrounding the defect using a suitable fixation means, such as suture or a soft-tissue anchor. The fixation procedure is preferably performed from the interior of the sealing means cavity 17 as depicted in FIGS. 19 and 20. A fixation delivery instrument 110 is delivered into cavity 17 through opening 8 in the sealing means 51. Fixation devices 14 can then be deployed through a wall of the sealing means 53 into surrounding tissues. Once the fixation means 14 have been passed into surrounding tissue, the fixation delivery instrument 110 can be removed from the disc 15. This method eliminates the need for a separate entryway into the disc 15 for delivery of fixation means 14. It further minimizes the risk of material leaking through sealing means 51 proximate to the fixation means 14. One or more fixation means 14 can be delivered into one or any number of surrounding tissues including the superior 95 and inferior 95' vertebral bodies. Following fixation of the sealing means 51, the enlarging means 53 can be inserted into cavity 17 of the sealing means 51 to further expand the barrier means 12 construct as well as increase its stiffness, as depicted in FIGS. 21A and 21B. The opening 8 into the sealing means 51 can then be closed by a suture or other means, although this is not a requirement of the present invention. In certain cases, insertion of a separate enlarging means may not be necessary if adequate fixation of the sealing means 51 is achieved.

Another method of securing the barrier 12 to tissues is to affix the enlarging means 53 to tissues either surrounding or remote from the defect 16. The enlarging means 53 can have an integral fixation region 4 that facilitates securing it to tissues as depicted in FIGS. 22A, 22B, 32A and 43B. This fixation region 4 can extend exterior to sealing means 51 either through opening 8 or through a separate opening. Fixation region 4 can have a hole through which a fixation means or fixation device 14 can be passed. In a preferred embodiment, the barrier 12 is affixed to at least one of the surrounding vertebral bodies (95 and 95') proximate to the defect using a bone anchor 14'. The bone anchor 14' can be deployed into the vertebral bodies 50, 50' at some angle between 0E and 180E relative to a bone anchor deployment tool. As shown the bone anchor 14' is mounted at 90E relative to the bone anchor deployment tool. Alternatively, the enlarging means 53 itself can have an integral fixation device 14 located at a site or sites along its length.

Figure 23A:
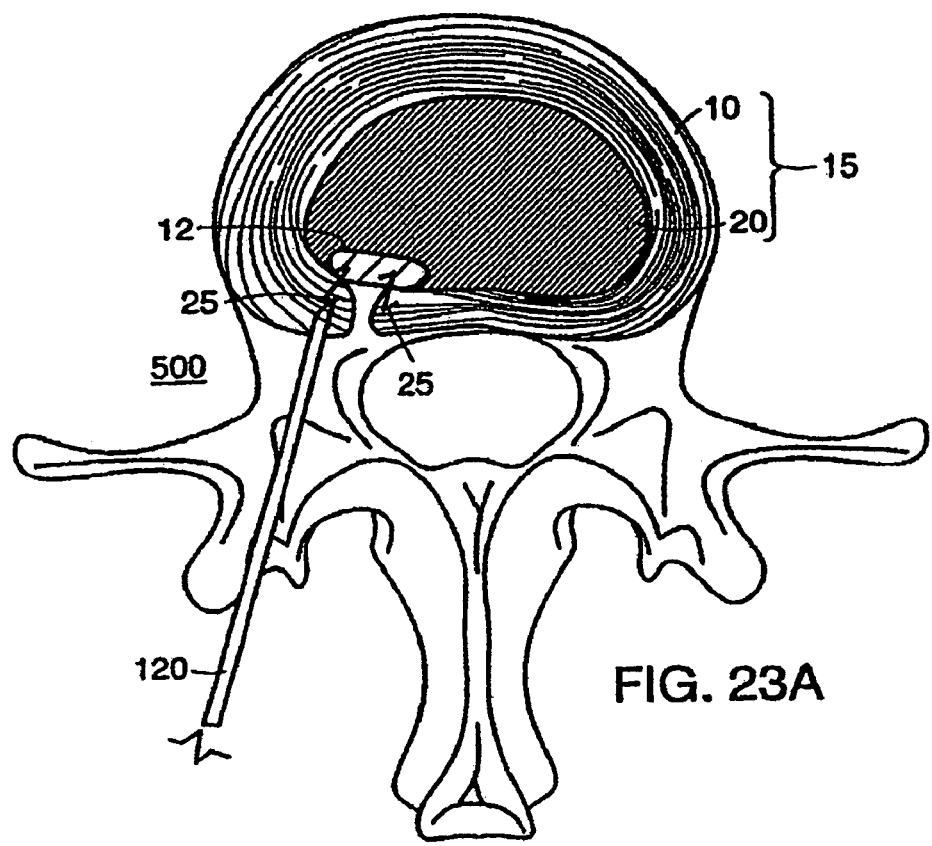
FIG. 23A depicts an embodiment of the barrier means of the present invention being secured to an anulus using fixation means, as shown in one embodiment.
Figure 23B:
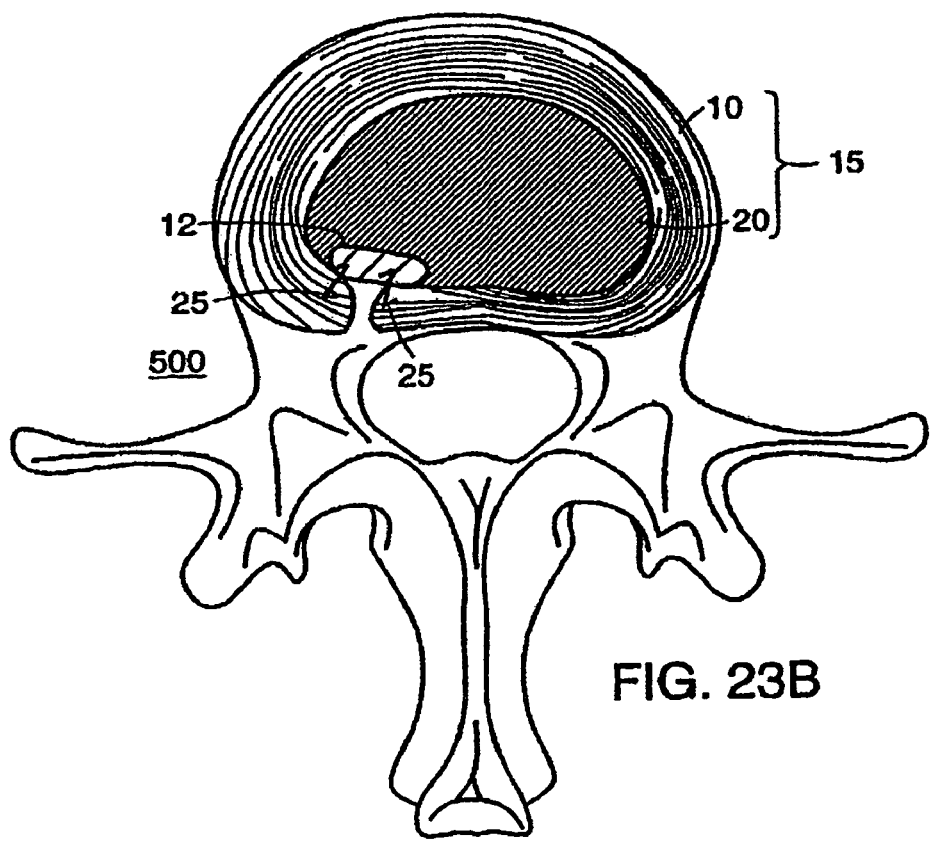
FIG. 23B depicts an embodiment of the barrier means of FIG. 23A secured to an anulus by two fixation darts wherein the fixation tool has been removed.

Another method of securing the barrier means 12 is to insert the barrier means 12 through the defect 16 or another opening into the disc 15, position it proximate to the interior aspect 36 of the defect 16, and pass at least one fixation means 14 through the anulus 10 and into the barrier 12. In a preferred embodiment of this method, the fixation means 14 can be darts 15 and are first passed partially into anulus 10 within a fixation device 120, such as a hollow needle. As depicted in FIGS. 23A and 23B, fixation means 25 can be advanced into the barrier means 12 and fixation device 120 removed. Fixation means 25 preferably have two ends, each with a means to prevent movement of that end of the fixation device. Using this method, the fixation means can be lodged in both the barrier 12 and anulus fibrosis 10 without any aspect of fixation means 25 exterior to the disc in the extradiscal region 500.

Figure 24A:
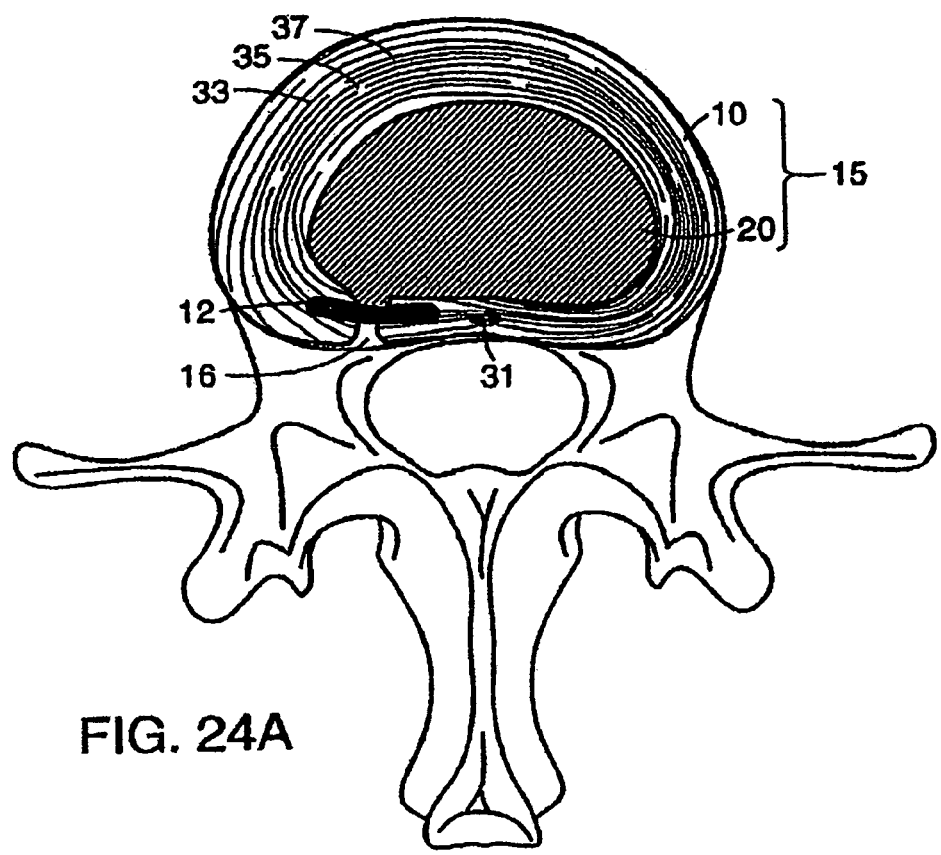
FIGS. 24A and 24B depict a barrier means positioned between layers of the anulus fibrosis on either side of a defect.
Figure 24B:
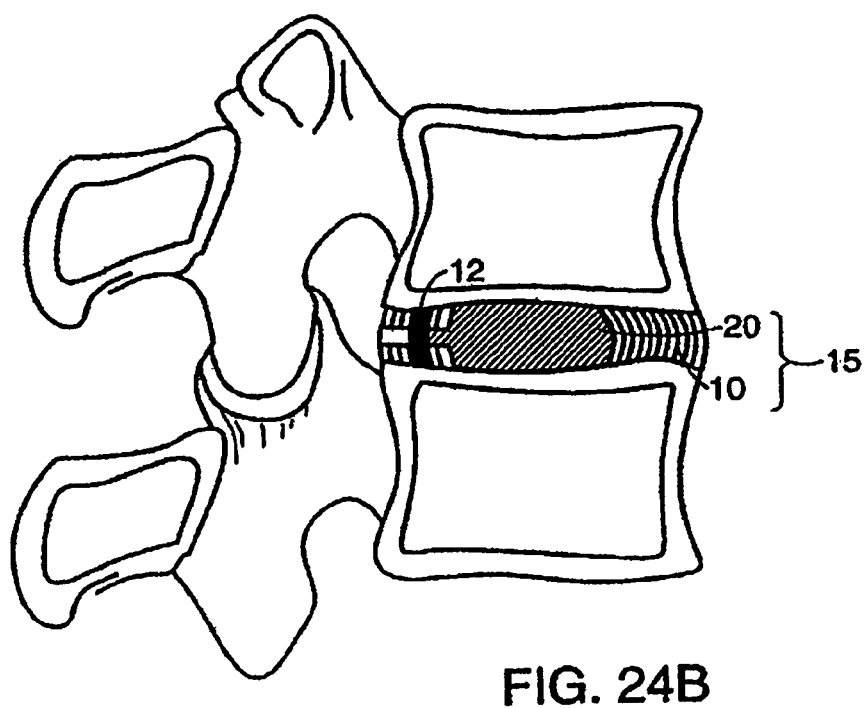

In several embodiments of the present invention, the barrier (or "patch") 12 can be placed between two neighboring layers 33, 37 (lamellae) of the anulus 10 on either or both sides of the defect 16 as depicted in FIGS. 24A and 24B. FIG. 24A shows an axial view while 24B shows a sagittal cross section. Such positioning spans the defect 16. The barrier means 12 can be secured using the methods outlined.

A dissecting tool can be used to form an opening extending circumferentially 31 within the anulus fibrosis such that the barrier can be inserted into the opening. Alternatively, the barrier itself can have a dissecting edge such that it can be driven at least partially into the sidewalls of defect 16, annulotomy 416, access hole 417 or opening in the anulus. This process can make use of the naturally layered structure in the anulus in which adjacent layers 33, 37 are defined by a circumferentially extending boundary 35 between the layers.

Figure 25:
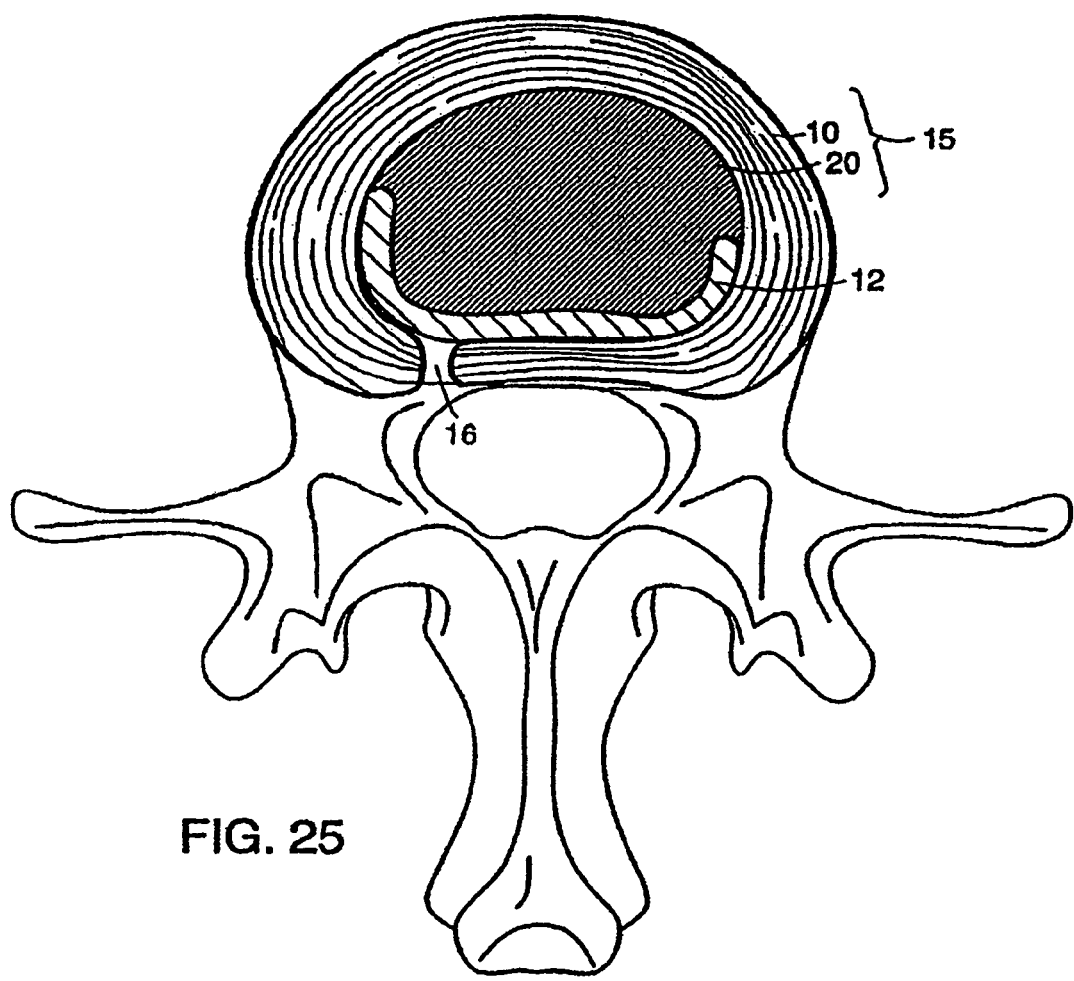
FIG. 25 depicts an axial cross section of a large version of a barrier means.

Another embodiment of the barrier 12 is a patch having a length, oriented along the circumference of the disc, which is substantially greater than its height, which is oriented along the distance separating the surrounding vertebral bodies. A barrier 12 having a length greater than its height is illustrated in FIG. 25. The barrier 12 can be positioned across the defect 16 as well as the entirety of the posterior aspect of the anulus fibrosis 10. Such dimensions of the barrier 12 can help to prevent the barrier 12 from slipping after insertion and can aid in distributing the pressure of the nucleus 20 evenly along the posterior aspect of the anulus 10.

Figure 26:
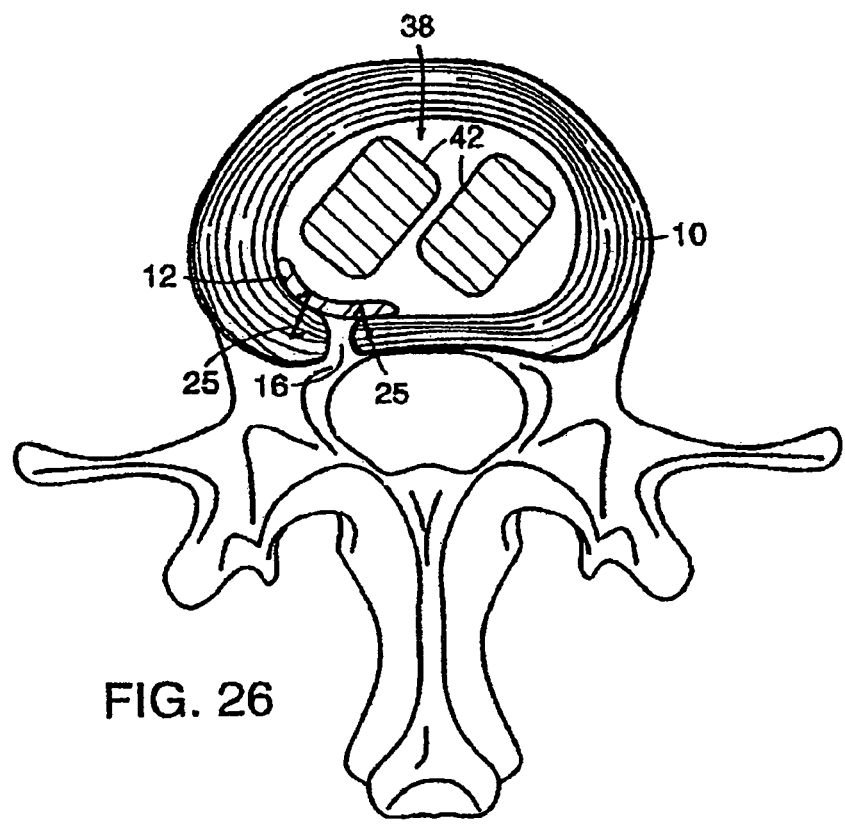
FIG. 26 depicts an axial cross section of a barrier means in position across a defect following insertion of two augmentation devices.
Figure 27:
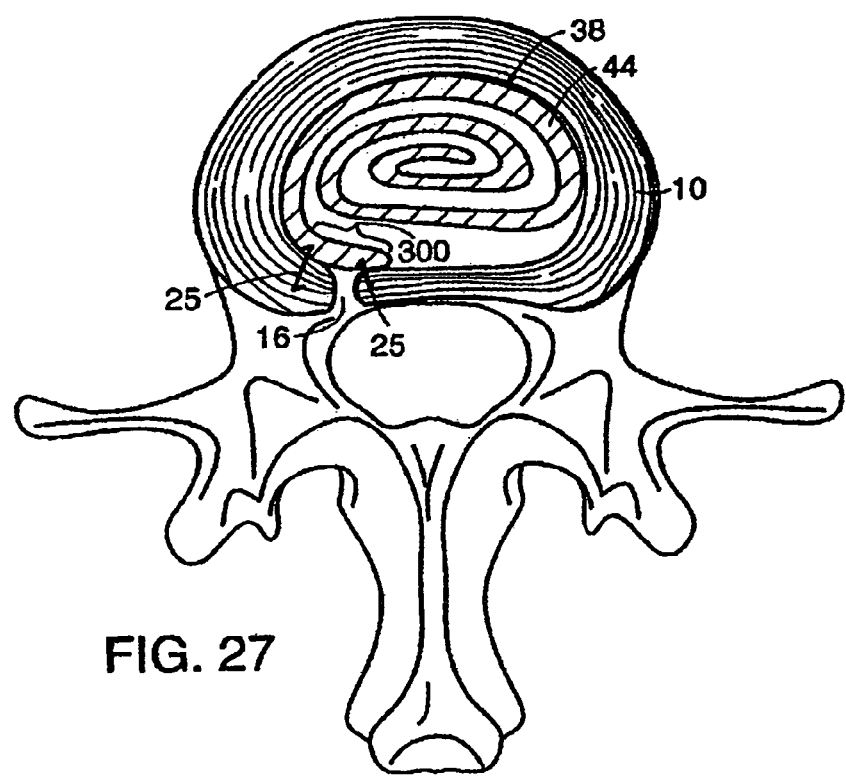
FIG. 27 depicts the barrier means as part of an elongated augmentation device.
Figure 28A:
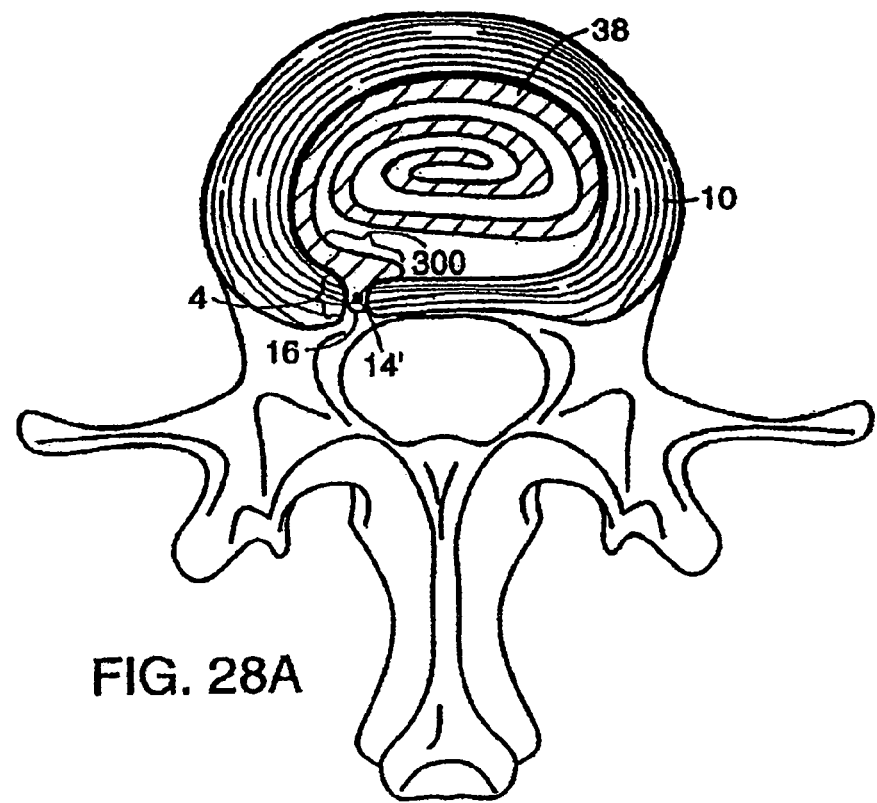
FIG. 28A depicts an axial section of an alternate configuration of the augmentation device of FIG. 27.
Figure 28B:
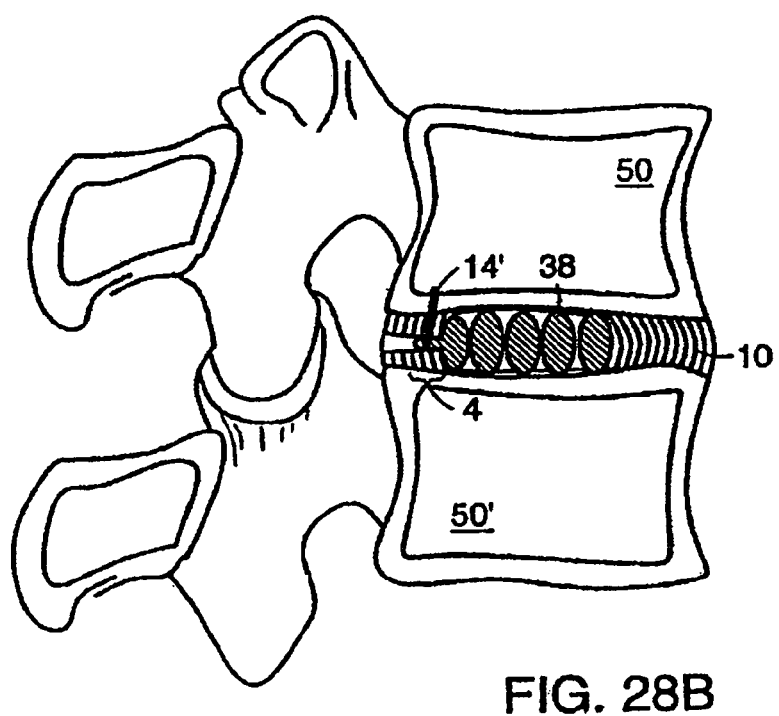
FIG. 28B depicts a sagittal section of an alternate configuration of the augmentation device of FIG. 27.

The barrier 12 can be used in conjunction with an augmentation device 11 inserted within the anulus 10. The augmentation device 11 can include separate augmentation devices 42 as shown in FIG. 26. The augmentation device 11 can also be a single augmentation device 44 and can form part of the barrier 12 as barrier region 300, coiled within the anulus fibrosis 10, as shown in FIG. 27. Either the barrier 12 or barrier region 300 can be secured to the tissues surrounding the defect 16 by fixation devices or darts 25, or be left unconstrained In another embodiment of the present invention, the barrier or patch 12 may be used as part of a method to augment the intervertebral disc. In one aspect of this method, augmentation material or devices are inserted into the disc through a defect (either naturally occurring or surgically generated). Many suitable augmentation materials and devices are discussed above and in the prior art. As depicted in FIG. 26, the barrier means is then inserted to aid in closing the defect and/or to aid in transferring load from the augmentation materials/devices to healthy tissues surrounding the defect. In another aspect of this method, the barrier means is an integral component to an augmentation device. As shown in FIGS. 27, 28A and 28B, the augmentation portion may comprise a length of elastic material that can be inserted linearly through a defect in the anulus. A region 300 of the length forms the barrier means of some embodiments of the present invention and can be positioned proximate to the interior aspect of the defect once the nuclear space is adequately filled. Barrier region 300 may then be affixed to surrounding tissues such as the AF and/or the neighboring vertebral bodies using any of the methods and devices described above.

FIGS. 28A and 28B illustrate axial and sagittal sections, respectively, of an alternate configuration of an augmentation device 38. In this embodiment, barrier region 300 extends across the defect 16 and has fixation region 4 facilitating fixation of the device 13 to superior vertebral body 50 with anchor 14'.

Figure 29A:
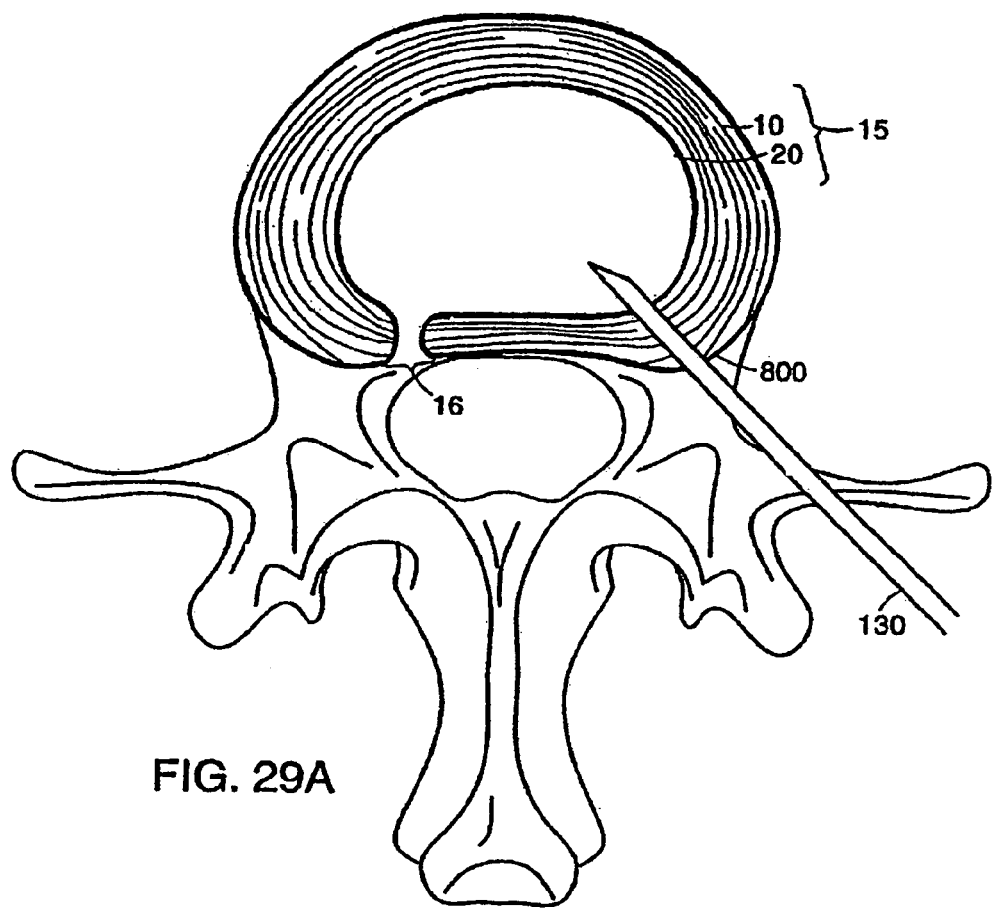
FIGS. 29A-D depict deployment of a barrier from an entry site remote from the defect in the anulus fibrosis.
Figure 29B:
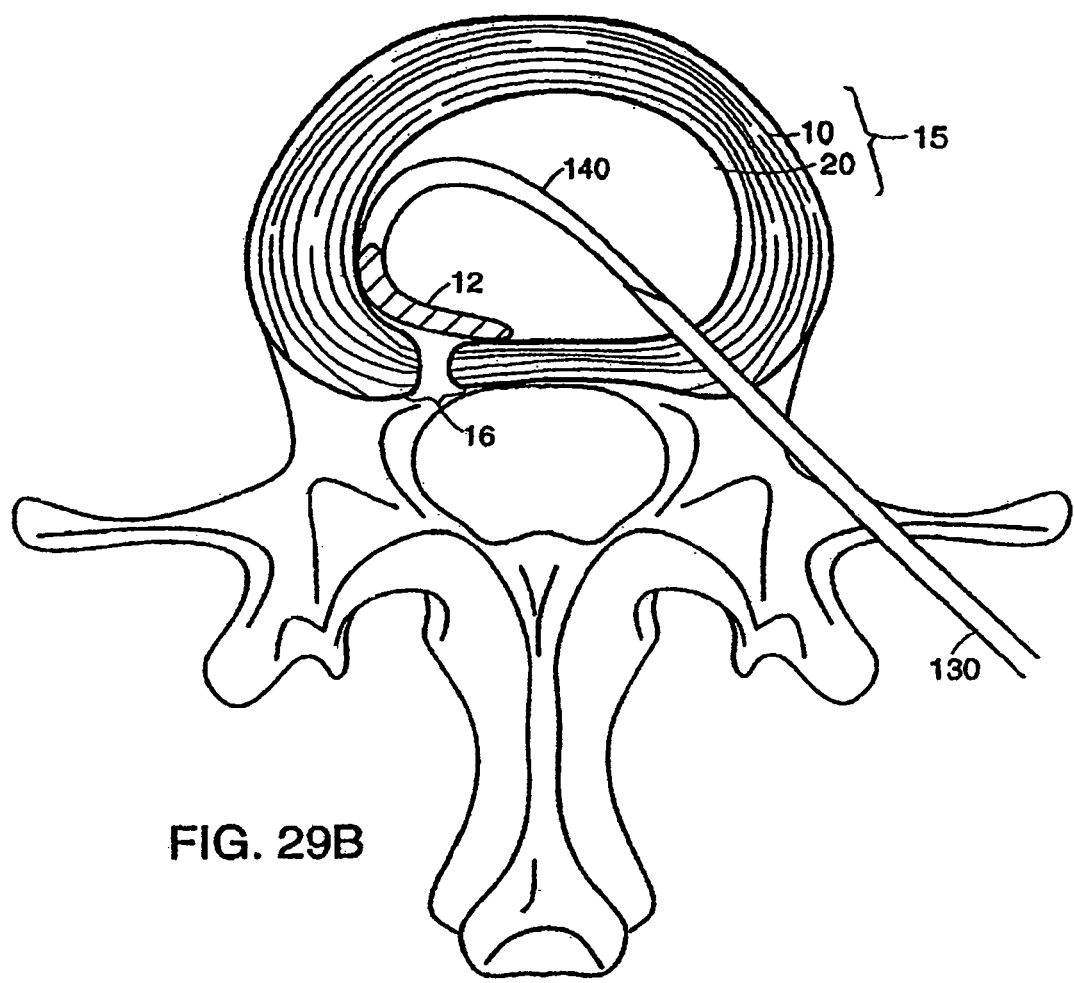
Figure 29C:
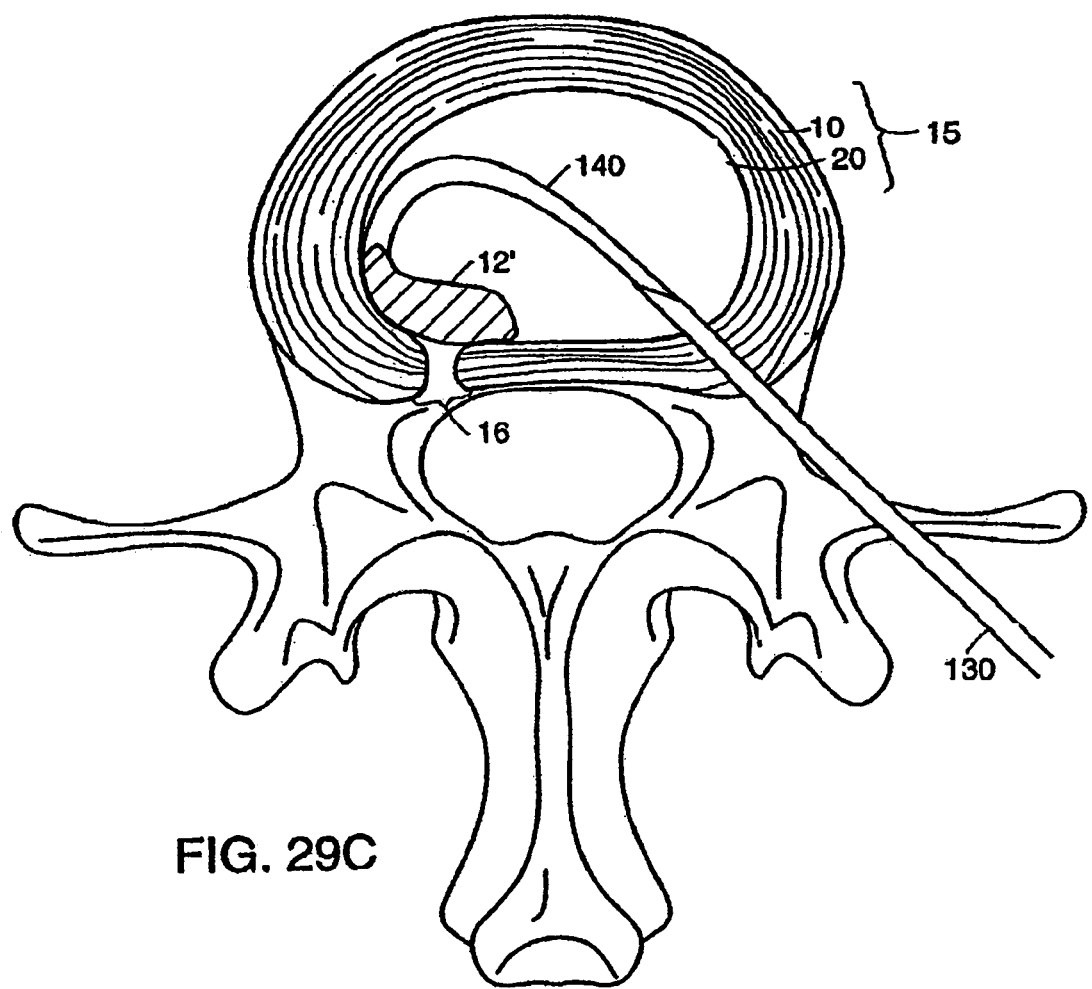
Figure 29D:
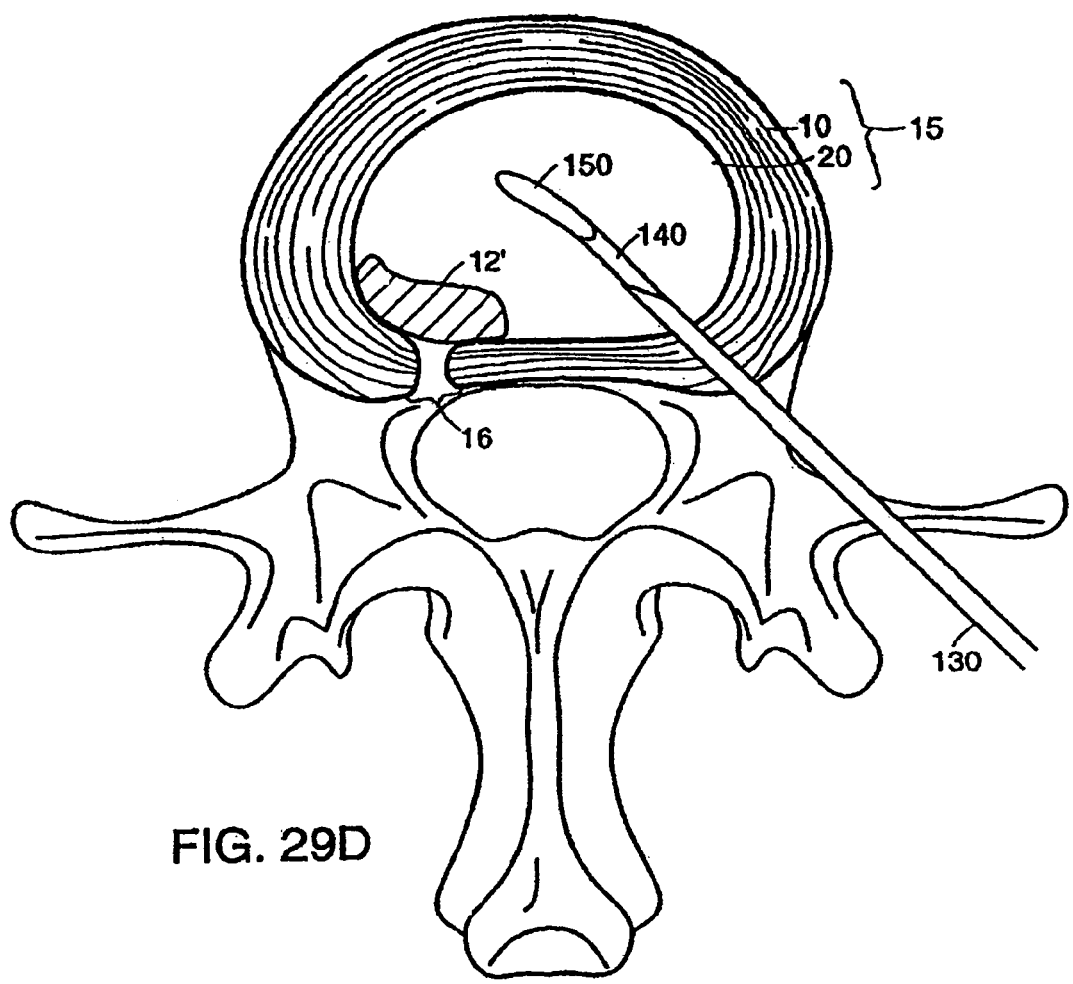

FIGS. 29A-D illustrate the deployment of a barrier 12 from an entry site 800 remote from the defect in the anulus fibrosis 10. FIG. 29A shows insertion instrument 130 with a distal end positioned within the disc space occupied by nucleus pulposus 20. FIG. 29B depicts delivery catheter 140 exiting the distal end of insertion instrument 130 with barrier 12 on its distal end. Barrier 12 is positioned across the interior aspect of the defect 16. FIG. 29C depicts the use of an expandable barrier 12' wherein delivery catheter 140 is used to expand the barrier 12' with balloon 150 on its distal end. Balloon 150 may exploit heat to further adhere barrier 12' to surrounding tissue. FIG. 29D depicts removal of balloon 150 and delivery catheter 140 from the disc space leaving expanded barrier means 12' positioned across defect 16.

Figure 47:
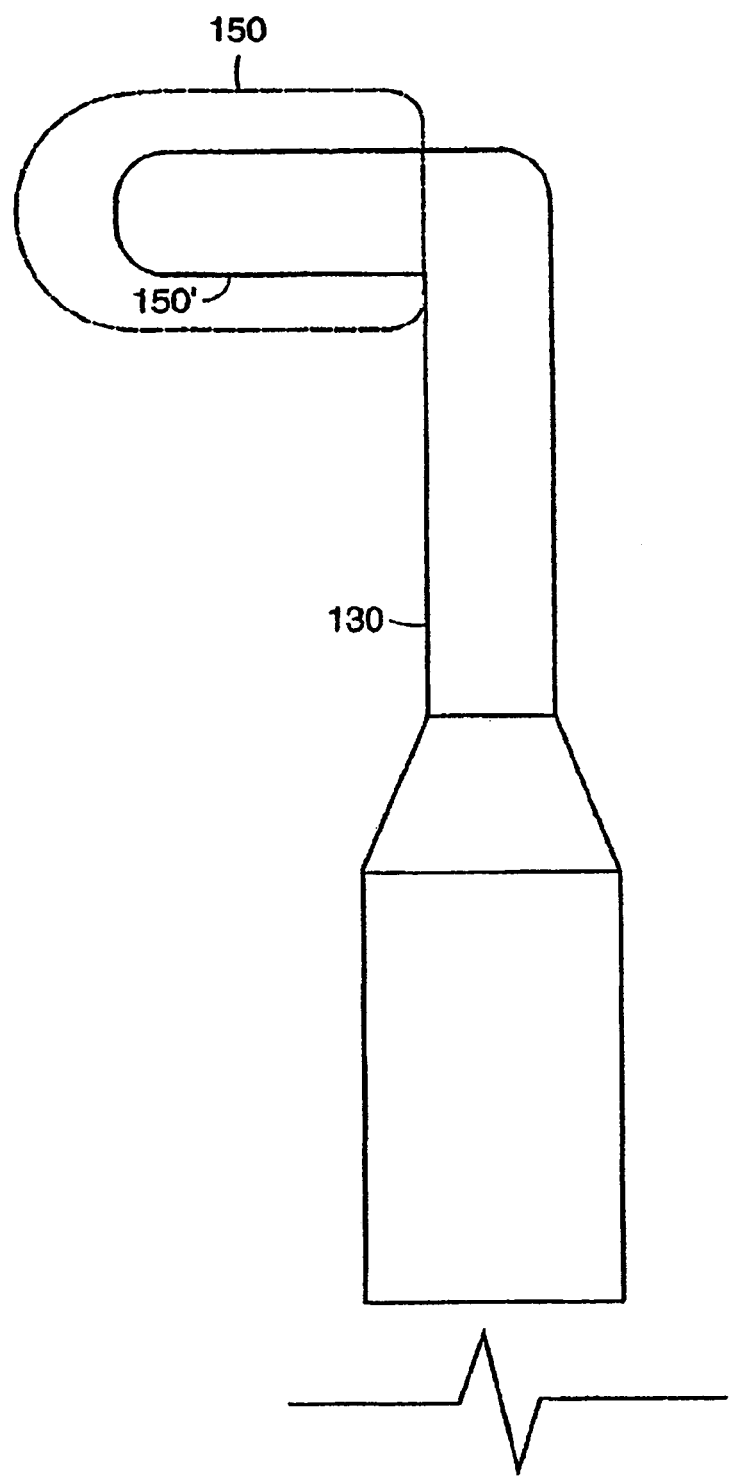
FIG. 47 depicts an expandable thermal element that can be used to adhere sealing means to tissues surrounding a defect.

Another method of securing the barrier means 12 is to adhere it to surrounding tissues through the application of heat. In this embodiment, the barrier means 12 includes a sealing means 51 comprised of a thermally adherent material that adheres to surrounding tissues upon the application of heat. The thermally adherent material can include thermoplastic, collagen, or a similar material. The sealing means 51 can further comprise a separate structural material that adds strength to the thermally adherent material, such as a woven Nylon™ or Marlex™. This thermally adherent sealing means preferably has an interior cavity 17 and at least one opening 8 leading from the exterior of the barrier means into cavity 17. A thermal device can be attached to the insertion instrument shown in FIGS. 29C and 29D. The insertion instrument 130 having a thermal device can be inserted into cavity 17 and used to heat sealing means 51 and surrounding tissues. This device can be a simple thermal element, such as a resistive heating coil, rod or wire. It can further be a number of electrodes capable of heating the barrier means and surrounding tissue through the application of radio frequency (RF) energy. The thermal device can further be a balloon 150, 150', as shown in FIG. 47, capable of both heating and expanding the barrier means. Balloon 150, 150' can either be inflated with a heated fluid or have electrodes located about its surface to heat the barrier means with RF energy. Balloon 150, 150' is deflated and removed after heating the sealing means. These thermal methods and devices achieve the goal of adhering the sealing means to the AF and NP and potentially other surrounding tissues. The application of heat can further aid the procedure by killing small nerves within the AF, by causing the defect to shrink, or by causing cross-linking and/or shrinking of surrounding tissues. An expander or enlarging means 53 can also be an integral component of barrier 12 inserted within sealing means 51. After the application of heat, a separate enlarging means 53 can be inserted into the interior cavity of the barrier means to either enlarge the barrier 12 or add stiffness to its structure. Such an enlarging means is preferably similar in make-up and design to those described above. Use of an enlarging means may not be necessary in some cases and is not a required component of this method.

Figure 44A:
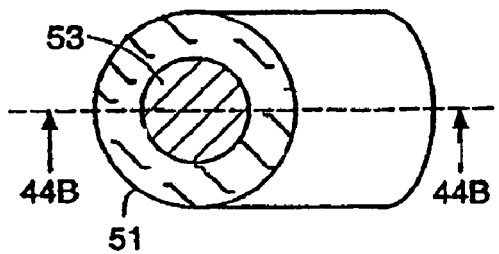
FIGS. 44A and 44B depict an alternative shape of the barrier means.
Figure 44B:
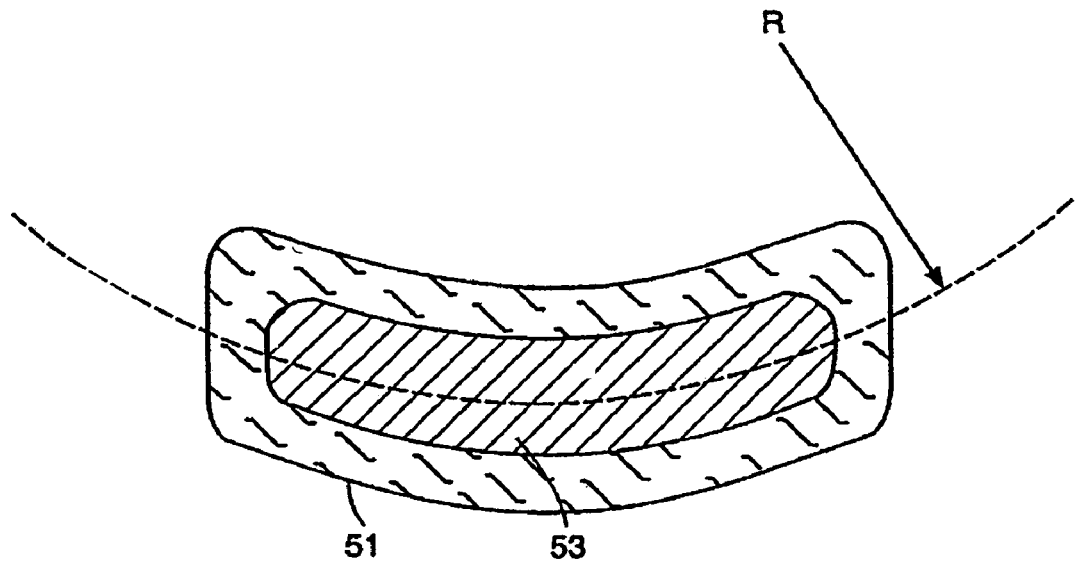

The barrier means 12 shown in FIG. 25 preferably has a primary curvature or gentle curve along the length of the patch or barrier 12 that allows it to conform to the inner circumference of the AF 10. This curvature may have a single radius R as shown in FIGS. 44A and 44B or may have multiple curvatures. The curvature can be fabricated into the barrier 12 and/or any of its components. For example, the sealing means can be made without an inherent curvature while the enlarging means can have a primary curvature along its length. Once the enlarging means is placed within the sealing means the overall barrier means assembly takes on the primary curvature of the enlarging means. This modularity allows enlarging means with specific curvatures to be fabricated for defects occurring in various regions of the anulus fibrosis.

The cross section of the barrier 12 can be any of a number of shapes. Each embodiment exploits a sealing means 51 and an enlarging means 53 that may further add stiffness to the overall barrier construct. FIGS. 30A and 30B show an elongated cylindrical embodiment with enlarging means 53 located about the long axis of the device. FIGS. 31A and 31B depict a barrier means comprising an enlarging means 53 with a central cavity 49. FIGS. 32A and 32B depict a barrier means comprising a non-axisymmetric sealing means 51. In use, the longer section of sealing means 51 as seen on the left side of this figure would extend between opposing vertebra 50 and 50'. FIGS. 33A and 33B depict a barrier means comprising a non-axisymmetric sealing means 51 and enlarger 53. The concave portion of the barrier means preferably faces nucleus pulposus 20 while the convex surface faces the defect 16, annulotomy 416, or access hole 417 and the inner aspect of the anulus fibrosis 10. This embodiment exploits pressure within the disc to compress sealing means 51 against neighboring vertebral bodies 50 and 50' to aid in sealing. The 'C' shape as shown in FIG. 33A is the preferred shape of the barrier wherein the convex portion of the patch rests against the interior aspect of the AF while the concave portion faces the NP. Used in this manner, the barrier or patch 12 serves to partially encapsulate the nucleus puporsus 20 by conforming to the gross morphology of the inner surface of the anulus 10 and presenting a concave or cupping surface toward the nucleus 20. To improve the sealing ability of such a patch, the upper and lower portions of this 'C' shaped barrier means are positioned against the vertebral endplates or overlying cartilage. As the pressure within the nucleus increases, these portions of the patch are pressurized toward the endplates with an equivalent pressure, preventing the passage of materials around the barrier means. Dissecting a matching cavity prior to or during patch placement can facilitate use of such a 'C' shaped patch.

FIGS. 34 through 41 depict various enlarging or expansion devices 53 that can be employed to aid in expanding a sealing element 51 within the intervertebral disc 15. Each embodiment can be covered by, coated with, or cover the sealing element 51. The sealing means 51 can further be woven through the expansion means 53. The sealing element 51 or membrane can be a sealer which can prevent flow of a material from within the anulus fibrosis of the intervertebral disc through a defect in the anulus fibrosis. The material within the anulus can include nucleus pulposus or a prosthetic augmentation device, such as a hydrogel.

FIGS. 34 through 38 depict alternative patterns to that illustrated in FIG. 33A. FIG. 33A shows the expansion devices 53 within the sealing means 51. The sealing means can alternatively be secured to one or another face (concave or convex) of the expansion means 53. This can have advantages in reducing the overall volume of the barrier means 12, simplifying insertion through a narrow cannula. It can also allow the barrier means 12 to induce ingrowth of tissue on one face and not the other. The sealing means 51 can be formed from a material that resists ingrowth such as expanded polytetrafluoroethylene (e-PTFE). The expansion means 53 can be constructed of a metal or polymer that encourages ingrowth. In several embodiments, if the e-PTFE sealing means 51 is secured to the concave face of the expansion means 53, tissue can grow into the expansion means 53 from outside of the disc 15, helping to secure the barrier means 12 in place and seal against egress of materials from within the disc 15.

The expansion means 53 shown in FIG. 33A can be inserted into the sealing means 51 once the sealing means 51 is within the disc 15. Alternatively, the expansion means 53 and sealing means 51 can be integral components of the barrier means 12 that can be inserted as a unit into the disc.

The patterns shown in FIGS. 34 through 38 can preferably be formed from a relatively thin sheet of material. The material may be a polymer, metal, or gel, however, the superelastic properties of nickel titanium alloy (NITINOL) makes this metal particularly advantageous in this application. Sheet thickness can generally be in a range of about 0.1 mm to about 0.6 mm and for certain embodiments has been found to be optimal if between about 0.003" to about 0.015" (0.0762 mm to 0.381 mm), for the thickness to provide adequate expansion force to maintain contact between the sealing means 51 and surrounding vertebral endplates. The pattern may be Wire Electro-Discharge Machined, cut by laser, chemically etched, or formed by other suitable means.

Figure 34:
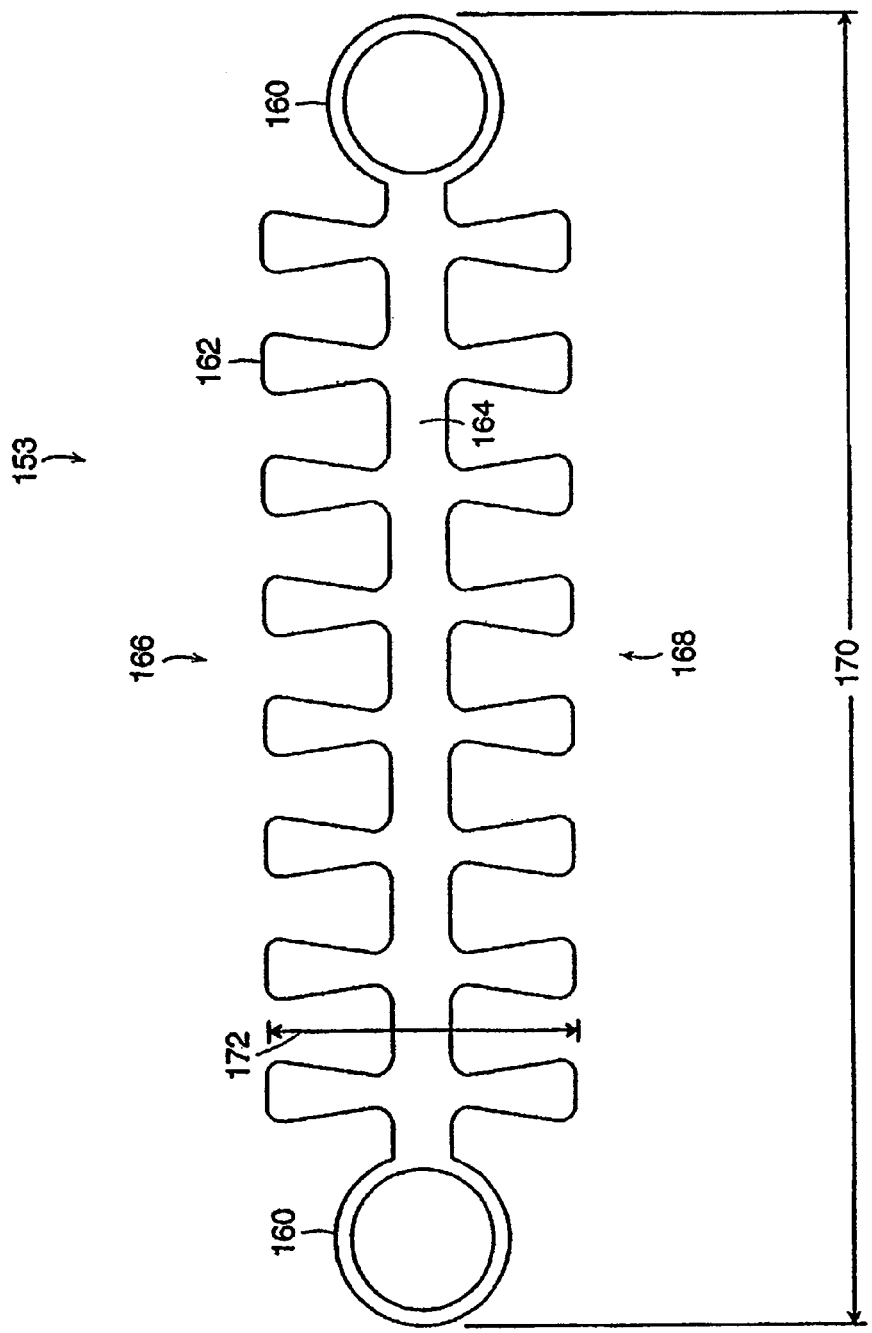
FIG. 34 shows a non-axisymmetric expansion means or frame.

FIG. 34 shows an embodiment of a non-axisymmetric expander 153 having a superior edge 166 and an inferior edge 168. The expander 153 can form a frame of barrier 12. This embodiment comprises dissecting surfaces or ends 160, radial elements or fingers 162 and a central strut 164. The circular shape of the dissecting ends 160 aids in dissecting through the nucleus pulposus 20 and/or along or between an inner surface of the anulus fibrosis 10. The distance between the left-most and right-most points on the dissecting ends is the expansion means length 170. This length 170 preferably lies along the inner perimeter of the posterior anulus following implantation. The expander length 170 can be as short as about 3 mm and as long as the entire interior perimeter of the anulus fibrosis. The superior-inferior height of these dissecting ends 160 is preferably similar to or larger than the posterior disc height.

This embodiment employs a multitude of fingers 162 to aid in holding a flexible sealer or membrane against the superior and inferior vertebral endplates. The distance between the superior-most point of the superior finger and the inferior-most point on the inferior finger is the expansion means height 172. This height 172 is preferably greater than the disc height at the inner surface of the posterior anulus. The greater height 172 of the expander 153 allows the fingers 162 to deflect along the superior and inferior vertebral endplates, enhancing the seal of the barrier means 12 against egress of material from within the disc 15.

The spacing between the fingers 162 along the expander length 170 can be tailored to provide a desired stiffness of the expansion means 153. Greater spacing between any two neighboring fingers 162 can further be employed to insure that the fingers 170 do not touch if the expansion means 153 is required to take a bend along its length. The central strut 164 can connect the fingers and dissecting ends and preferably lies along the inner surface of the anulus 10 when seated within the disc 15. Various embodiments may employ struts 164 of greater or lesser heights and thicknesses to vary the stiffness of the overall expansion means 153 along its length 170 and height 172.

Figure 35:
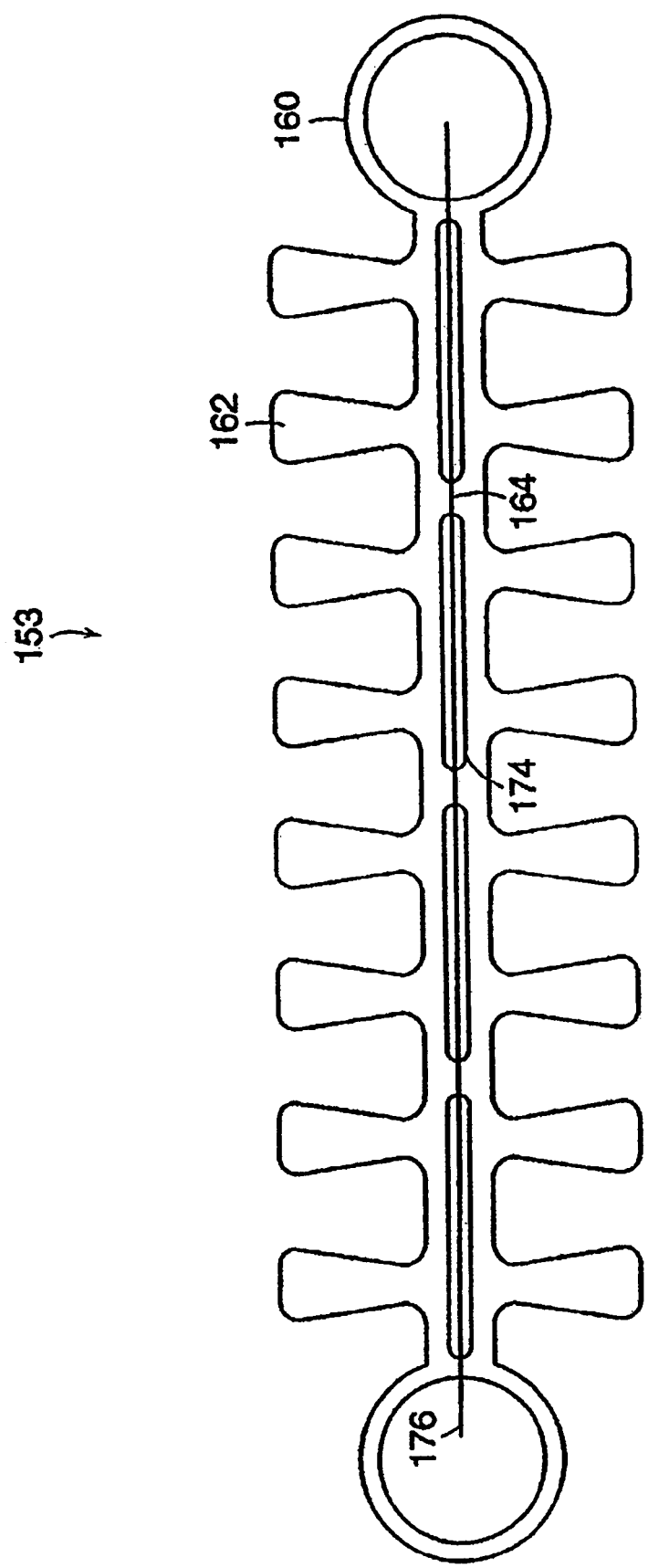
FIGS. 35 and 36 illustrate alternate embodiments of the expansion means shown in FIG. 34.

FIG. 35 depicts an alternative embodiment to the expander 153 of FIG. 34. Openings or slots 174 can be included along the central strut 164. These slots 174 promote bending of the expander 153 and fingers 162 along a central line 176 connecting the centers of the dissecting ends 160. Such central flexibility has been found to aid against superior or inferior migration of the barrier means or barrier 12 when the barrier 12 has not been secured to surrounding tissues.

Figure 34B:
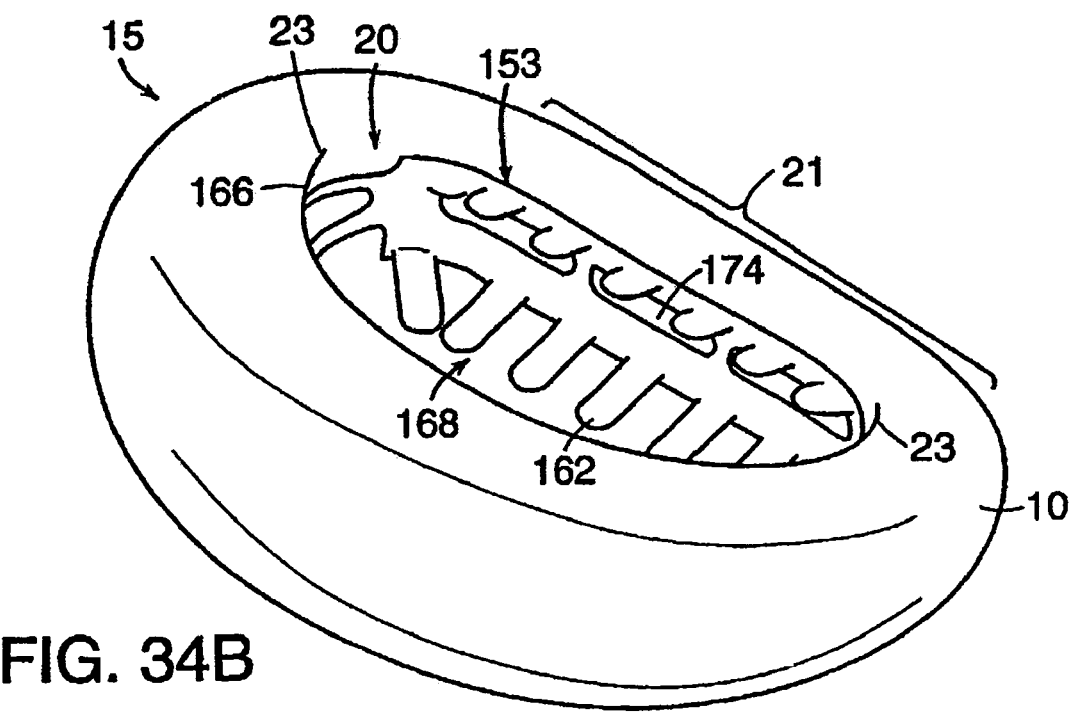
FIGS. 34B and 34C illustrate perspective views of a frame mounted within an intervertebral disc.
Figure 34C:
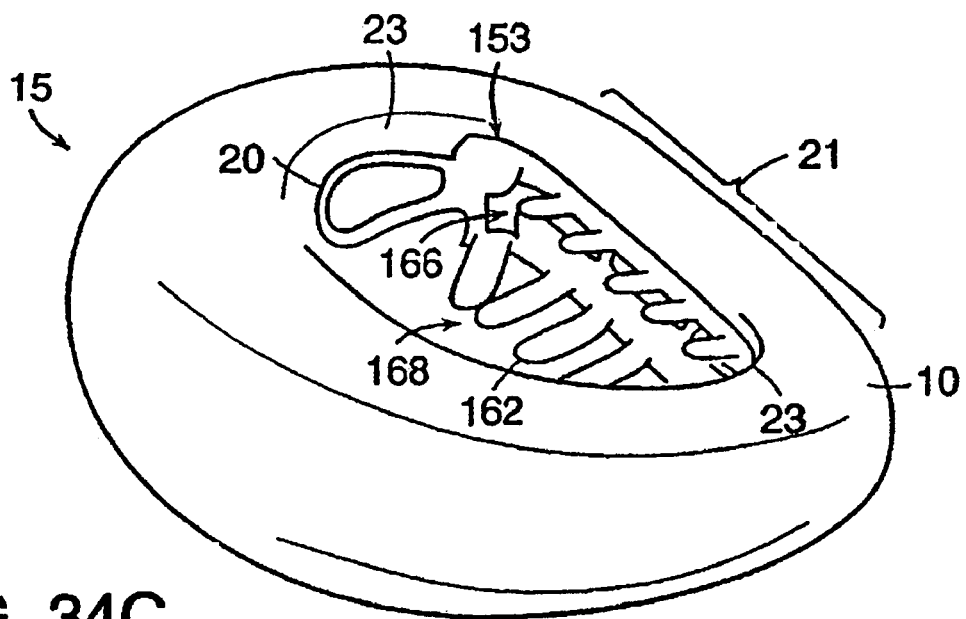

FIGS. 34B and 34C depict different perspective views of a preferred embodiment of the expander/frame 153 within an intervertebral disc 15. Expander 53 is in its expanded condition and lies along and/or within the posterior wall 21 and extends around the lateral walls 23 of the anulus fibrosis 10. The superior 166 and inferior 168 facing fingers 162 of expander 153 extend along the vertebral endplates (not shown) and/or the cartilage overlying the endplates. The frame 153 can take on a 3-D concave shape in this preferred position with the concavity generally directed toward the interior of the intervertebral disc and specifically a region occupied by the nucleus pulposus 20.

The bending stiffness of expander 153 can resist migration of the implant from this preferred position within the disc 15. The principle behind this stiffness-based stability is to place the regions of expander 153 with the greatest flexibility in the regions of the disc 153 with the greatest mobility or curvature. These flexible regions of expander 153 are surrounded by significantly stiffer regions. Hence, in order for the implant to migrate, a relatively stiff region of the expander must move into a relatively curved or mobile region of the disc.

For example, in order for expander 153 of FIG. 34B to move around the inner circumference of anulus fibrosis 10 (e.g., from the posterior wall 21 onto the lateral 23 and/or anterior 27 wall), the stiff central region of expander 153 spanning the posterior wall 21 would have to bend around the acute curves of the posterior lateral corners of anulus 10. The stiffer this section of expander 153 is, the higher the forces necessary to force it around these corners and the less likely it is to migrate in this direction. This principle was also used in this embodiment to resist migration of fingers 162 away from the vertebral endplates: The slots 174 cut along the length of expander 153 create a central flexibility that encourages expander 153 to bend along an axis running through these slots as the posterior disc height increases and decreased during flexion and extension. In order for the fingers 162 to migrate away from the endplate, this central flexible region must move away from the posterior anulus 21 and toward an endplate. This motion is resisted by the greater stiffness of expander 153 in the areas directly inferior and superior to this central flexible region.

The expander 153 is preferably covered by a membrane that acts to further restrict the movement of materials through the frame and toward the outer periphery of the anulus fibrosis.

Figure 36:
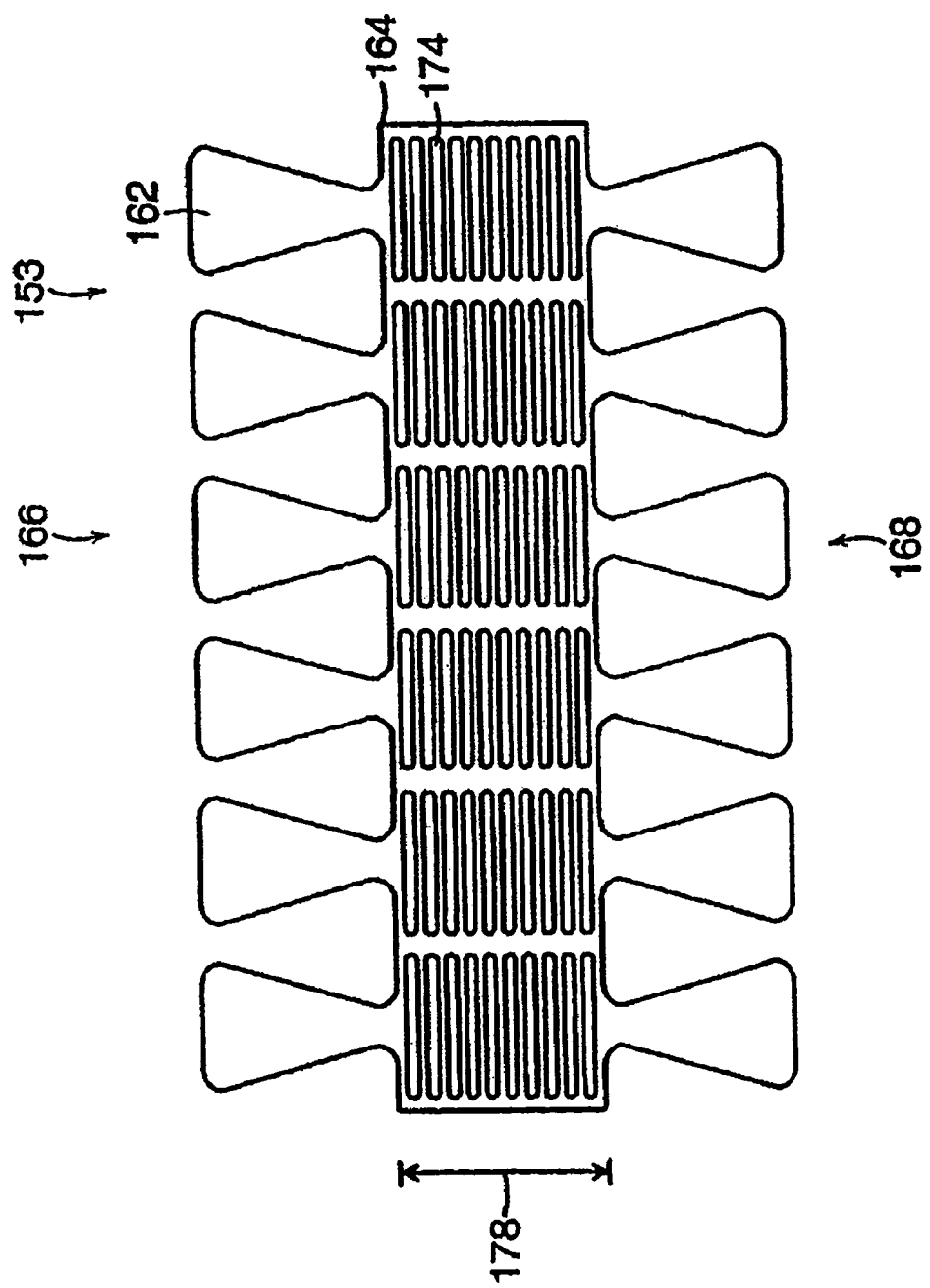

FIG. 36 depicts an embodiment of the expander 153 of FIG. 33A with an enlarged central strut 164 and a plurality of slots 174. This central strut 164 can have a uniform stiffness against superior-inferior 166 and 168 bending as shown in this embodiment. The strut 164 can alternatively have a varying stiffness along its height 178 to either promote or resist bending at a given location along the inner surface of the anulus 10.

Figure 37A:
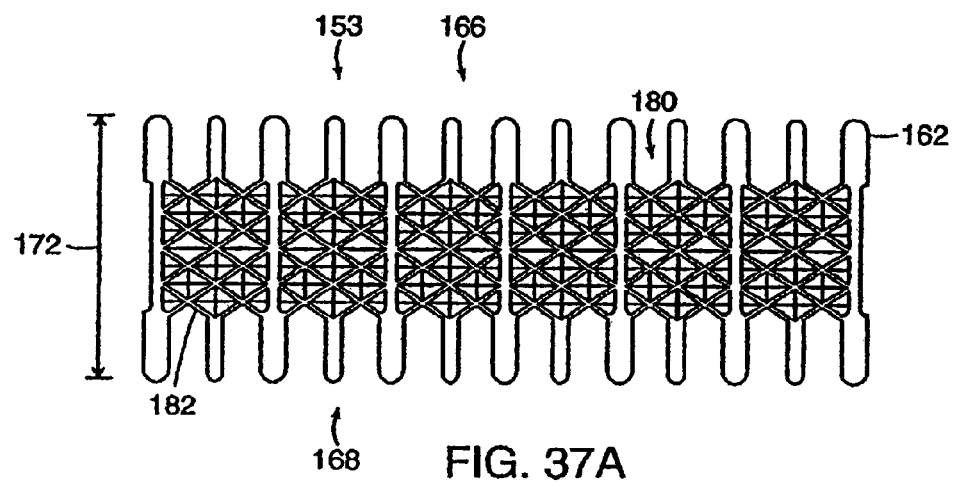
FIGS. 37A-C illustrate a front, side, and perspective view, respectively, of an alternate embodiment of the expansion means shown in FIG. 34.
Figure 37B:
Figure 37C:
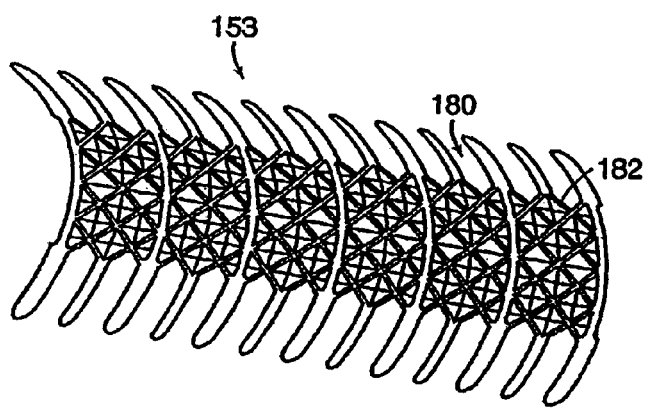

FIGS. 37A-C depict a further embodiment of the frame or expander 153. This embodiment employs a central lattice 180 consisting of multiple, fine interconnected struts 182. Such a lattice 180 can provide a structure that minimizes bulging of the sealing means 51 under intradiscal pressures. The orientation and location of these struts 182 have been designed to give the barrier 12 a bend-axis along the central area of the expander height 172. The struts 182 support inferior 168 and superior 166 fingers 162 similar to previously described embodiments. However, these fingers 162 can have varying dimensions and stiffness along the length of the barrier 12. Such fingers 162 can be useful for helping the sealer 51 conform to uneven endplate geometries. FIG. 37B illustrates the curved cross section 184 of the expander 153 of FIG. 37A. This curve 184 can be an arc segment of a circle as shown. Alternatively, the cross section can be an ellipsoid segment or have a multitude of arc segments of different radii and centers. FIG. 37C is a perspective view showing the three dimensional shape of the expander 153 of FIGS. 37A and 37B.

The embodiment of the frame 153 as shown in FIGS. 37A-C, can also be employed without the use of a covering membrane. The nucleus pulposus of many patients with low back pain or disc herniation can degenerate to a state in which the material properties of the nucleus cause it to behave much more like a solid than a gel. As humans age, the water content of the nucleus declines from roughly 88% to less than 75%. As this occurs, there is an increase in the cross linking of collagen within the disc resulting in a greater solidity of the nucleus. When the pore size or the largest open area of any given gap in the lattice depicted in FIGS. 37A-37C is between about 0.05 mm$^2$ (7.75×10$^{-5}$ in$^2$) and about 0.75 mm$^2$ (1.16× 10$^{-3}$ in$^2$), the nucleus pulposus is unable to extrude through the lattice at pressures generated within the disc (between about 250 KPa and about 1.8 MPa). The preferred pore size has been found to be approximately 0.15 mm$^2$ (2.33×10$^{-4}$ in$^2$). This pore size can be used with any of the disclosed embodiments of the expander or any other expander that falls within the scope of embodiments of the invention to prevent movement of nucleus toward the outer periphery of the disc without the need for an additional membrane. The membrane thickness is preferably in a range of about 0.025 mm to about 2.5 mm.

Figure 38:
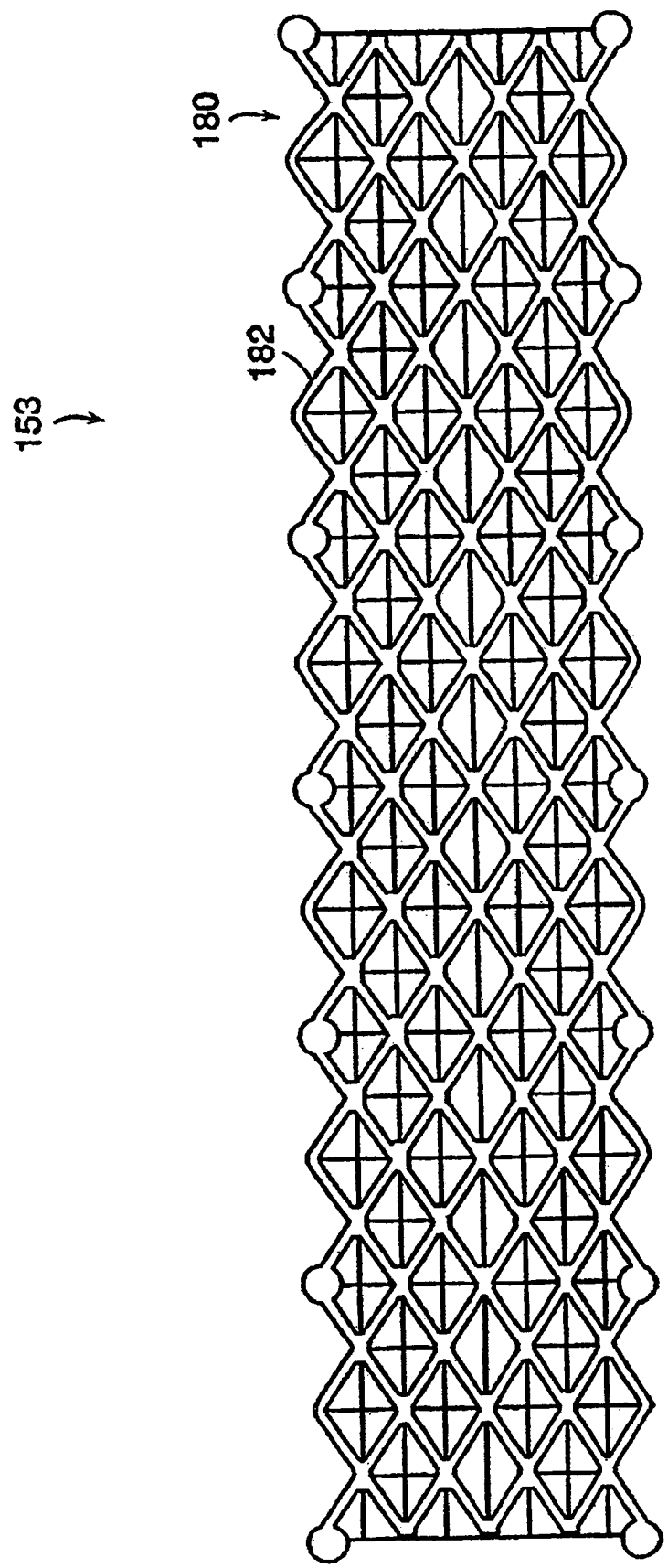
FIG. 38 shows an alternate expansion means to that shown in FIG. 37A.
Figure 39A:
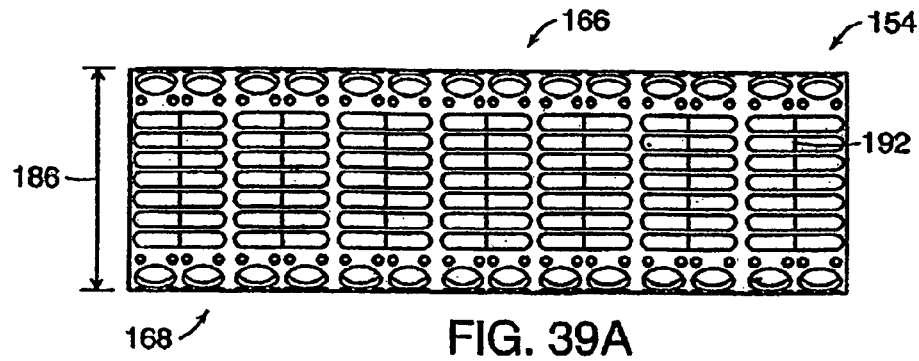
FIGS. 39A-D illustrate a tubular expansion means having a circular cross-section.
Figure 39B:
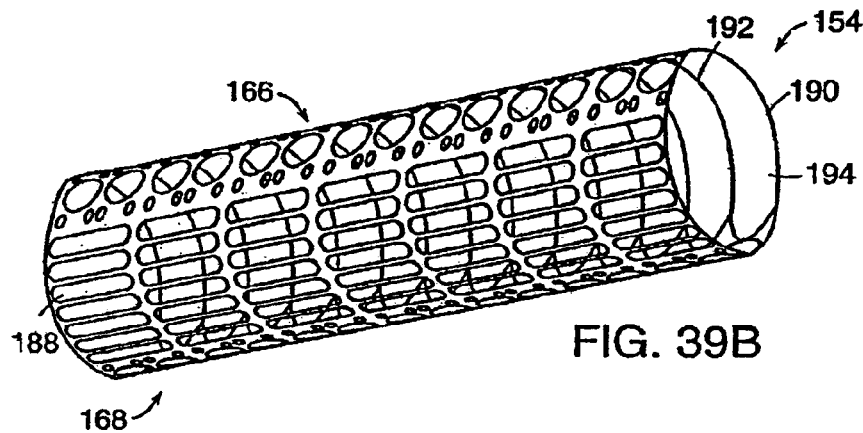
Figure 39C:
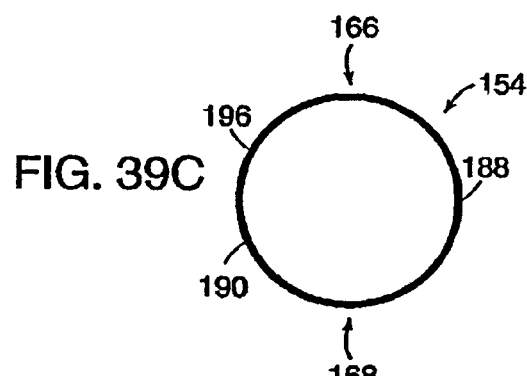
Figure 39D:
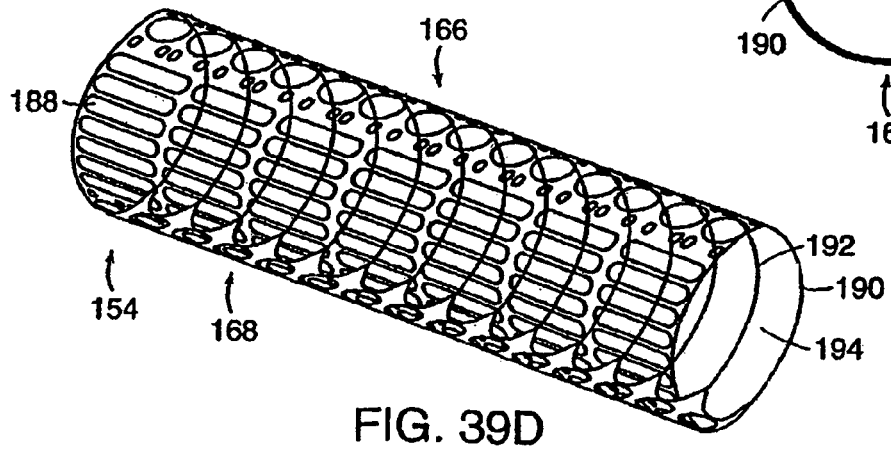

FIG. 38 depicts an expander 153 similar to that of FIG. 37A without fingers. The expander 153 includes a central lattice 180 consisting of multiple struts 182.

FIGS. 39 through 41 depict another embodiment of the expander 153 of some embodiments of the present invention. These tubular expanders can be used in the barrier 12 embodiment depicted in FIG. 31A. The sealer 51 can cover the expander 153 as shown in FIG. 31A. Alternatively, the sealer 51 can cover the interior surface of the expander or an arc segment of the tube along its length on either the interior or exterior surface.

FIG. 39 depicts an embodiment of a tubular expander 154. The superior 166 and inferior surfaces 168 of the tubular expander 154 can deploy against the superior and inferior vertebral endplates, respectively. The distance 186 between the superior 166 and inferior 168 surfaces of the expander 154 are preferably equal to or greater than the posterior disc height at the inner surface of the anulus 10. This embodiment has an anulus face 188 and nucleus face 190 as shown in FIGS. 39B, 39C and 39D. The anulus face 188 can be covered by the sealer 51 from the superior 166 to inferior 168 surface of the expander 154. This face 188 lies against the inner surface of the anulus 10 in its deployed position and can prevent egress of materials from within the disc 15. The primary purpose of the nucleus face 190 is to prevent migration of the expander 154 within the disc 15. The struts 192 that form the nucleus face 190 can project anteriorly into the nucleus 20 when the barrier 12 is positioned across the posterior wall of the anulus 10. This anterior projection can resist rotation of the tubular expansion means 154 about its long axis. By interacting with the nucleus 20, the struts 192 can further prevent migration around the circumference of the disc 15.

The struts 192 can be spaced to provide nuclear gaps 194. These gaps 194 can encourage the flow of nucleus pulposus 20 into the interior of the expander 154. This flow can insure full expansion of the barrier 12 within the disc 15 during deployment.

The embodiments of FIGS. 39, 40 and 41 vary by their cross-sectional shape. FIG. 39 has a circular cross section 196 as seen in FIG. 39C. If the superior-inferior height 186 of the expander 154 is greater than that of the disc 15, this circular cross section 196 can deform into an oval when deployed, as the endplates of the vertebrae compress the expander 154. The embodiment of the expander 154 shown in FIG. 40 is preformed into an oval shape 198 shown in FIG. 40C. Compression by the endplates can exaggerate the unstrained oval 198. This oval 198 can provide greater stability against rotation about a long axis of the expander 154. The embodiment of FIGS. 41B, 41C and 41D depict an 'egg-shaped' cross section 202, as shown in FIG. 41C, that can allow congruity between the curvature of the expander 154 and the inner wall of posterior anulus 10. Any of a variety of alternate cross sectional shapes can be employed to obtain a desired fit or expansion force without deviating from the spirit of the present invention.

Figure 40A:
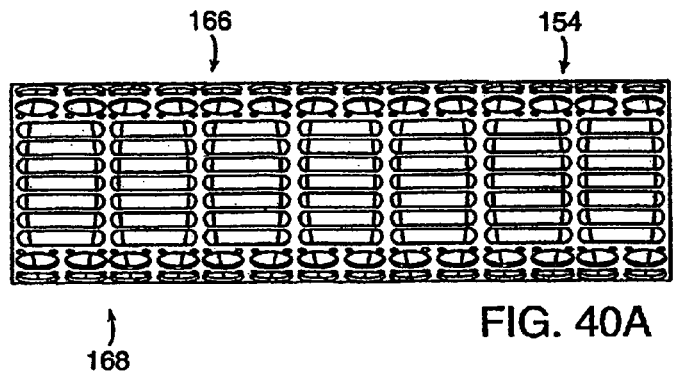
FIGS. 40A-I illustrate tubular expansion means.
Figure 40B:
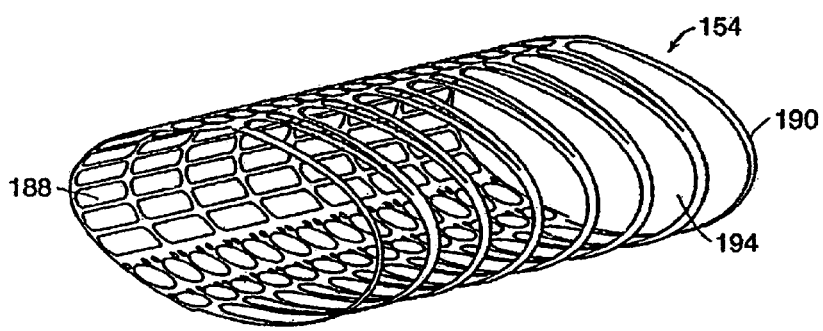
Figure 40C:
Figure 40D:
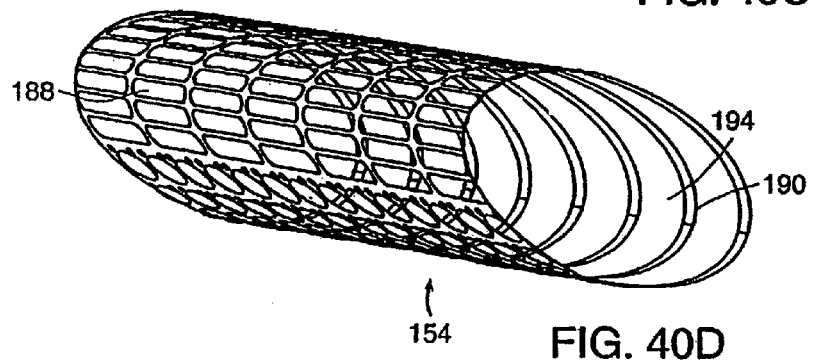
Figure 40E:
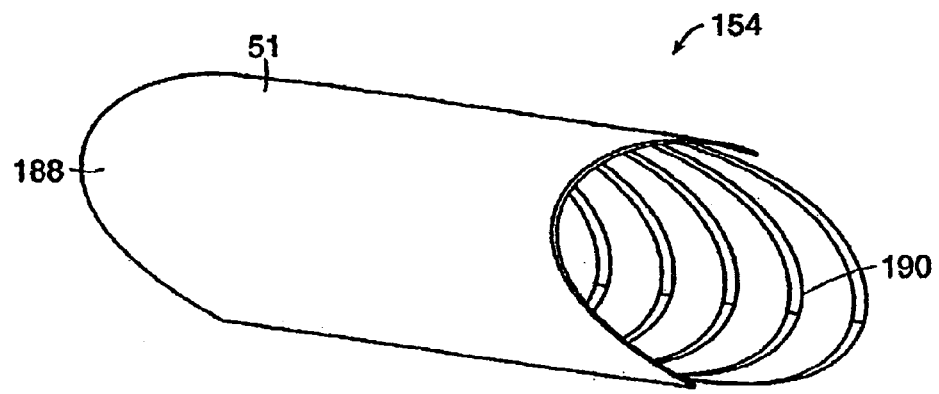
Figure 40F:
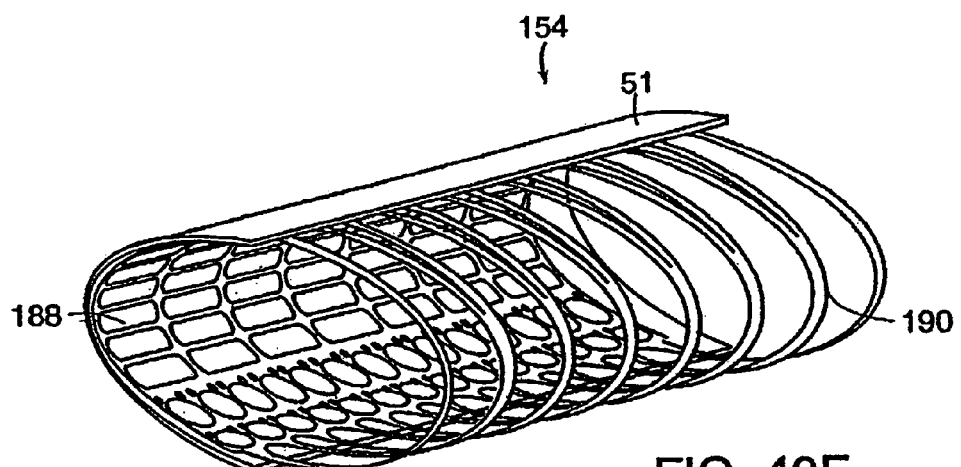
Figure 40G:
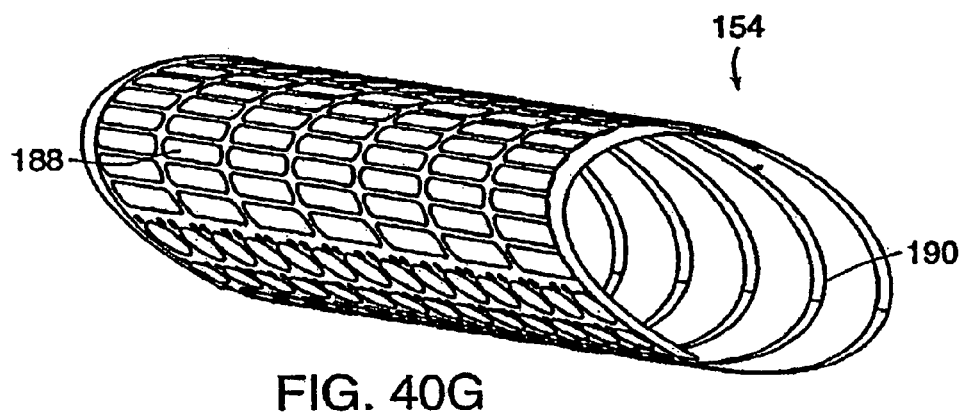
Figure 40H:
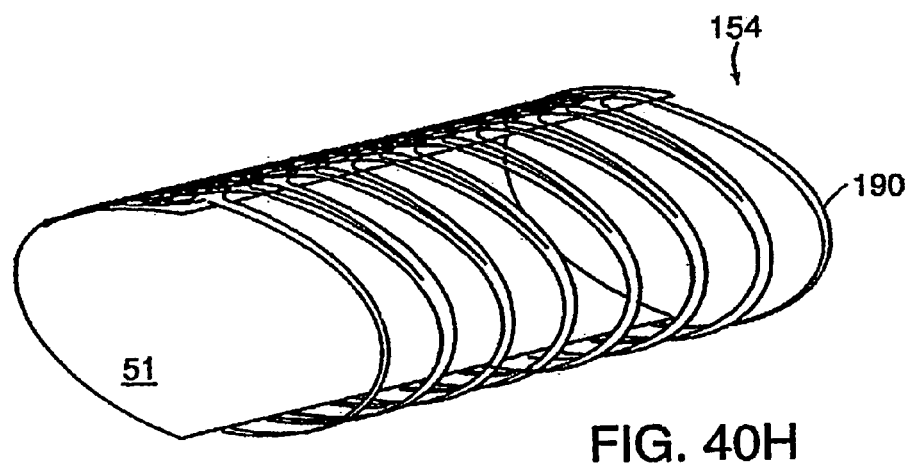
Figure 40I:
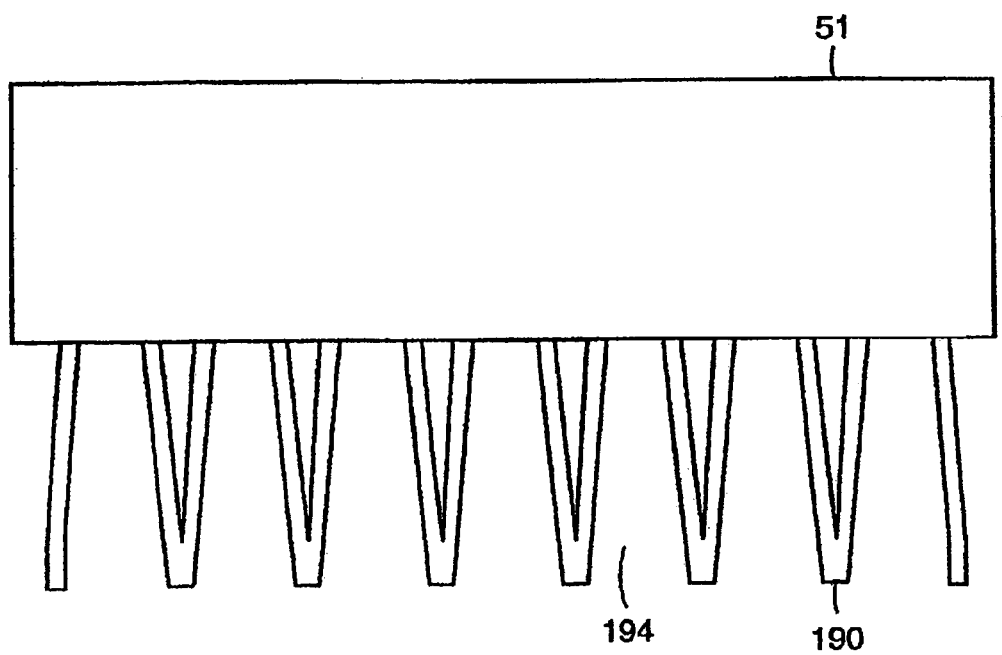
Figure 41A:
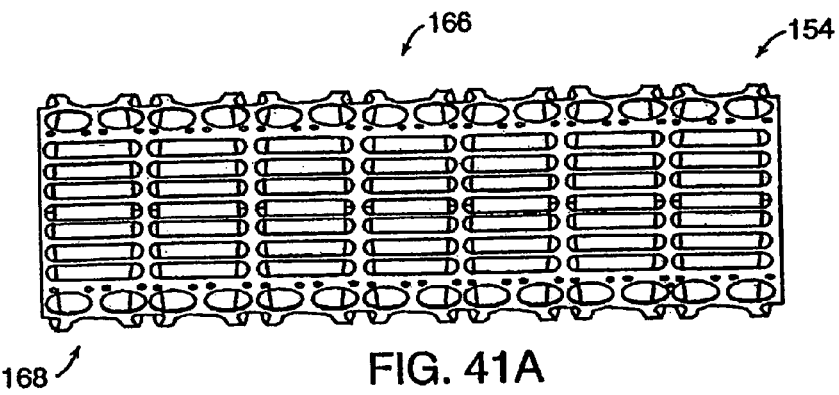
FIGS. 41A-D illustrate a tubular expansion means having an egg-shaped cross-section.
Figure 41B:
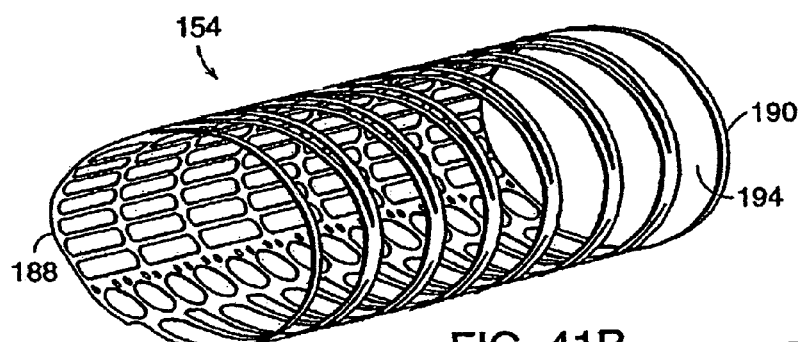
Figure 41C:
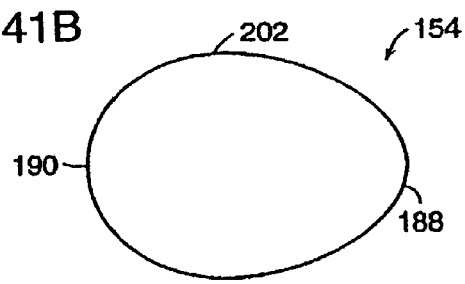
Figure 41D:
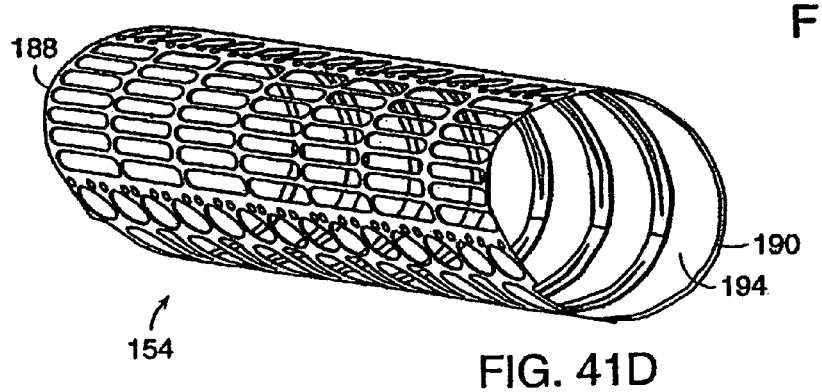

FIGS. 40E, 40F, and 40I depict the expander 154 of FIGS. 40A-D having a sealing means 51 covering the exterior surface of the anulus face 188. This sealing means 51 can be held against the endplates and the inner surface of the posterior anulus by the expander 154 in its deployed state.

FIGS. 40G and 40H depict the expander 154 of FIG. 40B with a sealer 51 covering the interior surface of the anulus face 188. This position of the sealer 51 can allow the expander 154 to contact both the vertebral endplates and inner surface of the posterior anulus. This can promote ingrowth of tissue into the expander 154 from outside the disc 15. Combinations of sealer 51 that cover all or part of the expander 154 can also be employed without deviating from the scope of the present invention. The expander 154 can also have a small pore size thereby allowing retention of a material such as a nucleus pulposus, for example, without the need for a sealer as a covering.

FIGS. 42A-D depict cross sections of a preferred embodiment of sealing means 51 and enlarging means 53. Sealing means 51 has internal cavity 17 and opening 8 leading from its outer surface into internal cavity 17. Enlarger 53 can be inserted through opening 8 and into internal cavity 17.

FIGS. 43A and 43B depict an alternative configuration of enlarger 53. Fixation region 4 extends through opening 8 in sealing means 51. Fixation region 4 has a through-hole that can facilitate fixation of enlarger 53 to tissues surrounding defect 16.

FIGS. 44A and 44B depict an alternative shape of the barrier. In this embodiment, sealing means 51, enlarger 53, or both have a curvature with radius R. This curvature can be used in any embodiment of the present invention and may aid in conforming to the curved inner circumference of anulus fibrosis 10.

Figure 45:
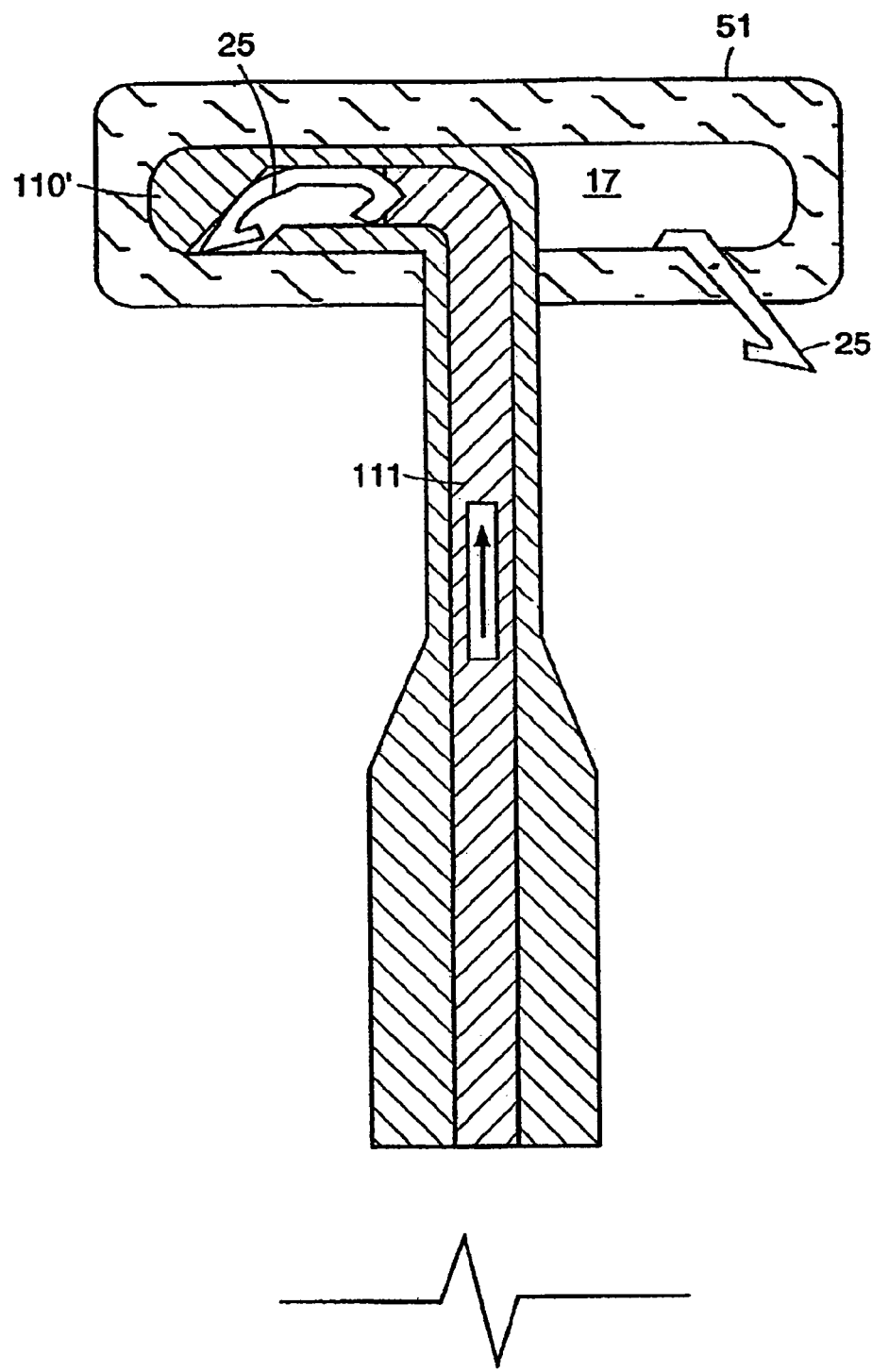
FIG. 45 is a section of a device used to affix sealing means to tissues surrounding a defect.

FIG. 45 is a section of a device used to affix sealing means 51 to tissues surrounding a defect. In this figure, sealing means 51 would be positioned across interior aspect 50 of defect 16. The distal end of device 110' would be inserted through defect 16 and opening 8 into the interior cavity 17. On the right side of this figure, fixation dart 25 has been passed from device 110', through a wall of sealing means 51 and into tissues surrounding sealing means 51. On the right side of the figure, fixation dart 25 is about to be passed through a wall of sealing means 51 by advancing pusher 111 relative to device 110' in the direction of the arrow.

Figure 46:
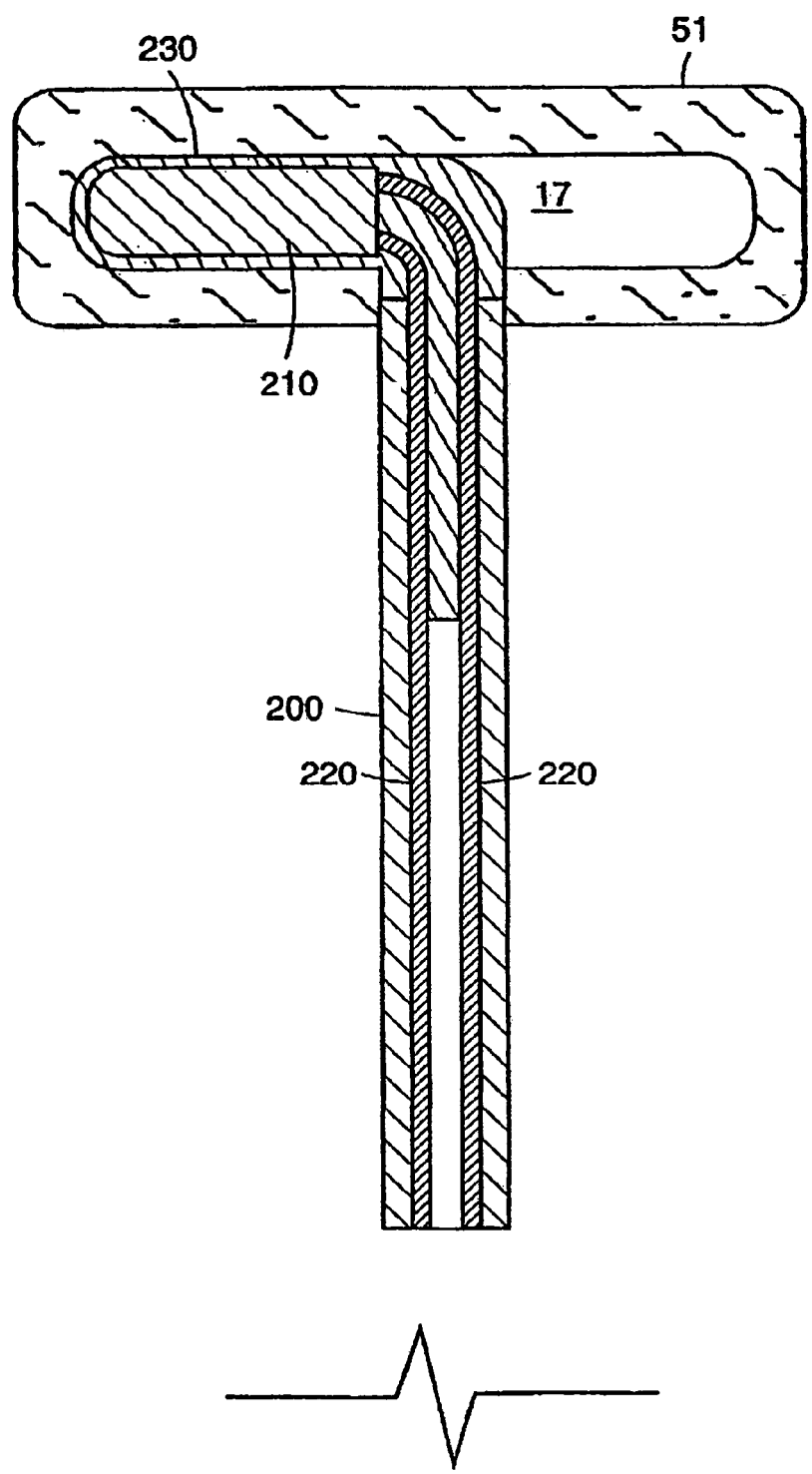
FIG. 46 depicts the use of a thermal device to heat and adhere sealing means to tissues surrounding a defect.

FIG. 46 depicts the use of thermal device 200 to heat sealing means 51 and adhere it to tissues surrounding a defect. In this figure, sealing means 51 would be positioned across the interior aspect 36 of a defect 16. The distal end of thermal device 200 would be inserted through the defect and opening 8 into interior cavity 17. In this embodiment, thermal device 200 employs at its distal end resistive heating element 210 connected to a voltage source by wires 220. Covering 230 is a non-stick surface such as Teflon tubing that ensures the ability to remove device 200 from interior cavity 17. In this embodiment, device 200 would be used to heat first one half, and then the other half of sealing means 51.

FIG. 47 depicts an expandable thermal element, such as a balloon, that can be used to adhere sealing means 51 to tissues surrounding a defect. As in FIG. 18, the distal end of device 130 can be inserted through the defect and opening 8 into interior cavity 17, with balloon 150' on the distal end device 130 in a collapsed state. Balloon 150' is then inflated to expanded state 150, expanding sealing means 51. Expanded balloon 150 can heat sealing means 51 and surrounding tissues by inflating it with a heated fluid or by employing RF electrodes. In this embodiment, device 130 can be used to expand and heat first one half, then the other half of sealing means 51.

Figure 48:
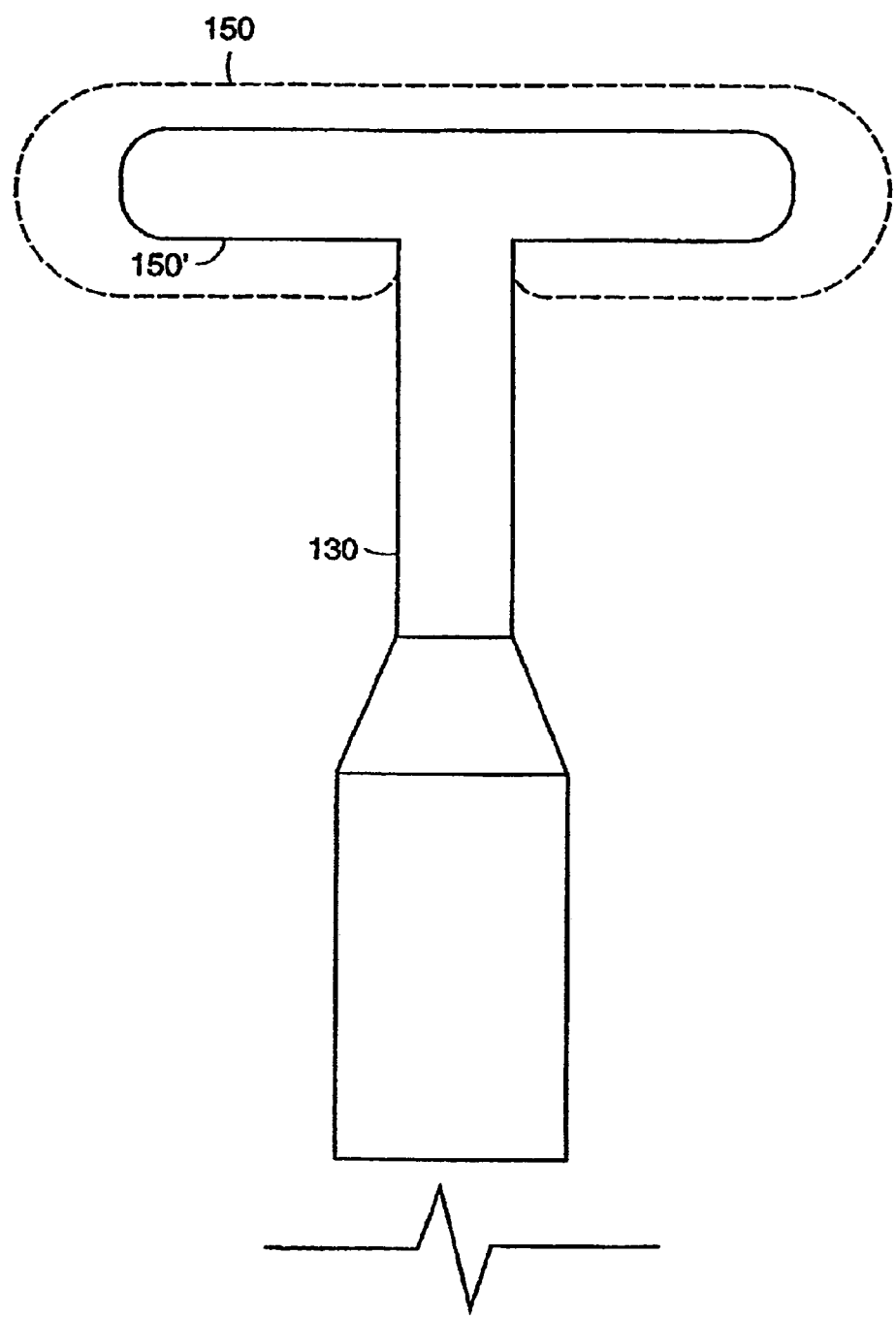
FIG. 48 depicts an alternative embodiment to the thermal device of FIG. 46.

FIG. 48 depicts an alternative embodiment to device 130. This device employs an elongated, flexible balloon 150' that can be inserted into and completely fill internal cavity 17 of sealing means 51 prior to inflation to an expanded state 150. Using this embodiment, inflation and heating of sealing means 51 can be performed in one step.

Figure 49C:
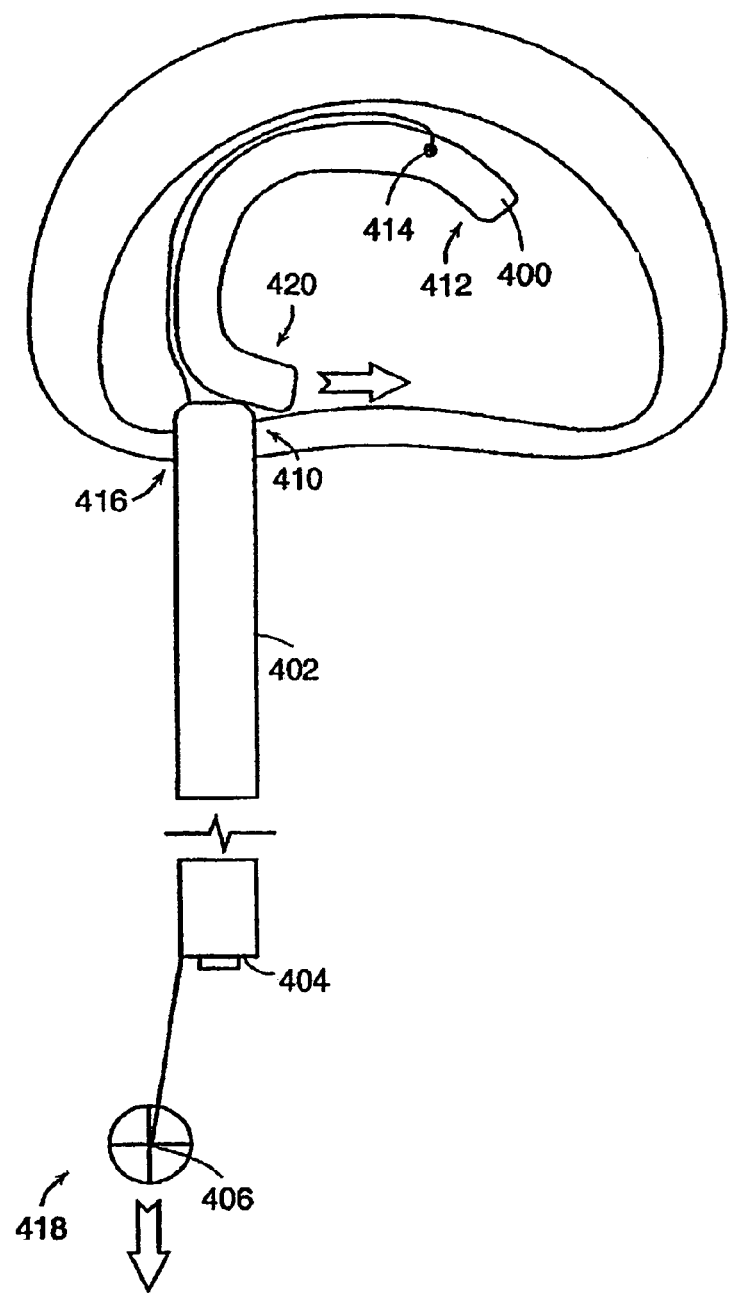

FIGS. 49A through 49G illustrate a method of implanting an intradiscal implant. An intradiscal implant system consists of an intradiscal implant 400, a delivery device or cannula 402, an advancer 404 and at least one control filament 406. The intradiscal implant 400 is loaded into the delivery cannula 402 which has a proximal end 408 and a distal end 410. FIG. 49A illustrates the distal end 410 advanced into the disc 15 through an annulotomy 416. This annulotomy 416 can be through any portion of the anulus 10, but is preferably at a site proximate to a desired, final implant location. The implant 400 is then pushed into the disc 15 through the distal end 410 of the cannula 402 in a direction that is generally away from the desired, final implant location as shown in FIG. 49B. Once the implant 400 is completely outside of the delivery cannula 402 and within the disc 15, the implant 400 can be pulled into the desired implant location by pulling on the control filament 406 as shown in FIG. 49C. The control filament 406 can be secured to the implant 400 at any location on or within the implant 400, but is preferably secured at least at a site 414 or sites on a distal portion 412 of the implant 400, e.g., that portion that first exits the delivery cannula 402 when advanced into the disc 15. These site or sites 414 are generally furthest from the desired, final implant location once the implant has been fully expelled from the interior of the delivery cannula 402.

Figure 49D:
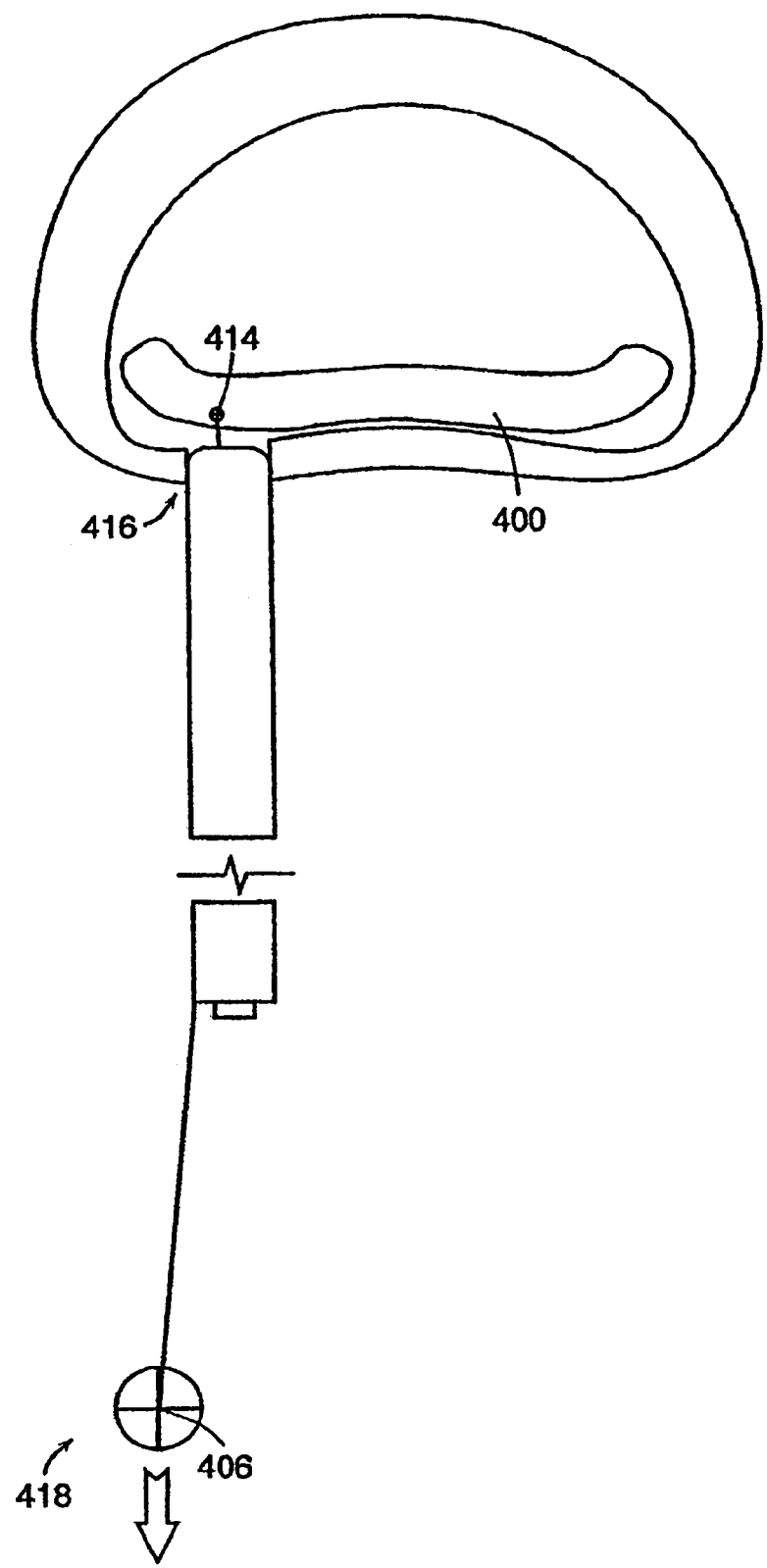
Figure 49E:
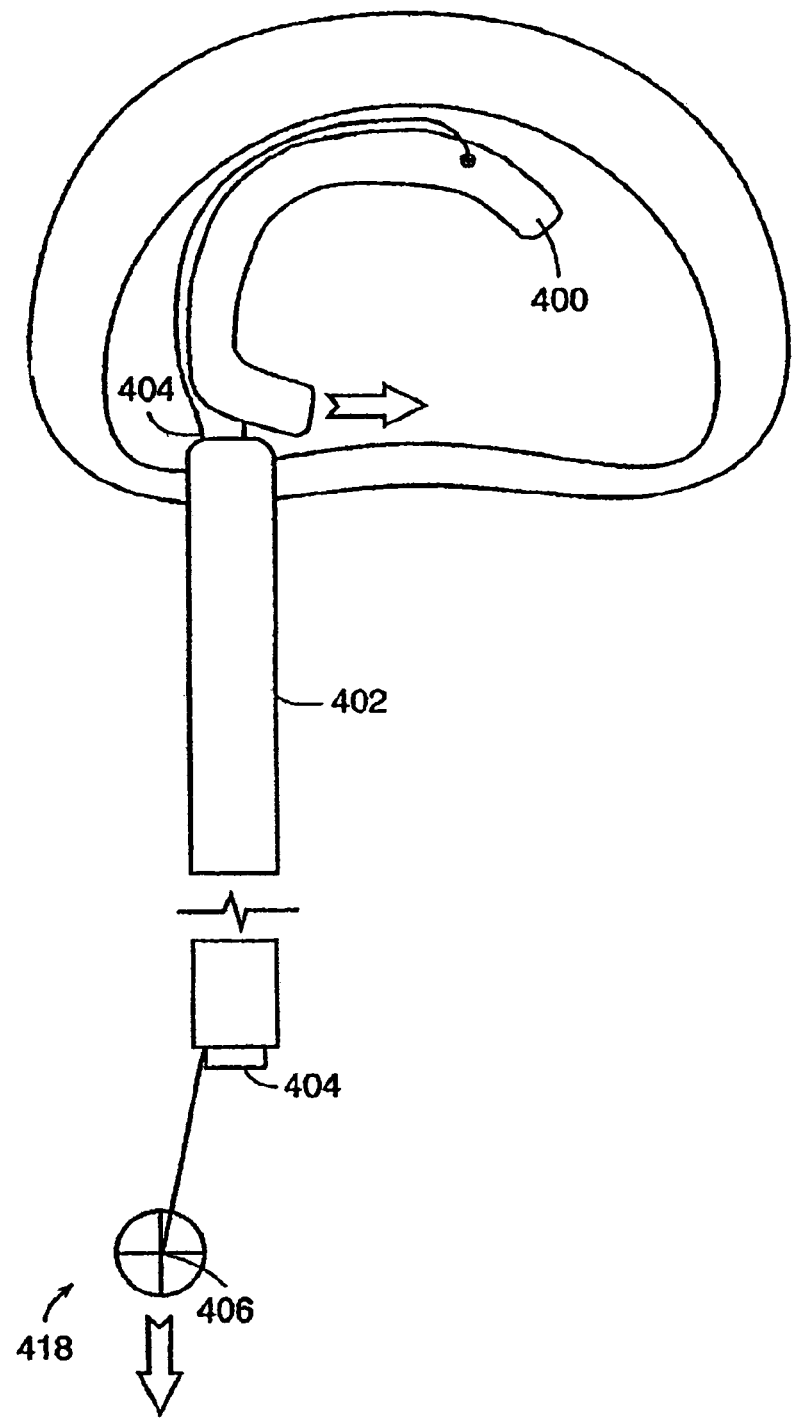
Figure 49F:
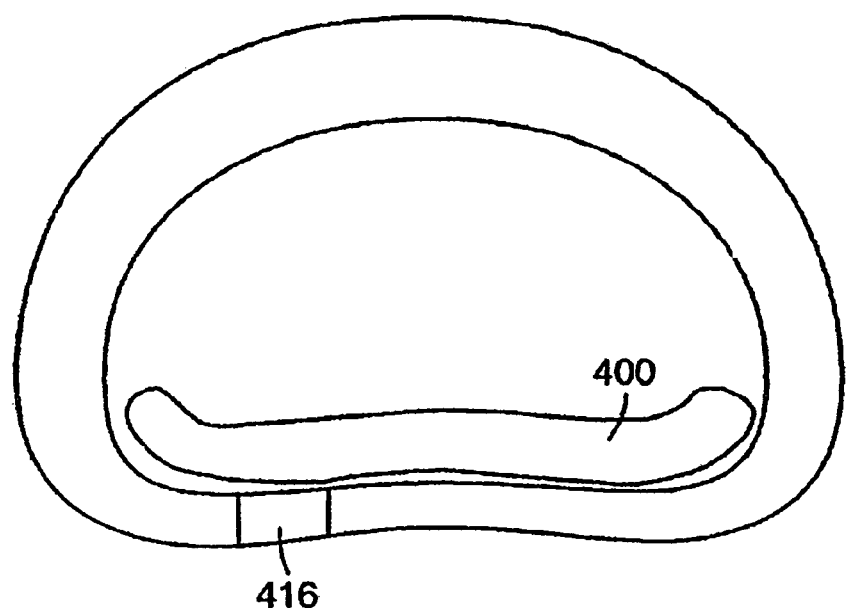

Pulling on the control filament 406 causes the implant 400 to move toward the annulotomy 416. The distal end 410 of the delivery cannula 402 can be used to direct the proximal end 420 of the implant 400 (that portion of the implant 400 that is last to be expelled from the delivery cannula 402) away from the annulotomy 416 and toward an inner aspect of the anulus 10 nearest the desired implant location. Alternately, the advancer 404 can be used to position the proximal end of the implant toward an inner aspect of the anulus 20 near the implant location, as shown in FIG. 49E. Further pulling on the control filament 406 causes the proximal end 426 of the implant 400 to dissect along the inner aspect of the anulus 20 until the attachment site 414 or sites of the guide filament 406 to the implant 400 has been pulled to the inner aspect of the annulotomy 416, as shown in FIG. 49D. In this way, the implant 400 will extend at least from the annulotomy 416 and along the inner aspect of the anulus 10 in the desired implant location, illustrated in FIG. 49F.

The implant 400 can be any one of the following (including a combination of two or more of the following): nucleus replacement device, nucleus augmentation device, anulus augmentation device, anulus replacement device, the barrier of the present invention or any of its components, drug carrier device, carrier device seeded with living cells, or a device that stimulates or supports fusion of the surrounding vertebra. The implant 400 can be a membrane which prevents the flow of a material from within the anulus fibrosis of an intervertebral disc through a defect in the disc. The material within the anulus fibrosis can be, for example, a nucleus pulposus or a prosthetic augmentation device, such as hydrogel. The membrane can be a sealer. The implant 400 can be wholly or partially rigid or wholly or partially flexible. It can have a solid portion or portions that contain a fluid material. It can comprise a single or multitude of materials. These materials can include metals, polymers, gels and can be in solid or woven form. The implant 400 can either resist or promote tissue ingrowth, whether fibrous or bony.

The cannula 402 can be any tubular device capable of advancing the implant 400 at least partially through the anulus 10. It can be made of any suitable biocompatible material including various known metals and polymers. It can be wholly or partially rigid or flexible. It can be circular, oval, polygonal, or irregular in cross section. It must have an opening at least at its distal end 410, but can have other openings in various locations along its length.

The advancer 404 can be rigid or flexible, and have one of a variety of cross sectional shapes either like or unlike the delivery cannula 402. It may be a solid or even a column of incompressible fluid, so long as it is stiff enough to advance the implant 400 into the disc 15. The advancer 404 can be contained entirely within the cannula 402 or can extend through a wall or end of the cannula to facilitate manipulation.

Advancement of the implant 400 can be assisted by various levers, gears, screws and other secondary assist devices to minimize the force required by the surgeon to advance the implant 400. These secondary devices can further give the user greater control over the rate and extent of advancement into the disc 15.

Figure 49G:
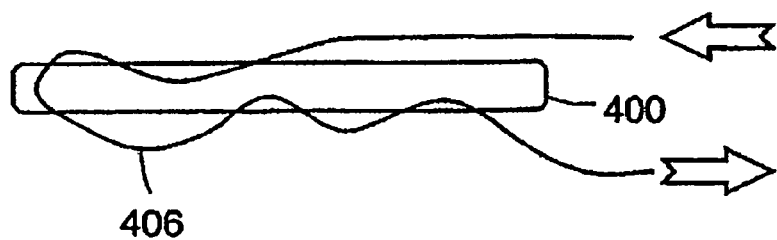

The guide filament 406 may be a string, rod, plate, or other elongate object that can be secured to and move with the implant 400 as it is advanced into the disc 15. It can be constructed from any of a variety of metals or polymers or combination thereof and can be flexible or rigid along all or part of its length. It can be secured to a secondary object 418 or device at its end opposite that which is secured to the implant 400. This secondary device 418 can include the advancer 404 or other object or device that assists the user in manipulating the filament. The filament 406 can be releasably secured to the implant 400, as shown in FIG. 49G or permanently affixed. The filament 406 can be looped around or through the implant; Such a loop can either be cut or have one end pulled until the other end of the loop releases the implant 400. It may be bonded to the implant 400 using adhesive, welding, or a secondary securing means such as a screw, staple, dart, etc. The filament 406 can further be an elongate extension of the implant material itself. If not removed following placement of the implant, the filament 406 can be used to secure the implant 400 to surrounding tissues such as the neighboring anulus 10, vertebral endplates, or vertebral bodies either directly or through the use of a dart, screw, staple, or other suitable anchor.

Figure 50B:
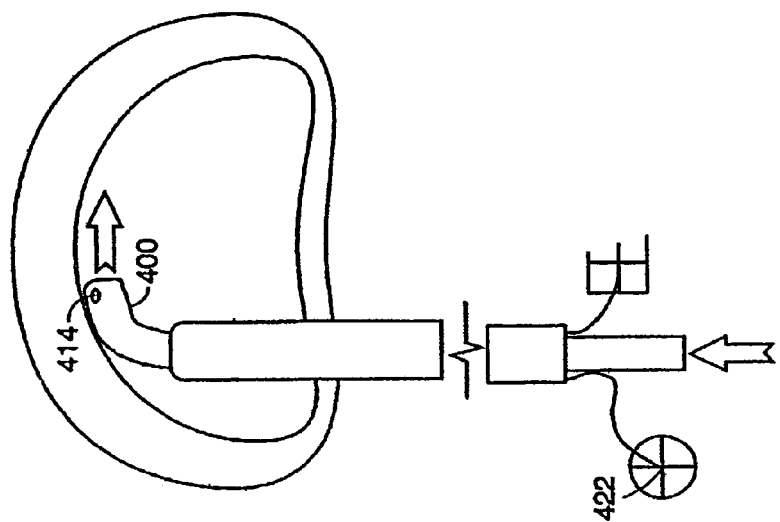
FIGS. 50A-F show an alternate method of implanting an intradiscal implant.
Figure 50A:
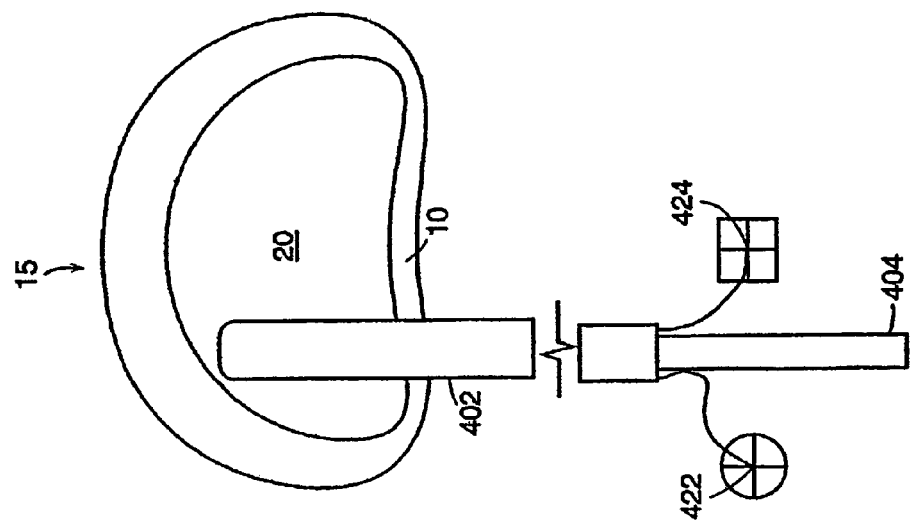
Figure 50D:
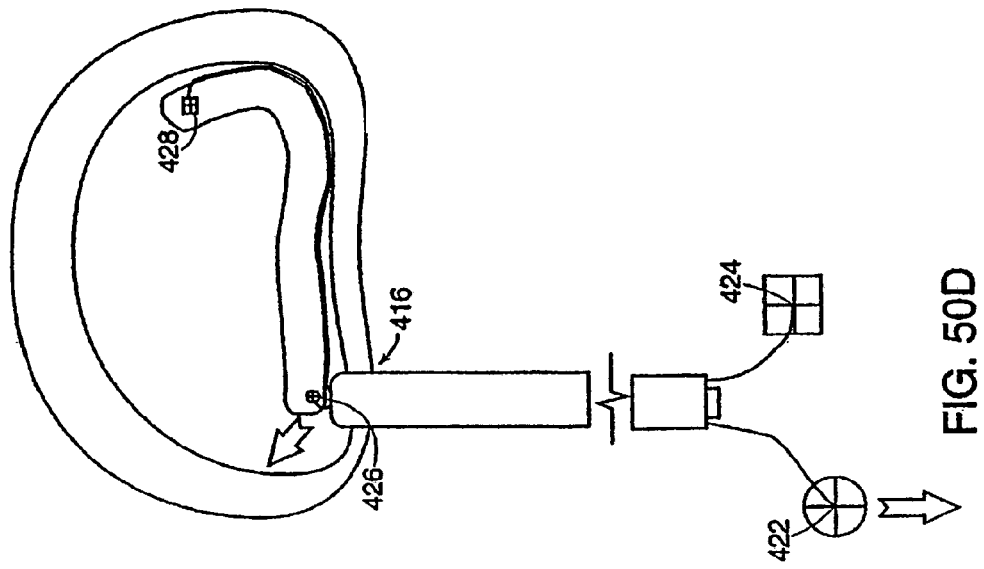
Figure 50C:
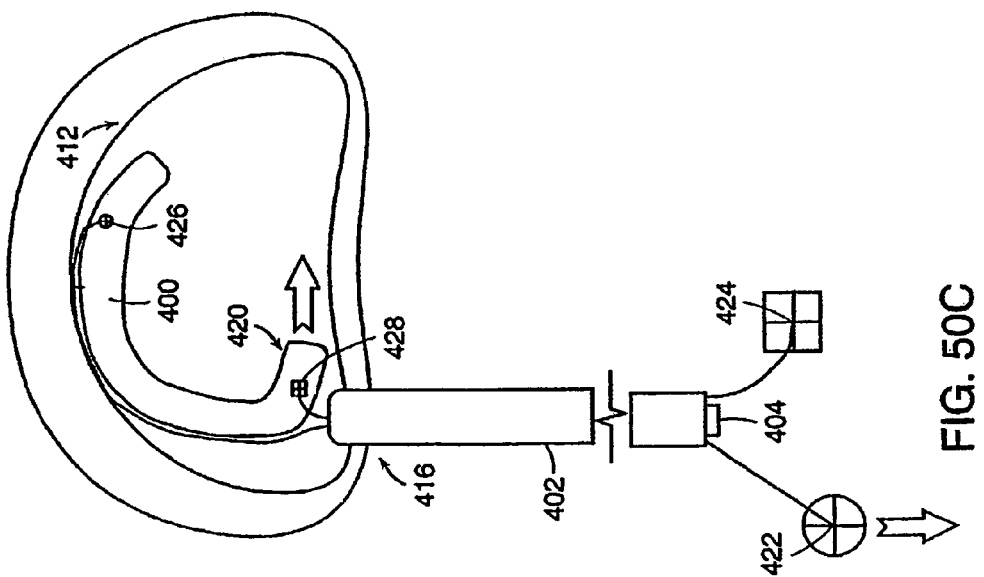

Multiple guide filaments can be secured to the implant 400 at various locations. In one preferred embodiment, a first or distal 422 and a second or proximal 424 guide filament are secured to an elongate implant 400 at or near its distal 412 and proximal 420 ends at attachment sites 426 and 428, respectively. These ends 412 and 420 correspond to the first and last portions of the implant 400, respectively, to be expelled from the delivery cannula 402 when advanced into the disc 15. This double guide filament system allows the implant 400 to be positioned in the same manner described above in the single filament technique, and illustrated in FIGS. 50A-C. However, following completion of this first technique, the user may advance the proximal end 420 of the device 400 across the annulotomy 416 by pulling on the second guide filament 424, shown in FIG. 50D. This allows the user to controllably cover the annulotomy 416. This has numerous advantages in various implantation procedures. This step may reduce the risk of herniation of either nucleus pulposus 20 or the implant itself. It may aid in sealing the disc, as well as preserving disc pressure and the natural function of the disc. It may encourage ingrowth of fibrous tissue from outside the disc into the implant. It may further allow the distal end of the implant to rest against anulus further from the defect created by the annulotomy. Finally, this technique allows both ends of an elongate implant to be secured to the disc or vertebral tissues.

Figure 50E:
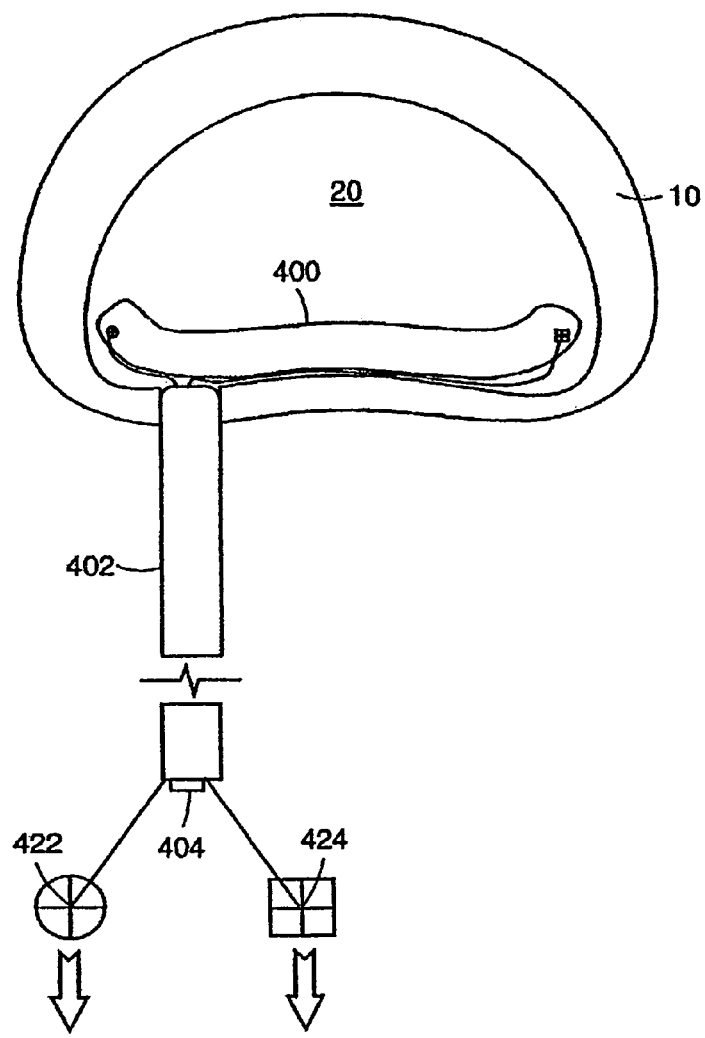
Figure 50F:
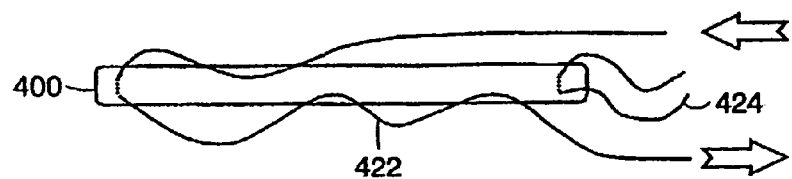

Both the first 422 and second 424 guide filaments can be simultaneously tensioned, as shown in FIG. 50E, to ensure proper positioning of the implant 400 within the anulus 10. Once the implant 400 is placed across the annulotomy, the first 422 and second 424 guide filaments can be removed from the input 400, as shown in FIG. 50F. Additional control filaments and securing sites may further assist implantation and/or fixation of the intradiscal implants.

Figure 51A:
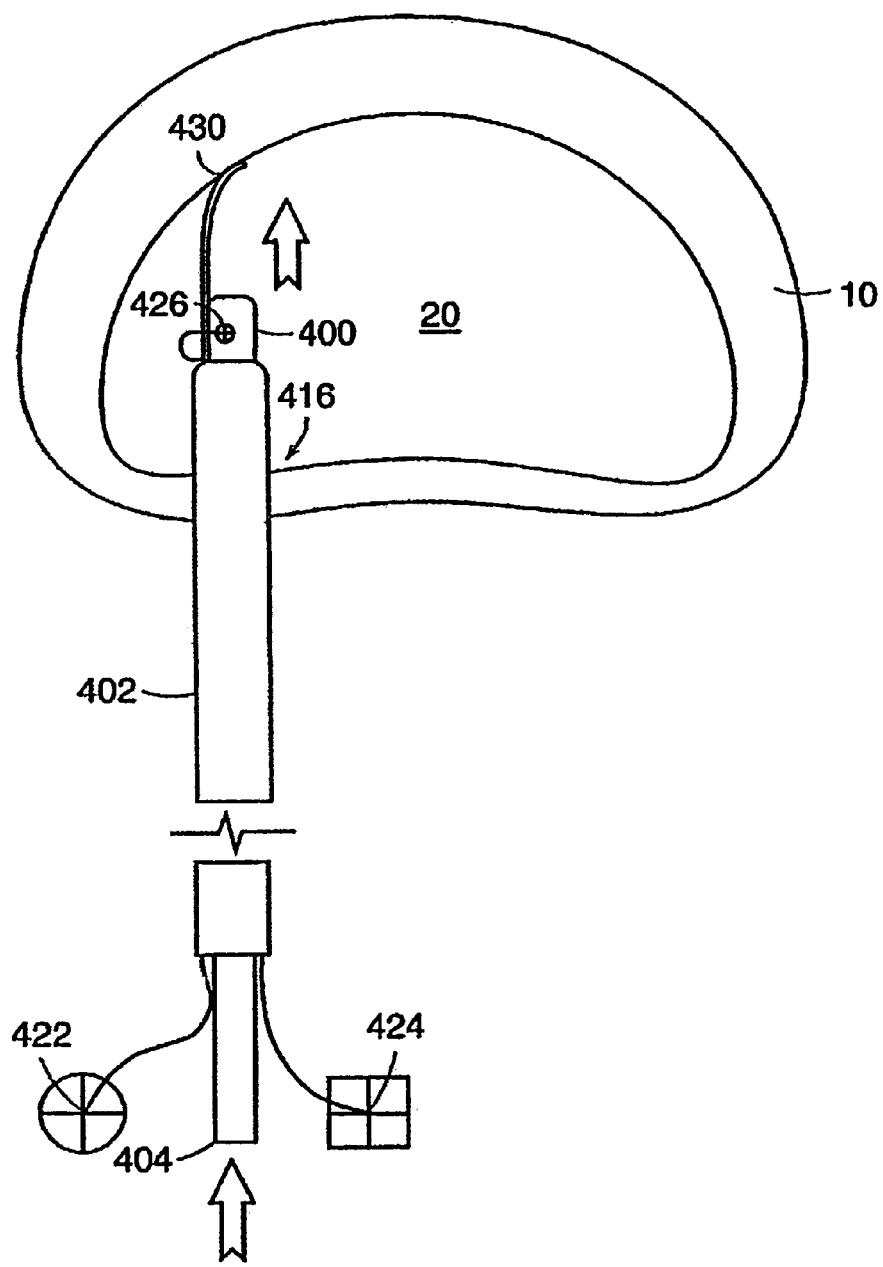
FIGS. 51A-C show another alternate method of implanting an intradiscal implant.
Figure 51B:
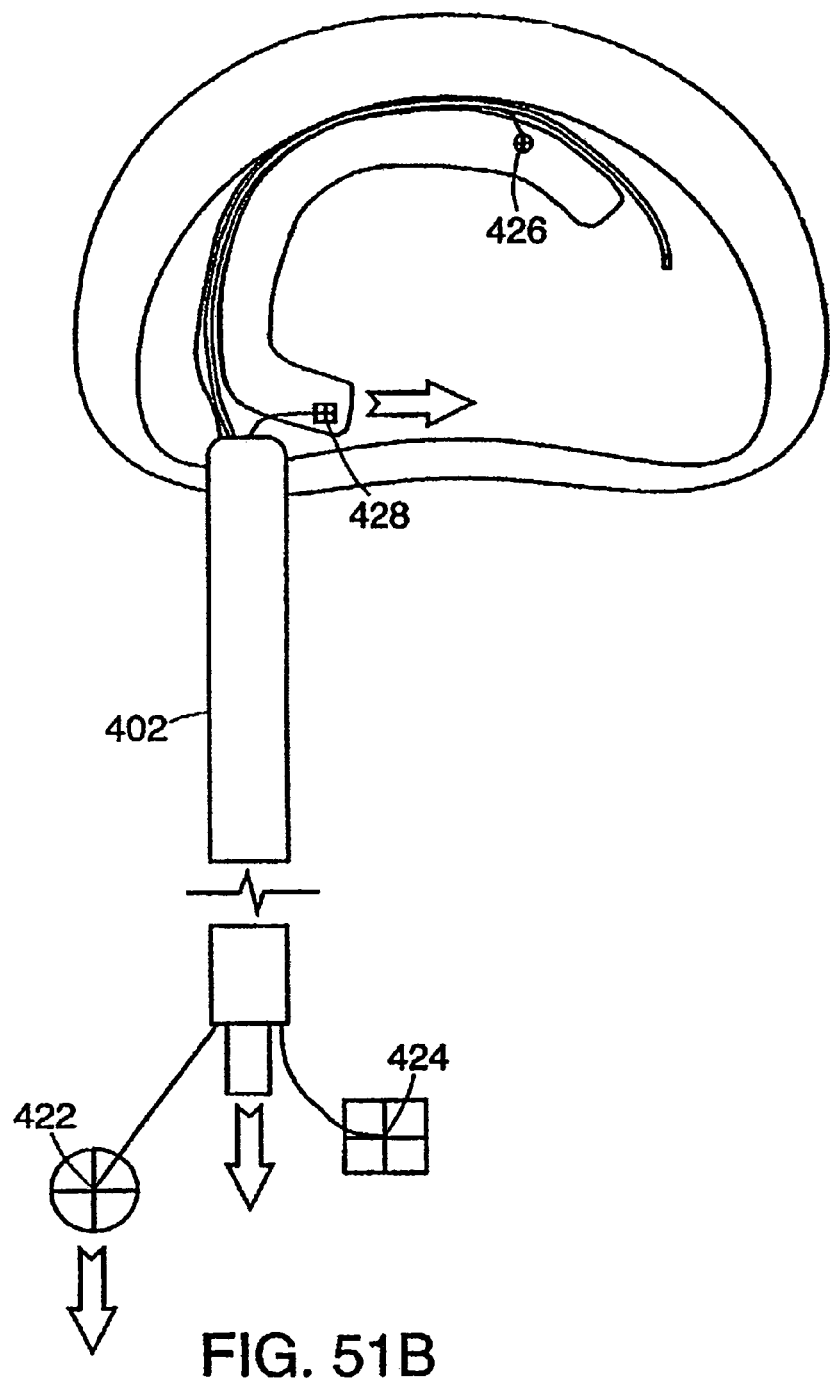
Figure 51C:
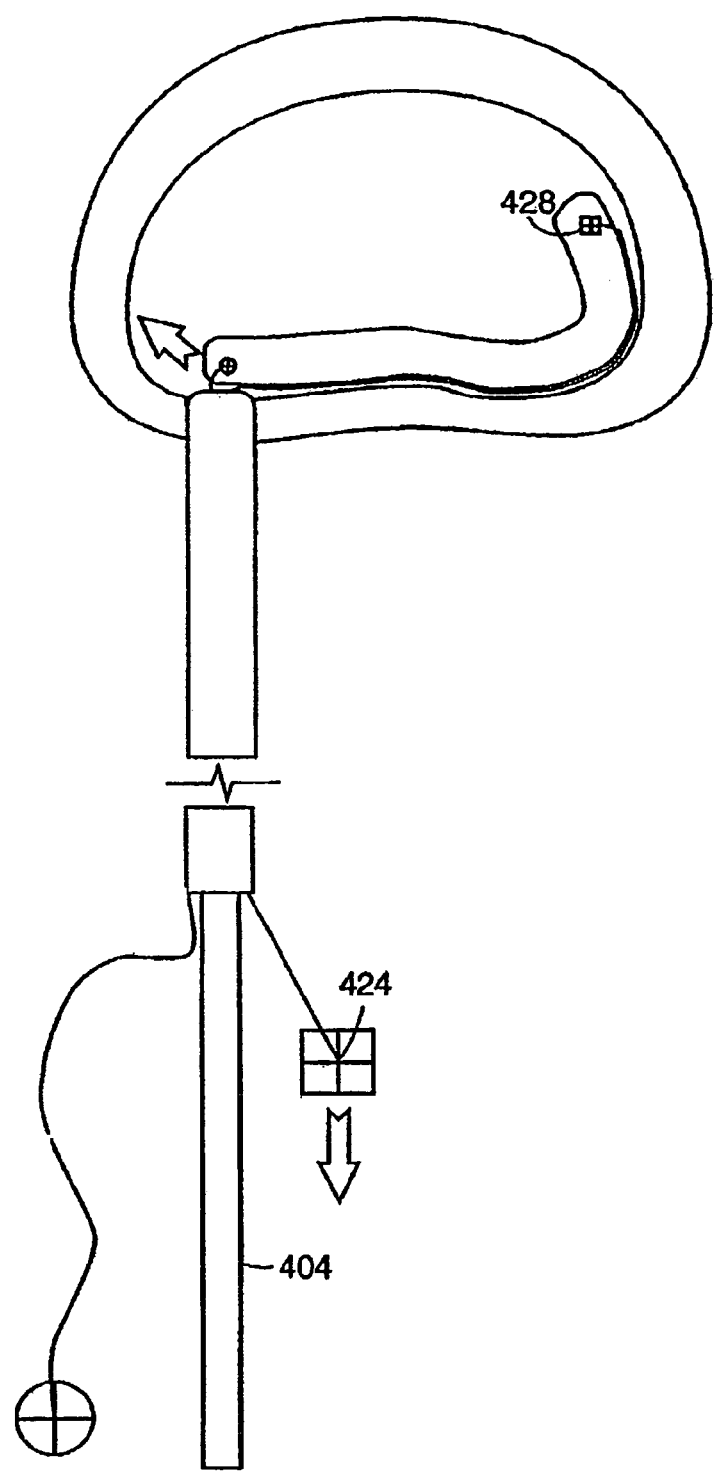
Figure 52A:
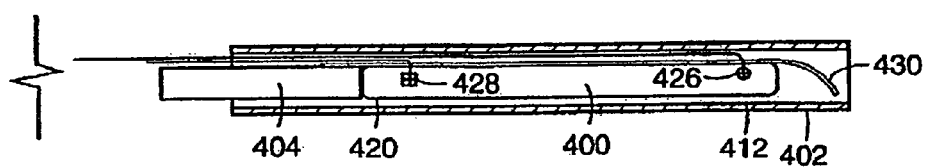
FIGS. 52A and 52B illustrate an implant guide used with the intradiscal implant system.
Figure 52B:
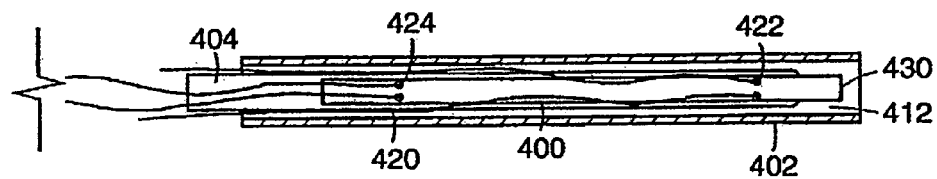

In another embodiment of the present invention, as illustrated in FIGS. 51A-C, an implant guide 430 may be employed to aid directing the implant 400 through the annulotomy 416, through the nucleus pulposus 10, and/or along the inner aspect of the anulus 10. This implant guide 430 can aid in the procedure by dissecting through tissue, adding stiffness to the implant construct, reducing trauma to the anulus or other tissues that can be caused by a stiff or abrasive implant, providing 3-D control of the implants orientation during implantation, expanding an expandable implant, or temporarily imparting a shape to the implant that is beneficial during implantation. The implant guide 430 can be affixed to either the advancer 404 or the implant 406 themselves. In a preferred embodiment shown in FIGS. 52A and 52B, the implant guide 430 is secured to the implant 400 by the first 424 and second 426 guide filaments of the first 426 and the second 428 attachment sites, respectively. The guide filaments 424 and 426 may pass through or around the implant guide 430. In this embodiment, the implant guide 430 may be a thin, flat sheet of biocompatible metal with holes passing through its surface proximate to the site or sites 426 and 428 at which the guide filaments 422 and 424 are secured to the implant 400. These holes allow passage of the securing filament 422 and 424 through the implant guide 430. Such an elongated sheet may run along the implant 400 and extend beyond its distal end 412. The distal end of the implant guide 430 may be shaped to help dissect through the nucleus 10 and deflect off of the anulus 10 as the implant 400 is advanced into the disc 15. When used with multiple guide filaments, such an implant guide 430 can be used to control rotational stability of the implant 400. It may also be used to retract the implant 400 from the disc 15 should this become necessary. The implant guide 430 may also extend beyond the proximal tip 420 of the implant 400 to aid in dissecting across or through the anulus 10 proximate to the desired implantation site.

The implant guide 430 is releasable from the implant 400 following or during implantation. This release may be coordinated with the release of the guide filaments 422 and 424. The implant guide 430 may further be able to slide along the guide filaments 422 and 424 while these filaments are secured to the implant 400.

Various embodiments of the barrier 12 or implant 400 can be secured to tissues within the intervertebral disc 15 or surrounding vertebrae. It can be advantageous to secure the barrier means 12 in a limited number of sites while still insuring that larger surfaces of the barrier 12 or implant juxtapose the tissue to which the barrier 12 is secured. This is particularly advantageous in forming a sealing engagement with surrounding tissues.

FIGS. 53-57 illustrate barriers 12 having stiffening elements 300. The barrier 12 can incorporate stiffening elements 300 that run along a length of the implant required to be in sealing engagement. These stiffening elements 300 can be one of a variety of shapes including, but not limited to, plates 302, rods 304, or coils. These elements are preferably stiffer than the surrounding barrier 12 and can impart their stiffness to the surrounding barrier. These stiffening elements 300 can be located within an interior cavity formed by the barrier. They can further be imbedded in or secured to the barrier 12.

Each stiffening element can aid in securing segments of the barrier 12 to surrounding tissues. The stiffening elements can have parts 307, including through-holes, notches, or other indentations for example, to facilitate fixation of the stiffening element 300 to surrounding tissues by any of a variety of fixation devices 306. These fixation devices 306 can include screws, darts, dowels, or other suitable means capable of holding the barrier 12 to surrounding tissue. The fixation devices 306 can be connected either directly to the stiffening element 300 or indirectly using an intervening length of suture, cable, or other filament for example. The fixation device 306 can further be secured to the barrier 12 near the stiffening element 300 without direct contact with the stiffening element 300.

The fixation device 306 can be secured to or near the stiffening element 300 at opposing ends of the length of the barrier 12 required to be in sealing engagement with surrounding tissues. Alternatively, one or a multitude of fixation devices 306 can be secured to or near the stiffening element 300 at a readily accessible location that may not be at these ends. In any barrier 12 embodiment with an interior cavity 17 and an opening 8 leading thereto, the fixation sites may be proximal to the opening 8 to allow passage of the fixation device 306 and various instruments that may be required for their implantation.

Figure 53A:
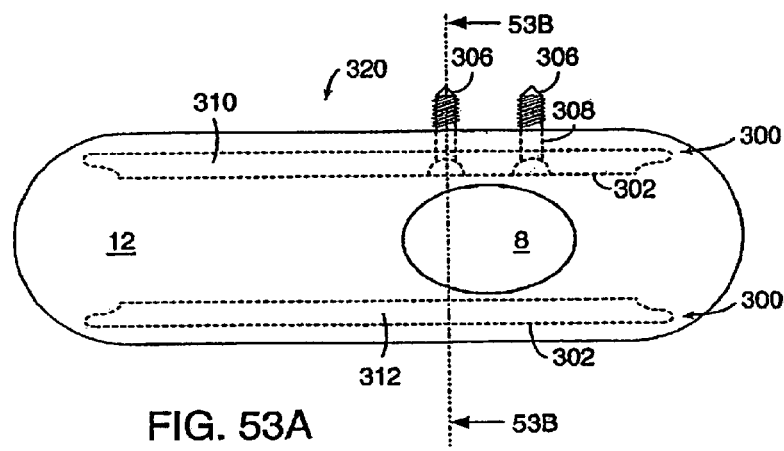
FIG. 53A illustrates a barrier having stiffening plate elements.
Figure 53B:
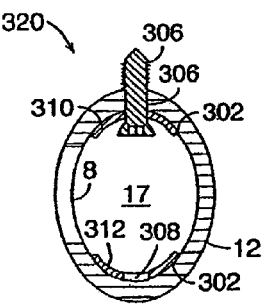
FIG. 53B illustrates a sectional view of the barrier of FIG. 53A.
Figure 54A:
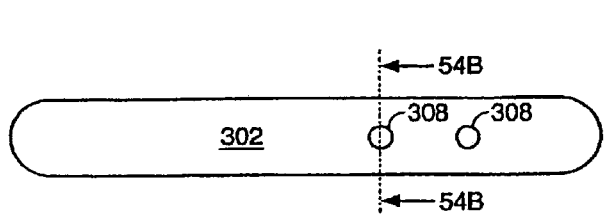
FIG. 54A shows a stiffening plate.
Figure 54B:
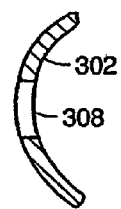
FIG. 54B shows a sectional view of the stiffening plate of FIG. 54A.

FIGS. 53A and 53B illustrate one embodiment of a barrier 12 incorporating the use of a stiffening element 300. The barrier 12 can be a plate and screw barrier 320. In this embodiment, the stiffening element 300 consists of two fixation plates, superior 310 and inferior 312, an example of which is illustrated in FIGS. 54A and 54B with two parts 308 passing through each plate. The parts 308 are located proximal to an opening 8 leading into an interior cavity 17 of the barrier 12. These parts 8 allow passage of a fixation device 306 such as a bone screw. These screws can be used to secure the barrier means 12 to a superior 50 and inferior 50' vertebra. As the screws are tightened against the vertebral endplate, the fixation plates 310, 312 compress the intervening sealing means against the endplate along the superior and inferior surfaces of the barrier 12. This can aid in creating a sealing engagement with the vertebral endplates and prevent egress of materials from within the disc 15. As illustrated in FIGS. 53A and 53B, only the superior screws have been placed in the superior plate 310, creating a sealing engagement with the superior vertebra.

FIGS. 55A and 55B illustrate another embodiment of a barrier 12 having stiffening elements 300. The barrier 12 can be an anchor and rod barrier 322. In this embodiment, the stiffening elements 300 consist of two fixation rods 304, an example of which is shown in FIGS. 56A and 56B, imbedded within the barrier 12. The rods 304 can include a superior rod 314 and an inferior rod 316. Sutures 318 can be passed around these rods 314 and 316 and through the barrier means 10. These sutures 318 can in turn, be secured to a bone anchor or other suitable fixation device 306 to draw the barrier 12 into sealing engagement with the superior and inferior vertebral endplates in a manner similar to that described above. The opening 8 and interior cavity 17 of the barrier 12 are not required elements of the barrier 12.

Figure 57:
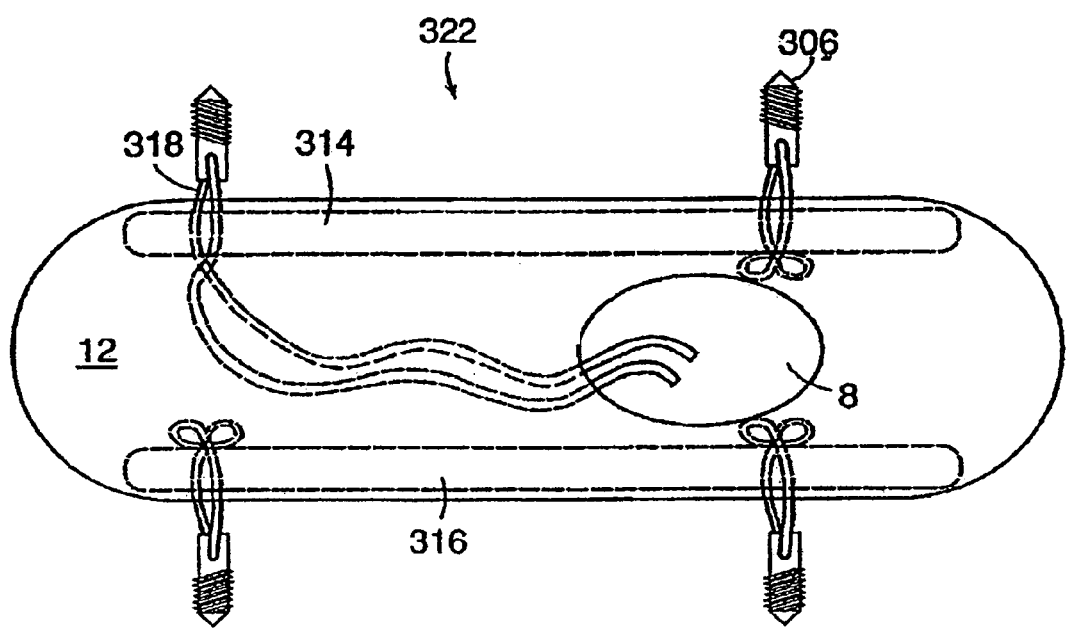
FIG. 57 shows an alternate configuration for the location of the fixation devices of the barrier of FIG. 44A.

FIG. 57 illustrates the anchor and rod barrier 322, described above, with fixation devices 306 placed at opposing ends of each fixation rod 316 and 318. The suture 18 on the left side of the superior rod 318 has yet to be tied.

Various methods may be employed to decrease the forces necessary to maneuver the barrier 12 into a position along or within the lamellae of the anulus fibrosis 10. FIGS. 58A, 58B, 59A and 59B depict two preferred methods of clearing a path for the barrier 12.

Figure 58A:
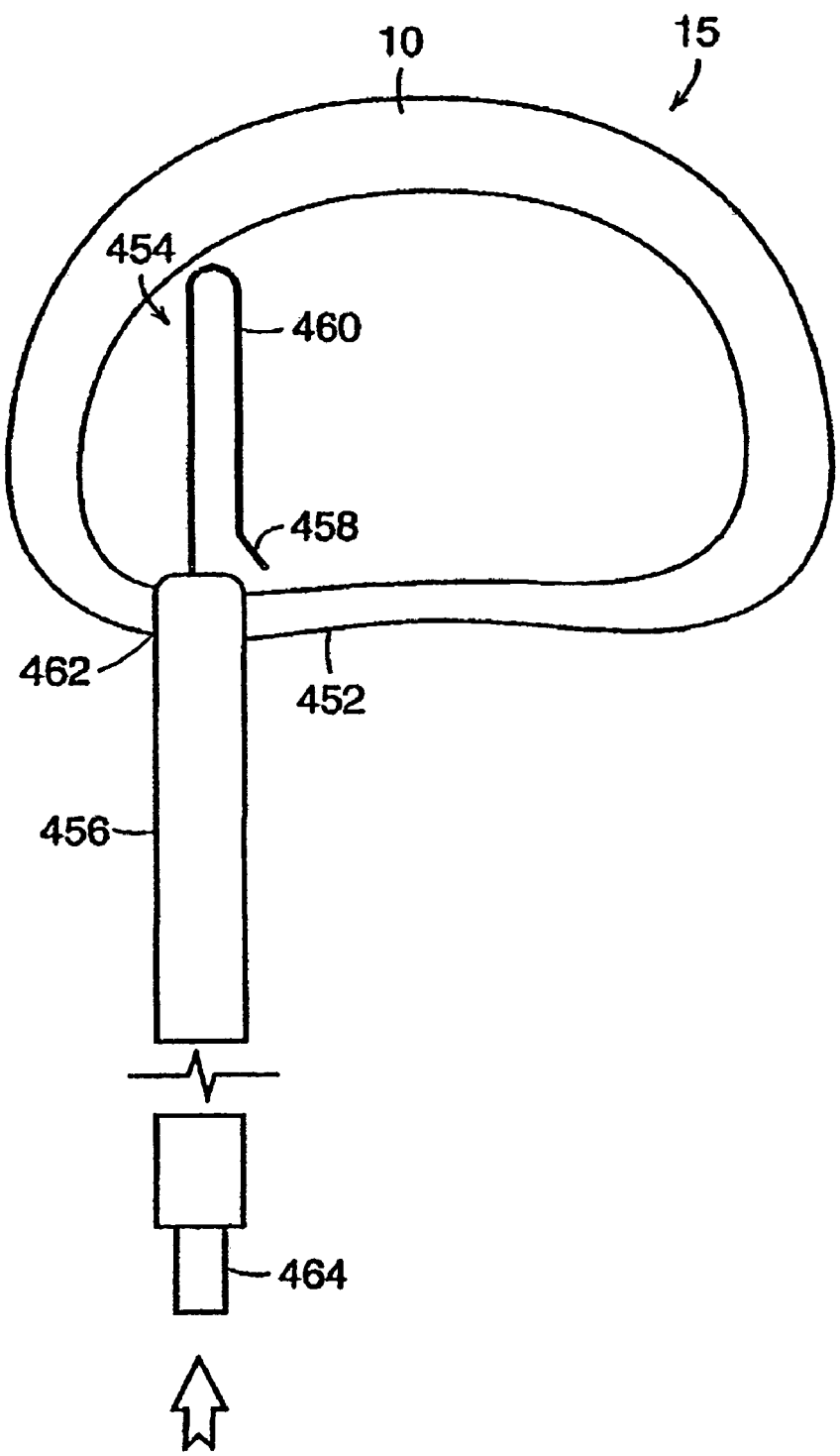
FIGS. 58A and 58B illustrate a dissection device for an intervertebral disc.
Figure 58B:
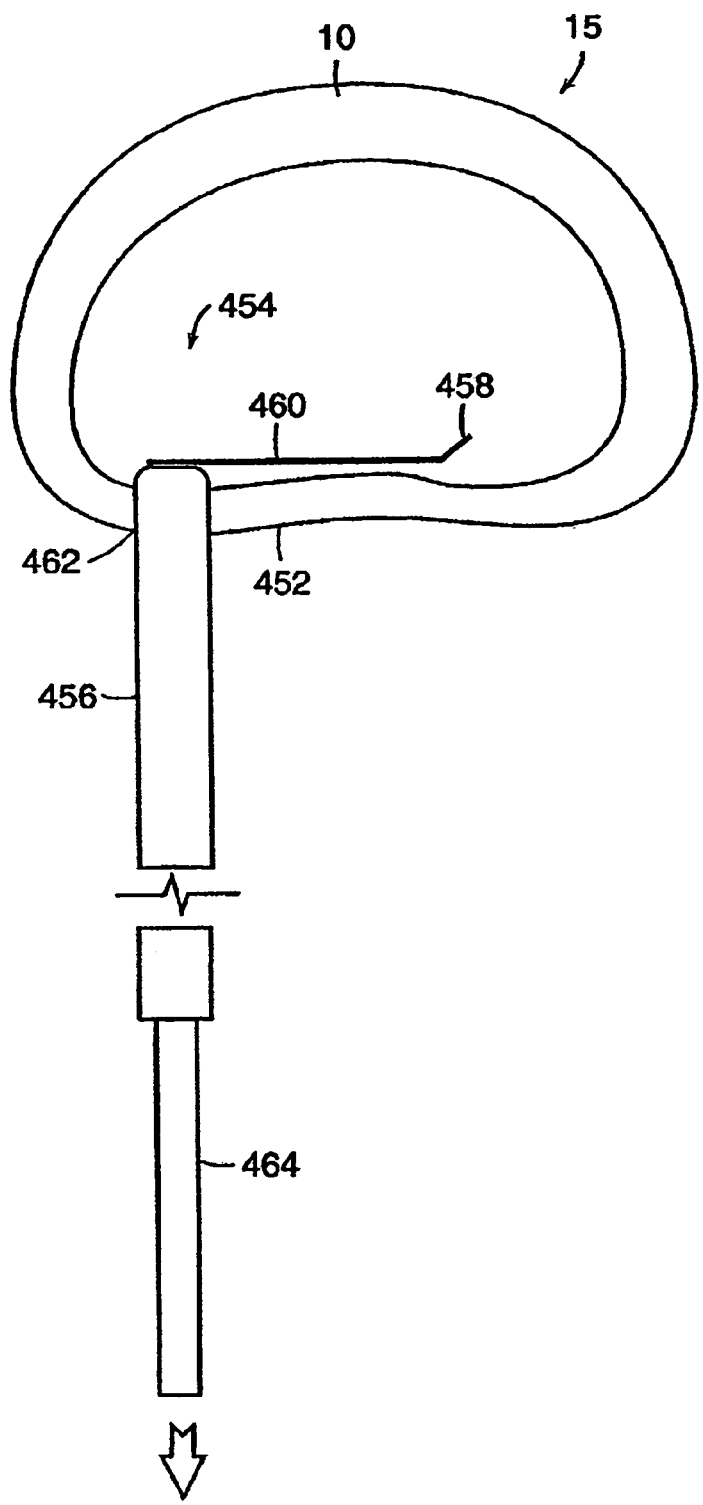

FIGS. 58A and 58B depict one such method and an associated dissector device 454. In these figures, the assumed desired position of the implant is along the posterior anulus 452. In order to clear a path for the implant, a hairpin dissector 454 can be passed along the intended implantation site of the implant. The hairpin dissector 454 can have a hairpin dissector component 460 having a free end 458. The dissector can also have an advancer 464 to position the dissector component 460 within the disc 15. The dissector 454 can be inserted through cannula 456 into an opening 462 in the anulus 10 along an access path directed anteriorly or anterior-medially. Once a free-end 458 of the dissector component 460 is within the disc 15, the free-end 458 moves slightly causing the hairpin to open, such that the dissector component 460 resists returning into the cannula 456. This opening 462 can be caused by pre-forming the dissector to the opened state. The hairpin dissector component 460 can then be pulled posteriorly, causing the dissector component 460 to open, further driving the free-end 458 along the posterior anulus 458. This motion clears a path for the insertion of any of the implants disclosed in the present invention. The body of dissector component 460 is preferably formed from an elongated sheet of metal. Suitable metals include various spring steels or nickel titanium alloys. It can alternatively be formed from wires or rods.

Figure 59A:
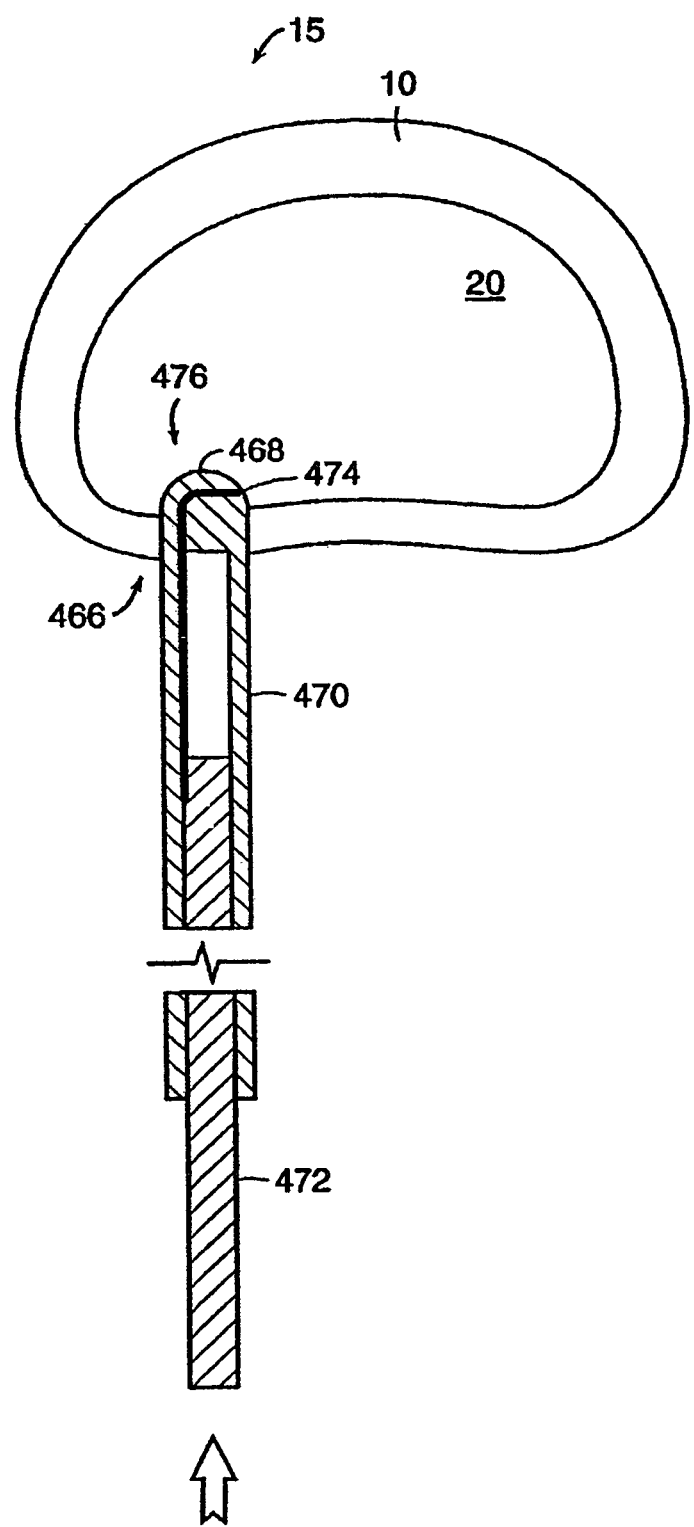
FIGS. 59A and 59B illustrate an alternate dissection device for an intervertebral disc.
Figure 59B:
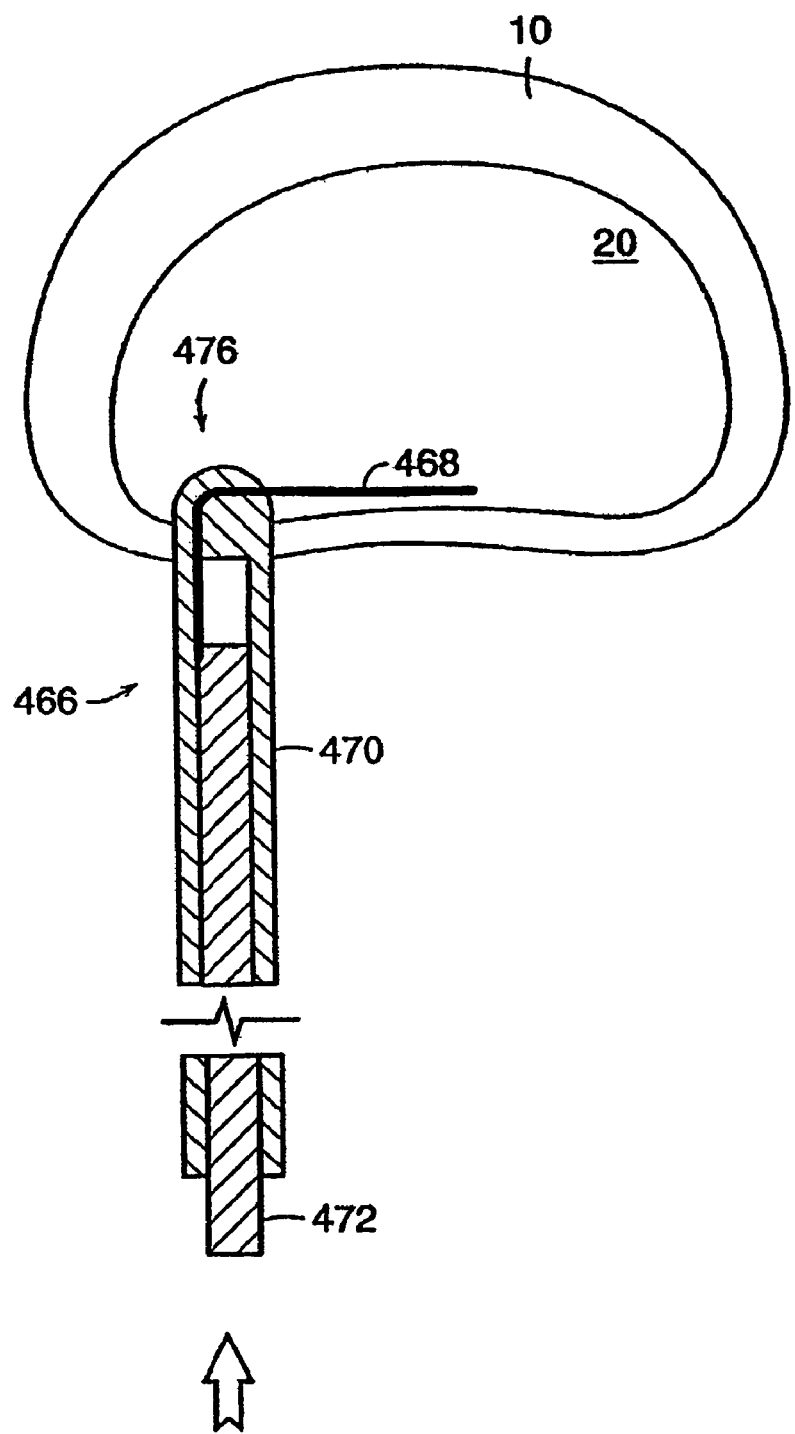

FIGS. 59A and 59B depict another method and associated dissector device 466 suitable for clearing a path for implant insertion. The dissector device 466 is shown in cross section and consists of a dissector component 468, an outer cannula 470 and an advancer or inner push rod 472. A curved passage or slot 474 is formed into an intradiscal tip 476 of outer cannula 470. This passage or slot 474 acts to deflect the tip of dissector component 468 in a path that is roughly parallel to the lamellae of the anulus fibrosis 10 as the dissector component 468 is advanced into the disc 15 by the advancer. The dissector component 468 is preferably formed from a superelastic nickel titanium alloy, but can be constructed of any material with suitable rigidity and strain characteristics to allow such deflection without significant plastic deformation. The dissector component 468 can be formed from an elongated sheet, rods, wires or the like. It can be used to dissect between the anulus 10 and nucleus 20, or to dissect between layers of the anulus 10.

Figure 60C:
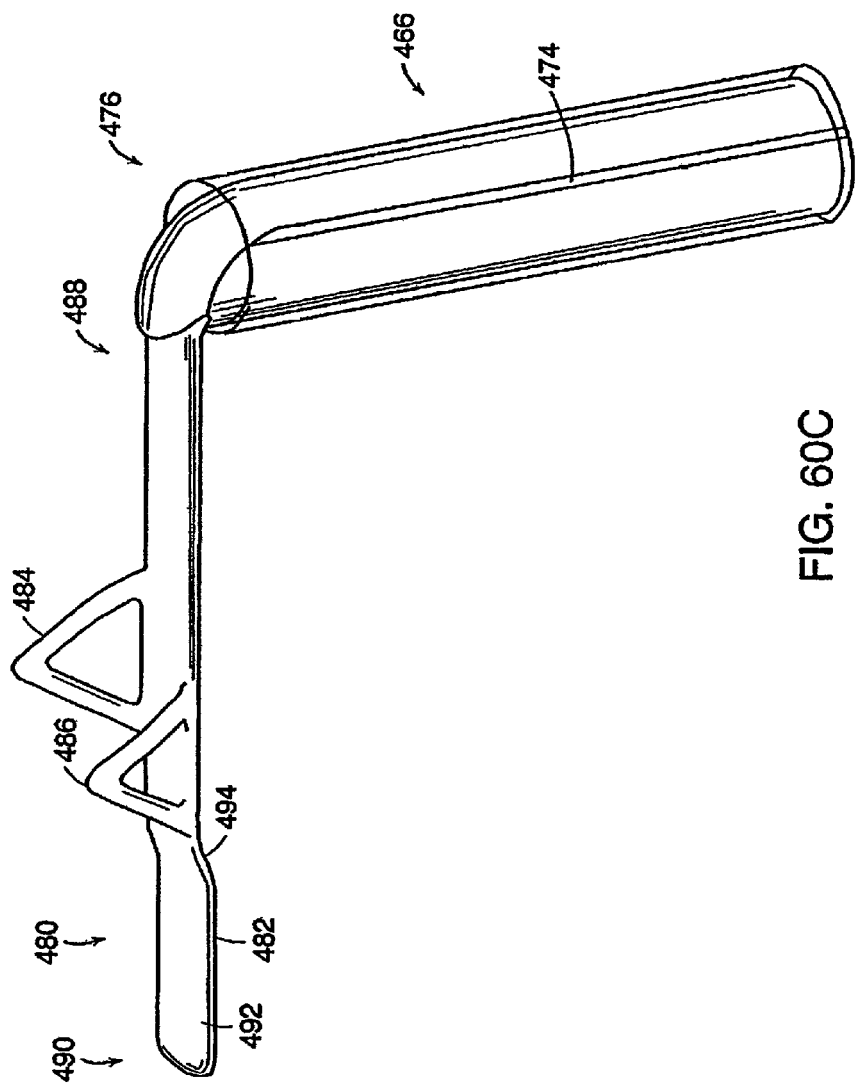

FIGS. 60A-C depict an alternate dissector component 480 of FIGS. 59A and 59B. Only the intradiscal tip 476 of device 460 and regions proximal thereto are shown in these figures. A push-rod 472 similar to that shown in FIG. 59A can be employed to advance dissector 480 into the disc 15. Dissector 480 can include an elongated sheet 482 with superiorly and inferiorly extending blades (or "wings") 484 and 486, respectively. This sheet 482 is preferably formed from a metal with a large elastic strain range such as spring steel or nickel titanium alloy. The sheet 482 can have a proximal end 488 and a distal end 490. The distal end 490 can have a flat portion which can be flexible. A step portion 494 can be located between the distal end 490 and the proximal end 488. The proximal end 488 can have a curved shape. The proximal end can also include blades 484 and 486.

In the undeployed state depicted in FIGS. 60A and 60B, wings 484 and 486 are collapsed within outer cannula 470 while elongated sheet 482 is captured within deflecting passage or slot 474. As the dissector component 480 is advanced into a disc 15, passage or slot 478 directs the dissector component 480 in a direction roughly parallel to the posterior anulus (90 degrees to the central axis of sleeve 470 in this case) in a manner similar to that described for the embodiment in FIGS. 59A and 59B. Wings 484 and 486 open as they exit the end of sleeve 470 and expand toward the vertebral endplates. Further advancement of dissector component 480 allows the expanded wings 484 and 486 to dissect through any connections of nucleus 20 or anulus 10 to the endplates that may present an obstruction to subsequent passage of the implants of the present invention. When used to aid in the insertion of a barrier, the dimensions of dissector component 480 should approximate those of the barrier such that the minimal amount of tissue is disturbed while reducing the forces necessary to position the barrier in the desired location.

Figure 61A:
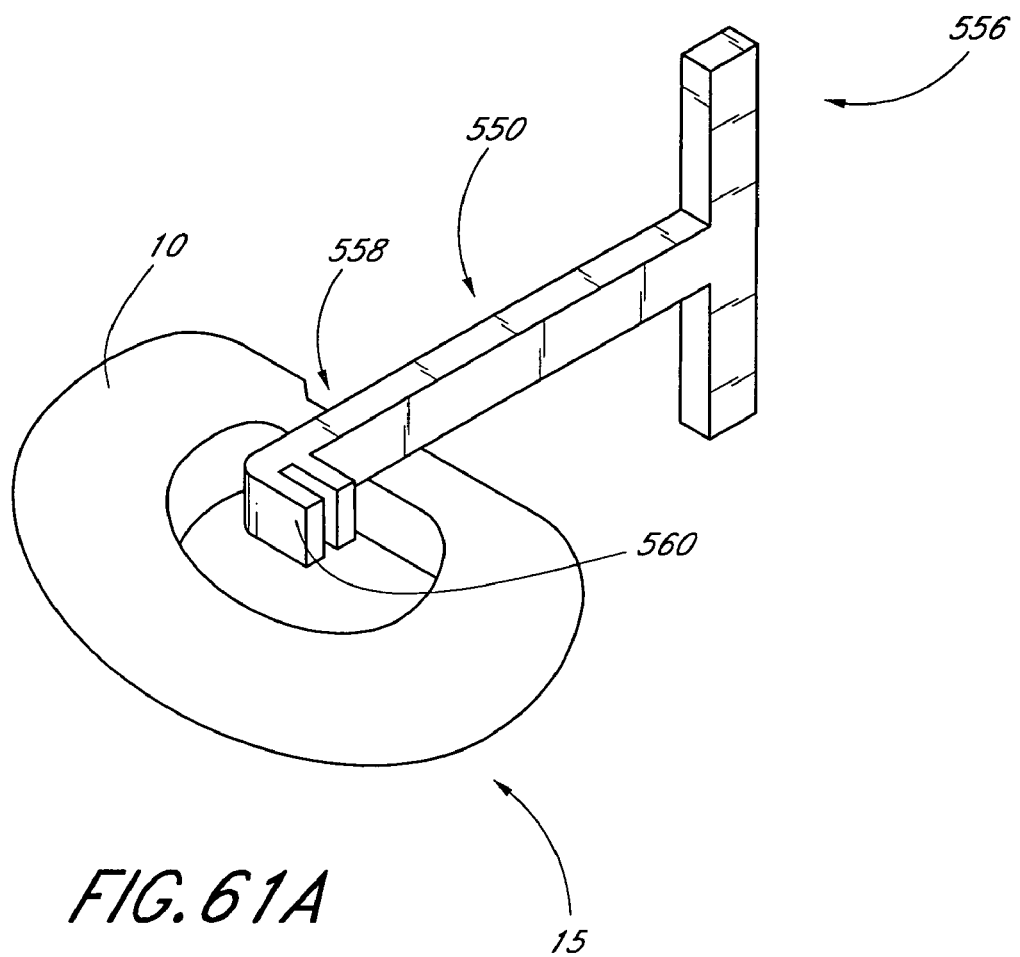
FIGS. 61A-D illustrate a method of inserting a disc implant within an intervertebral disc.
Figure 61B:
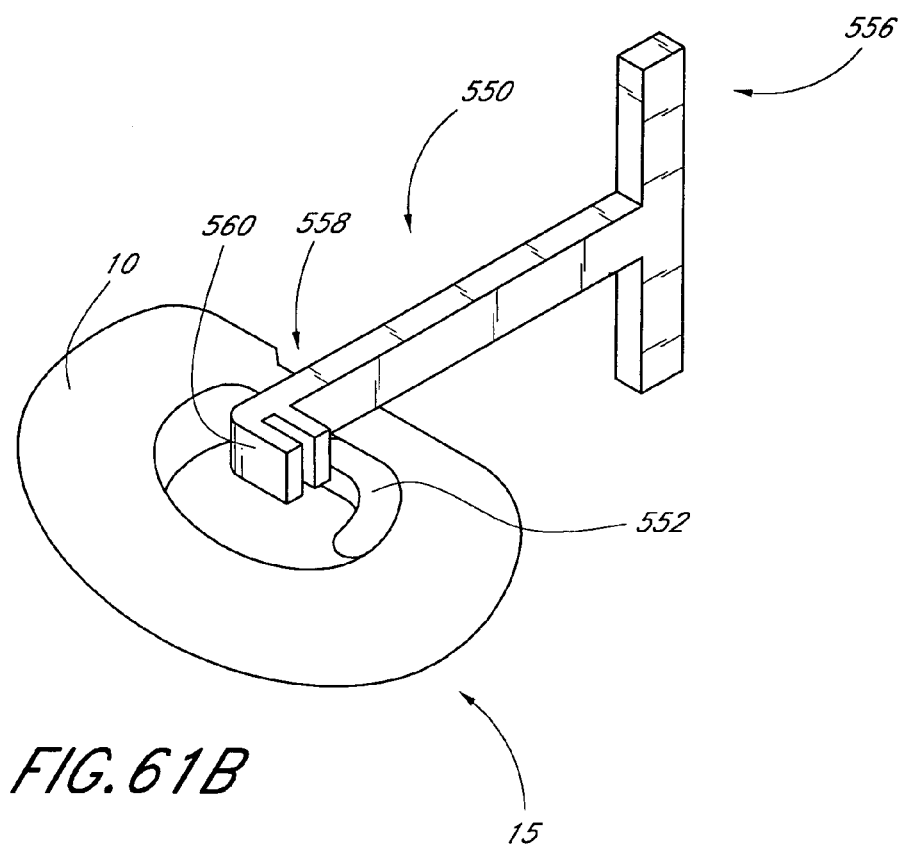
Figure 61C:
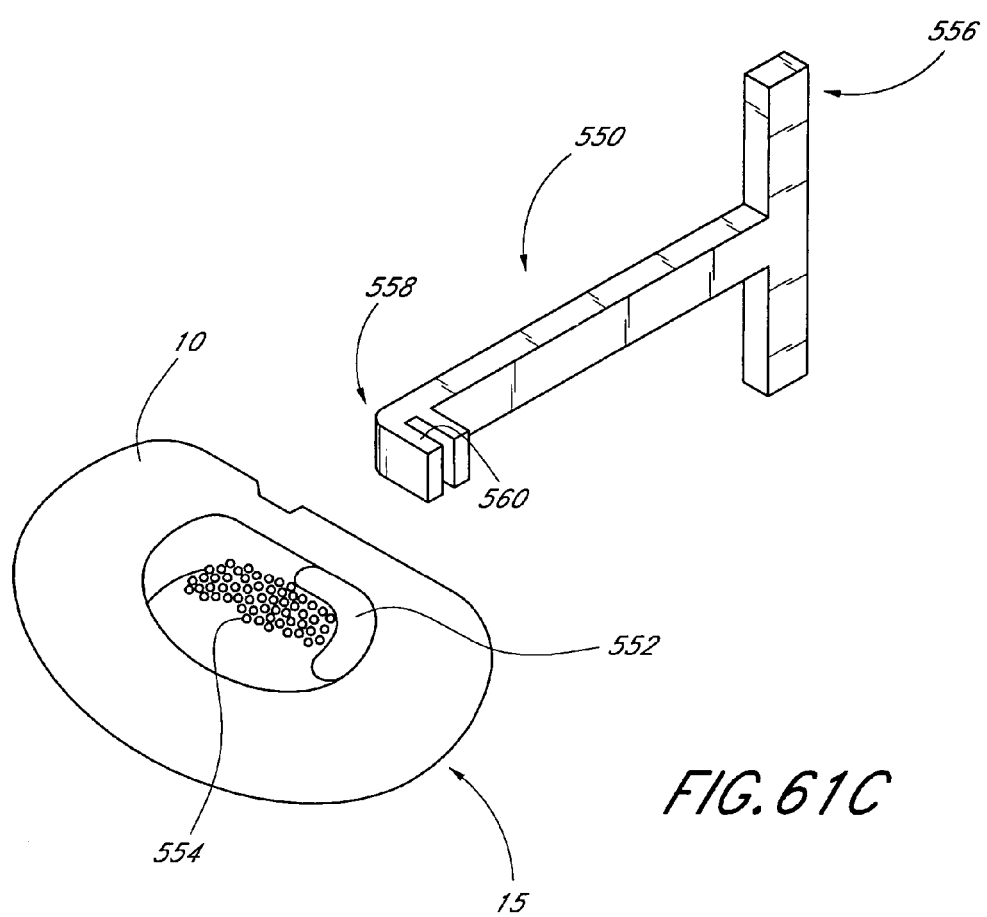
Figure 61D:
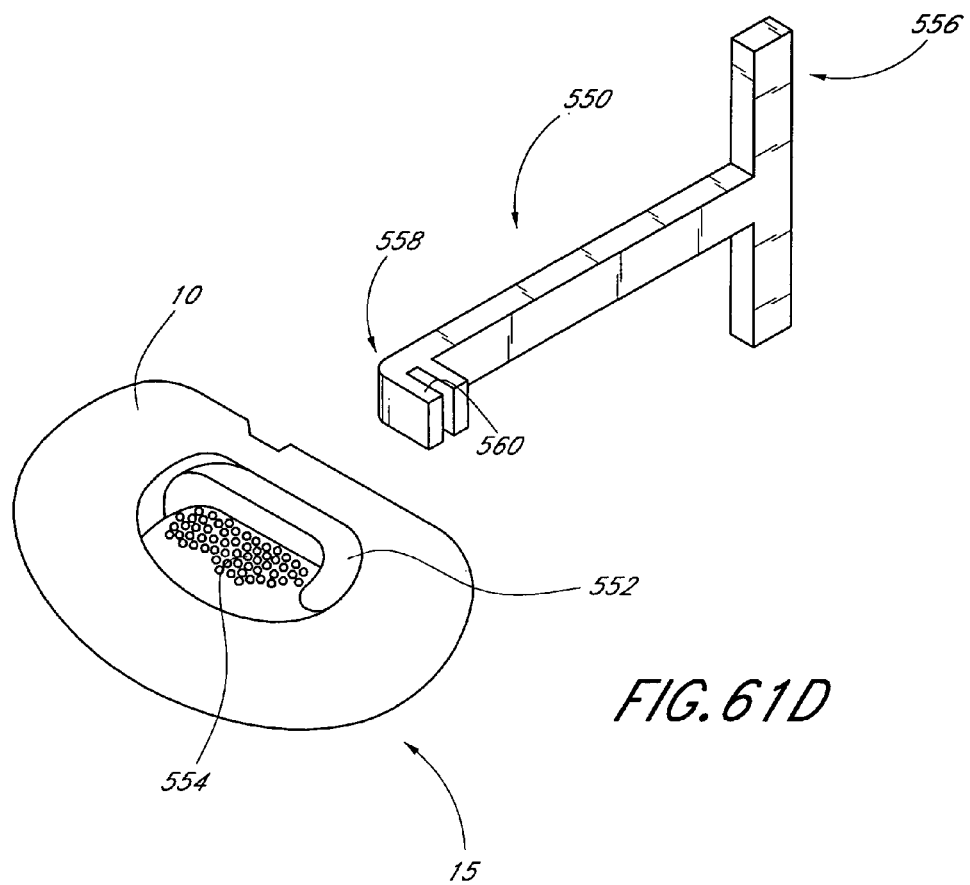

FIGS. 61A-61D illustrate a method of implanting a disc implant. A disc implant 552 is inserted into a delivery device 550. The delivery device 550 has a proximal end 556 and a distal end 558. The distal end 558 of the delivery device 550 is inserted into an annulotomy illustrated in FIG. 61A. The annulotomy is preferably located at a site within the anulus 10 that is proximate to a desired, final implant 552 location. The implant 400 is then deployed by being inserted into the disc 15 through the distal end 558 of the delivery device 550. Preferably the implant is forced away from the final implant location, as shown in FIG. 61B. An implant guide 560 can be used to position the implant 400. Before, during or after deployment of the implant 400, an augmentation material 7 can be injected into the disc 15. Injection of augmentation after deployment is illustrated in FIG. 61C. The augmentation material 7 can include a hydrogel or collagen, for example. In one embodiment, the delivery device 550 is removed from the disc 15 and a separate tube is inserted into the annulotomy to inject the flowable augmentation material 7. Alternately, the distal end 558 of the delivery device 550 can remain within the annulotomy and the fluid augmentation material 554 injected through the delivery device 550. Next, the delivery device 550 is removed from the annulotomy and the intradiscal implant 400 is positioned over the annulotomy in the final implant location, as shown in FIG. 61D. The implant 400 can be positioned using control filaments described above.

Certain embodiments, as shown in FIGS. 62-66, depict anulus and nuclear augmentation devices which are capable of working in concert to restore the natural biomechanics of the disc. A disc environment with a degenerated or lesioned anulus cannot generally support the load transmission from either the native nucleus or from prosthetic augmentation. In many cases, nuclear augmentation materials 7 bulge through the anulus defects, extrude from the disc, or apply pathologically high load to damaged regions of the anulus. Accordingly, in one aspect of the current invention, damaged areas of the anulus are protected by shunting the load from the nucleus 20 or augmentation materials 7 to healthier portions of the anulus 10 or endplates. With the barrier-type anulus augmentation 12 in place, as embodied in various aspects of the present invention, nuclear augmentation materials 7 or devices can conform to healthy regions of the anulus 10 while the barrier 12 shields weaker regions of the anulus 10. Indeed, the anulus augmentation devices 12 of several embodiments of the present invention are particularly advantageous because they enable the use of certain nuclear augmentation materials and devices 7 that may otherwise be undesirable in a disc with an injured anulus.

Figure 62:
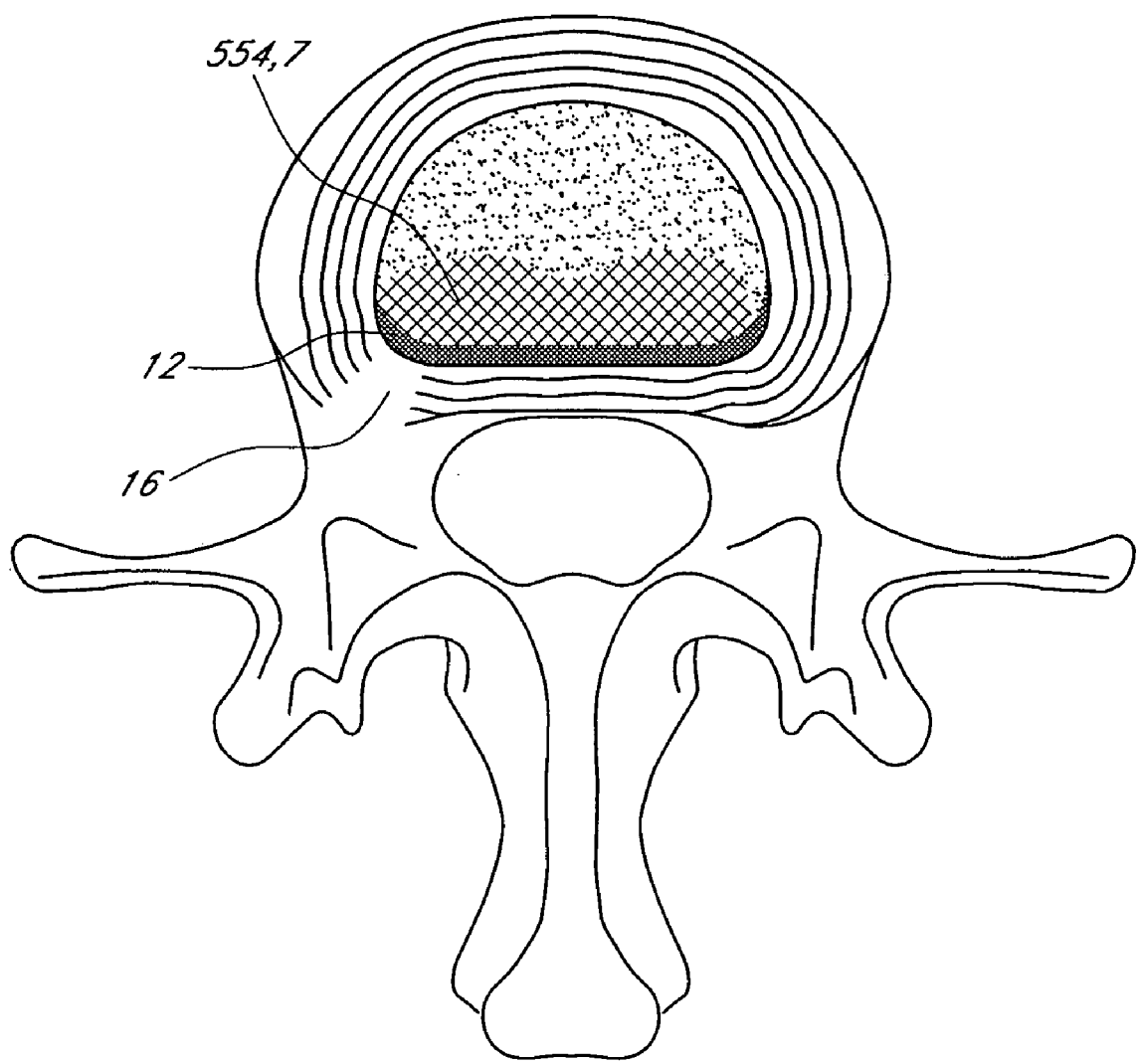
FIG. 62 depicts a cross-sectional transverse view of a barrier device implanted within a disc along the inner surface of a lamella. Implanted conformable nuclear augmentation is also shown in contact with the barrier.

FIG. 62 is a cross-sectional transverse view of an anulus barrier device 12 implanted within a disc 15 along the inner surface of a lamella 16. Implanted conformable nuclear augmentation 7 is also shown in contact with the barrier 12. The barrier device 12 is juxtapositioned to the innermost lamella of the anulus. Conformable nuclear augmentation material 7 is inserted into the cavity which is closed by the barrier 12, in an amount sufficient to fill the disc space in an unloaded supine position. As shown, in one embodiment, fluid nuclear augmentation 554, such as hyaluronic acid, is used.

Fluid nuclear augmentation 554 is particularly well-suited for use in various aspects of the current invention because it can be delivered with minimal invasiveness and because it is able to flow into and fill minute voids of the intervertebral disc space. Fluid nuclear augmentation 554 is also uniquely suited for maintaining a pressurized environment that evenly transfers the force exerted by the endplates to the anulus augmentation device and/or the anulus. However, fluid nuclear augmentation materials 554 used alone may perform poorly in discs 15 with a degenerated anulus because the material can flow back out through anulus defects 8 and pose a risk to surrounding structures. This limitation is overcome by several embodiments of the current invention because the barrier 12 shunts the pressure caused by the fluid augmentation 554 away from the damaged anulus region 8 and toward healthier regions, thus restoring function to the disc 15 and reducing risk of the extrusion of nuclear augmentation materials 7 and fluid augmentation material 554.

Exemplary fluid nuclear augmentation materials 554 include, but are not limited to, various pharmaceuticals (steroids, antibiotics, tissue necrosis factor alpha or its antagonists, analgesics); growth factors, genes or gene vectors in solution; biologic materials (hyaluronic acid, non-crosslinked collagen, fibrin, liquid fat or oils); synthetic polymers (polyethylene glycol, liquid silicones, synthetic oils); and saline. One skilled in the art will understand that any one of these materials may be used alone or that a combination of two or more of these materials may be used together to form the nuclear augmentation material.

Any of a variety of additional additives such as thickening agents, carriers, polymerization initiators or inhibitors may also be included, depending upon the desired infusion and long-term performance characteristics. In general, "fluid" is used herein to include any material which is sufficiently flowable at least during the infusion process, to be infused through an infusion lumen in the delivery device into the disc space. The augmentation material 554 may remain "fluid" after the infusion step, or may polymerize, cure, or otherwise harden to a less flowable or nonflowable state.

Additional additives and components of the nucleus augmentation material are recited below. In general, the nature of the material 554 may remain constant during the deployment and post-deployment stages or may change, from a first infusion state to a second, subsequent implanted state. For example, any of a variety of materials may desirably be infused using a carrier such as a solvent or fluid medium with a dispersion therein. The solvent or liquid carrier may be absorbed by the body or otherwise dissipate from the disc space post-implantation, leaving the nucleus augmentation material 554 behind. For example, any of a variety of the powders identified below may be carried using a fluid carrier. In addition, hydrogels or other materials may be implanted or deployed while in solution, with the solvent dissipating post-deployment to leave the hydrogel or other media behind. In this type of application, the disc space may be filled under higher than ultimately desired pressure, taking into account the absorption of a carrier volume. Additional specific materials and considerations are disclosed in greater detail below.

Figure 63:
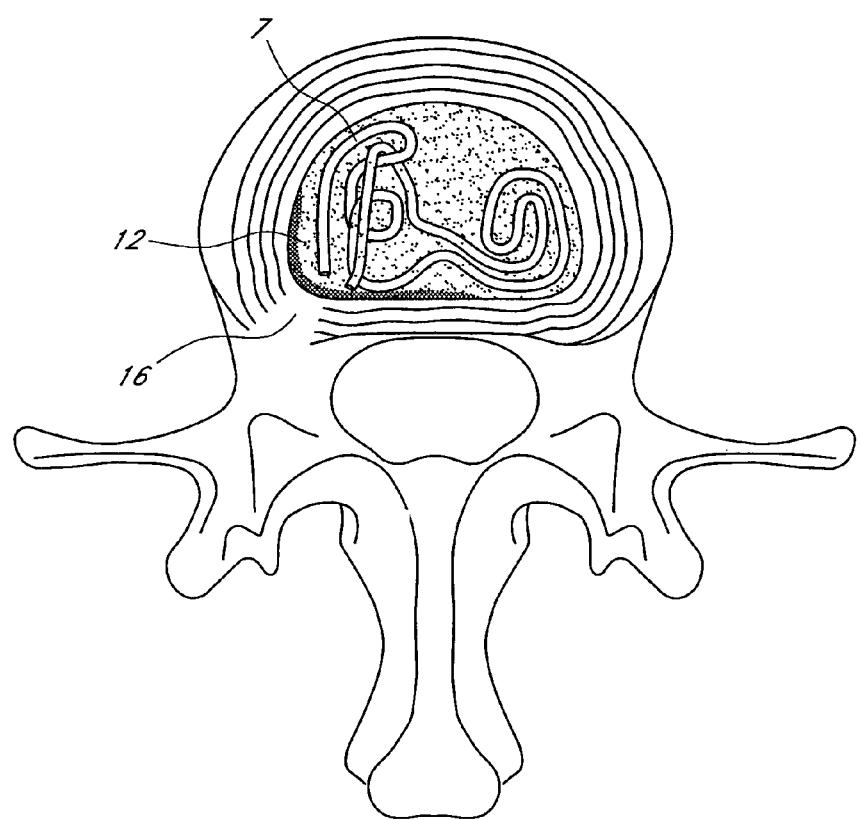
FIG. 63 shows a cross-sectional transverse view of a barrier device implanted within a disc along an inner surface of a lamella. Implanted nuclear augmentation comprised of a hydrophilic flexible solid is also shown.

FIG. 63 is a cross-sectional transverse view of anulus barrier device 12 implanted within a disc 15 along an inner surface of a lamella 16. Implanted nuclear augmentation 7 comprised of a hydrophilic flexible solid is also shown. Nuclear augmentation materials include, but are not limited to, liquids, gels, solids, gases or combinations thereof. Nuclear augmentation devices 7 may be formed from one or more materials, which are present in one or more phases. FIG. 63 shows a cylindrical flexible solid form of nuclear augmentation 7. Preferably, this flexible solid is composed of a hydrogel, including, but not limited to, acrylonitrile, acrylic acid, polyacrylimide, acrylimide, acrylimidine, polyacrylonitrile, polyvinylalcohol, and the like.

FIG. 63 depicts nuclear augmentation 7 using a solid or gel composition. If required, these materials can be designed to be secured to surrounding tissues by mechanical means, such as glues, screws, and anchors, or by biological means, such as glues and in growth. Solid but deformable augmentation materials 7 may also be designed to resist axial compression by the endplates rather than flowing circumferentially outward toward the anulus. In this way, less force is directed at the anulus 10. Solid nuclear augmentation 7 can also be sized substantially larger than the annulotomy 416 or defect 8 to decrease the risk of extrusion. The use of solid materials or devices 7 alone is subject to certain limitations. The delivery of solid materials 7 may require a large access hole 417 in the anulus 10, thereby decreasing the integrity of the disc 15 and creating a significant risk for extrusion of either the augmentation material 7 or of natural nucleus 20 remaining within the disc 15. Solid materials or devices 7 can also overload the endplates causing endplate subsidence or apply point loads to the anulus 10 from corners or edges that may cause pain or further deterioration of the anulus 10. Several embodiments of the present invention overcome the limitations of solid materials and are particularly well-suited for use with liquid augmentation materials 7. The barrier device 12 of various embodiments of this invention effectively closes the access hole 417 and can be adapted to partially encapsulate the augmented nucleus, thus mitigating the risks posed by solid materials.

Solid or gel nuclear augmentation materials 7 used in various embodiments of the current invention include single piece or multiple pieces. The solid materials 7 may be cube-like, spheroid, disc-like, ellipsoid, rhombohedral, cylindrical, or amorphous in shape. These materials 7 may be in woven or non-woven form. Other forms of solids including minute particles or even powder can be considered when used in combination with the barrier device. Candidate materials 7 include, but are not limited to: metals, such as titanium, stainless steels, nitinol, cobalt chrome; resorbable or non-resorbing synthetic polymers, such as polyurethane, polyester, PEEK, PET, FEP, PTFE, ePTFE, Teflon, PMMA, nylon, carbon fiber, Delrin, polyvinyl alcohol gels, polyglycolic acid, polyethylene glycol; silicon gel or rubber, vulcanized rubber or other elastomer; gas filled vesicles, biologic materials such as morselized or block bone, hydroxy apetite, cross-linked collagen, muscle tissue, fat, cellulose, keratin, cartilage, protein polymers, transplanted or bioengineered nucleus pulposus or anulus fibrosus; or various pharmacologically active agents in solid form. The solid or gel augmentation materials 7 may be rigid, wholly or partially flexible, elastic or viscoelastic in nature. The augmentation device or material 7 may be hydrophilic or hydrophobic. Hydrophilic materials, mimicking the physiology of the nucleus, may be delivered into the disc in a hydrated or dehydrated state. Biologic materials may be autologous, allograft, zenograft, or bioengineered.

In various embodiments of the present invention, the solid or gel nuclear augmentation material 7, as depicted in FIG. 63, are impregnated or coated with various compounds. Preferably, a biologically active compound is used. In one embodiment, one or more drug carriers are used to impregnate or coat the nuclear augmentation material 7. Genetic vectors, naked genes or other therapeutic agents to renew growth, reduce pain, aid healing, and reduce infection may be delivered in this manner. Tissue in-growth, either fibrous (from the anulus) or bony (from the endplates), within or around the augmentation material can be either encouraged or discouraged depending on the augmentation used. Tissue in-growth may be beneficial for fixation and can be encouraged via porosity or surface chemistry. Surface in-growth or other methods of fixation of the augmentation material 7 can be encouraged on a single surface or aspect so as to not interfere with the normal range of motion of the spinal unit. In this way, the material is stabilized and safely contained within the anulus 10 without resulting in complete fixation which might cause fusion and prohibit disc function.

Figure 64:
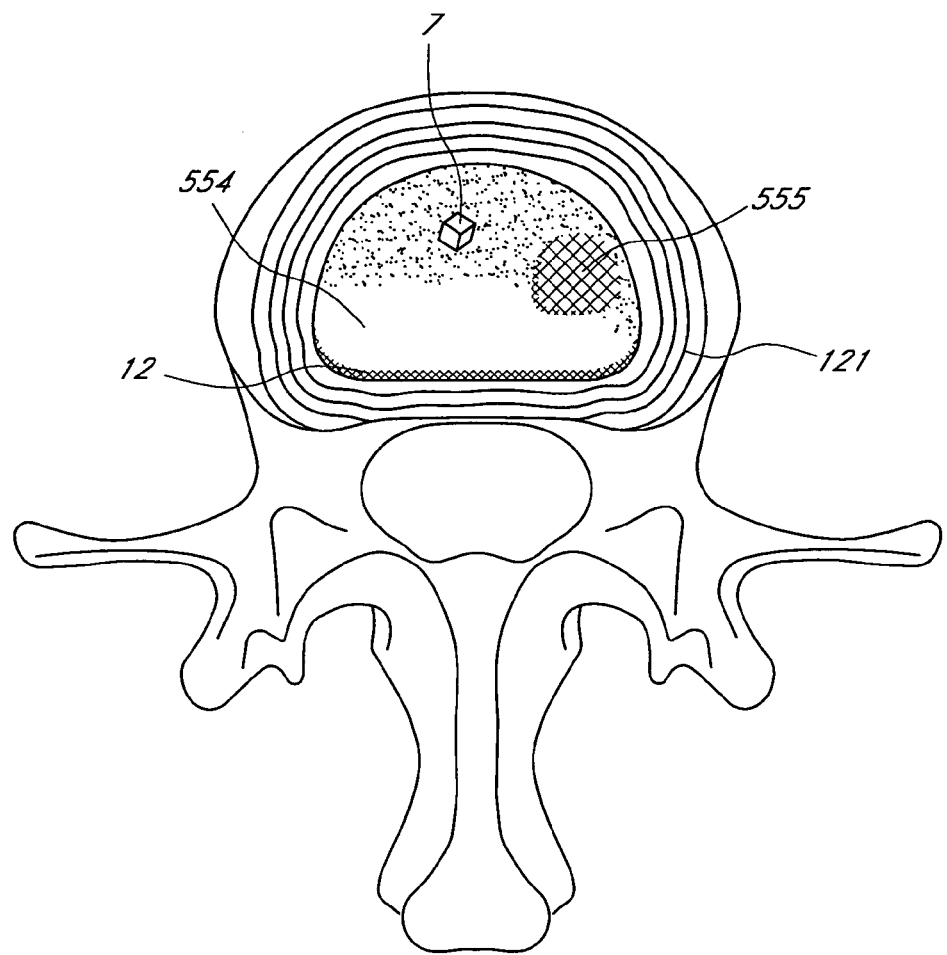
FIG. 64 shows a cross-sectional transverse view of a barrier device implanted within a disc along an inner surface of a lamella. Several types of implanted nuclear augmentation including a solid geometric shape, a composite solid, and a free flowing liquid are also shown.

FIG. 64 is a cross-sectional transverse view of anulus barrier device 12 implanted within a disc 15 along an inner surface of a lamella 16. Several types of implanted nuclear augmentation 7, including a solid cube, a composite cylindrical solid 555, and a free flowing liquid 554 are shown. The use of multiple types of nuclear augmentation with the barrier 12 is depicted in FIG. 64. The barrier device 12 is shown in combination with fluid nuclear augmentation 554, solid nuclear augmentation 7, in the form of a cube, and a cross-linked collagen sponge composite 555 soaked in a growth factor. In several embodiments of the present invention, a multiphase augmentation system, as shown in FIG. 64, is used. A combination of solids and liquids is used in a preferred embodiment. Nuclear augmentation 7 comprising solids and liquids 554 can be designed to create primary and secondary levels of flexibility within an intervertebral disc space. In use, the spine will flex easily at first as the intervertebral disc pressure increases and the liquids flows radially, loading the anulus. Then, as the disc height decreases and the endplates begin to contact the solid or gelatinous augmentation material, flexibility will decrease. This combination can also prevent damage to the anulus 10 under excessive loading as the solid augmentation 7 can be designed to resist further compression such that the fluid pressure on the anulus is limited. In a preferred embodiment, use of multiphase augmentation allows for the combination of fluid medications or biologically active substances with solid or gelatinous carriers. One example of such a preferable combination is a cross-linked collagen sponge 555 soaked in a growth factor or combination of growth factors in liquid suspension.

In one embodiment, the nuclear augmentation material or device 7, 554 constructed therefrom is phase changing, e.g., from liquid to solid, solid to liquid, or liquid to gel. In situ polymerizing nuclear augmentation materials are well-known in the art and are described in U.S. Pat. No. 6,187,048, herein incorporated by reference. Phase changing augmentation preferably changes from a liquid to a solid or gel. Such materials may change phases in response to contact with air, increases or decreases in temperature, contact with biologic liquids or by the mixture of separate reactive constituents. These materials are advantageous because they can be delivered through a small hole in the anulus or down a tube or cannula placed percutaneously into the disc. Once the materials have solidified or gelled, they can exhibit the previously described advantages of a solid augmentation material. In a preferred embodiment, the barrier device is used to seal and pressurize a phase changing material to aid in its delivery by forcing it into the voids of the disc space while minimizing the risk of extrusion of the material while it is a fluid. In this situation, the barrier or anulus augmentation device 12 may be permanently implanted or used only temporarily until the desired phase change has occurred.

In another embodiment, an anulus augmentation device 12 that exploits the characteristics of nucleus augmentation devices or materials to improve its own performance is provided. Augmenting the nucleus 20 pressurizes the intervertebral disc environment which can serve to fix or stabilize an anulus repair device in place. The nucleus 20 can be pressurized by inserting into the disc 15 an adequate amount of augmentation material 7, 554. In use, the pressurized disc tissue and augmentation material 7, 554 applies force on the inwardly facing surface of the anulus augmentation device 12. This pressure may be exploited by the design of the anulus prosthesis or barrier 12 to prevent it from dislodging or moving from its intended position. One exemplary method is to design the inwardly facing surface of the anulus prosthesis 12 to expand upon the application of pressure. As the anulus prosthesis 12 expands, it becomes less likely to be expelled from the disc. The prosthesis 12 may be formed with a concavity facing inward to promote such expansion.

In several embodiments, the anulus augmentation device 12 itself functions as nuclear augmentation 7. In a preferred embodiment, the barrier 12 frame is encapsulated in ePTFE. This construct typically displaces a volume of 0.6 cubic centimeters, although thicker coatings of ePTFE or like materials may be used to increase this volume to 3 cubic centimeters. Also, the anulus augmentation device may be designed with differentially thickened regions along its area.

Figure 65:
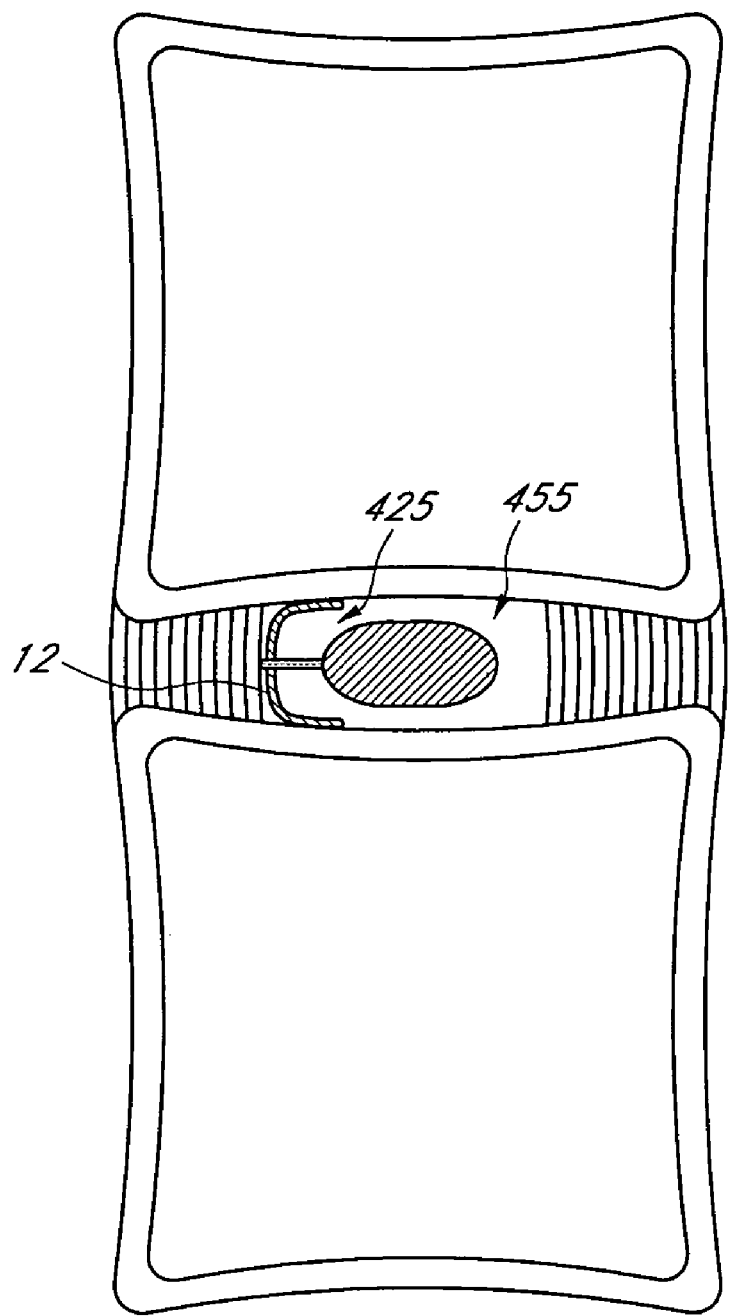
FIG. 65 illustrates a sagittal cross-sectional view of a barrier device connected to an inflatable nuclear augmentation device.

FIG. 65 depicts a sagittal cross-sectional view of the barrier device connected to an inflatable nuclear augmentation device 455. The barrier device 12 is shown connected via hollow delivery and support tube 425 to an nuclear augmentation sack 455 suitable for containing fluid material 554. The tube 425 has a delivery port or valve 450 that extends through the barrier device and can be accessed from the access hole 417 after the barrier device 12 and augmentation sack 455 has been delivered. This nuclear and anulus augmentation combination is particularly advantageous because of the ease of deliverability, since the sack 455 and the barrier 12 are readily compressed. The connection of the barrier 12 and the augmentation sack 455 also serves to stabilize the combination and prevent its extrusion from the disc 15. The nuclear augmentation 7 may be secured to the anulus augmentation prosthesis 12 to create a resistance to migration of the overall construct. Such attachment may also be performed to improve or direct the transfer of load from the nuclear prosthesis 7 through the anulus prosthesis 12 to the disc tissues. The barrier 12 and augmentation 7 can be attached prior to, during, or after delivery of the barrier 12 into the disc 15. They may be secured to each other by an adhesive or by a flexible filament such as suture. Alternatively, the barrier 12 may have a surface facing the augmentation material 7 that bonds to the augmentation material 7 though a chemical reaction. This surface may additionally allow for a mechanical linkage to a surface of the augmentation material 7. This linkage could be achieved through a porous attachment surface of the barrier 12 that allows the inflow of a fluid augmentation material 7 that hardens or gels after implantation.

Alternatively, the anulus augmentation device 12 and nuclear augmentation material 7 may be fabricated as a single device with a barrier 12 region and a nuclear augmentation region 7. As an example, the barrier 12 may form at least a portion of the surface of an augmentation sack 455 or balloon. The sack 455 may be filled with suitable augmentation materials 7 once the barrier has been positioned along a weakened inner surface of the anulus 10.

The sequence of inserting the barrier 12 and nuclear augmentation 7 in the disc can be varied according to the nuclear augmentation 7 used or requirements of the surgical procedure. For example, the nuclear augmentation 7 can be inserted first and then sealed in place by the barrier device 12. Alternatively, the disc 15 can be partially filled, then sealed with the barrier device 12, and then supplied with additional material 7. In a preferred embodiment, the barrier device 12 is inserted into the disc 15 followed by the addition of nuclear augmentation material 7 through or around the barrier 12. This allows for active pressurization. A disc 15 with a severely degenerated anulus can also be effectively treated in this manner.

In an alternative embodiment, the nuclear augmentation material 7 is delivered through a cannula inserted through an access hole 417 in the disc 15 formed pathologically, e.g. an anular defect 8, or iatrogenically, e.g. an anuulotomy 416 that is distinct from the access hole 417 that was used to implant the barrier 12. Also, the same or different surgical approach including transpsoas, presacral, transsacral, tranpedicular, translaminar, or anteriorly through the abdomen, may be used. Access hole 417 can be located anywhere along the anulus surface or even through the vertebral endplates.

In alternative embodiments, the anulus augmentation device 12 includes features that facilitate the introduction of augmentation materials 554 following placement. The augmentation delivery cannula may simply be forcibly driven into an access hole 417 proximal to the barrier 12 at a slight angle so that the edge of the barrier 12 deforms and allows passage into the disc space. Alternatively, a small, flexible or rigid curved delivery needle or tube may be inserted through an access hole 417 over (in the direction of the superior endplate) or under (in the direction of the inferior endplate) the barrier 12 or around an edge of the barrier 12 contiguous with the anulus 15.

In several embodiments, ports or valves are installed in the barrier 12 device that permit the flow of augmentation material into, but not out of, the disc space. One-way valves 450 or even flaps of material held shut by the intervertebral pressure may be used. A collapsible tubular valve may be fashioned along a length of the barrier. In one embodiment, multiple valves or ports 450 are present along the device 12 to facilitate alignment with the access hole 417 and delivery of augmentation material. Flow channels within or on the barrier 12 to direct the delivery of the material 554 (e.g. to the ends of the barrier) can be machined, formed into or attached to the barrier 12 along its length. Alternatively, small delivery apertures (e.g. caused by a needle) can be sealed with a small amount of adhesive or sutured shut.

Figure 66:
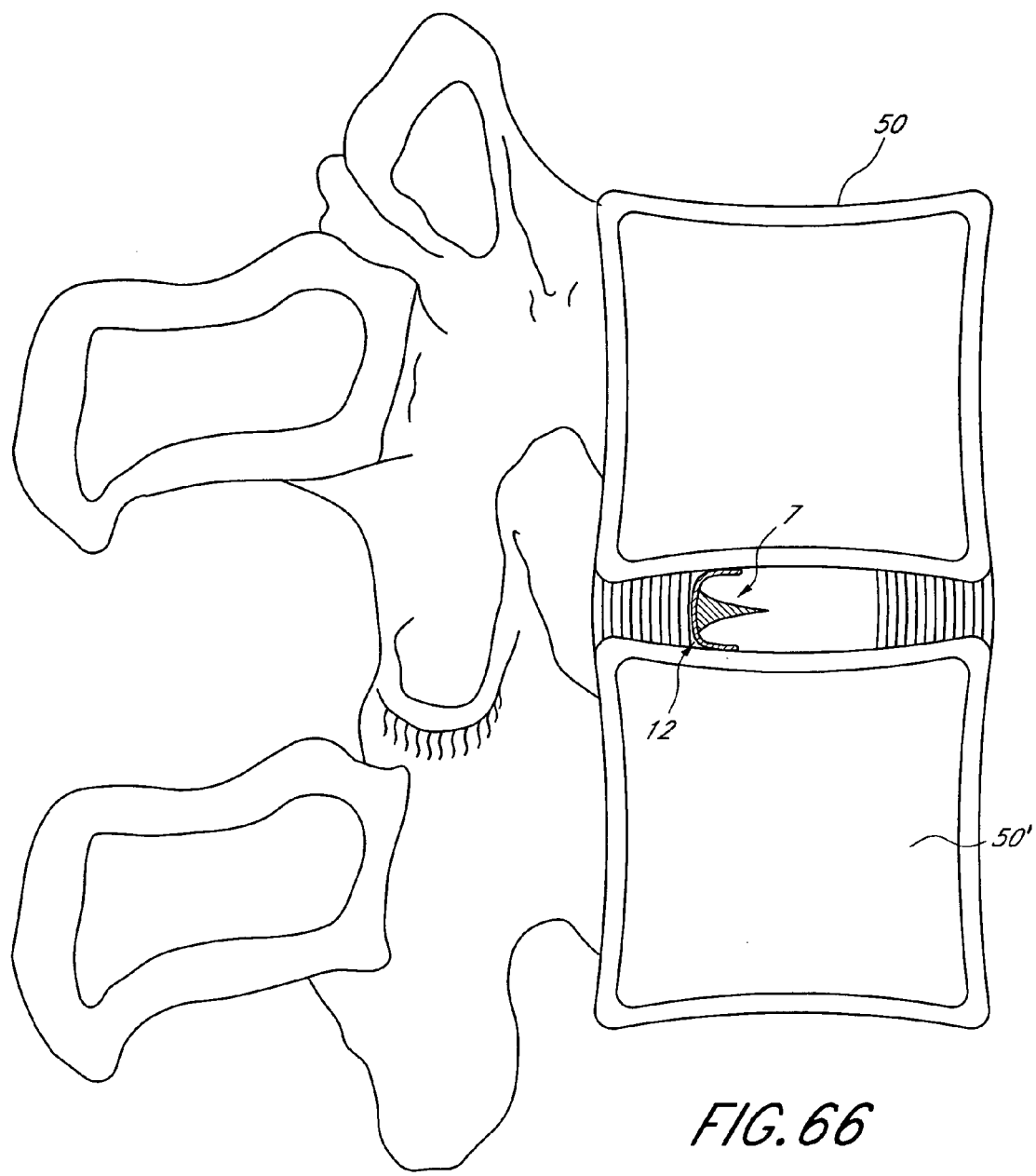
FIG. 66 depicts a sagittal cross-sectional view of a functional spine unit containing a barrier device unit connected to a wedge shaped nuclear augmentation device.

FIG. 66 is sagittal cross-sectional view of a functional spine unit containing the barrier device unit 12 connected to a wedge-shaped nuclear augmentation 7 device. FIG. 66 illustrates that the geometry of the nuclear augmentation 7 can be adapted to improve the function of the barrier. By presenting nuclear augmentation 7 with a wedge-shaped or hemicircular profile towards the interior of the intervertebral disc space, and attaching it in the middle of the barrier device 12 between the flexible finger-like edges of the barrier device, the force exerted by the pressurized environment is focused in the direction of the edges of the barrier device sealing them against the endplates. Accordingly, this wedge-shaped feature improves the function of the device 12. One skilled in the art will understand that the nuclear augmentation material 7 may also be designed with various features that improve its interaction with the barrier, such as exhibiting different flexibility or viscosity throughout its volume. For example, in certain applications, it may be preferable for the augmentation 7 to be either stiff at the interface with the barrier 12 and supple towards the center of the disc, or vice versa. The augmentation 7 can also serve to rotationally stabilize the barrier 12. In this embodiment, the augmentation is coupled to the inward facing surface of the barrier and extends outward and medially into the disc forming a lever arm and appearing as "T-shaped" unit. The augmentation device 7 of this embodiment can extend from the middle of the disc 15 to the opposite wall of the anulus.

Figure 67:
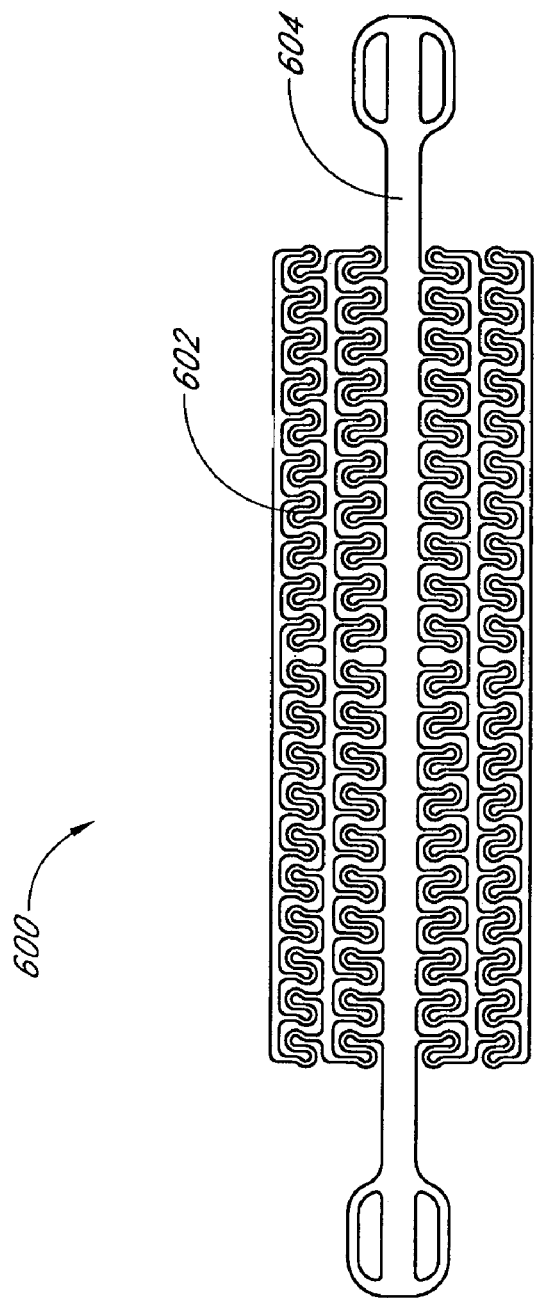
FIG. 67 shows an anulus augmentation device (such as a mesh) mesh having a series of curvilinear elements.

In one embodiment, the anulus augmentation device comprises a mesh. FIG. 67 shows one example of a meshed anulus augmentation device. In one embodiment, a repair mesh that is resilient is provided. In some embodiments, the mesh is particularly advantageous because it can withstand millions of motion cycles within the disc environment, and is resistant to fatigue. In several embodiments, fatigue resistance is accomplished by material properties, structural design, or a combination thereof. For a given material, a fatigue resistant structure can be designed to distribute the strain of deformation as evenly as possible over as much material as possible so as to minimize stress concentrations that could initiate fatigue cracks. For example, a coiled spring may deform millions of times without failure or cracking because the strain is distributed evenly over a length of metal. For an anulus repair mesh, the same effect maybe achieved by means such as, but not limited to, providing more material for a given deformation site by having mesh members curved throughout their lengths, alternating mesh curves in a sine-wave or zigzag pattern to provide more material and distributed strains, or having longer non linear members such that a given deformation results in less material strain, or pre-shaping the implant to minimize strain at the implantation site. The curvilinear, nonlinear, coiled, or angled members can be interconnected, woven, networked, or emanate from or be attached to rails or members to form a framework or define a mesh or barrier.

In one embodiment, a mesh can be used in a variety of locations in and around the intervertebral disc. It can be placed on an external surface of the anulus, along an endplate, within the anulus, between the anulus and nucleus, within the nucleus, or within both the anulus and nucleus. The mesh can be held in place via counteracting forces of the mesh as it flexes from its unstressed shape to stressed shape or friction with disc tissue, between disc and vertebral body tissue or between disc augmentation material or another implant and disc tissue. The mesh can also have a porosity or macrotexture including ridges, spikes or spirals to increase bioincorporation and fixation. Fixation devices, including but not limited to, sutures, glue, screws, and staples can be used to permanently fix the mesh in place.

In one embodiment, the anulus augmentation device is a barrier comprising a membrane and a frame. In some embodiments, the frame is the mesh. In other embodiment, the mesh is coated with the membrane. In another embodiment, the anulus augmentation device comprises only a frame.

In one embodiment, the mesh or frame region of the implant can preferably be formed from a relatively thin sheet of material. The material may be a polymer (including in-situ polymerizing), metal, or gel. However, as discuss infra, the superelastic properties of nickel titanium alloy (NITINOL) makes this metal particularly advantageous in this application. Other materials suitable for this application include one or more of the following: nylon, polyvinyl alcohol, polyethylene, polyurethane, polypropylene, polycaprolactone, polyacrylate, ethylene-vinyl acetates, polystyrene, polyvinyl oxide, polyvinyl fluoride, polyvinyl imidazole, chlorosulphonated polyolefins, polyethylene oxide, polytetrafluoroethylene and nylon, and copolymers and combinations thereof, polycarbonate, Kevlar™, acetal, cobalt chrome, carbon, graphite, metal matrix composites, stainless steel and other metals, alloys and composites. Some materials may be coated to achieve biocompatibility. These materials can also be used for frames or support member that do not comprise meshes.

In some embodiments, the mesh or frame designs may have sharp edges or have gaps that may allow for tissue transfer outside of the disc. In one embodiment, a membrane may be secured to one or more sides or portions of the mesh or frame in order to resist transfer of particles across its periphery and outside of the disc or to shield the body from the mesh's sharp edges. Also, a membrane can prevent the flow of a material bounded by the anulus fibrosis of the intervertebral disc through a defect in the anulus fibrosis if the device is positioned across the defect.

In a preferred embodiment, the size of the mesh device is dictated by the particular region of the functional spinal unit sought to be treated. For example, In one embodiment, a mesh intended for coverage the interior surface of the posterior lateral anulus can be about 2 cm to about 4 cm in length and about 2 mm to about 15 mm in height. Likewise, the mesh can be sized to cover the entire exterior or interior surface of a disc. Also, if a defect or weakened segment of the disc is pre-opertively identified, the size of the mesh can be selected to adequately span it in more than one direction. In one embodiment, the mesh is sized such that it spans all directions by at least about 2 mm. The overlap provided by the about 2 mm or more mesh, in some embodiments, provides mechanical means by which the mesh resists extrusion through a defect. Where a case dictates that a device is not available for full coverage of a portion of the anulus, the surgeon can select a mesh, barrier, or patch that is sized such that even if the barrier shifts along an axis in either direction, the selected width ensures that there remains about 2 mm or more of the device beyond the edge of the defect in all positions along that portion of the anulus. In this way a surgeon can determine a minimum implant size that will still be efficacious.

In one embodiment, the anulus augmentation device, such as a mesh or a membrane/frame combination, has a thickness in a range between about 0.025 mm to about 3 mm. Nucleus pulposus particles have been measured at around 0.8 mm$^2$. Accordingly, in one embodiment, the anulus augmentation device, such as a mesh or a membrane/frame combination, has pores slightly smaller (e.g., about 0.05 mm$^2$ to about 0.75 mm²) and still function as a means to prevent extrusion of nuclear material from the disc. Alternatively, one of ordinary skill in the art can through experimentation determine the size of disc particles sought to be contained by the mesh and size the pores slightly smaller. Such a design affords the fluid transfer of other smaller particles and especially water, blood, and other tissue fluids.

In several embodiments, the cross-section of the mesh can be flat, concave, convex or hinged (or flexibly connected) along at least a portion of one or more horizontal axes or vertical axes. One of skill in the art will understand that other cross-sections can also be used in accordance with several embodiments of the invention.

It has been determined that in procedures wherein only a limited amount of nucleus or anulus tissue is removed from a pathologic disc, approximately 0.2 to about 2.0 cc of tissue is typically removed. Accordingly, to replace this volume loss and contribute to the biomechanical function of the spine, spinal implants can be designed to replace this volume (about 0.2 to 2.0 cc) through selection of materials and their dimensions. Accordingly, in one embodiment, an implant having a volume of about 0.2 to about 2.0 cc is provided. The implant can include an anulus augmentation device, a nuclear augmentation device or an anulus augmentation/nuclear augmentation combination device. Preferably, a device having an overall volume of about 0.5 cc is provided because this is the most typical volume removed. Also, greater volumes may be used to further increase the volume of the disc in cases where disc height has decreased over time and the fragments have been metabolized (and thus do not require removal).

In one embodiment, an implant comprising a frame and a membrane is provided. In other embodiments, the implant comprises only one or more membranes. In one embodiment, the implant comprises only one or more frames. The frame may be coated. The membrane (or coating) can be comprised of any suitably durable and flexible material including polymers, elastomers, hydrogels and gels such as polyvinyl alcohol, polyethylene, polyurethane, polypropylene, polycaprolactone, polyacrylate, ethylene-vinyl acetates, polystyrene, polyvinyl oxides, polyvinyl fluorides, polyvinyl imidazole, chlorosulphonated polyolefin, polyethylene oxide, polytetrafluoroethylene, a nylon, silicone, rubber, polylactide, polyglycolic acid, polylactide-co-glycolide, polycaprolactone, polycarbonate, polyamide, polyanhydride, polyamino acid, polyortho ester, polyacetal, polycyanoacrylate, degradable polyurethane, copolymers and derivatives and combinations thereof. Biological materials including keratin, albumin collagen, elastin, prolamines, engineered protein polymers, and derivatives and combinations thereof, may also be used.

In one embodiment, at least a portion of the anulus augmentation device (e.g., the membrane, mesh, barrier, etc,) can be impregnated with, coated with, or designed to carry and deliver diagnostic agents and/or therapeutic agents. Diagnostic agents include, but are not limited to, radio-opaque materials suitable to permit imaging by MRI or X-ray. Therapeutic agents include, but are not limited to, steroids, genetic vectors, antibodies, antiseptics, growth factors such as somatomedins, insulin-like growth factors, fibroblast growth factors, bone morphogenic growth factors, endothelial growth factors, transforming growth factors, platelet derived growth factors, hepatocytic growth factors, keratinocyte growth factors, angiogenic factors, immune system suppressors, antibiotics, living cells such as fibroblasts, chondrocytes, chondroblasts, osteocytes, mesenchymal cells, epithelial cells, and endothelial cells, and cell-binding proteins and peptides. In other embodiments, the nuclear augmentation device can be impregnated, coated, or designed to carry diagnostic and/or therapeutic agents.

In one embodiment, as shown in FIG. 67, a mesh having a series of curvilinear elements 602 is provided. In one embodiment, the curvilinear elements 602 are interconnected. One of skill in the art will understand that the curvilinear elements 602 can exist independently of each other, or only be partially connected. The interconnections 602 can be distributed to form one or more contiguous horizontal bands, rails, members, struts, or axes 604. FIG. 67 shows such a device with a central horizontal axis 604 and "S" shaped curvilinear elements 602. In one embodiment, the "S" shaped elements 602 tend to distribute the stress generated under compression over a larger area. In one embodiment, only portions of the "S" move out of plane during loading providing stiffness. In some embodiments, the curvilinear elements are particularly advantageous because they provide flexibility, resilience and/or rigidity.

In some embodiments, the curvilinear elements 602 can be oriented about 90 degrees (curving in the ventral/dorsal axis) such that the curves appear in the overall horizontal cross-section of the implant. In other embodiments, the curvilinear elements 602 are substantially flat. The curvilinear elements 602 can also be oriented at any angle (e.g., from about 1 degree to about 179 degrees) from the plane. The mesh 600 can be straight, convex or concave in cross-section. FIGS. 68A-G show the profile of a mesh with various curvilinear elements. FIGS. 68D-G show top cross-sectional views of the mesh being elongated "U" shaped, "C" shaped, curvilinear shaped (like a typical posterior anulus interior surface), and "D" shaped to extend along and cover the entire inner anulus surface.

Figure 69:
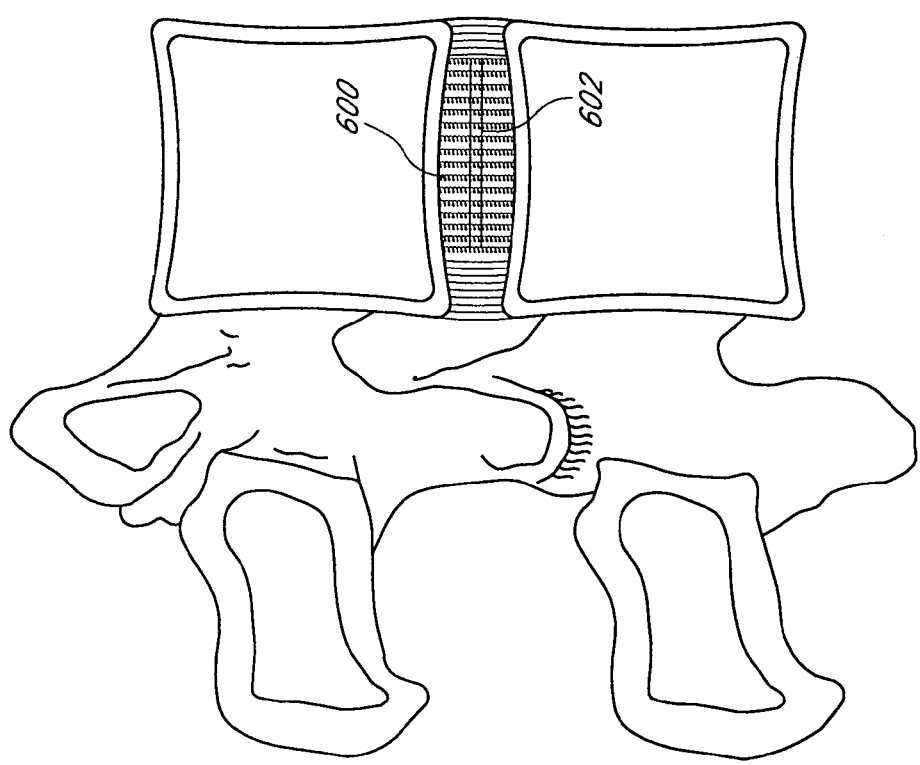
FIG. 69 shows one embodiment of a mesh with curvilinear elements implanted in an intervertebral disc.

FIG. 69 shows yet another embodiment of a mesh 600 implanted in an intervertebral disc. Here, the curvilinear elements 602 comprise springs, coils, or telescopic members that are adapted to compress axially (like pneumatic pistons or coil springs) under loading rather than bending and conforming to a tissue surface, e.g. the inner surface of the anulus. One advantage of a spring or coil-type mesh is that the mesh can be fairly rigid and resistant to lateral or transverse force but is flexible enough to span around the curvatures of the disc while maintaining contact with the endplates under compression and expansion. Like other curvilinear elements, the springs or coils can be interconnected, linked in a loose or hinge-like arrangement, attached to a horizontal band or axis, attached to a membrane, or encapsulated within a membrane, or portions thereof.

Figure 70:
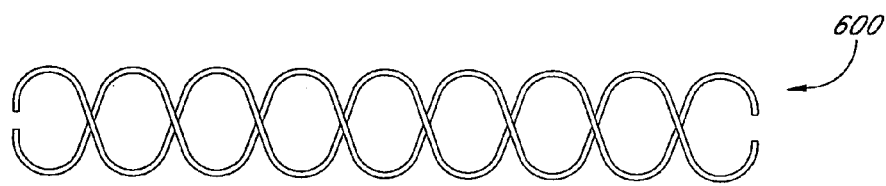
FIG. 70 shows a wire-type anulus augmentation device.

In one embodiment, the mesh may also be configured (e.g., from wire or stock) in a pattern comprising a series of repeating curved peaks and valleys oriented in a lateral manner. Two or more curved wires may be superimposed out of phase such that one peak is inferior to the adjacent wires valley. The two wires can be independent, contiguous and formed from a single wire, connected at one or more points, attached to a membrane, or encapsulated within a membrane. FIG. 70 shows a wire-type anulus augmentation device.

Figure 71A:
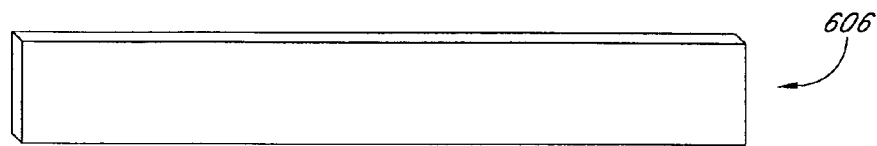
FIGS. 71A-E show a frame (e.g., mesh) that has been encapsulated by a membrane or cover to produce an encapsulated mesh.
Figure 71B:
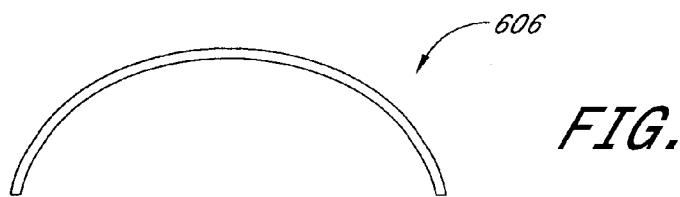
Figure 71C:
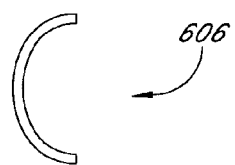
Figure 71D:
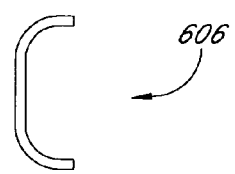
Figure 71E:
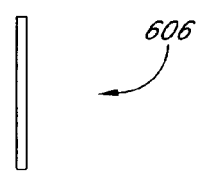

As discussed above, an annulus augmentation device can comprise, for example, a frame, a membrane or a frame/membrane combination. FIG. 70 shows just the frame, which can be, for example, a wire or mesh-like device. FIGS. 71A-E show a mesh that has been encapsulated by a membrane or cover to produce an encapsulated mesh 606. FIGS. 71C shows a top view cross-section wherein the mesh is elongated U shaped and 71D through 71F show various side view cross-sections wherein the mesh is straight or possesses varying degrees of concavity. As with other barriers disclosed herein, the membrane or encapsulation material may be of substantial thickness or may be substantially thin. Indeed, the encapsulation material may simply be a coating.

Figure 72A:
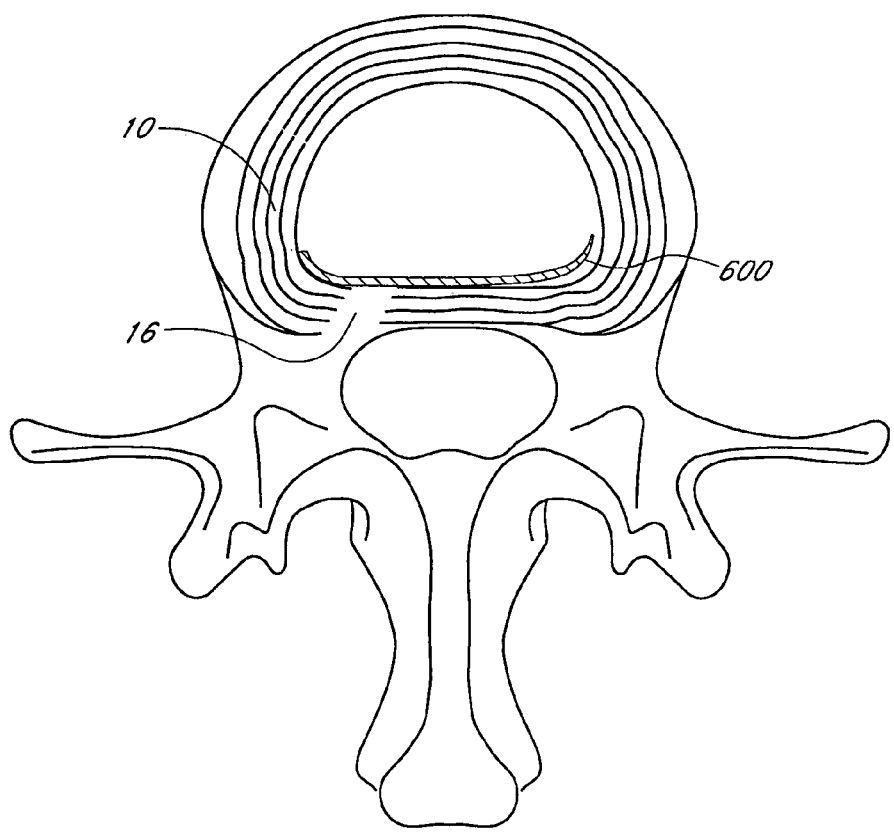
FIGS. 72A-B show a mesh having a double-wishbone frame.
Figure 72B:
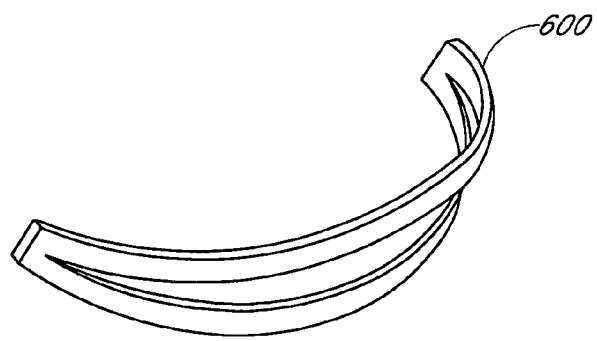
Figure 75B:
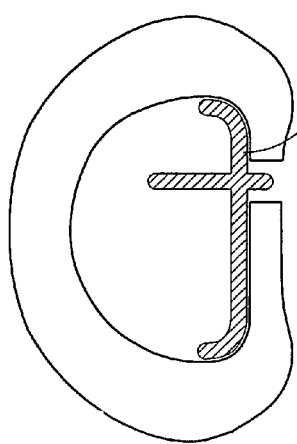
FIGS. 75A-L show an implant an annulus augmentation device such as a mesh having one or more projections extending into the disc or into a defect.
Figure 75D:
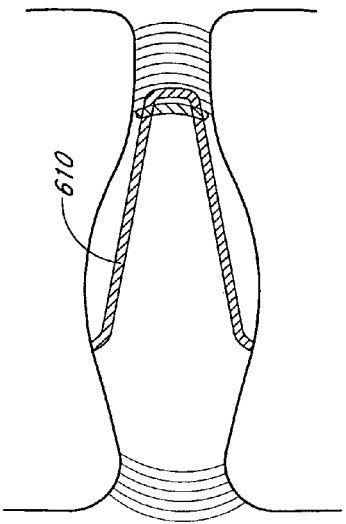
Figure 75A:
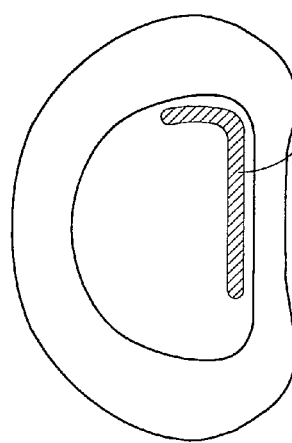
Figure 75C:
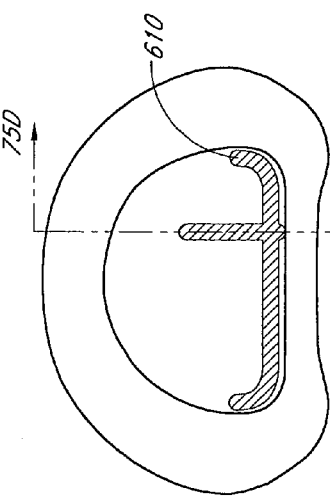
Figure 75F:
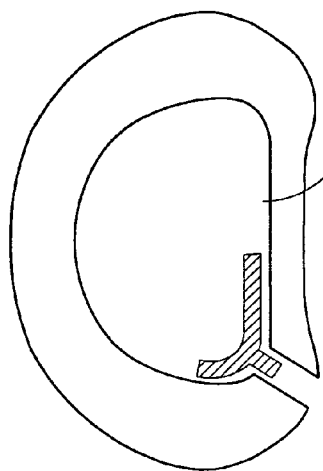
Figure 75H:
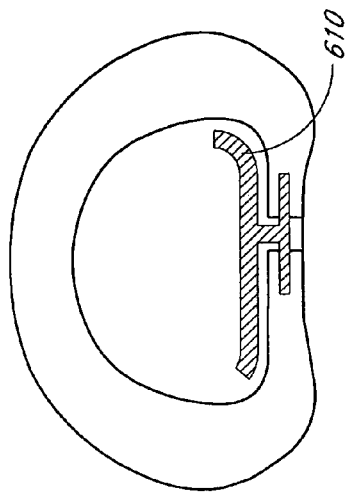
Figure 75E:
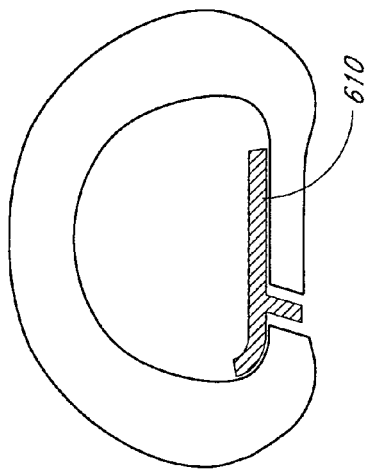
Figure 75G:
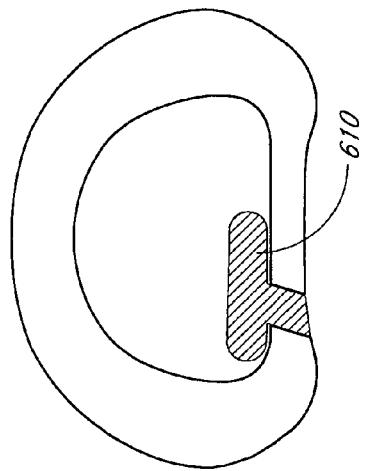
Figure 75I:
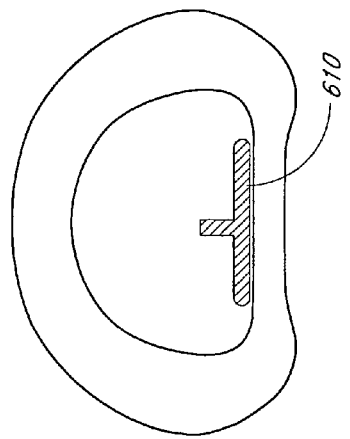
Figure 75J:
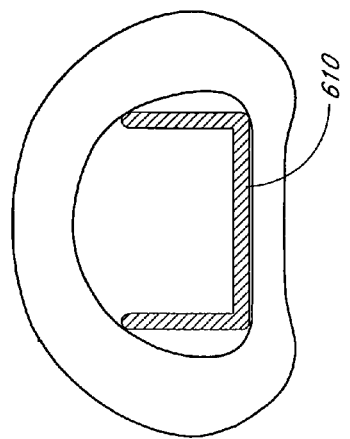
Figure 75K:
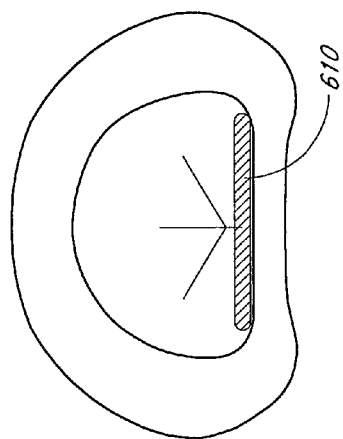
Figure 75L:
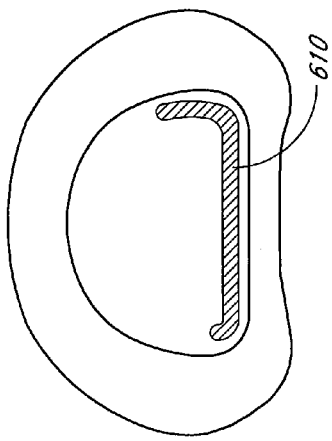

In another embodiment, as shown in FIGS. 72A-B, a mesh 600 having a double-wishbone frame with or without membrane cover is provided. In some embodiments, this design is particularly advantageous because it reduces the compression and stress experienced by the implant under flexion, extension, and lateral bending. FIG. 72A shows the frame without a membrane situated along a posterior portion of the disc. The implant (e.g., the frame) can also be placed on the outside of the anulus, within the anulus, between the nucleus and anulus or within the nucleus. Also shown is a defect 16 in the anulus 10 and placement of the frame 600 across the defect and spanning beyond it in more than a single direction. FIG. 72B shows the mesh in a perspective view outside of the disc. The frame (e.g., mesh) can be flat or an elongated "U" shaped corresponding to the inner surface of the posterior anulus. In one embodiment, the frame can be a single continuous band or wire forming two ends, a first end and a second end. In one embodiment, each end functions as a living hinge and forms an apex which may be in the form of a curve, a bend, or series of bends such that the wire is generally redirected in the opposite direction. Accordingly, if a load is applied along the vertical axis at the midpoint of the frame, e.g., the midpoint of the top and bottom (superior, inferior) rail, each corner or apex is loaded equally and the wire rails act as levers.

In one embodiment, the mesh 600 can be implanted such that the midpoint of the mesh frame 600 is in the posterior of the disc and the ends reside medially or even in the anterior portion of the disc. In this way the portion of the mesh 600 that undergoes the greatest compression is furthest away from each end. Accordingly, a relatively large range of motion can be traversed by the middle of the device but this will only translate to limited motion at each end or living hinge, thus reducing stress and fatigue. Also, by placing each end (which has a relatively small profile) at opposing sides at the midline of the disc (the center of rotation) it is subjected to almost no direct loading under lateral bending, flexion, extension, or compression by the endplates.

FIGS. 73A-C shows other embodiments for the end or natural hinge portion of the frame (e.g., mesh 600), including a loop formation.

FIGS. 74A-C show some embodiments of the central band or strut 604. FIGS. 74A-B show a central reinforcement band 604 disposed between the ends or apexes of the frame (e.g., mesh). As shown in FIG. 74B, the central band 604 can be positioned between the top rail (or wire) 603 and bottom rail (or wire) 605. As shown in FIG. 74C, the central band 604 can be elongated to form a concave cross-section between the top and bottom rail or wire.

In several embodiments of the invention, an implant (e.g., an anulus augmentation device, such as a mesh) can exhibit different mechanical properties along various axes. For example, an implant can exhibit rigidity along a first axis and flexibility (or less rigidity) along a second axis transverse or perpendicular to the first. Such an implant might find particular utility along the wall of an anulus between two adjacent vertebrae because such an environment will subject the implant to vertical compression (e.g., along the superior/inferior axis) yet will not compress the implant laterally. As such, the implant can retain its rigidity along its horizontal axis. Rigidity along the horizontal axis of anulus augmentation device is especially useful in some embodiments if the implant is placed in front of a weakened or defective surface of the anulus because a point load will like form at that region when the disc is compressed under loading and could cause the implant to bend and extrude. Accordingly, an implant having a certain degree of rigidity along its lateral axis resists such bending and extrusion. Moreover, because of the less rigid and more flexible behavior of the implant along its vertical axis loads caused flexion and extension of the spine will allow the implant to flex naturally with the spine and not injure the endplates.

In some embodiments, to achieve the differences in mechanical properties, any number of construction, material selection or fabrication techniques known in the art can be used. For example, the implant may be made thicker or thinner at points along a particular axis or voids or patterns may be cut into the material. Also, a composite implant having different material sandwiched together can also be used. Struts, members, rails and the like may be added to, secured to, or integral to the implant to provide stiffness and rigidity. Further, such stiffening elements can be added during the implantation procedure.

In one embodiment, the implant can also be corrugated along an axis or otherwise be provided with bents or curves to provide stiffness. A gentle curve or "C" shaped cross-section that could also conform or correspond to the inner curved surface of an anulus is also preferable for making a seal with the anulus and for resisting bending along the implant horizontal axis e.g., the curve would resist flattening out, flexing or bending laterally. Also, in some embodiments the implant can be oversized such that it remains in compression along one or more of its axes in its implanted state such that even under flexion and extension of the spine the corrugations or curved sections never flatten out and thus retain rigidity (or less flexibility) along an axis perpendicular to the curves.

One of skill in the art will understand that, in several embodiments, the implant (e.g., an anulus augmentation device, such as a mesh) can be more or less rigid or flexible, according to the preference of the practitioner or disc environment. The degree of desired rigidity and flexibility along each axis can be determined based on factors such as defect size, intervertebral pressure, implant deliverability, desired degree of compression and disc height.

According to one embodiment of the invention, an implant has a "C" cross-section, a central rail and top and bottom rails, and curvilinear elements connect the rails. The frame or mesh can be comprised of any of the suitable materials discussed herein, (e.g. nickel titanium) and can also be coated, covered, bonded, or coupled to a cover or membrane. In one embodiment, the implant is more rigid along its lateral axis because of its "C" cross-section or the rails and less rigid along its vertical axis because of the void caused by the pattern and lack of corrugations or stiffening elements.

Though some embodiments of the invention disclose a mesh frame, patch, plate, biocompatible support member or barrier adapted to extend along the inner circumference of an anulus fibrosus, other embodiments contemplate partial coverage of the anulus or tissue surface. For some embodiments that that cover less than the entire inner surface of the anulus or that are not fully anchored in place, and are susceptible to migration, one or more projections extending outward from, or off-angle to the implant can be configured to resist migration or movement of the implant within the disc under cyclical loading and movement of the spine. One advantage of such embodiments is that they can reduce or prevent migration. Undesired migration may render the implant ineffective or cause it to pathologically interfere with adjacent tissue including the anulus, nucleus, endplates and spinal cord.

According to one embodiment, an implant can be stabilized within an intervertebral disc by providing a support member or patch with an off-angle projection functioning as a lever arm or keel. In some embodiments, even a slightly angled projection (e.g., about 5 to about 10 degrees) can serve to reduce the tendency of the device to rotate or migrate if it has sufficient surface area and length (about 3 mm to about 30 mm). As shown previously in FIGS. 25 and 34, one embodiment of an anulus augmentation device can have one or more corners, sides or projections connected at the opposing end of the devices midsection or middle portion. Such a configuration is especially effective when implanted into an intervertebral disc such that the midsection of the barrier is inserted along the posterior anulus and the corners and side projections are inserted along the posterio-lateral corners and lateral anulus respectively. In one embodiment, the corner sections extend away from the posterior anulus toward the anterior of the disc. The projections that project away from the posterior anulus at an angle (about 90 degrees or through a radius of curvature resulting in an angle from about 30 to about 150 degrees) are substantially parallel with or adjacent to the lateral anulus. Thus, the projection portion of the implant in its implanted orientation is at once off-angle to the posterior anulus or midsection of the barrier and parallel to the lateral anulus. Because the anulus defines a bounded area such a projection may indeed collide with or be parallel with another adjacent or opposing surface of the anulus but still function to stabilize the device along the other surface. The device can also be designed with one or more projections that are angled toward the medial, anterior, posterior, or lateral portion of the disc such that the projection contacts mostly or exclusively nucleus tissue or endplate. For example, a looped projection connected at the top and bottom and/or opposing ends of the support member, frame, or patch can be configured to extend across the disc from about 3 mm to about 30 mm and only contact nucleus tissue. In another embodiment, one or more projections can be oriented into a defect in the anulus and occupy less than or all of its volume. In another embodiment, a projection situated within a defect may be anchored into an endplate adjacent the defect. FIGS. 75A-L show an implant 610 (e.g., an annulus augmentation device such as a mesh) having one or more projections extending into the disc or into a defect.

A stabilizing projection according to one or more embodiments of the invention can be integral or affixed to the surgical mesh, patch, plate, biocompatible support member or barrier device. The stabilizing projection can also be independent of or coupled to at least a portion of the frame or the membrane. The stabilizing projection can be constructed from the same material as the frame or the membrane, or it can be constructed from different material. The stabilizing projection can extend from any point or points along the device or device frame including its opposing ends, mid-section, along the top edge or along the bottom edge. The projection can also form a loop in one or more planes including parallel and perpendicular to the face of the device. For example, in one embodiment opposing end projections are connected to, or are integral to, the barrier and extend out from the barrier at an angle from about 0 to about 160 degrees. In another embodiment, the projections are joined or are simply contiguous and form a bow-shaped or curved projection extending away from the barrier. In this embodiment, the barrier can be placed along a portion of the anulus and the bow would extend medially into the disc. In another embodiment, the barrier can be placed along at least a portion of the posterior anulus and the bowed projection, attached at the opposing ends of the barrier frame or membrane, would extend toward the anterior of the disc.

Figure 76:
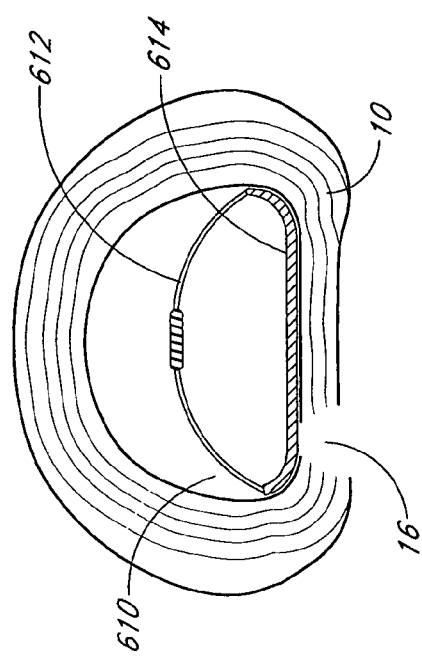
FIG. 76 shows an implant comprising a bow-like anterior projection that extends outwardly from a posterior support member.
Figure 77A:
FIGS. 77A-H show various cross-sectional side views along a horizontal axis of an implant comprising a bow, band or projection.
Figure 77E:
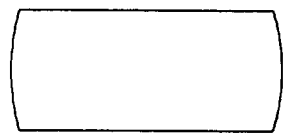
Figure 77B:
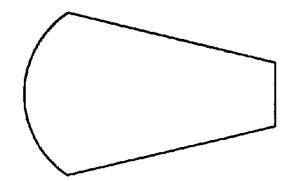
Figure 77F:
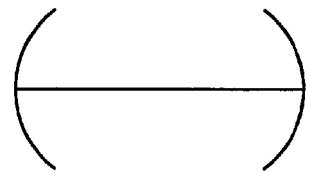
Figure 77C:
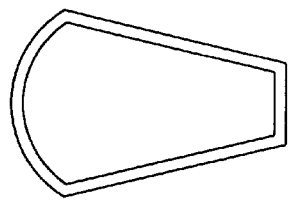
Figure 77G:
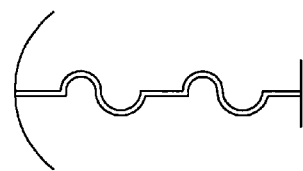
Figure 77D:
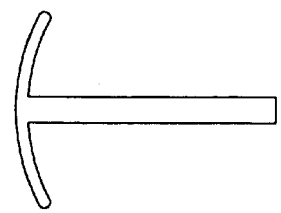
Figure 77H:
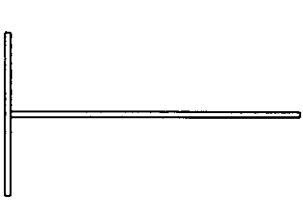

FIG. 76 shows an implant 610 according to one embodiment of the invention. Here, a bow-like anterior projection 612 extends outwardly from a posterior support member 614 (e.g., a patch, barrier or mesh). The projection 612 can be connected at each end of the posterior support member 614 along its horizontal axis. The projection 612 can be attached at any point along the vertical axis of the end including its midline, ends, or its entirety. The projection 612 may be integral to the posterior support member 614 such that the posterior support member 614 is simply formed as a band or attached separately. As shown the implant 610 can be shaped like a bow. The bow can be a gentle arc, curved, re-curved one or more times, triangular, rectangular, octagonal, linked multiple sided, oval or circular. Though in some embodiments, an arc or smooth bow may be advantageous for transferring loads evenly, a rigid mid-section portion or a comparatively flexible hinge-like mid-section along the bow is also presented. The mid-section of the bow projection can have a different height than the remainder of the bow and be the same or different (less than or greater than) height than the midsection patch or biocompatible support member portion of the device.

Various embodiments of the bow or arcurate member or projection 612 can act like a spring to aid in holding the ends of the patch open and against the anulus wall. Similarly, in one embodiment, the profile of the projection 612 can provide resistance to anterior travel of the implant through the nucleus or through the opposite wall of the anulus. In another embodiment of the invention, the projection or stabilizer 612 can also provide torsional resistance to the barrier 614. Finally, because the projection or bow 612 extends across the endplates it creates an elongated profile functioning as a lever arm and thus resists rotation along the anulus wall within the disc.

The projection, bow or band portion 612 of the implant 610 can be tubular, wire-like, flat, mesh-like, curvilinear, bent, comprised of one or more rails, or contain voids. The bow can define concavities facing inward or outward and be opposite or the same as the concavities defined by the biocompatible support member portion 614 of the implant 610. The projection 612 can simply be angled projections of the biocompatible support member and be made of the same material and have the same properties. Alternatively the projection can have different properties such as less flexibility or more rigidity along one or more axes. Although one projection is shown in FIG. 76, more than one bow-like projections may be used.

Different bow or loop projection profiles may be useful for retaining nucleus tissue within the area bounded by the implant, soft anchoring to the nucleus or at least resisting travel through or along the nucleus, or for mechanically displacing nucleus tissue. Mechanical displacement (through pinching or pressing) of the nucleus can increase disc height and serve to more uniformly load the anulus and improve the performance of the implant. Also, the gap within the disc created by the bow or projection can be left vacant or filled in with suitable nucleus augmentation either through, or around a periphery of the implant. The bow projection 612 can also act as a piston or shock absorber that deforms under compressive loading of the disc relieving some of the load on the anulus caused by the nucleus being compressed between the endplates.

The stabilizing projection 612 can be made of the same material as the biocompatible support member 614 (e.g., barrier, patch or mesh). In one embodiment, the stabilizing projection 612 is an off-angle projection of the biocompatible support member 614 and forms a continuous loop or band. In another embodiment, the stabilizing projection 612 can be made of a different biocompatible material, including polymers, metals, bio-materials, and grafts.

FIGS. 77A-H show various cross-sectional side views of an implant 610 along a horizontal axis according to one or more embodiments of the invention. Accordingly, a bow, band or projection can be uniform in height or non-uniform. It can be the same height, shorter or taller than the patch portion of the implant. For example, in one embodiment, a projection is narrow at the point where it connects to the posterior support member component of the implant and then flairs near the midline of the anterior bow until its height exceeds the posterior member height. Such a configuration might be favorable between cupped or concave vertebral endplates when the posterior member portion of the implant is positioned against the posterior anulus. Further, in one or more embodiments of the invention, a projection can have different mechanical properties than the support member or patch section of the implant. For example, in one embodiment, a projection is more or less flexible along one or more axes compared to the patch or biocompatible support member portion of the implant. In another embodiments, a projection can be concave along one or more axes, or can have variable regions of concavity along the same axis.

Figure 78A:
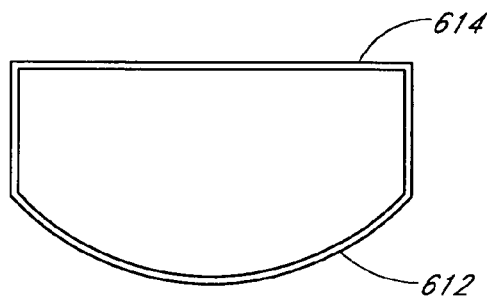
FIGS. 78A-J show various cross-sectional top views of implants along a vertical axis.
Figure 78B:
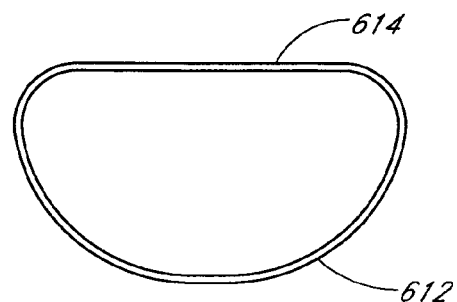
Figure 78C:
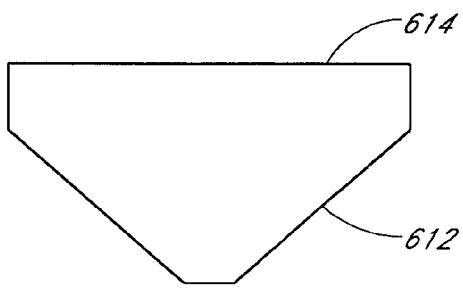
Figure 78D:
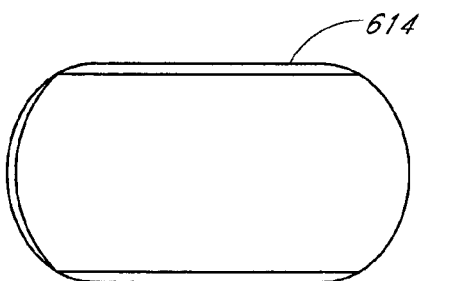
Figure 78E:
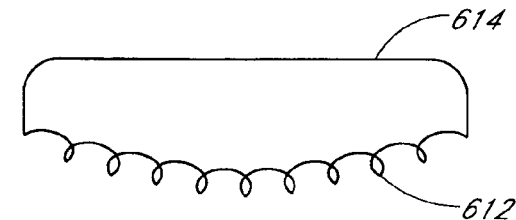
Figure 78F:
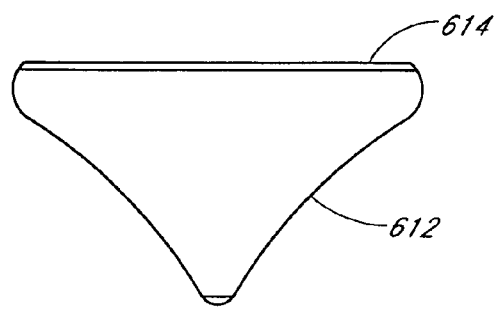
Figure 78G:
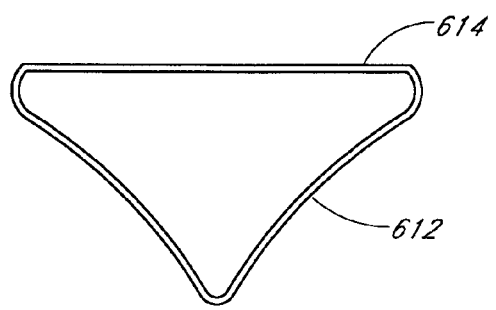
Figure 78H:
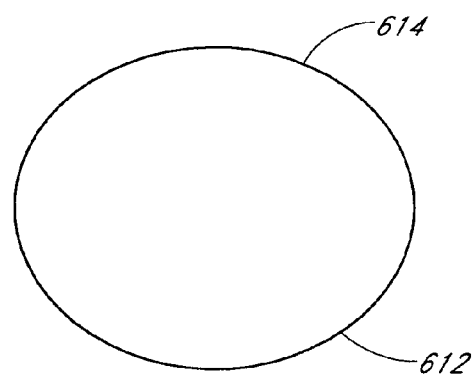
Figure 78I:
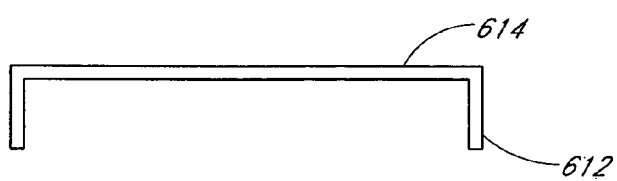
Figure 78J:
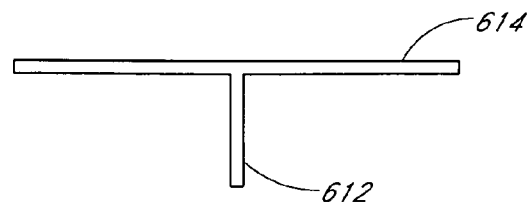
Figure 79A:
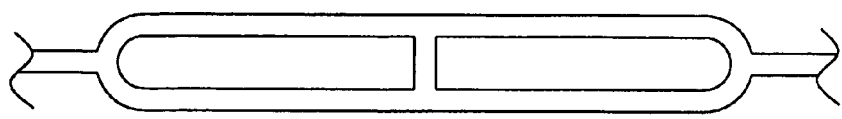
FIGS. 79A-F show a frontal view of a portion of several embodiments of an implant projection.
Figure 79B:
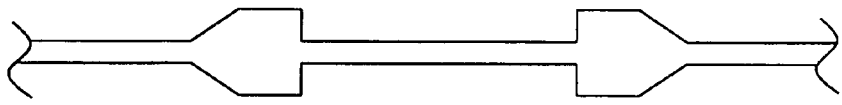
Figure 79C:
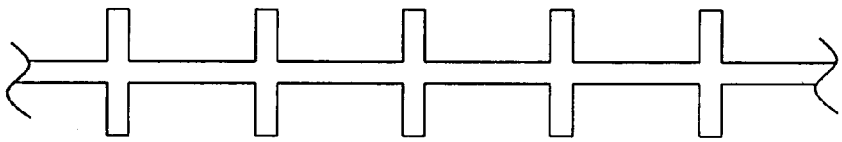
Figure 79D:
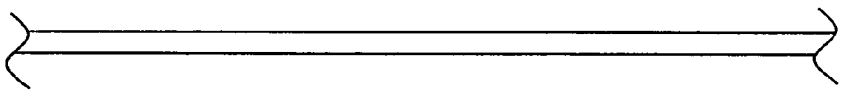
Figure 79E:
Figure 79F:
Figure 80A:
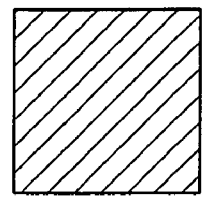
FIGS. 80A-D show various cross-sections of an implant projection.
Figure 80B:
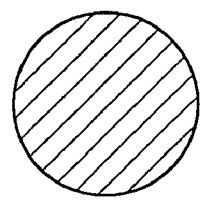
Figure 80C:
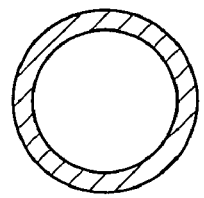
Figure 80D:
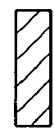

FIGS. 78A-J show various cross-sectional top views of implants 610 along a vertical axis according to some embodiments of the invention. For example, FIG. 78G shows an implant (e.g., an anulus augmentation device such as a mesh) that has a puckered bow-like projection that is well-suited for disc morphology.

FIGS. 79A-F show a frontal view of a portion of various embodiments of projections according to one or more embodiments of the invention.

FIGS. 80A-D show various cross-sections of projection 612, according to some embodiments of the invention.

Figure 81A:
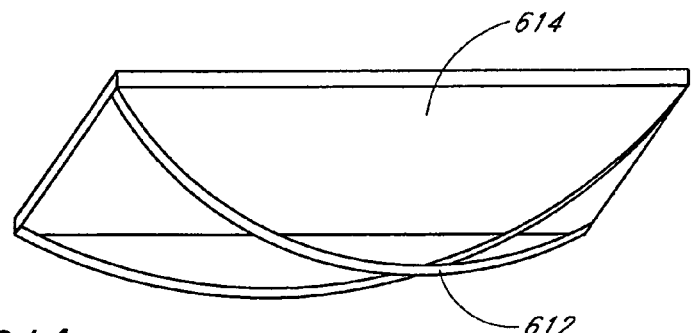
FIGS. 81A-D show looped or bent bow-type projections.
Figure 81B:
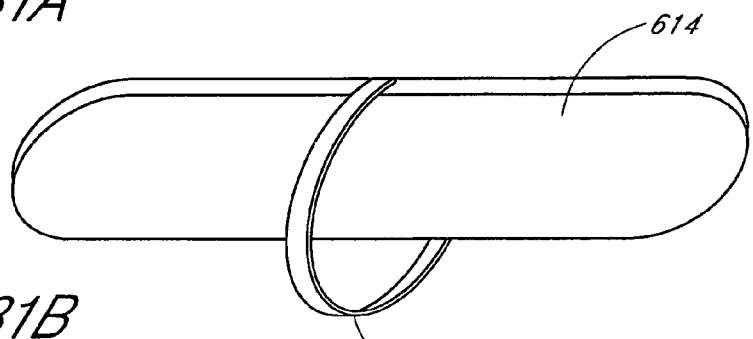
Figure 81C:
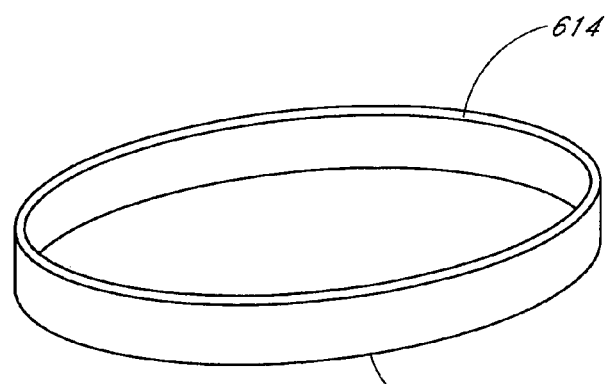
Figure 81D:
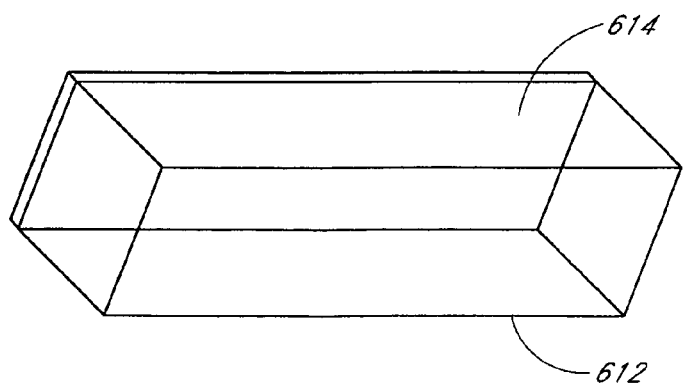

FIGS. 81A-D show looped or bent bow-type projections 612 that are contiguous or integral with, or are connected to the biocompatible support member 614 at two or more points along a vertical or horizontal axis. FIG. 81A shows a criss-cross loop projection. FIG. 81B shows a strap-like projection. FIG. 81C shows a projection that is integral with the support member such that the implant forms a circular band that serves to stabilize the device. FIG. 81D shows a box-frame type projection.

One skilled in the art will appreciate that any of the above procedures involving nuclear augmentation and/or anulus augmentation may be performed with or without the removal of any or all of the autologous nucleus. Further, the nuclear augmentation materials and/or the anulus augmentation device may be designed to be safely and efficiently removed from the intervertebral disc in the event they are no longer required.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reinforcing an intervertebral disc comprising:
    locating a defect in an anulus fibrosis, wherein said defect is proximate a herniated segment,
    wherein the herniated segment comprises anulus fibrosis tissue; delivering a support member through said defect, wherein the support member comprises a plate or bar shaped device;
    positioning the plate or bar shaped device to close the defect;
    securely establishing said plate or bar shaped device adjacent said defect;
    securely establishing said plate or bar shaped device to a region substantially opposite said defect with an anchor; and
    returning at least part of the herniated segment to a position substantially within a pre-herniated border of the herniated segment by pulling the support member towards the anchor.

2. The method of claim 1, further comprising providing a tightening connection member between the support member and the anchor, wherein the connection member is configured for transmission of a tensile force along the length of the connection member, thereby causing the herniated segment to move in the direction of its pre-herniated borders.

3. The method of claim 1, further comprising positioning said support member along an innermost layer of the anulus.

4. The method of claim 1, wherein said plate or bar shaped device comprises one or more barbs.

5. The method of claim 1, wherein the step of securely establishing said plate or bar shaped device to a region substantially opposite said defect with an anchor comprises affixing said plate or bar shaped device into an endplate with said anchor.

6. The method of claim 1, further comprising positioning said support member to span the defect in more than one direction.

* * * * *

UNITED STATES PATENT AND TRADEMARK OFFICE
CERTIFICATE OF CORRECTION

PATENT NO.       : 7,658,765 B2                                              Page 1 of 1
APPLICATION NO. : 10/972106
DATED            : February 9, 2010
INVENTOR(S)      : Gregory H. Lambrecht It is certified that error appears in the above-identified patent and that said Letters Patent is hereby corrected as shown below:

In the Specifications:

At column 4, line 66, please delete "polyp-phenyleneterephtalamide)" and insert therefore, -- poly(p-phenyleneterephthalamide) --

At column 27, line 60, please delete "implant," and insert -- implant. --

In the Claims:

At column 46, line 32 claim 2, please delete "borders" and insert -- border --

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,658,765 B2 | Page 1 of 1 |
| APPLICATION NO. | : 10/972106 | |
| DATED | : February 9, 2010 | |
| INVENTOR(S) | : Lambrecht et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 918 days.

Signed and Sealed this

Twenty-eighth Day of December, 2010

David J. Kappos
*Director of the United States Patent and Trademark Office*